US011898149B2

(12) United States Patent
Chen et al.

(10) Patent No.: US 11,898,149 B2
(45) Date of Patent: Feb. 13, 2024

(54) METHODS AND COMPOSITIONS FOR IDENTIFYING AND ENRICHING FOR CELLS COMPRISING SITE SPECIFIC GENOMIC MODIFICATIONS

(71) Applicant: SYNGENTA PARTICIPATIONS AG, Basel (CH)

(72) Inventors: Zhongying Chen, Research Triangle Park, NC (US); Myoung Kim, Cary, NC (US); Mary-Dell Chilton, Chapel Hill, NC (US); Heng Zhong, Research Triangle Park, NC (US); Weining Gu, Research Triangle Park, NC (US); Yaping Jiang, Research Triangle Park, NC (US); Qiudeng Que, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 18/181,704

(22) Filed: Mar. 10, 2023

(65) Prior Publication Data

US 2023/0265446 A1 Aug. 24, 2023

Related U.S. Application Data

(62) Division of application No. 17/177,291, filed on Feb. 17, 2021, now Pat. No. 11,643,664, and a division of application No. 15/942,859, filed on Apr. 2, 2018, now abandoned, which is a division of application No. 14/974,247, filed on Dec. 18, 2015, now Pat. No. 9,963,710.

(60) Provisional application No. 62/096,442, filed on Dec. 23, 2014.

(51) Int. Cl.
*C12N 15/82* (2006.01)
*C12N 15/10* (2006.01)

(52) U.S. Cl.
CPC ..... *C12N 15/8213* (2013.01); *C12N 15/1058* (2013.01); *C12N 15/8205* (2013.01); *C12N 15/8207* (2013.01)

(58) Field of Classification Search
None
See application file for complete search history.

(56) References Cited

U.S. PATENT DOCUMENTS

| | | | |
|---|---|---|---|
| 6,455,315 B1 | 9/2002 | Baszczynski et al. | |
| 7,361,813 B2 | 4/2008 | Steiner et al. | |
| 7,935,862 B2 | 5/2011 | Que | |
| 8,329,986 B2 | 12/2012 | Butler et al. | |
| 8,354,519 B2 | 1/2013 | Steiner et al. | |
| 8,399,254 B2 | 3/2013 | Que | |
| 8,470,973 B2 | 6/2013 | Bonas et al. | |
| 8,586,363 B2 | 11/2013 | Voytas et al. | |
| 8,586,526 B2 | 11/2013 | Gregory et al. | |
| 8,697,359 B1 | 4/2014 | Zhang et al. | |
| 8,697,853 B2 | 4/2014 | Voytas et al. | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 2005/0216970 A1 | 9/2005 | Steiner et al. | |
| 2006/0253918 A1 | 11/2006 | Que | |
| 2009/0133152 A1 | 5/2009 | Lyznik et al. | |
| 2010/0218278 A1* | 8/2010 | Kaster, Jr. .......... | C12N 15/8271 800/301 |
| 2011/0165679 A1 | 7/2011 | Gordon-Kamm et al. | |
| 2011/0191899 A1 | 8/2011 | Ainley et al. | |
| 2011/0201055 A1 | 8/2011 | Doyon et al. | |
| 2011/0201118 A1 | 8/2011 | Yang et al. | |
| 2014/0068797 A1 | 3/2014 | Doudna et al. | |
| 2014/0090113 A1 | 3/2014 | Cogan et al. | |
| 2014/0273235 A1 | 9/2014 | Voytas et al. | |
| 2014/0298547 A1 | 10/2014 | Sastry-Dent et al. | |
| 2015/0128309 A1 | 5/2015 | Sastry-Dent et al. | |

FOREIGN PATENT DOCUMENTS

| | | |
|---|---|---|
| WO | 2007142840 A2 | 12/2007 |
| WO | 2011154158 A1 | 12/2011 |
| WO | 2011154159 A1 | 12/2011 |
| WO | 2012129373 A2 | 9/2012 |
| WO | 2013019411 A1 | 2/2013 |
| WO | 2013026740 A2 | 2/2013 |
| WO | 2013066423 A2 | 5/2013 |
| WO | 2013112686 A1 | 8/2013 |
| WO | 2013141680 A1 | 9/2013 |
| WO | 2013160230 A1 | 10/2013 |
| WO | 2013169802 A1 | 11/2013 |
| WO | 2014161821 A1 | 10/2014 |
| WO | 2014199358 A1 | 12/2014 |

OTHER PUBLICATIONS

Yang et al., Plant Mol Biol, 2009, 70, 669-679.
Version et al., Jun. 1, 2014, Retrieved from the Internet: URL:http://www.bc-diagnostics.com/downloads/products/bpz/Z_720_06_20_foodproof_SL_GMO_MIR604_Maize_Detection_Kit_V1-1.pfd [retrieved on Mar. 7, 2016].
International Search Report for International Application No. PCT/US2015/066619 dated Mar. 29, 2016.
Ainley et al. 2013, Plant Biotechnology Journal, 11, 1126-1134.
Ayar et al., Plant Biotechnology Journal, 2013, 11, 305-314.
Belhaj et al., Plant Methods, 2013, 9, 39.
Bortesi and Fischer, Biotechnology Advances, 33, 2015, 41-52.
Cai et al., Plant Mol Biol, 2009, 69, 699-709.
Cermak et al., Nucleic Acids Research, 2011, 39, 12, e82.

(Continued)

*Primary Examiner* — Brent T Page
(74) *Attorney, Agent, or Firm* — Amanda W. Bublitz

(57) ABSTRACT

The present invention relates to methods and compositions for modifying a target site in the genome of a plant cell. Such modifications include integration of a transgene and mutations. The present invention also relates to methods and compositions for identifying and enriching for cells which comprise a modified target site.

3 Claims, 13 Drawing Sheets

Specification includes a Sequence Listing.

(56) References Cited

OTHER PUBLICATIONS

Chen and Gao, Plant Cell Rep, 2014, 33, 575-583.
Christian et al., Genetics, 186, 757-761 (Oct. 2010).
Cibulskis et al., Nature Biotechnology, vol. 31, No. 3, Mar. 2013, 213-221.
Curtin et al., The Plant Genome, Jul. 2012, vol. 5, No. 2, 42-50.
Dahlem et al., PLOS Genetics, Aug. 2012, vol. 8, Issue 8, e1002861.
D'Halluin et al., Plant Biotechnology Journal, 2008, 6, 93-102.
D'Halluin et al., Plant Biotechnology Journal, 2013, 11, 933-941.
Djukanovic et al., The Plant Journal, 2013, 76, 888-899.
Doudna and Charpentier, Science, Nov. 28, 2014, vol. 346, Issue 6213, 1077-1086.
Grove, Journal of Biomolecular Techniques, vol. 10, Issue 1, Mar. 1999, 11-16.
Ishida et al., Nature Protocols, vol. 2, No. 7, 2007, 1614-1621.
Jiang et al., Nucleic Acids Research, 2013, 1-12.
Li et al., Nucleic Acids Research, 2011, vol. 39, No. 14, 6315-6325.
Liang et al., Journal of Genetics and Genomics, 41, 2014, 63-68.
Malnoy et al., Tree Genetics and Genomes, 2010, 6, 423-433.
Marton et al., Plant Physiology, Nov. 2010, vol. 154, 1079-1087.
Negrotto et al., Plant Cell Reports, 2000, 19, 798-803.
Nekrasov et al., Nature Biotechnology, vol. 31, No. 8, Aug. 2013, 691-693.
Papapetrou et al., Nature Biotechnology, vol. 29, No. 1, Jan. 2011, 73-81.
Permingeat et al., Plant Molecular Biology, 52, 415-419, 2003.
Puchta and Fauser, The Plant Journal, 2014, 78, 727-741.
Qi et al., Genome Research, 2013, 1-8.
Qiu et al., BioTechniques, 2004, 36, 4, 702-707.
Que et al., Frontiers in Plant Science, Aug. 2014, 6, 379, 1-19.
Sadelain et al., Nature Reviews, Jan. 2012, 12, 51-58.
Saika et al., Plant Physiology, Jul. 2011, 156, 1269-1277.
Shukla et al., Nature, May 21, 2009, 459, 437-443.
Townsend et al., Nature, May 21, 2009, 459, 442-446.
Tzfira et al., Plant Biotechnology Journal, 2012, 10, 373-389.
Voytas, Annu. Rev. Plant Biol., 2013, 64, 327-50.
Voytas and Gao, PLOS Biology, Jun. 2014, 12, 6, e1001877.
Voytas and Joung, Science, 2009, 326, 1491-1492.

* cited by examiner

| Mutation type | M assay copy number call |
|---|---|
| WT | 2 |
| Small InDel in one allele | 1 |
| Small InDel in both alleles | 0 |
| Small InDel and large deletion in each allele | 0 |

Interpretation of Taqman results

| Taqman Readings | Target Site Modification Status |
|---|---|
| 2 | both copies aren't modified |
| 1 | one copy is modified, one copy isn't |
| 0 | both copies are modified |

(B) Copy number call of different types of events

| Event type | T assay copy number call | M assay copy number call | G assay copy number call |
|---|---|---|---|
| Event with no targeted insertion | | | |
| a) WT, no mutation in both alleles | 2 | 2 | $\geq 0$ |
| b) Small indel in one allele | 2 | 1 | $\geq 0$ |
| c) Small indel in both alleles | 2 | 0 | $\geq 0$ |
| d) Small indel in one allele and large deletion in another allele | 1 | 0 | $\geq 0$ |
| e) Large insertion in both alleles | 0 | 0 | $\geq 0$ |
| Event with targeted insertion | | | |
| f) No mutation in one allele, targeted insertion in another allele | 1 | 1 | $\geq 1$ |
| g) Small indel in each allele, targeted insertion in another allele | 1 | 0 | $\geq 1$ |
| h) Large deletion in in each allele, targeted insertion in another allele | 0 | 0 | $\geq 1$ |
| i) Targeted insertion in both alleles | 0 | 0 | $\geq 2$ |

FIG. 8B

MIR604 RBFS_pNOV2130 T-DNA insert_LBFS

11632 bp

METHODS AND COMPOSITIONS FOR IDENTIFYING AND ENRICHING FOR CELLS COMPRISING SITE SPECIFIC GENOMIC MODIFICATIONS

RELATED APPLICATIONS

This application is a divisional of U.S. patent application Ser. No. 17/177,291, filed Feb. 17, 2021, which is a divisional of U.S. patent application Ser. No. 15/942,859, filed Apr. 2, 2018, which is a divisional of U.S. patent application Ser. No. 14/974,247, filed Dec. 18, 2015, now U.S. Pat. No. 9,963,710, which claims priority from provisional application 62/096,442, filed Dec. 23, 2014 and incorporated by reference in its entirety herein.

SEQUENCE LISTING

A Sequence Listing in ASCII text format, submitted under 37 C.F.R. § 1.821, entitled "80484_ST25.txt", 409 kilobytes in size, generated on Dec. 15, 2015 and filed via EFS-Web is provided in lieu of a paper copy. This Sequence Listing is hereby incorporated by reference into the specification for its disclosures.

FIELD OF THE INVENTION

The present invention relates to methods and compositions for modifying a target site in the genome of a plant cell. Such modifications include transgene integration and mutations. The present invention further relates to methods and compositions for identifying and enriching for a cell with one or more transgenes integrated at a target site within the genome of the cell, as well as for identifying and enriching for a cell comprising a mutation introduced at a target site within the genome of the cell without integration into the genome of a heterologous nucleotide sequence encoding a nuclease for site specific cleavage at the target site within the genome.

BACKGROUND OF THE INVENTION

Recent advances in the field of targeted modifications of a genome have made is so that routine targeted modifications may soon be possible. Significant advances have been made in the last few years towards the development of methods and compositions to target and cleave genomic DNA by site specific nucleases (e.g., Zinc Finger Nucleases (ZFNs), Meganucleases, Transcription Activator-Like Effector Nucelases (TALENS) and Clustered Regularly Interspaced Short Palindromic Repeats/CRISPR-associated nuclease (CRISPR/Cas) with an engineered crRNA/tracr RNA), to induce targeted mutagenesis, induce targeted deletions of cellular DNA sequences, and facilitate targeted recombination of an exogenous donor DNA polynucleotide, such as a transgene, within a predetermined genomic locus. This predetermined genomic locus is not obvious. Many sites in the genome are non-ideal for, for example, transgene insertion, due to highly repetitive nucleotide sequence, methylation, and other characteristics that result in a very high or very low level of recombination or poor expression of genes on introduced transgenes. Therefore, there is a need in the art to identify ideal target sites within a genome for targeted modifications, such as transgene insertion.

Once a target site has been used for targeted modification, there is a need to determine if the desired targeted modification was successfully created. Existing methods of screening for targeted genomic modifications in cells are primarily based on polymerase chain reaction (PCR) protocols, nucleic acid sequencing and Southern analysis. In the case of PCR amplification, the screening process of handling the complexity of gene insertion or modification at a specific site is inefficient due to the complexity of PCR primer settings and inherent ambiguity of PCR amplification due to the resulting complexity of genome rearrangement and genome ploidy. Some of the problems with PCR include: 1) no clear distinction between one copy and two copy insertions due to ploidy of the genome; 2) a requirement for complex primer design and large sets of primer combinations to deal with the complexity of gene insertion or modification at the specific site(s); and 3) low throughput of gel electrophoresis and ambiguity of amplification bands. Although subsequent sequencing can help in identifying the characteristics of PCR amplification products, there are problems with large scale sequencing efforts and interpretation of results for large sample numbers. Further gene segregation analysis is required to isolate homozygous progeny for further screening. These steps require large scale operations for screening of commercial crops in order to capture less than 2% of potential candidates and the inventory scale of plants in greenhouses require commercial scales of space and operational costs until the plant growth stage is mature enough to carry out Southern analyses.

The present invention addresses these shortcomings in the art by providing an ideal target site for a maize genome. The present invention also provides a more strategic and efficient approach to identify and enrich for cells with a targeted genomic insertion or a targeted genomic mutation, which reduces the number of candidate plants with high accuracy at the very early stages of the screening process, avoiding a large scale sequencing effort and reducing greenhouse operational costs for plant maintenance.

SUMMARY OF THE INVENTION

In one aspect, the present invention provides a method of integrating a transgene into a genomic nuclease cleavage site in a maize genome, comprising introducing into a maize cell: a) a first nucleic acid molecule comprising at least about 100 contiguous nucleotides, wherein said contiguous nucleotides have at least about 90% identity with a target site in the nucleotide sequence of SEQ ID NO:1 or the nucleotide sequence of SEQ ID NO:2, and further comprising a transgene; and b) a second nucleic acid molecule comprising a nucleotide sequence encoding a nuclease for site-directed cleavage at a genomic nuclease cleavage site adjacent to the nucleotide sequence of SEQ ID NO:1 or the nucleotide sequence of SEQ ID NO:2 that corresponds to the contiguous nucleotides of (a), under conditions wherein expression of the second nucleic acid molecule can occur to produce the nuclease and the nuclease can cleave the nucleotide sequence at the genomic nuclease cleavage site, whereby the transgene is integrated at the genomic nuclease target cleavage site in the maize genome. The present invention also provides a method of producing a maize plant, plant part, or progeny thereof comprising a transgene integrated into a genomic nuclease cleavage site in the maize genome, comprising regenerating a maize plant from the maize cell produced by the method described above. The present invention further provides a maize plant, plant part, or progeny thereof comprising a transgene integrated into a genomic nuclease cleavage site in the maize genome, produced by the method described.

In a further aspect, the present invention provides a method of enriching for a cell comprising a transgene inserted into a nuclease cleavage site in a genome of the cell, comprising: a) introducing into a plurality of cells: i) a first nucleic acid molecule comprising at least 100 contiguous nucleotides, wherein the at least 100 contiguous nucleotides have at least 90% identity with a target site in the genome of the cell, and further comprising a transgene; and ii) a second nucleic acid molecule encoding a nuclease for site-directed cleavage at a nuclease cleavage site in the genome of the cell adjacent to the nucleotide sequence in the genome of the cell that corresponds to the at least 100 contiguous nucleotides of (a), under conditions wherein expression of the second nucleic acid molecule can occur to produce the nuclease and the nuclease can cleave at the nuclease cleavage site in the genome of the cell and integrate the transgene into the nuclease cleavage site in the genome of the cell; b) culturing the cells of (a) to produce a cell line or tissue; c) extracting a genomic DNA sample from the cell line or tissue of (b); d) performing real-time quantitative polymerase chain reaction (qPCR) assays T and G on the sample of (c), wherein the assays T and G respectively comprise the following probes: i) a first probe comprising a nucleotide sequence that is complementary to a nucleotide sequence of the target site, at least five base pairs away from the nuclease cleavage site for carrying out assay T, and ii) a second probe comprising a nucleotide sequence that is complementary to a nucleotide sequence of the transgene for carrying out assay G; e) obtaining a DNA copy number of the target site from the results of assay T and a DNA copy number of the transgene from the results of assay G; and f) enriching for a cell line or tissue that has reduced copy number in assay T relative to a reference and a copy number greater than zero for assay G, thereby enriching for the cell comprising the transgene inserted into the nuclease cleavage site in the genome of the cell.

Furthermore, the present invention provides a method of identifying a cell comprising a transgene inserted into a nuclease cleavage site in a genome of the cell, comprising: a) introducing into a plurality of cells: i) a first nucleic acid molecule comprising at least 100 contiguous nucleotides having at least 90% identity with a target site in the genome of the cell, and further comprising a transgene; and ii) a second nucleic acid molecule encoding a nuclease for site-directed cleavage at a nuclease cleavage site in the genome of the cell adjacent to the nucleotide sequence in the genome corresponding to the at least 100 contiguous nucleotides of (a), under conditions wherein expression of the second nucleic acid molecule can occur to produce the nuclease and the nuclease can cleave at the nuclease cleavage site in the genome of the cell and integrate the transgene into the nuclease cleavage site in the genome of the cell; b) culturing the cells of (a) to produce a cell line or tissue; c) extracting a genomic DNA sample from the cell line or tissue of (b); d) performing real-time quantitative polymerase chain reaction (qPCR) assays T and G on the sample of (c), wherein the assays T and G respectively comprise the following probes: i) a first probe comprising a nucleotide sequence that is complementary to a nucleotide sequence of the target site, at least five base pairs away from the nuclease cleavage site for carrying out assay T, and ii) a second probe comprising a nucleotide sequence that is complementary to a nucleotide sequence of the transgene for carrying out assay G; e) obtaining a DNA copy number of the target site from the results of assay T and a DNA copy number of the transgene from the results of assay G; and f) identifying a cell line or tissue that has reduced copy number in assay T relative to a reference and a copy number greater than zero for assay G, thereby identifying the cell comprising the transgene inserted into the nuclease cleavage site in the genome of the cell. The present invention also provides for a cell line or tissue that is enriched for or identified by the described methods, and further provides for a plant, plant part, or progeny thereof derived from the cell line or tissue.

In further aspects of this invention, a method is provided of enriching for a cell comprising a mutation introduced into a nuclease cleavage site in a genome of the cell and lacking integration of a heterologous nucleotide sequence encoding a nuclease for site-directed cleavage of a nucleotide sequence at the nuclease cleavage site into the genome of the cell, comprising: a) introducing a nucleic acid molecule comprising a heterologous sequence encoding a nuclease for site-directed cleavage of the nucleotide sequence at the nuclease cleavage site in the genome of the cell into a plurality of cells under conditions wherein expression of the nucleic acid molecule can occur to produce the nuclease and the nuclease can cleave the nucleotide sequence at the nuclease cleavage site in the genome of the cell, thereby introducing a mutation at the nuclease cleavage site in the genome of the cell without integration of the heterologous nucleotide sequence encoding the nuclease into the genome of the cell; b) culturing the plurality of cells of (a) to produce a cell line or tissue; c) extracting a genomic DNA sample from the cell line or tissue of (b); d) performing real-time quantitative polymerase chain reaction (qPCR) assays 1 and 2 on the sample of (c), wherein the assays respectively comprise the following probes: i) a first probe comprising a nucleotide sequence that is complementary to the nucleotide sequence comprising the nuclease cleavage site to carry out assay 1, and ii) a second probe comprising a nucleotide sequence that is complementary to the heterologous nucleotide sequence encoding the nuclease to carry out assay 2; e) obtaining a DNA copy number of the nuclease cleavage site from the results of assay 1 and a DNA copy number of the heterologous nucleotide sequence encoding the nuclease from the results of assay 2; and f) enriching for a cell line or tissue that has a reduced copy number for assay 1 relative to a reference and a copy number equal to zero for assay 2, thereby enriching for the cell comprising the mutation introduced into the nuclease cleavage site in the genome of the cell and lacking integration of the heterologous nucleotide sequence encoding the nuclease into the genome of the cell.

Also provided as an aspect of this invention is a method of identifying a cell comprising a mutation introduced into a nuclease cleavage site in a genome of the cell and lacking integration of a heterologous nucleotide sequence encoding a nuclease for site-directed cleavage of a nucleotide sequence at the nuclease cleavage site into the genome of the cell, comprising: a) introducing a nucleic acid molecule comprising a heterologous sequence encoding a nuclease for site-directed cleavage of the nucleotide sequence at the nuclease cleavage site in the genome of the cell into a plurality of cells under conditions wherein expression of the nucleic acid molecule can occur to produce the nuclease and the nuclease can cleave the nucleotide sequence at the nuclease cleavage site in the genome of the cell, thereby introducing a mutation at the nuclease cleavage site in the genome of the cell without integration of the heterologous nucleotide sequence encoding the nuclease into the genome of the cell; b) culturing the plurality of cells of (a) to produce a cell line or tissue; c) extracting a genomic DNA sample from the cell line or tissue of (b); d) performing real-time quantitative polymerase chain reaction (qPCR) assays 1 and 2 on the sample of (c), wherein the assays respectively comprise the following probes: i) a first probe comprising a nucleotide sequence that is complementary to the nucleotide sequence comprising the nuclease cleavage site to carry out assay 1, and ii) a second probe comprising a nucleotide sequence that is complementary to the heterologous nucleotide sequence encoding the nuclease to carry out assay 2; e) obtaining a DNA copy number of the nuclease cleavage site from the results of assay 1 and a DNA copy number of the heterologous nucleotide sequence encoding the nuclease from the results of assay 2; and f) identifying a cell line or tissue that has a reduced copy number for assay 1 relative to a reference and a copy number equal to zero for assay 2, thereby identifying the cell comprising the mutation introduced into the nuclease cleavage site in the genome of the cell and lacking integration of the heterologous nucleotide sequence encoding the nuclease into the genome of the cell. The present invention also provides for a cell line or tissue that is enriched for or identified by the described methods, and further provides for a plant, plant part, or progeny thereof derived from the cell line or tissue.

In additional aspects, the present invention provides a method of producing a plant, plant part, or progeny thereof comprising a mutation introduced at a nuclease cleavage site in a genome of a plant cell and lacking integration of a heterologous nucleotide sequence encoding a nuclease for site-directed cleavage of a nucleotide sequence at the nuclease cleavage site in the genome of the plant cell, comprising: a) introducing into the plant cell a nucleic acid molecule comprising a heterologous nucleotide sequence encoding a nuclease for site-directed cleavage of the nucleotide sequence at the nuclease cleavage site in the genome of the plant cell under conditions wherein expression of the nucleic acid molecule occurs transiently to produce the nuclease and the nuclease can cleave the nucleotide sequence at the nuclease cleavage site in the genome of the plant cell, thereby introducing a mutation at the nuclease cleavage site in the genome of the plant cell without integration of the heterologous nucleotide sequence encoding the nuclease into the genome of the plant cell; and b) regenerating a plant, plant part, or progeny thereof from the plant cell of (a). The present invention further provides the plant, plant part, or progeny thereof produced by the method described.

The present invention also provides a method for modifying a target site in the genome of a plant cell, comprising: a) introducing into the plant cell a first nucleic acid comprising at least 100 contiguous nucleotides, wherein the at least 100 contiguous nucleotides have at least 90% identity with a target site in the genome of the cell, and further comprising a transgene; and b) a second nucleic acid molecule encoding nuclease for site-directed cleavage at a nuclease cleavage site in the genome of the cell adjacent to the nucleotide sequence in the genome of the cell that corresponds to the at least 100 contiguous nucleotides of (a), wherein the nuclease is a modified Cas9 nuclease comprising SEQ ID NO: 30, under conditions wherein expression of the second nucleic acid molecule can occur to produce the nuclease and the nuclease can cleave at the nuclease cleavage site in the genome of the cell and modify the target site in the genome of the plant cell.

The present invention also provides a method of producing a maize plant, plant part, or progeny thereof comprising a modification at a target site in the genome of the plant cell, comprising: a) introducing into the plant cell a first nucleic acid comprising at least 100 contiguous nucleotides, wherein the at least 100 contiguous nucleotides have at least 90% identity with a target site in the genome of the cell, and further comprising a transgene; b) a second nucleic acid molecule encoding nuclease for site-directed cleavage at a nuclease cleavage site in the genome of the cell adjacent to the nucleotide sequence in the genome of the cell that corresponds to the at least 100 contiguous nucleotides of (a), wherein the nuclease is a modified Cas9 nuclease comprising SEQ ID NO: 30, under conditions wherein expression of the second nucleic acid molecule can occur to produce the nuclease and the nuclease can cleave at the nuclease cleavage site in the genome of the cell and modify the target site in the genome of the plant cell; and c) regenerating a plant, plant part, or progeny thereof from the plant cell of (a). The present invention further provides the plant, plant part, or progeny thereof produced by the method described.

The present invention also provides a method of integrating a transgene into a genomic nuclease cleavage site in an event MIR604 transgenic maize genome, comprising introducing into an event MIR604 maize cell: a) a first nucleic acid molecule comprising at least 100 contiguous nucleotides, wherein said at least 100 contiguous nucleotides have at least 90% identity with a target site in a nucleotide sequence selected from the group comprising SEQ ID NO:133, SEQ ID NO: 134, SEQ ID NO: 135, SEQ ID NO: 136, SEQ ID NO: 137, SEQ ID NO: 138, and SEQ ID NO: 139, and further comprising a transgene; and b) a second nucleic acid molecule comprising a nucleotide sequence encoding a nuclease for site-directed cleavage at a genomic nuclease cleavage site adjacent to a nucleotide sequence with at least 90% identity to a nucleotide sequence selected from the group comprising SEQ ID NO:133, SEQ ID NO: 134, SEQ ID NO: 135, SEQ ID NO: 136, SEQ ID NO: 137, SEQ ID NO: 138, and SEQ ID NO: 139, that corresponds to the at least 100 contiguous nucleotides of (a), under conditions wherein expression of the second nucleic acid molecule can occur to produce the nuclease and the nuclease can cleave the nucleotide sequence at the genomic nuclease cleavage site, whereby the transgene is integrated at the genomic nuclease target cleavage site in the maize genome. The present invention further provides a method of producing a maize plant, plant part, or progeny thereof comprising a transgene integrated into a genomic nuclease cleavage site in an event MIR604 maize genome, comprising regenerating a maize plant from the maize cell produced by the method described. The present invention further provides a maize plant, plant part, or progeny thereof comprising comprising a transgene integrated into a genomic nuclease cleavage site in the event MIR604 maize genome, produced by the method described.

BRIEF DESCRIPTION OF THE DRAWINGS

FIGS. 8A-B. Strategies to enrich for potential targeted insertion events based on copy number reduction of target sequences. (A) Schematic representation of potential types of mutations and targeted insertion as a result of targeted nuclease cleavage at the target locus in a targeted insertion experiment. M is the site-directed nuclease cleavage site; T is a sequence located away from M by at least 5 nucleotides in the region of the target locus and it should be as far away as possible from M but within the region replaced by targeted insertion. However, T can sit within the same amplicon as assay for M. G is an assay target for transgenic sequences (gene of interest (GOI)). (B) Copy number call of different assays in plants with different kinds of mutations or insertions in the target site as shown in (A) using real-time qPCR assays.

BRIEF DESCRIPTION OF THE SEQUENCES IN THE SEQUENCE LISTING

Figure 1:
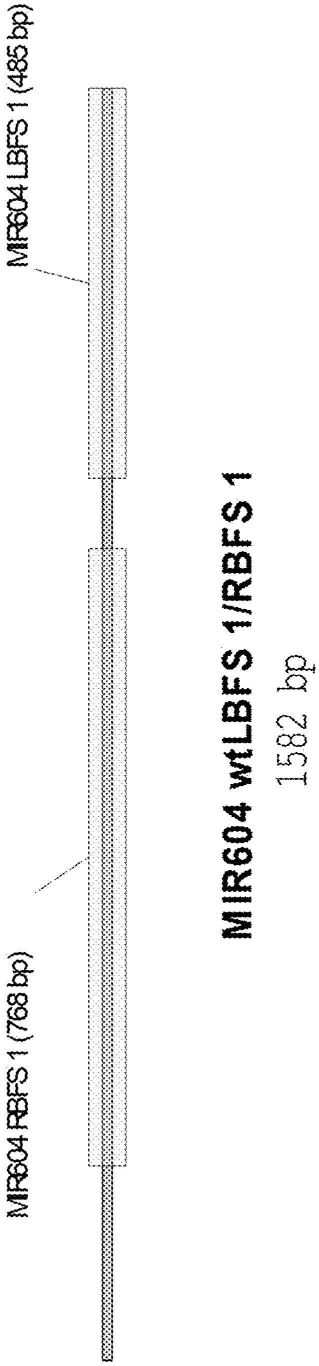
FIG. 1. Schematic diagram showing MIR604 insertion site flanking sequences. 88 base pairs of sequences between MIR604RBFS1 and MIR604LBFS1 are deleted in MIR604 event during T-DNA integration. This MIR604 insertion site does not contain the event MIR604 transgene.

SEQ ID NO: 1 is a nucleotide sequence of the MIR604 insertion site sequence from maize line A188. This the MIR604 insertion site without an event MIR604 transgene.

SEQ ID NO: 2 is maize elite line NP2222 genomic sequences corresponding to the A188 MIR604 insertion site and its flanking sequences.

SEQ ID NO: 3-27 are nucleotide sequences that are potential target sequences for Cas9-mediated cleavage proximal to the MIR604 insertion site.

SEQ ID NO: 28 is a maize genomic target sequence, MIR604FR2.

SEQ ID NO: 29 is a nucleotide sequence encoding a Type II Cas9 gene from *Streptococcus pyogenes* SF370 optimized with maize-preferred codons.

SEQ ID NO: 30 is an amino acid sequence comprising a modified Cas9 protein.

SEQ ID NO: 31-34 are nucleotide sequences that can be used to guide Cas9 cleavage of the MIR604 insertion site.

SEQ ID NO: 35 is a nucleotide sequence encoding tracRNA scaffold and PolIII termination sequences.

SEQ ID NO: 36 is a nucleotide sequence encoding a single guide RNA (sgRNA).

SEQ ID NO: 37 is a nucleotide sequence comprising an expression cassette comprising prOsU3 and coding sequences for the sgRNA of SEQ ID NO: 36.

SEQ ID NO: 38 is a nucleotide sequence comprising xJHAX-03.

SEQ ID NO: 39 is a nucleotide sequence comprising xJHAX-04.

SEQ ID NO: 40-65 are nucleotide sequences selected as TALEN target sequences based on NP2222 genomic sequences (SEQ ID NO: 2).

SEQ ID NO: 66 is a nucleotide sequence comprising the TALEN target sequence MIR604FR1.

SEQ ID NO: 67 is a nucleotide sequence comprising the TALEN target sequence MIR604FR2.

SEQ ID NO: 68 is an amino acid sequence of the artificial nuclease cTNmir604Fw1-01 which recognizes target sequence SEQ ID NO: 42.

SEQ ID NO: 69 is an amino acid sequence of the artificial nuclease cTNmir604Fw1-02 which recognizes target sequence SEQ ID NO: 42.

SEQ ID NO: 70 is an amino acid sequence of the artificial nuclease cTNmirFw1-03 which recognizes target sequence SEQ ID NO: 42.

SEQ ID NO: 71 is an amino acid sequence of the artificial nuclease cTNmir604Rv1-01 which recognizes target sequence SEQ ID NO: 43.

SEQ ID NO: 72 is an amino acid sequence of the artificial nuclease cTNmir604Rv1-02 which recognizes target sequence SEQ ID NO: 43.

SEQ ID NO: 73 is an amino acid sequence of the artificial nuclease cTNmir604Rv1-03 which recognizes target sequence SEQ ID NO: 43.

SEQ ID NO: 74 is an amino acid sequence of the artificial nuclease cTNmir604Fw2-01 which recognizes target sequence SEQ ID NO: 53.

SEQ ID NO: 75 is an amino acid sequence of the artificial nuclease cTNmir604Fw2-02 which recognizes target sequence SEQ ID NO: 53.

SEQ ID NO: 76 is an amino acid sequence of the artificial nuclease cTNmir604Fw2-03 which recognizes target sequence SEQ ID NO: 53.

SEQ ID NO: 77 is an amino acid sequence of the artificial nuclease cTNmire604RV2-01 which recognizes target sequence SEQ ID NO: 54.

SEQ ID NO: 78 is an amino acid sequence of the artificial nuclease cTNmir604RV2-02 which recognizes target sequence SEQ ID NO: 54.

SEQ ID NO: 79 is an amino acid sequence of the artificial nuclease cTNmir604Rv2-03 which recognizes target sequence SEQ ID NO: 54.

SEQ ID NO: 80 is an amino acid sequence of the artificial nuclease cTNmir604Fw2-05 which recognizes target sequence SEQ ID NO: 53.

SEQ ID NO: 81 is an amino acid sequence of the artificial nuclease cTNmir604Rv2-04 which recognizes target sequence SEQ ID NO: 65.

SEQ ID NO: 82 is a nucleotide sequence encoding for the full length artificial nuclease molecule cTNmir604Fw1-01 (SEQ ID NO:68).

SEQ ID NO: 83 is a nucleotide sequence encoding for the truncated artificial nuclease molecule cTNmir604Fw1-03 (SEQ ID NO:70).

SEQ ID NO: 84 is a nucleotide sequence encoding for the full length artificial nuclease molecule cTNmir604Rv1-01 (SEQ ID NO:71).

SEQ ID NO: 85 is a nucleotide sequence encoding for the truncated artificial nuclease molecule cTNmir604Rv1-03 (Seq.ID No.72).

SEQ ID NO: 86 is a nucleotide sequence encoding for the full length artificial nuclease molecule cTNmir604Fw2-01 (SEQ ID NO:72).

SEQ ID NO: 87 is a nucleotide sequence encoding for the truncated artificial nuclease molecule cTNmir604Fw2-03 (SEQ ID NO:73).

SEQ ID NO: 88 is a nucleotide sequence encoding for the truncated artificial nuclease molecule cTNmir604Fw2-05 (SEQ ID NO:80).

SEQ ID NO: 89 is a nucleotide sequence encoding for the full length artificial nuclease molecule cTNmir604Rv2-01 (SEQ ID NO:77).

SEQ ID NO: 90 is a nucleotide sequence encoding for the truncated artificial nuclease molecule cTNmir604Rv2-03 (SEQ ID NO:79).

SEQ ID NO: 91 is a nucleotide sequence encoding for the truncated artificial nuclease molecule cTNmir604Rv2-04 (SEQ ID NO.81).

SEQ ID NO: 92-97 are nucleotide sequences useful for using qPCR for the detection of mutations within the SEQ ID NO: 67 target sequence.

SEQ ID NO: 98 is a nucleotide sequence comprising a gene encoding phosphomannose isomerase (cPMI-01).

SEQ ID NO: 99-101 are nucleotide sequences comprising PMI target sequences for genomic modification meditated by TALENs SEQ ID NO: 102-107 are nucleotide sequences comprising TALEN sequence targets within SEQ ID NO: 98.

SEQ ID NO: 108 is an amino acid sequence of the artificial nuclease protein TLN_PMIFW1a which recognizes SEQ ID NO: 102

SEQ ID NO: 109 is an amino acid sequence of the artificial nuclease protein TLN_PMIRV1a which recognizes SEQ ID NO: 103.

SEQ ID NO: 110 is an amino acid sequence of the artificial nuclease protein TLN_PMIFW3 which recognizes SEQ ID NO: 106

SEQ ID NO: 111 is an amino acid sequence of the artificial nuclease protein TLN_PMIRV3 which recognizes SEQ ID NO: 107.

SEQ ID NO: 112 is a nucleotide sequence which encodes for the artificial nuclease protein TLN_PMIFW1a.

SEQ ID NO: 113 is a nucleotide sequence which encodes for the artificial nuclease protein TLN_PMIRV1a.

SEQ ID NO: 114 is a nucleotide sequence which encodes for the artificial nuclease protein TLN_PMIFW3.

SEQ ID NO: 115 is a nucleotide sequence which encodes for the artificial nuclease protein TLN_PMIRV3.

SEQ ID NO: 116-118 are nucleotide sequences comprising the artificial nuclease target sequences.

SEQ ID NO: 119 is an amino acid sequence of the artificial nuclease protein TLN_rPMIFW1-01 which recognizes SEQ ID NO: 117.

SEQ ID NO: 120 is an amino acid sequence of the artificial nuclease protein TLN_rPMIRv1-01 which recognizes SEQ ID NO: 118.

SEQ ID NO: 121 is an amino acid sequence of the artificial nuclease protein TLN_rPMIFw1-02 which recognizes SEQ ID NO: 117.

SEQ ID NO: 122 is an amino acid sequence of the artificial nuclease protein TLN_rPMIRv1-02 which recognizes SEQ ID NO: 118.

SEQ ID NO: 123 is a nucleotide sequence encoding the artificial nuclease protein TLNrPMIFW1-01.

SEQ ID NO: 124 is a nucleotide sequence encoding the artificial nuclease protein TLN_rPMIRv1-01.

SEQ ID NO: 125 is a nucleotide sequence encoding the artificial nuclease protein TLNrPMIFW1-02.

SEQ ID NO: 126 is a nucleotide sequence encoding the artificial nuclease protein TLN_rPMIRv1-02.

SEQ ID NO: 127-132 are nucleotide sequences useful for the detection of targeted integration.

Figure 9:
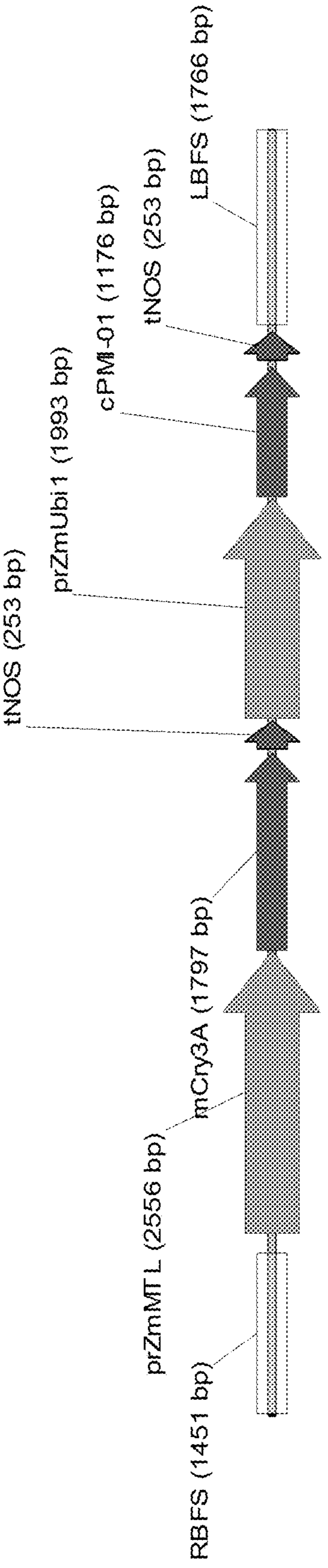
FIG. 9. Schematic drawing of MIR604 transgenic event T-DNA insertions and flanking regions. MIR604 RB FS: maize genomic region flanking the T-DNA right border; MIR604 LB FS: maize genomic region flanking the T-DNA left border; prUbi1 maize ubiquitin-1 promoter; cPMI-01: PMI coding sequence; tNOS: Nopaline synthase terminator; mCry3A: synthetic form of Cry3A gene sequence (mCry3A) from *Bacillus thuringiensis*. (U.S. Pat. No. 7,897,748)

SEQ ID NO: 133 is a nucleotide sequence of the PMI expression cassette (prZmUbi1-cPMI-tNOS) present in the T-DNA insert of event MIR604 transgenic plants (FIG. 9).

SEQ ID NO: 134 is a nucleotide sequence of the T-DNA insert present in event MIR604 and of the right and left border regions (FIG. 9).

SEQ ID NO: 135 is a nucleotide sequence of event MIR604 transgene locus including the whole T-DNA insert and the flanking genomic DNA regions, including RBFS and LBFS (FIG. 9).

SEQ ID NO: 136 is a nucleotide sequence of the B73 maize genomic region proximal to the MIR604 T-DNA insertion right border (RB) region (RBFS in FIG. 9).

SEQ ID NO: 137 is a nucleotide sequence of the B73 maize genomic region proximal to the MIR604 T-DNA insertion left border (LB) region (LBFS in FIG. 9).

SEQ ID NO: 138 is a nucleotide sequence of the elite maize line NP2222 genomic sequence corresponding to the B73 MIR604 insertion site locus sequences proximal to the RB region including the RBFS (FIG. 9).

SEQ ID NO: 139 is a nucleotide sequence of the elite maize line NP2222 genomic sequence corresponding to the B73 MIR604 T-DNA insertion site locus sequences proximal to the LB region including the LBFS (FIG. 9).

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., *Glossary of Genetics: Classical and Molecular,* 5$^{th}$ edition, Springer-Verlag: New York, 1994.

"Accuracy" of an amplification method such as a polymerase chain reaction (PCR) method (e.g., TaqMan) means the closeness of agreement between a test result and an accepted reference value.

As used herein, the term "amplified" means the construction of multiple copies of a nucleic acid molecule or multiple copies complementary to the nucleic acid molecule using at least one of the nucleic acid molecules as a template. See, e.g., Diagnostic Molecular Microbiology: Principles and Applications, D. H. Persing et al., Ed., American Society for Microbiology, Washington, D.C. (1993). The product of amplification is termed an amplicon.

A "coding sequence" is a nucleic acid sequence that is transcribed into RNA such as mRNA, rRNA, tRNA, snRNA, sense RNA or antisense RNA. In some embodiments, the RNA is then translated in an organism to produce a protein.

The "coefficient of linearity ($R^2$)" is the correlation coefficient of a standard curve obtained by linear regression analysis.

"Dynamic range" as used herein means the range of DNA concentrations over which the method of the invention performs in a linear manner with an acceptable level of accuracy and precision.

"Detection kit" as used herein refers to a kit used to detect target DNA from the events of interest in a sample comprising nucleic acid probes and primers of the present invention, which will be processed specifically under optimum conditions to a target DNA sequence, and other materials necessary to enable nucleic acid hybridization and/or amplification methods.

As used herein the term transgenic "event" refers to a recombinant plant produced by transformation and regeneration of a single plant cell with heterologous DNA, for example, an expression cassette that includes one or more genes of interest (e.g., transgenes). The term "event" refers to the original transformant and/or progeny of the transformant that include the heterologous DNA. The term "event" also refers to progeny produced by a sexual outcross between the transformant and another line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Thus, "event MIR604," "MIR604" or "MIR604 event" as used herein, means the original MIR604 transformant and/or progeny of the MIR604 transformant (U.S. Pat. Nos. 7,361,813, 7,897,748, 8,354,519, and 8,884,102, incorporated by references herein).

The insertion site of event MIR604 has many characteristics which make it a good candidate for a target site for genomic modifications. Such characteristics include that the site does not interrupt native genes, the site is not in a highly repetitive region of nucleotide sequence, the nucleotide sequence of the site is not significantly repeated elsewhere in the maize genome, and transgenes introduced at this site are known to have good expression levels, both in the initially transformed plant, in other maize varieties into which event MIR604 has been introduced, and in the progeny of event MIR604 plants, for multiple generations. Additionally, the success of event MIR604 as a commercial product and in a successful commercial-level breeding program, where event MIR604 is introduced into at least dozens of maize varieties and has shown excellent expression of the transgenes in multiple environmental conditions, indicates that the event MIR604 insertion site is a good candidate for targeted insertion.

"Expression cassette" as used herein means a nucleic acid molecule capable of directing expression of a particular nucleotide sequence in an appropriate host cell, comprising a promoter operably linked to the nucleotide sequence of interest, typically a coding region, which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

"Genotype" as used herein is the genetic material inherited from parent plants not all of which is necessarily expressed in the descendant plants. By way of example, the MIR604 genotype refers to the heterologous genetic material transformed into the genome of a plant as well as the genetic material flanking the inserted sequence.

As used herein, "heterologous" refers to a nucleic acid molecule or nucleotide sequence not naturally associated with a host cell into which it is introduced, that either originates from another species or is from the same species or organism but is modified from either its original form or the form primarily expressed in the cell, including non-naturally occurring multiple copies of a naturally occurring nucleic acid sequence. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., present in a different copy number, and/or under the control of different regulatory sequences than that found in the native state of the nucleic acid molecule. A nucleic acid sequence can also be heterologous to other nucleic acid sequences with which it may be associated, for example in a nucleic acid construct, such as e.g., an expression vector. As one nonlimiting example, a promoter may be present in a nucleic acid construct in combination with one or more regulatory element and/or coding sequences that do not naturally occur in association with that particular promoter, i.e., they are heterologous to the promoter.

A "homologous" nucleic acid sequence is a nucleic acid sequence naturally associated with a host cell into which it is introduced. A homologous nucleic acid sequence can also be a nucleic acid sequence that is naturally associated with other nucleic acid sequences that may be present, e.g., in a nucleic acid construct. As one nonlimiting example, a promoter may be present in a nucleic acid construct in combination with one or more regulatory elements and/or coding sequences that naturally occur in association with that particular promoter, i.e., they are homologous to the promoter.

"Operably-linked" refers to the association of nucleic acid sequences on a single nucleic acid sequence so that the function of one affects the function of the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences in sense or antisense orientation can be operably-linked to regulatory sequences.

"Primers" as used herein are isolated nucleic acids that are annealed to a complementary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other nucleic-acid amplification methods.

A "probe" is an isolated nucleic acid molecule that is complementary to a portion of a target nucleic acid molecule and is typically used to detect and/or quantify the target nucleic acid molecule. Thus, in some embodiments, a probe can be an isolated nucleic acid molecule to which is attached a detectable moiety or reporter molecule, such as a radioactive isotope, ligand, chemiluminescenc agent, fluorescence agent or enzyme. Probes according to the present invention can include not only deoxyribonucleic or ribonucleic acids but also polyamides and other probe materials that bind specifically to a target nucleic acid sequence and can be used to detect the presence of and/or quantify the amount of, that target nucleic acid sequence.

A TaqMan probe is designed such that it anneals within a DNA region amplified by a specific set of primers. As the Taq polymerase extends the primer and synthesizes the nascent strand from a single-strand template from 3' to 5' of the complementary strand, the 5' to 3' exonuclease of the polymerase extends the nascent strand through the probe and consequently degrades the probe that has annealed to the template. Degradation of the probe releases the fluorophore from it and breaks the close proximity to the quencher, thus relieving the quenching effect and allowing fluorescence of the fluorophore. Hence, fluorescence detected in the quantitative PCR thermal cycler is directly proportional to the fluorophore released and the amount of DNA template present in the PCR.

Primers and probes are generally between 5 and 100 nucleotides or more in length. In some embodiments, primers and probes can be at least 20 nucleotides or more in length, or at least 25 nucleotides or more, or at least 30 nucleotides or more in length. Such primers and probes hybridize specifically to a target sequence under optimum hybridization conditions as are known in the art. Primers and probes according to the present invention may have complete sequence complementarity with the target sequence, although probes differing from the target sequence and which retain the ability to hybridize to target sequences may be designed by conventional methods according to the invention.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

The polymerase chain reaction (PCR) is a technique for "amplifying" a particular piece of DNA. In order to perform PCR, at least a portion of the nucleotide sequence of the DNA molecule to be replicated must be known. In general, primers or short oligonucleotides are used that are complementary (e.g., substantially complementary or fully complementary) to the nucleotide sequence at the 3' end of each strand of the DNA to be amplified (known sequence). The DNA sample is heated to separate its strands and is mixed with the primers. The primers hybridize to their complementary sequences in the DNA sample. Synthesis begins (5' to 3' direction) using the original DNA strand as the template. The reaction mixture must contain all four deoxynucleotide triphosphates (dATP, dCTP, dGTP, dTTP) and a DNA polymerase. Polymerization continues until each newly-synthesized strand has proceeded far enough to contain the sequence recognized by the other primer. Once this occurs, two DNA molecules are created that are identical to the original molecule. These two molecules are heated to separate their strands and the process is repeated. Each cycle doubles the number of DNA molecules. Using automated equipment, each cycle of replication can be completed in less than 5 minutes. After 30 cycles, what began as a single molecule of DNA has been amplified into more than a billion copies ($23^{30}$=$1.02\times10^{9}$).

The oligonucleotides of an oligonucleotide primer pair are complementary to DNA sequences located on opposite DNA strands and flanking the region to be amplified. The annealed primers hybridize to the newly synthesized DNA strands. The first amplification cycle will result in two new DNA strands whose 5' end is fixed by the position of the oligonucleotide primer but whose 3' end is variable ('ragged' 3' ends). The two new strands can serve in turn as templates for synthesis of complementary strands of the desired length (the 5' ends are defined by the primer and the 3' ends are fixed because synthesis cannot proceed past the terminus of the opposing primer). After a few cycles, the desired fixed length product begins to predominate.

A quantitative polymerase chain reaction (qPCR), also referred to as real-time polymerase chain reaction, monitors the accumulation of a DNA product from a PCR reaction in real time. qPCR is a laboratory technique of molecular biology based on the polymerase chain reaction (PCR), which is used to amplify and simultaneously quantify a targeted DNA molecule. Even one copy of a specific sequence can be amplified and detected in PCR. The PCR reaction generates copies of a DNA template exponentially. This results in a quantitative relationship between the amount of starting target sequence and amount of PCR product accumulated at any particular cycle. Due to inhibitors of the polymerase reaction found with the template, reagent limitation or accumulation of pyrophosphate molecules, the PCR reaction eventually ceases to generate template at an exponential rate (i.e., the plateau phase), making the end point quantitation of PCR products unreliable. Therefore, duplicate reactions may generate variable amounts of PCR product. Only during the exponential phase of the PCR reaction is it possible to extrapolate back in order to determine the starting quantity of template sequence. The measurement of PCR products as they accumulate (i.e., real-time quantitative PCR) allows quantitation in the exponential phase of the reaction and therefore removes the variability associated with conventional PCR. In a real time PCR assay, a positive reaction is detected by accumulation of a fluorescent signal. For one or more specific sequences in a DNA sample, quantitative PCR enables both detection and quantification. The quantity can be either an absolute number of copies or a relative amount when normalized to DNA input or additional normalizing genes. Since the first documentation of real-time PCR, it has been used for an increasing and diverse number of applications including mRNA expression studies, DNA copy number measurements in genomic or viral DNAs, allelic discrimination assays, expression analysis of specific splice variants of genes and gene expression in paraffin-embedded tissues and laser captured micro-dissected cells.

As used herein, the phrase "Ct value" refers to "threshold cycle," which is defined as the "fractional cycle number at which the amount of amplified target reaches a fixed threshold." In some embodiments, it represents an intersection between an amplification curve and a threshold line. The amplification curve is typically in an "S" shape indicating the change of relative fluorescence of each reaction (Y-axis) at a given cycle (X-axis), which in some embodiments is recorded during PCR by a real-time PCR instrument. The threshold line is in some embodiments the level of detection at which a reaction reaches a fluorescence intensity above background. See Livak & Schmittgen (2001) 25 *Methods* 402-408. It is a relative measure of the concentration of the target in the PCR. Generally, good Ct values for quantitative assays such as qPCR are in some embodiments in the range of 10-40 for a given reference gene. Ct levels are inversely proportional to the amount of target nucleic acid in the sample (i.e., the lower the Ct level the greater the amount of detectable target nucleic acid in the sample). Additionally, good Ct values for quantitative assays such as qPCR show a linear response range with proportional dilutions of target gDNA.

In some embodiments, qPCR is performed under conditions wherein the Ct value can be collected in real-time for quantitative analysis. For example, in a typical qPCR experiment, DNA amplification is monitored at each cycle of PCR during the extension stage. The amount of fluorescence generally increases above the background when DNA is in the log linear phase of amplification. In some embodiments, the Ct value is collected at this time point.

The term "transformation" as used herein refers to the transfer of a nucleic acid molecule into the genome of a host cell, resulting in genetically stable inheritance. In some embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or any combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in *Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell Mol Biol Lett* 7:849-858 (2002)).

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. 1993, *Plant Cell* 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen and Willmitzer 1988, *Nucleic Acids Res* 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacteria or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The terms "nucleotide sequence" "nucleic acid," "nucleic acid sequence," "nucleic acid molecule," "oligonucleotide" and "polynucleotide" are used interchangeably herein to refer to a heteropolymer of nucleotides and encompass both RNA and DNA, including cDNA, genomic DNA, mRNA, synthetic (e.g., chemically synthesized) DNA or RNA and chimeras of RNA and DNA. The term nucleic acid molecule refers to a chain of nucleotides without regard to length of the chain. The nucleotides contain a sugar, phosphate and a base which is either a purine or pyrimidine. A nucleic acid molecule can be double-stranded or single-stranded. Where single-stranded, the nucleic acid molecule can be a sense strand or an antisense strand. A nucleic acid molecule can be synthesized using oligonucleotide analogs or derivatives (e.g., inosine or phosphorothioate nucleotides). Such oligonucleotides can be used, for example, to prepare nucleic acid molecules that have altered base-pairing abilities or increased resistance to nucleases. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. Unless otherwise indicated, a particular nucleic acid sequence of this invention also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid molecule is used interchangeably with gene, cDNA, and mRNA encoded by a gene.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). In some embodiments, a gene refers to only the coding region. A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 70%, least about 75%, at least about 80%, least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of this invention, the substantial identity exists over a region of the sequences that is at least about 50, about 60, about 70, about 80, about 90, about 100, about 110, about 120, about 130, about 140, about 150, or more residues in length. In some particular embodiments, the sequences are substantially identical over at least about 150 residues. In a further embodiment, the sequences are substantially identical over the entire length of the coding regions. Furthermore, in representative embodiments, substantially identical nucleotide or protein sequences perform substantially the same function (e.g., conferring increased resistance to a nematode plant parasite, reducing the growth of a nematode plant parasite, reducing cyst development).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the present invention. In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

"Wild-type" nucleotide sequence or amino acid sequence refers to a naturally occurring ("native") or endogenous nucleotide sequence or amino acid sequence. Thus, for example, a "wild-type mRNA" is an mRNA that is naturally occurring in or endogenous to the organism. A "homologous" nucleotide sequence is a nucleotide sequence naturally associated with a host cell into which it is introduced.

By the term "express" or "expression" of a polynucleotide coding sequence, it is meant that the sequence is transcribed, and optionally translated.

"Nucleotide sequence of interest" refers to any nucleotide sequence which, when introduced into a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "nucleotide sequence of interest" may also be one that is transferred to plants for the production of commercially valuable enzymes or metabolites in the plant.

As used herein, the phrases "operably linked," "operatively linked," "operatively associated" or "in operative association" and the like, mean that elements of a nucleic acid construct such as an expression cassette or nucleic acid molecule are configured so as to perform their usual function. Thus, regulatory or control sequences (e.g., promoters) operatively associated with a nucleotide sequence are capable of effecting expression of the nucleotide sequence. For example, a promoter in operative association with a nucleotide sequence encoding miR396c would be capable of effecting the expression of that miR396c nucleotide sequence.

The control sequences need not be contiguous with the nucleotide sequence of interest, as long as they function to direct the expression thereof. Thus, for example, intervening untranslated, yet transcribed, sequences can be present between a promoter and a coding sequence, and the promoter sequence can still be considered "operably linked" to the coding sequence.

As used herein, the terms "transformed" and "transgenic" refer to any plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term “recombinant” does not refer to alterations of polynucleotides that result from naturally occurring events, such as spontaneous mutations, or from non-spontaneous mutagenesis followed by selective breeding.

The term “introducing” or “introduce” in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term “transformation” as used herein refers to the introduction of a heterologous nucleic acid into a cell. Transformation of a cell may be stable or transient. Thus, a transgenic plant cell, plant and/or plant part of the invention can be stably transformed or transiently transformed.

The term “plant part,” as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, “shoot” refers to the above ground parts including the leaves and stems. Further, as used herein, “plant cell” refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

“Transient transformation” in the context of a polynucleotide means that a polynucleotide is introduced into the cell and does not integrate into the genome of the cell.

As used herein, “stably introducing,” “stably introduced,” “stable transformation” or “stably transformed” in the context of a polynucleotide introduced into a cell, means that the introduced polynucleotide is stably integrated into the genome of the cell, and thus the cell is stably transformed with the polynucleotide. As such, the integrated polynucleotide is capable of being inherited by the progeny thereof, more particularly, by the progeny of multiple successive generations. “Genome” as used herein includes the nuclear and/or plastid genome, and therefore includes integration of a polynucleotide into, for example, the chloroplast genome. Stable transformation as used herein can also refer to a polynucleotide that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods. Transformation can also be detected by direct sequencing and/or hybridization protocols well known in the art.

The terms “open reading frame” and “ORF” refer to the amino acid sequence encoded between translation initiation and termination codons of a coding sequence. The terms “initiation codon” and “termination codon” refer to a unit of three adjacent nucleotides (‘codon’) in a coding sequence that specifies initiation and chain termination, respectively, of protein synthesis (mRNA translation).

“Promoter” refers to a nucleotide sequence, usually upstream (5') to its coding sequence, which controls the expression of the coding sequence by providing the recognition for RNA polymerase and other factors required for proper transcription. “Promoter regulatory sequences” consist of proximal and more distal upstream elements. Promoter regulatory sequences influence the transcription, RNA processing or stability, or translation of the associated coding sequence. Regulatory sequences include enhancers, promoters, untranslated leader sequences, introns, and polyadenylation signal sequences. They include natural and synthetic sequences as well as sequences that may be a combination of synthetic and natural sequences. An “enhancer” is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. The meaning of the term “promoter” includes “promoter regulatory sequences.”

“Primary transformant” and “T0 generation” refer to transgenic plants that are of the same genetic generation as the tissue that was initially transformed (i.e., not having gone through meiosis and fertilization since transformation). “Secondary transformants” and the “T1, T2, T3, etc. generations” refer to transgenic plants derived from primary transformants through one or more meiotic and fertilization cycles. They may be derived by self-fertilization of primary or secondary transformants or crosses of primary or secondary transformants with other transformed or untransformed plants.

“Gene” refers to a nucleic acid fragment that expresses mRNA, functional RNA, or specific protein, including regulatory sequences. The term “native gene” refers to a gene as found in nature. The term “chimeric gene” refers to any gene that contains 1) DNA sequences, including regulatory and coding sequences that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A “transgene” refers to a nucleic acid molecule that has been introduced into the genome by transformation and is stably maintained. A transgene may comprise at least one expression cassette, typically comprises at least two expression cassettes, and may comprise ten or more expression cassettes. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but one that is introduced into the organism by gene transfer.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

"Exon" refers to a section of DNA which carries the coding sequence for a protein or part of it. Exons are separated by intervening, non-coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

Accordingly, in one embodiment, the present invention provides a method of integrating a transgene into a genomic nuclease cleavage site in a maize genome, comprising introducing into a maize cell: a) a first nucleic acid molecule comprising at least 80, at least 90, at least 100, at least 110, at least 120, at least 130, at least 140, or at least 150 contiguous nucleotides, wherein said contiguous nucleotides have at least 80%, at least 85%, at least 90%, at least 93%, at least 95%, at least 96%, at least 97%, at least 98%, at least 99%, or 100% identity with a target site in the nucleotide sequence of SEQ ID NO:1 or the nucleotide sequence of SEQ ID NO:2, and further comprising a transgene; and b) a second nucleic acid molecule comprising a nucleotide sequence encoding a nuclease for site-directed cleavage at a genomic nuclease cleavage site adjacent to the nucleotide sequence of SEQ ID NO:1 or the nucleotide sequence of SEQ ID NO:2 that corresponds to the contiguous nucleotides of (a), under conditions wherein expression of the second nucleic acid molecule can occur to produce the nuclease and the nuclease can cleave the nucleotide sequence at the genomic nuclease cleavage site, whereby the transgene is integrated at the genomic nuclease target cleavage site in the maize genome.

As used herein, a "target site" means a region of nucleotides in the genome that is the selected or preferred site for insertion of a nucleotide sequence (e.g., one or more transgenes, expression cassettes, or nucleotide sequences of interest) into the genome as well as a selected or preferred site for introducing a mutation (e.g., a substitution and/or a deletion, and/or an insertion such as an INDEL) into the genome. In some embodiments, a target site can comprise a nuclease cleavage site, also referred to as a genomic nuclease cleavage site. A nonlimiting example of a target site of this invention is the chromosome interval on chromosome 1 defined by and including base pair (bp) position 38,860,000 to base pair (bp) position 39,105,000 as defined by Maize B73 RefGen_V2 available in the Maize Genome Database.

As used herein, the terms "adjacent" or "adjacent to" with regard to one or more nucleotide sequences of this invention means immediately next to (e.g., with no intervening sequence) or separated by from about 1 base to about 10,000 bases (e.g., 1, 2, 3, 4, 5, 6, 7, 8, 9, 10, 15, 20, 30, 40, 50, 100, 200, 500, 1000, 2000, 3000, 4000, 5000, 6000, 7000, 8000, 9000, or 10,000 bases), including any values included within this range but not explicitly recited herein.

A "nuclease cleavage site" or "genomic nuclease cleavage site" is a region of nucleotides that comprise a nuclease cleavage sequence that is recognized by a specific nuclease, which acts to cleave the nucleotide sequence of the genomic DNA in one or both strands. Such cleavage by the nuclease enzyme initiates DNA repair mechanisms within the cell, which establishes an environment for homologous recombination to occur. In the methods herein wherein the first nucleic acid molecule comprises, for example, at least about 100 contiguous nucleotides having, for example, at least 90% identity with a target site in the genome of the cell, the first nucleic acid molecule is integrated into the genome of the cell via homologous recombination, thereby integrating the one or more transgenes into the genome of the cell.

In some embodiments of the above method, the first nucleic acid molecule can comprise at least about 100, 150, 200, 250, 300, 250, 400, 450, 500, 600, 700, 800, 900, 1000, 1500, 2000, 2500, 3000, 3500, 4000, 4500, 5000, 7500, 10000, 15,000 or 20,000 nucleotides, including any value within this range not explicitly recited herein.

In some embodiments of the above method, the nucleotide sequence comprising the genomic nuclease cleavage site in the maize genome can be the nucleotide sequence of SEQ ID NO:1, SEQ ID NO:2, SEQ ID NO:3, SEQ ID NO:28, SEQ ID NO:66, or SEQ ID NO:67.

In some embodiments of the above method, the genomic nuclease cleavage site is located within a chromosome interval on chromosome 1 defined by and including base pair (bp) position 38,860,000 to base pair (bp) position 39,015,000 as defined by Maize B73 RefGen_V2, available in the Maize Genome Database.

In some embodiments of the method above, the nuclease has cleavage specificity for a nuclease cleavage site in the nucleotide sequence selected from the group consisting of SEQ ID NO:1 (HiII-MIR604), SEQ ID NO:2 (AX-MIR604), SEQ ID NO:3, SEQ ID NO:28, SEQ ID NO:66, SEQ ID NO:67 and any combination thereof.

In some embodiments, the first nucleic acid molecule and the second nucleic acid molecule can be introduced into the maize cell by biolistic nucleic acid delivery, via an *Agrobacterium*, by co-transformation, and/or with a T-DNA vector in any combination and/or order.

In some embodiments, the first nucleic acid molecule and the second nucleic acid molecule can be present on a single nucleic acid construct and in some embodiments, the first nucleic acid molecule and the second nucleic acid molecule can be present on separate nucleic acid constructs.

In some embodiments, the first nucleic acid molecule and/or the second nucleic acid molecule can be transiently expressed in the maize cell.

In some embodiments, the first nucleic acid molecule and/or the second nucleic acid molecule can be stably integrated into the maize genome in the maize cell.

The present invention further provides a method of producing a maize plant, plant part, or progeny thereof comprising a transgene integrated into the genomic nuclease cleavage site in the maize genome, comprising regenerating a maize plant from the maize cell produced by the method described herein. Accordingly, the present invention provides a maize plant, plant part, or progeny thereof comprising the transgene integrated into the genomic nuclease cleavage site in the maize genome, produced by the method of this invention.

The present invention is based in some embodiments on the unexpected discovery and development of rapid (e.g., high throughput) methods to identify and enrich for cells that comprise one or more transgenes integrated into the genome at a target site that employ selective combinations of quantitative polymerase chain reaction (qPCR) assays.

The present invention further provides a method of identifying a cell and/or enriching for a cell comprising a transgene inserted into a nuclease cleavage site in a genome of the cell, comprising: a) introducing into a plurality of cells: i) a first nucleic acid molecule comprising at least 80, at least 90, at least 100, at least 110, at least 120, at least 130, at least 140, or at least 150 contiguous nucleotides, wherein the contiguous nucleotides have at least 80%, at least 85%, at least 90%, at least 93%, at least 95%, at least 96%, at least 97%, at least 98%, at least 99%, or 100% identity with a target site in the genome of the cell, and further comprising a transgene; and ii) a second nucleic acid molecule encoding a nuclease for site-directed cleavage at a nuclease cleavage site in the genome of the cell adjacent to the nucleotide sequence in the genome of the cell that corresponds to the contiguous nucleotides of (i), under conditions wherein expression of the second nucleic acid molecule can occur to produce the nuclease and the nuclease can cleave at the nuclease cleavage site in the genome of the cell and integrate the transgene into the nuclease cleavage site in the genome of the cell; b) culturing the cells of (a) to produce at least one cell line or tissue; c) extracting a genomic DNA sample from each of the cell lines or tissues of (b); d) performing real-time quantitative polymerase chain reaction (qPCR) assays T and G on the samples of (c), wherein the assays T and G respectively comprise the following probes: i) a first probe comprising a nucleotide sequence that is complementary to a nucleotide sequence of the target site, at least one, at least two, at least three, at least four, at least five, at least six, at least seven, at least eight, at least nine, at least ten, at least twelve, or at least fifteen base pairs away from the nuclease cleavage site for carrying out assay T, and ii) a second probe comprising a nucleotide sequence that is complementary to a nucleotide sequence of the transgene for carrying out assay G; e) obtaining a DNA copy number of the target site from the results of assay T and a DNA copy number of the transgene from the results of assay G; and f) identifying and/or enriching for a cell line or tissue that has reduced copy number in assay T relative to a reference and a copy number greater than zero for assay G, thereby identifying and/or enriching for the cell comprising the transgene inserted into the nuclease cleavage site in the genome of the cell.

In the methods described above directed to identifying and/or enriching for cells that comprise one or more transgenes inserted into a nuclease cleavage site in a genome of the cell, the qPCR assays can be performed in a high-throughput format as is well known in the art, such that a large volume of samples can be assayed rapidly and simultaneously. Such rapid and efficient screening allows for the identification and enrichment for the small percentage of cells (e.g., around 2%) among the plurality of cells employed in these methods, which would typically be a large volume of cells.

In the methods described above, the first probe (for carrying out assay T) can comprise, consist essentially of or consist of a nucleotide sequence that is complementary (e.g., at least about 90%, 95%, 98%, 99% or 100% complementary) to nucleotide sequence at least five (e.g., 4, 5, 6, 7, 8, 9, 10, 11, 12, 13, 14, 15, 16, 17, 18, 19, 20) base pairs away from the nuclease cleavage site and the second probe (for carrying out assay G) can comprise a nucleotide sequence that is complementary (e.g., at least about 90%, 95%, 98%, 99% or 100% complementary) to at least one of the one or more transgenes.

In some embodiments of the enriching and identifying methods described above, in addition to the step of identifying and/or enriching for a cell line or tissue that has reduced copy number in assay T relative to a reference and a copy number greater than zero (e.g., a copy number of about one, a copy number of about 2, or a copy number of about 3) for assay G, the methods in some embodiments can further comprise the step of discarding a cell line or tissue that has no change in the DNA copy number of assay T in comparison with a reference, and in some embodiments, can further comprise the step of discarding a cell line or tissue that has a copy number of zero (e.g., a copy number of less than one) for assay G.

As used herein, being "positive" or a positive result for an assay (e.g., assay G) means that the copy number is greater than zero and being "negative" for an assay (e.g., assay G) means that the copy number is zero or less than one.

As also used herein, a "reference" is a genome that has a fixed gene copy number. In some embodiments, the reference can be a "wild type" genome (e.g., a genome of a cell that has not had the first and second nucleic acid molecules of this invention introduced into it according to the methods of this invention)

In particular embodiments of the invention, the first and second probes are fluorescence probes and in some embodiments, the first and second probes are Taqman probes.

In some embodiments of the invention, the qPCR assays are performed in the same mixture and in some embodiments, the qPCR assays are performed in different mixtures, in any combination.

In embodiments in which the plant is a maize plant, the nuclease cleavage site is a maize MIR604 transgene insertion site, namely a nucleotide sequence with at least 80%, at least 85%, at least 90%, at least 93%, at least 95%, at least 96%, at least 97%, at least 98%, at least 99%, or 100% identity to the nucleotide sequence of SEQ ID NO:1 or SEQ ID NO:2.

In some embodiments of the methods described herein, the nuclease can be a non-engineered nuclease (e.g., a nuclease in its "native" form or "wild type" form without modifications). In some embodiments, the nuclease can be an engineered nuclease with programmable cleavage target specificity. Non-limiting examples of a nuclease of this invention include CRISPR gRNA-Cas9 nuclease, zinc finger nuclease, engineered meganuclease and/or TAL effector nuclease, singly or in any combination.

The present invention also provides a cell line or tissue that is identified and/or enriched by the methods described herein, wherein the cell line or tissue is derived from a plant or a plant part. In some embodiments, the cell line or tissue is derived from a monocot plant or monocot plant part. In some embodiments, the cell line or tissue is derived from a dicot plant or plant part. In some embodiments, the cell line or tissue is derived from a cereal plant or cereal plant part. In further embodiments, the cell line or tissue is derived from a maize plant or maize plant part. Other nonlimiting examples of a plant of this invention include rice, sugarcane, barley, sugarbeet, potato, tobacco, soybean, tomato, wheat and sunflower.

Further provided herein is a cell line or tissue that is identified and/or enriched by the methods described herein, wherein the cell line or tissue is derived from a eukaryotic organism.

In some embodiments of the enriching and identifying methods described above, in addition to the step of identifying and/or enriching for a cell line or tissue that has reduced copy number in assay T relative to a reference and is positive for assay G, the methods in some embodiments can further comprise the step of discarding a cell line or tissue that has no change in the DNA copy number of assay T in comparison with a reference, and in some embodiments, can further comprise the step of discarding a cell line or tissue that is negative for assay G.

As used herein, being "positive" for an assay (e.g., assay G) means that the copy number is greater than zero and being "negative" for an assay (e.g., assay G) means that the copy number is equal to zero.

As also used herein, a "reference" is a genome or other nucleic acid molecule that has a fixed gene copy number. In some embodiments, the reference can be a "wild type" genome (e.g., a genome of a cell that has not had the first and second nucleic acid molecules of this invention introduced into it according to the methods of this invention)

In particular embodiments of the invention, the first and second probes are fluorescence probes and in some embodiments the first and second probes are Taqman probes.

In some embodiments of the invention, the qPCR assays are performed in the same mixture and in some embodiments, the qPCR assays are performed in different mixtures, in any combination.

In embodiments in which the plant produced is a maize plant, the nuclease cleavage site is a maize MIR604 transgene insertion site, namely a nucleotide sequence with at least 80%, at least 85%, at least 90%, at least 93%, at least 95%, at least 96%, at least 97%, at least 98%, at least 99%, or 100% identity to the nucleotide sequence of SEQ ID NO:1 or SEQ ID NO:2

Further provided herein is a method of identifying a cell and/or for enriching for a cell comprising a mutation introduced into a nuclease cleavage site in a genome of the cell and lacking integration of a heterologous nucleotide sequence encoding a nuclease for site-directed cleavage of a nucleotide sequence at the nuclease cleavage site into the genome of the cell, comprising: a) introducing a nucleic acid molecule comprising a heterologous sequence encoding a nuclease for site-directed cleavage of the nucleotide sequence at the nuclease cleavage site in the genome of the cell into a plurality of cells under conditions wherein expression of the nucleic acid molecule can occur to produce the nuclease and the nuclease can cleave the nucleotide sequence at the nuclease cleavage site in the genome of the cell, thereby introducing a mutation at the nuclease cleavage site in the genome of the cell without integration of the heterologous nucleotide sequence encoding the nuclease into the genome of the cell; b) culturing the plurality of cells of (a) to produce at least one cell line or tissue; c) extracting a genomic DNA sample from each of the cell lines or tissues of (b); d) performing real-time quantitative polymerase chain reaction (qPCR) assays 1 and 2 on the samples of (c), wherein the assays respectively comprise the following probes: i) a first probe comprising a nucleotide sequence that is complementary to the nucleotide sequence comprising the nuclease cleavage site to carry out assay 1, and ii) a second probe comprising a nucleotide sequence that is complementary to the heterologous nucleotide sequence encoding the nuclease to carry out assay 2; e) obtaining a DNA copy number of the nuclease cleavage site from the results of assay 1 and a DNA copy number of the heterologous nucleotide sequence encoding the nuclease from the results of assay 2; and f) identifying and/or enriching for a cell line or tissue that has a reduced copy number for assay 1 relative to a reference and a copy number equal to zero for assay 2, thereby identifying and/or enriching for the cell comprising the mutation introduced into the nuclease cleavage site in the genome of the cell and lacking integration of the heterologous nucleotide sequence encoding the nuclease into the genome of the cell.

In some embodiments of the methods described herein, the cell line or tissue may be derived from a plant or plant part, for example a plant derived from tissue culture or germinated seeds. In some embodiments the plant can be a monocot and in some embodiments, the plant can be a dicot. In some embodiments, the plant can be a cereal. In particular embodiments, the plant can be a maize plant. Other nonlimiting examples of a plant of this invention include rice, sugarcane, barley, sugarbeet, potato, tobacco, soybean, tomato, wheat and sunflower. In some embodiments, the cell line or tissue that is identified and/or enriched by the methods described herein is derived from a eukaryotic organism.

In some embodiments of the enriching and identifying methods described above, in addition to the step of identifying and/or enriching for a cell line or tissue that has a reduced copy number in assay 1 relative to a reference and a copy number equal to zero (e.g., is less than one) for assay 2, the methods in some embodiments can further comprise the step of discarding a cell line or tissue that has no change in the DNA copy number of assay 1 relative to a reference, and in some embodiments, can further comprise the step of discarding a cell line or tissue that has a copy number greater than zero (e.g., a copy number of about 1, a copy number of about 2, or a copy number of about 3) for assay 2.

As used herein, being "positive" or a positive result for an assay (e.g., assay 2) means that the copy number is greater than zero (e.g., a copy number of about 1, a copy number of about 2, or a copy number of about 3) and being "negative" for an assay (e.g., assay 2) means that the copy number is equal to zero (e.g., is less than one).

As also used herein, a "reference" is a genome or other nucleic acid molecule that has a fixed gene copy number. In some embodiments, the reference can be a "wild type" genome (e.g., a genome of a cell that has not had the first and second nucleic acid molecules of this invention introduced into it according to the methods of this invention).

In particular embodiments of the invention, the first and second probes are fluorescence probes and in some embodiments, the first and second probes are Taqman probes.

In some embodiments of the invention, the qPCR assays are performed in the same mixture and in some embodiments, the qPCR assays are performed in different mixtures, in any combination.

In some embodiments of the methods described herein, the tissue can be a plant derived from tissue culture or germinated seeds. In some embodiments the plant can be a monocot and in some embodiments, the plant can be a dicot. In particular embodiments, the plant can be a maize plant. Other nonlimiting examples of a plant of this invention include rice, sugarcane, barley, sugarbeet, potato, tobacco, soybean, tomato, wheat and sunflower.

In some embodiments of the methods described herein, the nuclease can be a non-engineered nuclease (e.g., a nuclease in its "native" form or "wild type" form without modifications). In some embodiments, the nuclease can be an engineered nuclease with programmable cleavage target specificity. Non-limiting examples of a nuclease of this invention include CRISPR gRNA-Cas9 nuclease (for example, a Cas9 nuclease comprising SEQ ID NO: 30) zinc finger nuclease, engineered meganuclease and/or TAL effector nuclease, singly or in any combination.

In embodiments in which the plant is a maize plant, the nuclease cleavage site is a maize MIR604 transgene insertion site, namely a nucleotide sequence with at least 80%, at least 85%, at least 90%, at least 93%, at least 95%, at least 96%, at least 97%, at least 98%, at least 99%, or 100% identity to the nucleotide sequence of SEQ ID NO:1 or SEQ ID NO:2

The present invention additionally provides a kit of reagents and instructions for carrying out the methods and assay of this invention. In some embodiments, a kit or a package comprising the compositions, formulations and/or agents for carrying out the methods of the present invention is provided. For example, a kit may include means for obtaining a cell or tissue, as well as means for obtaining a nucleic acid sample. The kit may also contain reagents for carrying out the steps of the methods of this invention. Such reagents can include site-specific probes and/or primers that facilitate isolation and biochemical characterization of nucleic acid molecules of this invention. The kit can contain one or more separate containers.

Although the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container. For example, wherein the components of the kit are in lyophilized form, the kit may optionally contain a sterile and physiologically acceptable reconstitution medium such as water, saline, buffered saline, and the like.

In some embodiments, the containers of the kit can include at least one vial, test tube, flask, bottle, syringe or other containers, into which the compositions/formulations of the present invention, and any other desired agent, may be placed and suitably aliquoted.

In additional embodiments, the present invention provides a method of producing a plant, plant part, or progeny thereof comprising a mutation introduced at a nuclease cleavage site in a genome of a plant cell and lacking integration of a heterologous nucleotide sequence encoding a nuclease for site-directed cleavage of a nucleotide sequence at the nuclease cleavage site in the genome of the plant cell, comprising: a) introducing into the plant cell a nucleic acid molecule comprising a heterologous nucleotide sequence encoding a nuclease for site-directed cleavage of the nucleotide sequence at the nuclease cleavage site in the genome of the plant cell under conditions wherein expression of the nucleic acid molecule occurs transiently to produce the nuclease and the nuclease can cleave the nucleotide sequence at the nuclease cleavage site in the genome of the plant cell, thereby introducing a mutation at the nuclease cleavage site in the genome of the plant cell without integration of the heterologous nucleotide sequence encoding the nuclease into the genome of the plant cell; and b) regenerating a plant, plant part, or progeny thereof from the plant cell of (a). In another embodiment, the present invention provides for the plant cell produced by the method described above. In a further embodiment, the present invention provides for a plant or plant part regenerated or derived from the plant cell produced by the method described above.

In some embodiments of the method described above, the plant is a monocot. In other embodiments, the plant is a dicot. In some embodiments, the plant is a cereal. In further embodiments the plant is maize Other nonlimiting examples of a plant of this invention include rice, sugarcane, barley, sugarbeet, potato, tobacco, soybean, tomato, wheat and sunflower.

In some embodiments of the methods described above, the mutation comprises at least one nucleotide substitution, the deletion of at least one nucleotide, or a combination of substitution, deletion, and/or insertion, such as for example an INDEL.

In some embodiments of the methods described above, the nucleic acid molecule is biolistic nucleic acid delivery, *Agrobacterium*-mediated transformation, or any method of plant transformation known in the art.

In some embodiments of the methods described above, the nuclease for site-directed cleavage is a non-engineered nuclease. In some embodiments, the nuclease is an engineered nuclease with programmable cleavage target specificity. In some embodiments, the nuclease is a Cas9. In some embodiments, the nuclease is a Cas9 comprising SEQ ID NO: 30.

The present invention additionally provides a method of producing a plant, plant part, or progeny thereof comprising a transgene introduced at a nuclease cleavage site in a genome of a plant cell and lacking integration of a heterologous nucleotide sequence encoding a nuclease for site-directed cleavage of a nucleotide sequence at the nuclease cleavage site in the genome of the plant cell, comprising: a) introducing into the plant cell a nucleic acid molecule comprising a heterologous nucleotide sequence encoding a nuclease for site-directed cleavage of the nucleotide sequence at the nuclease cleavage site in the genome of the plant cell under conditions wherein expression of the nucleic acid molecule occurs transiently to produce the nuclease and the nuclease can cleave the nucleotide sequence at the nuclease cleavage site in the genome of the plant cell, thereby introducing a mutation at the nuclease cleavage site in the genome of the plant cell without integration of the heterologous nucleotide sequence encoding the nuclease into the genome of the plant cell; and b) regenerating a plant, plant part, or progeny thereof from the plant cell of (a). In another embodiment, the present invention provides for the plant cell produced by the method described above. In a further embodiment, the present invention provides for a plant or plant part regenerated or derived from the plant cell produced by the method described above.

In some embodiments of the method described above, the transgene may comprise at least one, at least two, at least three, at least four, at least five, at least six, at least seven, at least eight, at least nine, at least ten, or ten or more expression cassettes.

In some embodiments of the method described above, the nuclease cleavage site is or is adjacent to a nucleotide sequence that has at least 80%, at least 85%, at least 90%, at least 93%, at least 95%, at least 96%, at least 97%, at least 98%, at least 99%, or 100% identity to the nucleotide sequence of SEQ ID NO:1 or SEQ ID NO:2.

In some embodiments of the methods described above, the plant is a monocot. In other embodiments, the plant is a dicot. In some embodiments, the plant is a cereal. In further embodiments the plant is maize. Other nonlimiting examples of a plant of this invention include rice, sugarcane, barley, sugarbeet, potato, tobacco, soybean, tomato, wheat and sunflower.

In some embodiments of the methods described above, the first nucleic acid molecule and the second nucleic acid molecule are introduced at the same time, for example by co-transformation, biolistic nucleic acid delivery, or *Agrobacterium*-mediated transformation. In some embodiments, the first nucleic acid molecule and the second nucleic acid molecule are separate molecules. In some embodiments, a single nucleic acid molecule or construct comprises the first nucleic acid molecule and the second nucleic acid molecule described above.

In some embodiments of the methods described above, the nuclease for site-directed cleavage is a non-engineered nuclease. In some embodiments, the nuclease is an engineered nuclease with programmable cleavage target specificity. In some embodiments, the nuclease is a Cas9. In some embodiments, the nuclease is a Cas9 comprising SEQ ID NO: 30.

The present invention additionally provides a method for modifying a target site in the genome of a plant cell, comprising: a) introducing into the plant cell a first nucleic acid comprising at least 100 contiguous nucleotides, wherein the at least 100 contiguous nucleotides have at least 90% identity with a target site in the genome of the cell, and further comprising a transgene; and b) a second nucleic acid molecule encoding nuclease for site-directed cleavage at a nuclease cleavage site in the genome of the cell adjacent to the nucleotide sequence in the genome of the cell that corresponds to the at least 100 contiguous nucleotides of (a), wherein the nuclease is a modified Cas9 nuclease comprising SEQ ID NO: 30, under conditions wherein expression of the second nucleic acid molecule can occur to produce the nuclease and the nuclease can cleave at the nuclease cleavage site in the genome of the cell and modify the target site in the genome of the plant cell. In another embodiment, the present invention provides for the plant cell produced by the method described above. In a further embodiment, the present invention provides for a plant or plant part regenerated or derived from the plant cell produced by the method described above.

In some embodiments of the method described above, the plant is a monocot. In other embodiments, the plant is a dicot. In some embodiments, the plant is a cereal. In further embodiments the plant is maize. In some embodiments, the maize is transgenic. In further embodiments, the transgenic maize is event MIR604. Other nonlimiting examples of a plant of this invention include rice, sugarcane, barley, sugarbeet, potato, tobacco, soybean, tomato, wheat and sunflower.

In some embodiments of the methods described above, the modification of the target site comprises at least one nucleotide substitution, the deletion of at least one nucleotide, or a combination of substitution, deletion, and/or insertion, such as for example an INDEL. In other embodiments, the modification of the target site is an insertion, such as a transgene insertion.

In some embodiments of the methods described above, the nucleic acid molecule is biolistic nucleic acid delivery, *Agrobacterium*-mediated transformation, or any method of plant transformation known in the art.

The present invention additionally provides a method of integrating a transgene into a genomic nuclease cleavage site in an event MIR604 transgenic maize genome, comprising introducing into an event MIR604 maize cell: a) a first nucleic acid molecule comprising at least 100 contiguous nucleotides, wherein said at least 100 contiguous nucleotides have at least 90% identity with a target site in a nucleotide sequence selected from the group comprising SEQ ID NO:133, SEQ ID NO: 134, SEQ ID NO: 135, SEQ ID NO: 136, SEQ ID NO: 137, SEQ ID NO: 138, and SEQ ID NO: 139, and further comprising a transgene; and b) a second nucleic acid molecule comprising a nucleotide sequence encoding a nuclease for site-directed cleavage at a genomic nuclease cleavage site adjacent to a nucleotide sequence with at least 90% identity to a nucleotide sequence selected from the group comprising SEQ ID NO:133, SEQ ID NO: 134, SEQ ID NO: 135, SEQ ID NO: 136, SEQ ID NO: 137, SEQ ID NO: 138, and SEQ ID NO: 139, that corresponds to the at least 100 contiguous nucleotides of (a), under conditions wherein expression of the second nucleic acid molecule can occur to produce the nuclease and the nuclease can cleave the nucleotide sequence at the genomic nuclease cleavage site, whereby the transgene is integrated at the genomic nuclease target cleavage site in the maize genome.

The present invention further provides a method of producing a maize plant, plant part, or progeny thereof comprising a transgene integrated into a genomic nuclease cleavage site in an event MIR604 maize genome, comprising regenerating a maize plant from the maize cell produced by the method described in the proceeding paragraph. The present invention further provides a maize plant, plant part, or progeny thereof comprising a transgene integrated into a genomic nuclease cleavage site in an event MIR604 maize genome, produced by the method described above.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1. Regions Around the MIR604 Transgene Insertion Site as a Potential Safe Harbor The following artificially defined criteria are used to identify potential maize genomic safe harbor regions that are suitable for targeted transgene integration and stable expression: (1) Regions that contain mostly unique sequences so it is suitable for performing targeted integration mediated by homologous recombination; (2) Regions that are not part of a known functional gene including those encoding for miRNAs; Ideally, these regions should be at least 2 Kb upstream of any known open reading frame or 1 Kb downstream from the 3'-untranslated region (3'-UTR) of a gene; thus integration of transgene will not interrupt any endogenous gene sequences or affect function of neighboring endogenous genes; (3) Regions that are not close to heterochromatic regions with highly repetitive sequences such as pericentromeric regions that may result in unstable expression of transgenes or potential silencing of inserted transgenes; (4) Regions that do not contain known cis-acting elements such as enhancers or repressors so that transgene expression pattern and level is altered unexpectedly when inserted. (5) Regions that have empirical data showing good transgene expression.

Several candidate regions are identified using the above criteria in the maize genome, for example, in chromosome 1 between position 38,555,000 and 38,605,000, between position 38,640,000 and 38,715,000, and between position 38,860,000 and 39,015,000 (Maize B73 RefGen_V2). Since commercial transgenic events usually have good transgene expression, insertion sites of commercial events are also examined for their potential to serve as candidate safe harbors. However, almost all of them fail to meet the above criteria except for the root-worm resistance trait event MIR604. Interestingly, the transgene insert in MIR604 happens to be located at Chromosome 1 between position 39,014,056 and 39,014,148 close to the end of position 39,015,000. Regions flanking the MIR604 insertion site is unique in that it is the only one out of the many examined to meet all of the safe harbor criteria. Since MIR604 event has been on market for several years, the region around the insertion site is an ideal candidate as safe harbor for insertion of additional transgenes. However, it is shown before that transgene inserted into the previously generated transgene loci may also lead to expression variation (Day et al. "Transgene integration into the same chromosome location can produce alleles that express at a predictable level or alleles that are differentially silenced *Genes and Develop.* 14:2869-2880 (2000)). It is important to verify the hypothesis that the MIR604 insertion site region is a good safe harbor for expression of new transgene alleles at the same locus created via site-directed transformation using different site-directed nucleases and delivery approaches.

Example 2. Cloning of the Genomic Sequences Flanking the MIR604 Insertion Site in HiII The MIR604 transgenic event was generated from binary vector pNOV2130 using *Agrobacterium*-mediated transformation of A188 maize immature embryos using mannose as selection. Maize varieties containing MIR604 transgene are widely grown in the United States. MIR604 event contains single copy insertion of pNOV2130 T-DNA in the maize genome. The sequences of MIR604 insertion site and its flanking regions are described in U.S. Pat. No. 8,354,519, incorporated in its entirety herein, and are as in SEQ ID NO:1.

Example 3. Cloning of Chromosomal Sequences Corresponding to the Safe Harbor Locus 1 (MIR604 Insertion Site) Sequences from a Transformable Elite Maize Variety NP2222

The original MIR604 insertion site sequences (SEQ ID. NO:1) were derived from non-elite transformation variety A188. It is desirable to insert the transgene directly into an elite transformation variety. However, the sequences from the elite transformation target variety might be different than from A188 and thus will not be recognized by site-directed nucleases designed using the A188 genomic sequences. To obtain genomic sequences corresponding to the MIR604 insertion site flanking regions in the elite maize transformation variety NP2222 (U.S. Pat. No. 9,133,474, incorporated by reference herein), PCR primers were designed based on A188 MIR604 insertion site flanking sequences and used to amplify corresponding regions from NP2222 Amplified sequences were sequenced and assembled into a contig which was used for assembly of Hi-Seq whole genome deep sequencing reads around the insertion site. Finally, the NP2222 genomic sequences, named AX_MIR604, which corresponds to the A188 MIR604 insertion site were obtained and are as in SEQ ID NO:2. Sequence comparison shows that there are significant differences in the genomic sequences between NP2222 and A188, including many InDels (insertions/deletions) and nucleotide substitutions.

Example 4. Targeted Insertion of Transgenes at the MIR604 Insertion Site Safe Harbor Mediated by Programmable CRISPR-Cas9 Nuclease

Example 4.1. Introduction to CRISPR-Cas9 Nucleases for Mediating Targeted Insertion Targeted insertion of transgenic sequences for replacing short stretches of DNA sequences (allele replacement) or inserting large DNA fragments (transgene insertion) can be mediated by DNA breaks introduced by CRISPR-Cas9 nucleases via homologous recombination (Shan et al., *Nature Biotechnology* 31:686-688 (2013); Wang et al., *Cell* 153:910-918 (2013); Yang et al., *Cell* 154:1370-1379 (2013); Puchta and Fauser, *Plant Journal* 78:727-741 (2014); Chen and Gao, *Plant Cell Rep.* 33:575-583 (2014)). In this example, CRISPR-Cas9 nucleases are used to mediate the insertion of large DNA molecules into the desired chromosomal safe harbor target in corn plants. The MIR604 event insertion site in NP2222 corn line was chosen as the tentative transgene expression safe harbor for studying Cas9/gRNA-mediated transgene insertion.

Example 4.2. Candidate Safe Harbor (MIR604) Target Sequence Selection

The putative safe harbor regions at and surrounding the MIR604 insertion site are scanned for potential Cas9 cleavage sites by using the rule of 5'-G/A-$(N)_{18-20}$-NGG-3' in both strands so that the target template sequences $A(N)_{18-20}$ and $G(N)_{18-20}$ preceding the 5'-NGG-3' sequence motif can be conveniently placed under the control of a DNA PolIII promoter such as rice prOsU3 and prOsU6, respectively. Many sequences can be identified as potential Cas9-gRNA cleavage targets around the MIR604 insertion site. For example, the following potential target sequences were identified for Cas9-mediated cleavage: 5'-AGTGC AGTGC AGTGC AGGAC AGG-3' (SEQ ID. NO:3), 5'-ACTAA TCGTG CTTCA CGCAC AGG-3'(SEQ ID. NO:4), 5'-AGGCA CAGCA CGTAG TAGAC AGG-3'(SEQ ID. NO:5); 5'-ACATG TCGAT CCGAC GACGA CGG-3'(SEQ ID. NO:6), 5'-AGTTT TATTA TAATC CGAA ACGG-3' (SEQ ID. NO:7), 5'-AATCC GAAAC GGAGC ACGCA CGG-3' (SEQ ID. NO:8), 5'-AAACG GAGCA CGCAC GGCGG TGG-3'(SEQ ID. NO:9), 5'-GGAGC ACGCA CGGCG GTGG AGG-3' (SEQ ID. NO:10), 5'-ATCCA AAGCT ACATC CGTGC AGG-3'(SEQ ID. NO:11), 5'-GTGCA GTGCA GTGCA GTGC AGG-3'(SEQ ID. NO:12), 5'-GGACA GGACC TCCTT TGTTT AGG-3'(SEQ ID. NO:13), 5'-GCGTG CGCAG AGCGC CTGCT CGG-3'(SEQ ID. NO:14), 5'-GCGTC ATCCA TGTGT TC TGG-3'(SEQ ID. NO:15), 5'-GTCCA TCTCC ATTCA CTGGT T CGG-3'(SEQ ID. NO:16), 5'-AATGC CTGCA GAAGA GGCCG TGG-3'(SEQ ID. NO:17). Similarly, target sequences from the other strand were also identified, for example: 5'-GCGGC CGGCA CGTTG CTAAC C AGG-3' (SEQ ID. NO:18), 5'-AGAGA AGAAA AATTC GTCCA TGG-3'(SEQ ID. NO:19), 5'-GGCCT CTTCT GCAGG CATT TGG-3'(SEQ ID. NO:20), 5'-AAGGA ACCCG AACCA GTGAA TGG-3'(SEQ ID. NO:21), 5'-ATCGG TCCTAA ACAAA GG AGG-3'(SEQ ID. NO:22), 5'-GGATG CAGCT TTGGC AACG AGG-3'(SEQ ID. NO:23), 5'-GTCGC GCAGC GCTCC TGCA CGG-3'(SEQ ID. NO:24), 5'-GCTCC TGCAC GGATG TAGCT T TGG-3'(SEQ ID. NO:25), 5'-GGATG TAGCT TTGGA TTGC TGG-3'(SEQ ID. NO:26), 5'-AAATA AAAAA ATCGG ATTAA AGG-3'(SEQ ID. NO:27).

One of the above listed sequences, 5'-AGTGC AGTGC AGTGC AGGAC AGG-3'(SEQ ID NO:3), which is located very close to the MIR604 insert site, was chosen as a target sequence for testing Cas9-gRNA mediated transgene insertion. Sequences (20 bp) preceding the Cas9 recognition PAM motif (5'-NGG-3'), 5'-AGTGC AGTGC AGTGC AGGAC-3' (SEQ ID NO:28, aka. xMIR6041-R2) were used to construct sgRNA expression vector using the rice PolIII promoter prOsU3 in the example below.

Example 4.3. CRISPR-Cas9 and Guide RNA Design and Expression Vectors

Example 4.3.1. Optimization of Cas9 for Expression in Maize Cells

In order to achieve good expression in maize cells, Type II Cas9 gene from *Streptococcus pyogenes* SF370 was optimized with maize-preferred codons (cBCas9Nu-01, SEQ ID NO:29). A nuclear localization signal was also incorporated into the C-terminus of Cas9 to improve its targeting to nucleus (Cas9Nuc, SEQ ID NO:30). To express the modified Cas9 protein (Cas9Nuc) in maize cells, the maize-optimized Cas9 gene (cBCas9Nu-01, SEQ ID NO:29) was placed under the control of maize ubiquitin-1 promoter (prUbi1-10) followed by a terminator sequence (tNOS).

Example 4.3.2. Guide RNAs (gRNAs) for Mediating the MIR604 Insertion Site Safe Harbor Modification: gRNA Design and its Expression For targeted cleavage of the safe harbor #1 (MIR604 insertion site) target sequence (5'-AGTGC AGTGC AGTGC AGGAC AGG-3', SEQ ID NO:3), crRNAs of at least 17 nucleotides (nt) long were designed against the maize genomic target sequence (5'-AGTGC AGTGC AGTGC AGGAC-3', SEQ ID NO:28,) preceding the 5'-NGG-3' for Cas9-mediated target recognition. For example, crRNAs of 17-nt (5'-GC AGTGC AGTGC AGGAC-3', SEQ ID NO:31), 18-nt (5'-TGC AGTGC AGTGC AGGAC-3', SEQ ID NO:32), 19-nt (5'-GTGC AGTGC AGTGC AGGAC-3', SEQ ID NO:33), 20-nt (5'-AGTGC AGTGC AGTGC AGGAC-3', SEQ ID NO:28) or 21-nt (5'-C AGTGC AGTGC AGTGC AGGAC-3', SEQ ID NO:34) can be used to guide Cas9 cleavage of the safe harbor #1(MIR604 insertion site). The target crRNA is co-delivered with tracRNA and Cas9 protein or mRNA to mediate target site cleavage. Preferably, the crRNA molecule is fused with tracRNA molecule covalently into a single guide RNA (sgRNA). sgRNAs can be synthesized chemically or produced by in vitro transcription. In vitro produced sgRNAs can be used directly for physical delivery such as biolistic bombardment with Cas9 RNA or protein to mediate target cleavage and homology-directed target modification if repair donor oligonucleotide is co-delivered. More preferably, sgRNA is produced in planta from a DNA expression cassette comprising a RNA polymerase III (PolIII) promoter, for example the rice U3 or U6 promoters (prOsU3 and prOsU6). For prOsU3, the transcriptional start site begins with nucleotide A, whereas for prOsU6, the transcriptional start site begins with nucleotide G (Shan et al., (2013) *Nature Biotechnology* 31: 686-688; Xie and Yang, (2013) *Molecular Plant* 6:1975-1983). For example, to produce sgRNA targeting the safe harbor #1(MIR604 insertion site) sequence (5'-AGTGC AGTGC AGTGC AGGAC AGG-3', SEQ ID NO:3), 19-nt DNA oligonucleotides (5'-GTGC AGTGC AGTGC AGGAC-3', SEQ ID NO:33) or 20-nt oligonucleotides (5'-AGTGC AGTGC AGTGC AGGAC-3', SEQ ID NO:28) were fused to the DNA sequences encoding tracRNA scaffold and PolIII termination sequences (5'-GTTTT AGAGC TAGAA ATAGC AAGTT AAAAT AAGGC TAGTC CGTTA TCAAC TTGAA AAAGT GGCAC CGAGT CGGTG CTTTT TTTTT-3', SEQ ID NO:35) (Mali et al. (2013). *Science* 339:823-826) to form coding sequence for a single guide RNA (sgRNA) named rBsgRNA-01 (Seq. ID. NO:36) which was placed under the control of rice polymerase III promoter U3 (prOsU3) or U6 (prOsU6). For this example, the expression cassette comprised prOsU3 and coding sequences for the sgRNA rBsgRNA-01, comprising the 20-nt xMIR6041-R2 (SEQ ID NO:28) target RNA fused with tracRNA (SEQ ID NO:37). The expression cassette comprising prOsU3 promoter and rBsgRNA-01 sgRNA was cloned into a biolistic transformation vector along with the Cas9 expression cassette. This biolistic transformation vector is referred to as 22169.

Example 4.4. Generation of Targeted Insertion Events at the MIR604 Insertion Site Safe Harbor

Figure 2:
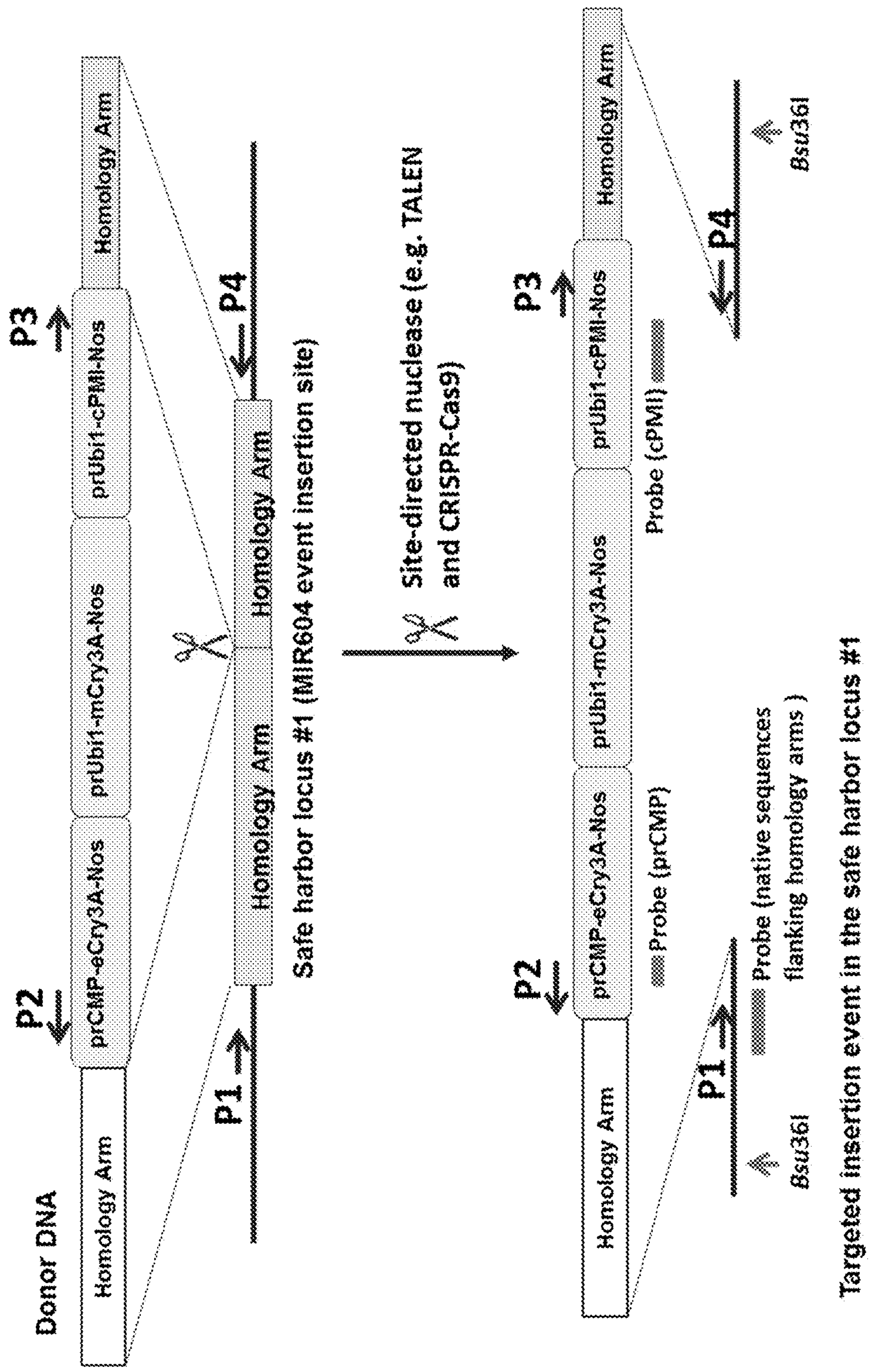
FIG. 2. Schematic representation of targeted insertion into MIR604 insertion site safe harbour locus and PCR reactions to identify potential targeted integration events with two primer pairs: P1 (FE4706)/P2 (FE4705) and P3 (FE4708)/P4 (FE4707). P1 (FE4706) and P4 (1-B4707) only binds to chromosomal regions outside the homology arms present in the donor and target region, whereas P2 (FE4705) and P3 (FE4708) only binds to donor molecules. Primer pair P1(FE4706) and P2 (FE4705) produces a fragment of 2.87 Kbp and primer pair P3(FE4708)/and P4(FE4707) amplifies a fragment of 2.0 Kbp only if targeted insertion is present at the safe harbor locus #1 (MIR604 insertion site). The approximate position of Bsu36I restriction sites and probes used in Southern DNA blot analysis (FIG. 5) are indicated in the targeted insertion event.

Example 4.4.1. Construction Donor Vector for Targeted Insertion Via Homologous Recombination A gene targeting donor vector (referred to as 21942) was constructed by inserting expression cassettes for 2 insect control genes (eCry3.1Ab and mCry3A) and the PMI selectable marker gene between two homology arms (xJHAX-03, SEQ ID NO:38 and xJHAX-04, SEQ ID NO:39). From the 5' end, the donor nucleic acid sequence comprises xJHAX-03 operably linked to an eCry3.1Ab expression cassette, which is operably linked to a mCry3A expression cassette, which is operably linked to a cPMI expression cassette, which is operably linked to xJHAX-04 (FIG. 2). The two homology arms (xJHAX-03 and xJHAX-04) have sequences identical to part of the safe harbor #1 (MIR604 insertion site) sequences (SEQ ID NO:2) and are for guiding the targeted insertion of the donor sequences to the Cas9 cleavage site at the target locus using homologous recombination (FIG. 2).

Figure 3:
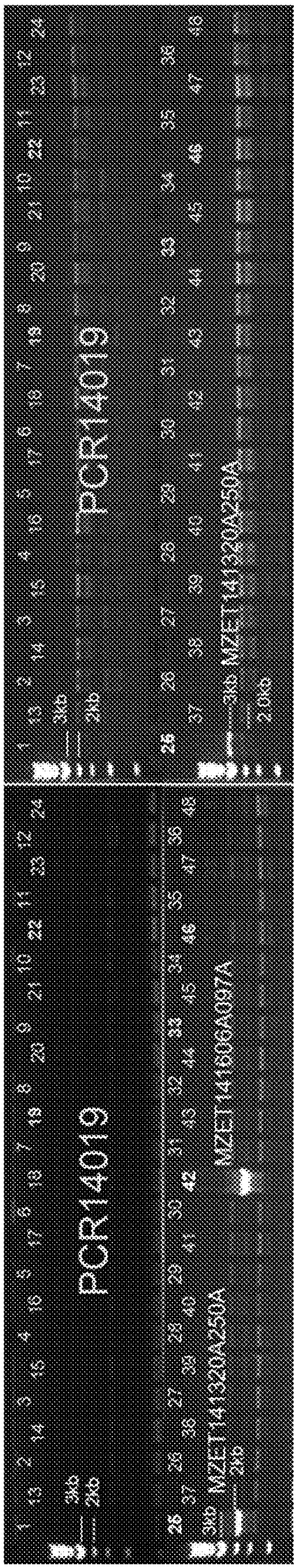
FIG. 3. An example of PCR screening assay as outlined in FIG. 2. In the left panel, PCR is done with P3(FE4708)/and P4(FE4707) which amplifies a fragment of 2.0 Kbp from 2 events (lane 25, MZET141320A250A and lane 42, event MZET141606A097A). In the right panel, PCR is done with pair P1 (FE4706) and P2 (FE4705) produces a fragment of 2.87 Kbp from only 1 event (lane 25, MZET141320A250A).
Figure 5:
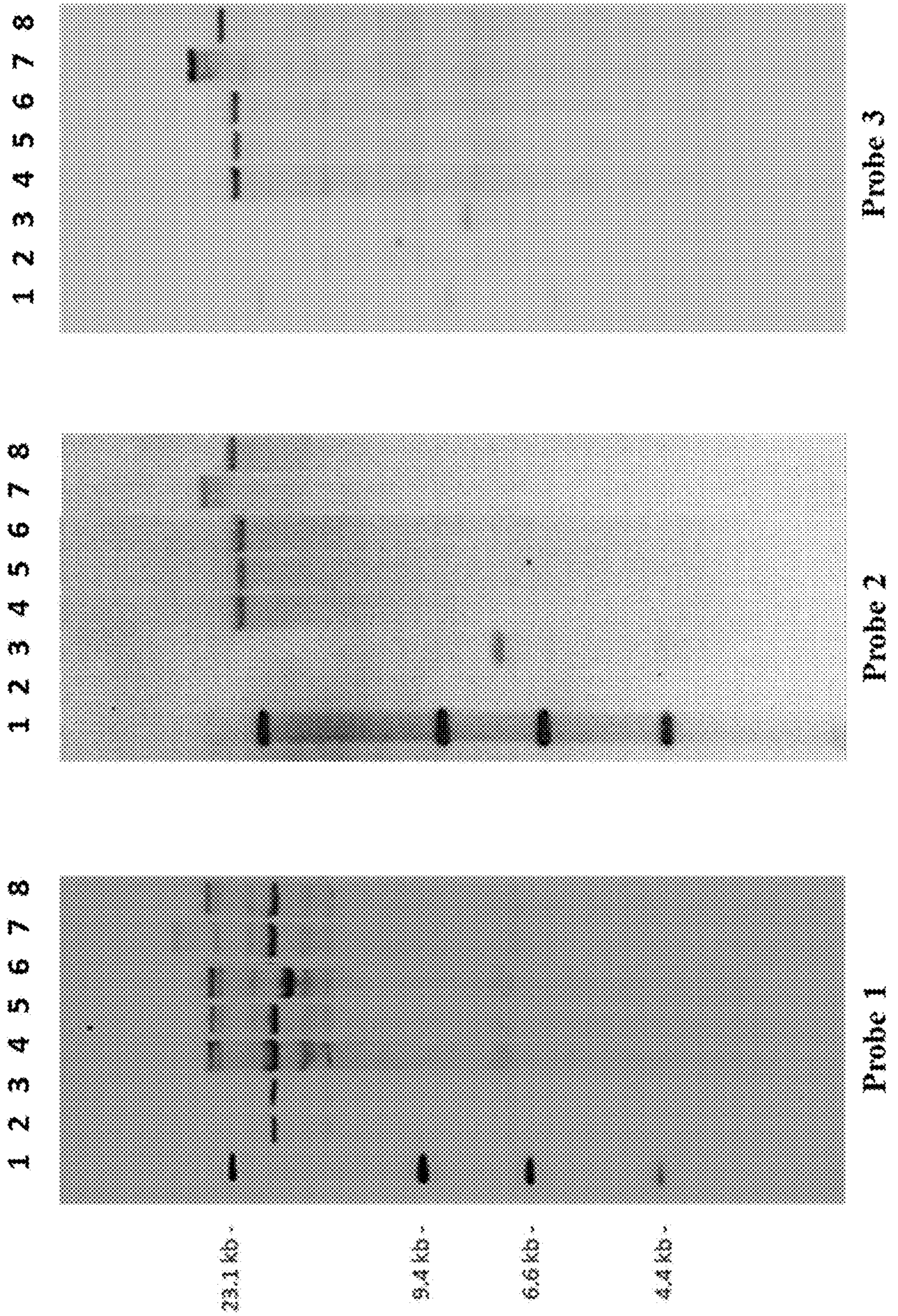
FIG. 5. DNA blot analysis of targeted insertion events at the safe harbor locus #1 (MIR604 insertion site). DNA Probe 1: against flanking native genomic sequences; Probe 2: probe against prCMP; Probe 3: Probe against cPMI (See FIG. 2 for probe locations in the schematic map). Lane 1: DIG-labeled markers; Lane 2: Wild type maize transformation line NP2222; Lane 3: NP2222 spiked with 21942; digested with HindIII (releasing a 8553 bp fragment); Lane 4: MZET134207E056A; Lane 5: MZET134300A679A; Lane 6: MZET134505A104A; Lane 7: MZET141322A015A; Lane 8: MZET141322B143A; All maize genomic DNAs in lane 2 to 8 were digested with Bsu36I restriction enzyme. Note: Probe 1 also hybridizes weakly to homologous sequences in other parts of the genome. WT safe harbor locus has the dominant 17.5 Kb band, whereas targeted insertion events have the fragment size increased to 28 Kb. For probe 2 and 3, the 28 Kb Bsu36I bands contain targeted insertion of donor DNA sequences through homologous recombination. In lane 7, the event likely contains an insertion of the rearranged donor DNA molecule.

Example 4.4.2. Generation of Targeted Insertion Events at the MIR604 Insertion Site Safe Harbor with Biolistic Bombardment For target gene sequence modification mediated by homology-directed repair, a donor DNA molecule needs to be co-delivered with Cas9 and sgRNA. To generate potential events carrying targeted insertion events at the safe harbor locus #1, plasmid DNA of a vector (22169) carrying an expression cassette for Cas9Nuc and sgRNA was mixed with a fragment of vector 21942 comprising the donor nucleic acid sequence (FIG. 2), which comprises the expression cassettes and homology arms described in example 4.4.1. The DNA (Cas9Nuc and sgRNA vector with donor nucleic acid sequence) was then precipitated onto gold particles and used to bombard immature maize embryos (line NP2222). Methods for maize immature embryo bombardment, callus induction tissue regeneration and rooting methods have been described previously (Wright et al., *Plant Cell Reports* 20:429-436 (2001)). Briefly, immature embryos were isolated from harvested immature ears at about 9-11 days after pollination and pre-cultured for 1 to 3 days on osmoticum media. Pre-cultured embryos were then bombarded with the DNA described above using BioRad PDS-1000 Biolistic particle delivery system. Bombarded embryos were then incubated in callus induction media and then moved onto mannose selection media. Mannose resistant calli were transferred to regeneration media to induce shoot formation. Shoots were then sub-cultured onto rooting media. Samples were then harvested from rooted plants for Taqman assays to detect mutations in the target site to enrich for potential targeted insertion events (described herein) and junction PCRs were performed to identify potential plants containing the targeted insertion (FIG. 2 and FIG. 3). Identified putative targeted insertion events were further characterized by more detailed PCR, sequencing and Southern analysis for confirmation (FIG. 5). Table 1 shows an experiment (MZET134300) that resulted in the recovery of a targeted insertion event MZET134300A679A. In this experiment, more than 80% of transgenic events positive for donor nucleic acid expression cassettes (384 out of 473 events) contain modifications at the target site sequence xMIR604FR2 (SEQ ID NO:28). PCR reactions were performed on a subset of events and identified one clean targeted insertion event through double crossover homologous recombination at both homology arms. Additional DNA sequencing and Southern blot analysis confirmed that the event was a clean targeted insertion event, meaning that this event comprises a single copy of the donor nucleic acid sequence described in example 4.4.1, specifically the eCry3.1Ab, mCry3A, and PMI expression cassettes, is backbone free, shows evidence of a double-crossover homologous recombination event, and has no integration of the vector DNA comprising the nuclease. This Example shows that the MIR604 insertion site is a good target site for targeted insertion.

TABLE 1

Targeting experiments in corn with sgRNA-Cas9 nuclease at the safe harbor locus #1(MIR604 insertion site) target sequence xMIR604FR2 (SEQ ID NO: 28)

| Experiment ID | DNA used for bombardment | No. of embryos | Total transgenic events | Events with target site mutation | Events with potential targeted insertion | Events with confirmed clean targeted insertion |
|---|---|---|---|---|---|---|
| MZET134300 | 22169, 21942 (1:1, $8 \times 10^{10}$ molecules of each) | 3620 | 473 | 384 | 29 | 1 |

To determine the efficiency of sgRNA-Cas9 mediated genome modification, we assayed for the presence of mutations in all 473 transgenic plants described in Table 1, using high throughput Taqman assays as described in the subsequent Examples. Since the transformation is done through co-delivery of repair donor and Cas9 nuclease constructs, we expect to see donor nucleic acid sequence in transgenic plants that do not contain the Cas9Nuc expression vector. Indeed, out of the 473 PMI-positive plants for donor nucleic acid sequence, 301 of them (63.6%) have and 172 of them (36.4%) do not have co-integrated Cas9 nuclease expression vector, respectively (Table 2). 83 plants (17.5%) without a co-integrated Cas9Nuc nuclease expression vector (22169) have their target site (xMIR6041-R2, SEQ ID NO:28) modified either in one allele (7 plants) or both alleles (76 plants) of the maize genome (Table 2).

In addition, we assayed for the presence of mutations in regenerated plants that escaped the mannose selection process or transformation escapes that do not contain donor nucleic acid sequence expression cassettes. As expected, out of 471 escapes, only 2 plants are positive for the Cas9Nuc nuclease expression vector and both of these 2 plants have biallelic mutations in the genomic target (Table 2). Surprisingly, a high percentage of escape plants (23.9%, 112 out of 469 plants) negative for any transgene (donor nucleic acid sequence expression cassettes or Cas9Nuc expression vector) have mutations at the safe harbor locus #1 (MIR604 insertion site) target sequence xMIR604FR2 (SEQ ID NO:28). 37 of these 112 events have biallelic mutations, i.e., both copies of the xMIR604FR2 sequence (SEQ ID NO:28) in the maize genome are mutated. The remaining 75 events have mutation in one of the copies of the sequence. This surprising result indicates that transient expression of Cas9 nuclease and sgRNA in the maize cells is sufficient for generating mutations at the chromosome targets. Also, selection is optional to obtain mutant plants. If sufficient number of regenerated plants is screened, targeted mutants can be easily identified through transient delivery and expression of Cas9Nuc protein and gRNA or gRNAs in plant cells.

TABLE 2

Breakdown of different types of events in regenerated plants with gRNA-Cas9 mediated targeted mutagenesis at the safe harbor locus #1(MIR604 insertion site) target sequence xMIR604FR2 (SEQ ID NO: 28)

| Experiment MZET13430 | Number | Percentage |
|---|---|---|
| Total immature embryo targets | 3620 | |
| Total regenerated plants | 944 | |
| Donor nucleic acid (PMI) positive plants (Transformants) | 473 | 13.1%[1] |
| Events with no target site modification | 89 | |
| Events with target site modification | 384 | 81.2% |
| Events with monoallelic modification | 20 | |

TABLE 2-continued

Breakdown of different types of events in regenerated plants with gRNA-Cas9 mediated targeted mutagenesis at the safe harbor locus #1(MIR604 insertion site) target sequence xMIR604FR2 (SEQ ID NO: 28)

| Experiment MZET13430 | Number | Percentage |
|---|---|---|
| Monoallelic modification with co-integration of Cas9 vector | 13 | |
| Monoallelic modification without co-integration of Cas9 vector | 7 | |
| Events with biallelic modification | 364 | |
| Biallelic modification with co-integration of Cas9 vector | 288 | |
| Biallelic modification without co-integration of Cas9 vector | 76 | |
| Donor nucleic acid (PMI) negative plants (Escapes) | 471 | 13.0%[2] |
| Events with no target site modification | 357 | 75.8% |
| Events with target site modification | 114 | 24.2% |
| Events with monoallelic modification | 75 | 15.9% |
| Monoallelic modification with co-integration of Cas9 vector (22169) | 0 | |
| Monoallelic modification without co-integration of Cas9 vector (22169) | 75 | 15.9% |
| Events with biallelic modification | 39 | 8.3% |
| Biallelic modification with co-integration of Cas9 vector (22169) | 2 | |
| Biallelic modification without co-integration of Cas9 vector (22169) | 37 | 7.9% |
| Total number of events with mutations at the target site | 498 | 52.7% |

[1]Transformation frequency is 13.1%

[2]Escape frequency is 13.0%

Example 4.4.3. Generation of Targeted Insertion Events at the MIR604 Insertion Site Safe Harbor with *Agrobacterium*-Mediated Transformation Targeted insertion of transgenes into the safe harbor locus can also be generated with DNA donor and expression vectors for Cas9 nuclease and sgRNA delivered via *Agrobacterium*. *Agrobacterium*-mediated transformation methods have been described elsewhere (Ishida et al., *Nat. Biotechnol.* 14:745-750 (1996)). Briefly, binary vectors for delivering donor DNA and expression cassettes of Cas9 and sgRNA are constructed. Donor DNA may be introduced in the same binary vector as expression cassettes of Cas9 and sgRNA, or may be introduced into separate T-DNA in the same binary vector, or may be introduced into separate binary vectors which can be transformed into the same *Agrobacterium* strain or separate *Agrobacterium* strains and delivered together through co-transformation. To construct a binary vector for *Agrobacterium*-mediated delivery of Cas9 and sgRNA, a DNA fragment containing the Cas9 and sgRNA expression cassettes is inserted into binary vector backbone to form pB-Cas9-U3-xMIR604FR2.

Similarly, a binary donor vector is constructed by inserting a nucleic acid fragment containing homology arms (xJHAX-03 and xJHAX-04), an eCry3.1Ab expression cassette, a mCry3A expression cassette, and a PMI marker expression cassettes into a binary vector. Both binary vectors are introduced into *Agrobacterium* strain LBA4404 containing a helper plasmid through electroporation. *Agrobacterium* strains containing these binary vectors are mixed and then used to co-infect maize immature embryos. Infected embryos are co-cultivated with *Agrobacterium* cells for 2-4 days and then used to induce calli. Calli are selected with mannose—containing media and mannose-resistant calli are regenerated into plantlets using a method similar to Negrotto et al. *Plant Cell Rep.* 19:798-803 (2000). Samples are taken from rooted plantlets for qPCR Taqman assays to enrich for potential targeted insertion events as described in the subsequent Examples and then junction PCR analyses are carried out to identify targeted insertion events as shown in FIG. 2 and FIG. 3. Identified putative targeted insertion events are further characterized in detail by Southern analysis and sequencing of PCR products.

Example 5. Targeted Insertion of Transgene Sequences to the MIR604 Insertion Site Safe Harbor Mediated by TALE Nucleases (TALENs)

Example 5.1. Selection of TALEN Recognition Target Against AX-MIR604 Sequences Target sequences were selected from the AX_MIR604 (SEQ ID NO:2) for TALEN design. Table 3 lists the selected sequences, their names and identifier numbers.

TABLE 3

Selected TALEN target sequences based on NP2222 genomic sequences (SEQ ID NO: 2)

| TALEN target name | Sequence (5' to 3') | Length | Sequence identifier |
|---|---|---|---|
| MIR604A1FW1 | TTGCT ACTCC ATGTG ACT | 18 | SEQ ID NO: 40 |
| MIR604A1RV1 | TTGTC ATATT CTTTT T | 16 | SEQ ID NO: 41 |
| MIR604A2FW1; aka. mir604Fw1 | TACAC GTACT AATCG TGCT | 19 | SEQ ID NO: 42 |
| MIR604A2RV1; aka. mir604Rv1 | TCCTG TCTAC TACGT GCT | 18 | SEQ ID NO: 43 |
| MIR604A2RV2 | TTGTT CCTGT CTACT ACGT | 19 | SEQ ID NO: 44 |
| MIR604A3FW1 | TTGGT CTTTG ATGAG GTGAT | 20 | SEQ ID NO: 45 |
| MIR604A3RV1 | TCGAC ATGTA CAAAG TAGGT | 20 | SEQ ID NO: 46 |
| MIR604A4FW1 | TTCGG AAACA TCCTT TAAT | 19 | SEQ ID NO: 47 |
| MIR604A4RV1 | TTATA ATAAA ACTAA TATT | 19 | SEQ ID NO: 48 |
| MIR604A5FW1 | TAATA AATAA ATAAA TAAAT | 20 | SEQ ID NO: 49 |

TABLE 3-continued

Selected TALEN target sequences based on NP2222 genomic sequences (SEQ ID NO: 2)

| TALEN target name | Sequence (5' to 3') | Length | Sequence identifier |
|---|---|---|---|
| MIR604A5RV1 | TTGGA TTGCT GGATA ATGT | 19 | SEQ ID NO: 50 |
| MIR604A6FW1 | TCGTT GCCAA AGCTG CAT | 18 | SEQ ID NO: 51 |
| MIR604A6RV1 | TCCTG TCCTG CACTG CACT | 19 | SEQ ID NO: 52 |
| MIR604A7FW1; aka. mir604Fw2 | TGCAT CCGTG CAGTG CAGT | 19 | SEQ ID NO: 53 |
| MIR604A7RV1; aka. mir604Rv2 | TCCTA AACAA AGGAG GT | 17 | SEQ ID NO: 54 |
| MIR604A8FW1 | TAGGA CGCGA TGCTG CT | 17 | SEQ ID NO: 55 |
| MIR604A8RV1 | TGCGC ACGCA AGTGT CGT | 18 | SEQ ID NO: 56 |
| MIR604A9FW1 | TCCAT CTCCA TTCAC TGGT | 19 | SEQ ID NO: 57 |
| MIR604A9RV1 | TTCTG CAGGC ATTTG GCAT | 19 | SEQ ID NO: 58 |
| MIR604A10FW1 | TTTTC TTCTC TTCTC GAT | 18 | SEQ ID NO: 59 |
| MIR604A10RV1 | TAACC AGGCT AGCTT CGTT | 19 | SEQ ID NO: 60 |
| MIR604A11FW1 | TAAGC TACAA AAGAA CGC | 18 | SEQ ID NO: 61 |
| MIR604A11RV1 | TGTTT CGCGG CCGGC CCT | 18 | SEQ ID NO: 62 |
| MIR604A12FW1 | TTTCC GTCCT GGCCT GTC | 18 | SEQ ID NO: 63 |
| MIR604A12RV1 | TCGTC CGACG ACGAT CGAT | 19 | SEQ ID NO: 64 |
| MIR604Rv2-LT | TCCTA AACAA AGGAG GTCC | 19 | SEQ ID NO: 65 |

Example 5.2. Design of TALEN Fusion Nucleases Against Selected the MIR604 Insertion Site Safe Harbor Sequences DNA binding specificity of TALENs is designed against the target sequences in Table 3. As an example, here is the design of two pairs of heterodimeric TALENs to cleave target sequences MIR604AXA2 (aka. MIR604FR1, SEQ ID NO:66, 5'-TACAC GTACT AATCG TGCTT CACGC ACAGG CACAG CACGT AGTAG ACAGG A-3') and MIR604AXA7 (aka. MIR604FR2, SEQ ID NO:67, 5'-TGCAT CCGTG CAGTG CAGTG CAGTG CAGGA CAGGA CCTCC TTTGT TTAGG A-3'). Individual TALEN monomers recognizing 2 targets, MIR604A2FW1 (aka. mir604Fw1, 5'-TACAC GTACT AATCG TGCT-3', SEQ ID NO:42) and MIR604A2RV1 (aka. mir604Rv1, 5'-TCCTG TCTAC TACGT GCT-3', SEQ ID NO:43) within the MIR604AXA2 sequence, were assembled individually. For TALEN against MIR604A2FW1 (aka. mir604Fw1, 5'-TACAC GTACT AATCG TGCT-3', SEQ ID NO:42), the specificity determining di-residues within the RVD (Repeat-Variable Di-residue) repeats are as the following,

| | RVD position | | | | | | | | | | | | | | | | | | |
|---|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 | 17 | 18 |
| RVD residue | N/A | NI | HD | NI | HD | NN | NG | NI | HD | NG | NI | NI | NG | HD | NN | NG | NN | HD | NG |
| Target nucleotide | T | A | C | A | C | G | T | A | C | T | A | A | T | C | G | T | G | C | T |

For TALEN against MIR604A2RV1 (aka. mir604Rv1, 5'-TCCTG TCTAC TACGT GCT-3', SEQ ID NO:43), the specificity determining di-residues within the DVR repeats are as the following,

| | RVD position | | | | | | | | | | | | | | | | | |
|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 | 17 |
| RVD residue | N/A | HD | HD | NG | NN | NG | HD | NG | NI | HD | NG | NI | HD | NN | NG | NN | HD | NG |
| Target nucleotide | T | C | C | T | G | T | C | T | A | C | T | A | C | G | T | G | C | T |

We constructed three versions of each TALEN containing the RVDs recognizing mir604Fw1 (SEQ ID NO:42), a first full-length version that keeps most of the TAL effector protein sequences such as the N-terminal T3SS and the NLSs after the RVD repeat region (cTNmir604Fw1-01, SEQ ID NO:68), a second shorter version that has removed the N-terminal T3SS (cTNmir604Fw1-02, SEQ ID NO:69), and a third short version with deletions in the N-terminal T3SS and also NLSs after the RVD repeat region (cTNmir604Fw1-03, SEQ ID NO:70). Similarly, we constructed three versions of each TALEN containing the RVDs recognizing mir604Rv1 (SEQ ID NO:43), a first full-length version that keeps most of the TAL effector protein sequences such as the N-terminal T3SS and the NLSs after the RVD repeat region (cTNmir604Rv1-01, SEQ ID NO:71), a second shorter version that has removed the N-terminal T3SS (cTNmir604Rv1-02, SEQ ID NO:72), and a third short version with deletions in the N-terminal T3SS and also NLSs after the DVR repeat region (cTNmir604Rv1-03, SEQ ID NO:73). The amino acid sequences of these engineered nucleases are shown in SEQ ID NO:68 (cTNmir604Fw1-01), SEQ ID NO:69 (cTNmir604Fw1-02), SEQ ID NO:70 (cTNmir604Fw1-03), SEQ ID NO:71 (cTNmir604Rv1-01), SEQ ID NO:72 (cTNmir604Rv1-02) and SEQ ID NO:73 (cTNmir604Rv1-03).

Individual TALEN monomers recognizing another 2 target sequences, MIR604A7FW1 (aka. mir604Fw2, 5'-TGCAT CCGTG CAGTG CAGT-3', SEQ ID. NO:53) and MIR604A7RV1 (aka. mir604Rv2, 5'-TCCTA AACAA AGGAG GT-3', SEQ ID NO:54) within the MIR604AXA7 (aka. mir604FR2, SEQ ID. NO:67) sequence, were also assembled individually. For TALENs against MIR604A7FW1 (aka. mir604Fw2, 5'-TGCAT CCGTG CAGTG CAGT-3', SEQ ID NO:53), the specificity determining di-residues within the RVD repeats are as the following,

| | RVD position | | | | | | | | | | | | | | | | | | |
|---|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 | 17 | 18 |
| RVD residue | N/A | NN | HD | NI | NG | HD | HD | NN | NG | NN | HD | NI | NN | NG | NN | HD | NI | NN | NG |
| Target nucleotide | T | G | C | A | T | C | C | G | T | G | C | A | G | T | G | C | A | G | T |

For TALENs against MIR604A7RV1 (aka. mir604Rv2, 5'-TCCTA AACAA AGGAG GT-3', SEQ ID NO:54), the specificity determining di-residues within the DVR repeats are as the following,

| | RVD position | | | | | | | | | | | | | | | | |
|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 |
| RVD residue | N/A | HD | HD | NG | NI | NI | NI | HD | NI | NI | NI | NN | NN | NI | NN | NN | NG |
| Target nucleotide | T | C | C | T | A | A | A | C | A | A | A | G | G | A | G | G | T |

We constructed three versions of each TALEN containing the RVDs recognizing mir604Fw2 (SEQ ID NO:53), a first full-length version (cTNmir604Fw2-01, SEQ ID NO.74) that keeps most of the TAL effector protein sequences such as the N-terminal T3SS and the NLSs after the RVD repeat region, a second shorter version (cTNmir604Fw2-02, SEQ ID NO.75) that has removed the N-terminal T3SS, and a third short version (cTNmir604Fw2-03, SEQ ID NO.76) that has deletions in the N-terminal T3SS and also NLSs after the RVD repeat region. Similarly, we constructed three versions of each TALEN containing the RVDs recognizing MIR604Rv2 (SEQ ID NO:50), a first full-length version (cTNmir604Rv2-01, SEQ ID NO.77) that keeps most of the TAL effector protein sequences such as the N-terminal T3SS and the NLSs after the RVD repeat region, a second shorter version (cTNmir604Rv2-02, SEQ ID NO.78) that has removed the N-terminal T3SS, and a third short version (cTNmir604Rv2-03, SEQ ID NO.79) with deletions in the N-terminal T3SS and also NLSs after the RVD repeat region.

For MIR604AXA7 (aka. mir6041-R2, SEQ ID NO:67) sequence cleavage, another pair of TALENS were assembled that have slightly different amino acid sequences and recognition specificity: cTNmir604Fw2-05 (SEQ ID NO.80) containing the RVDs recognizing mir604Fw2 (SEQ ID NO:53) and cTNmir604Rv2-04 (SEQ ID NO.81) containing the RVDs recognizing MIR604Rv2-LT (SEQ ID NO:65, 5'-TCCTA AACAA AGGAG GTCC-3'), respectively. The amino acid sequences of these engineered nucleases are in SEQ ID NO.74 (cTNmir604Fw2-01), SEQ ID NO.75 (cTNmir604Fw2-02), SEQ ID NO.76 (cTNmir604Fw2-03), SEQ ID NO.77 (cTNmir604Rv2-01), SEQ ID NO.78 (cTNmir604Rv2-02), SEQ ID NO.79 (cTNmir604Rv2-03), SEQ ID NO.80 (cTNmir604Fw2-05) and SEQ ID NO.81 (cTNmir604Rv2-04).

Example 5.3. Assembly of TALEN Against AX-MIR604 Insertion Locus Sequences

Artificial TALE fusion nuclease protein sequences (SEQ ID NO:68 to SEQ ID NO.81) were back-translated into DNA coding sequences using plant-preferred codons for maximizing expression in corn and other monocot plants. Some of examples are shown here. For example, SEQ ID NO:82 is the DNA coding sequence for cTNmir604Fw1-01 protein sequence (SEQ ID NO:68) and SEQ ID NO:84 is the DNA coding sequence for cTNmir604Rv1-01 protein sequence (SEQ ID NO:71). Artificial fusion nuclease DNA sequences were then assembled from library of fragments containing different RVD repeats, promoter and terminator to form TALEN expression cassettes directly after Type IIs enzyme digestion and ligation as described (Cermak et al., *Nucleic Acid Research* 39(12):e82 (2011); Zhang et al., *Nature Biotech* 29:149-154 (2011)). For example, the assembled reporter construct MIRA2R1FLA-GUUS contains the assembled TALEN sequence TLNMIR604A2RV1 (SEQ ID NO:84) encoding cTNmir604Rv1-01 (SEQ ID NO:71) under the control of maize ubiquitin promoter (prZmUbi1-10) and also has a nonfunctional GUS recombination assay substrate cassette containing a direct repeat of GUS fragment and an inverted repeat of the 18 bp TALEN recognition sequence MIR604A2RV1 (aka. mir604Rv1, 5'-TCCTG TCTAC TACGT GCT-3', SEQ ID NO:43). Similarly, expression constructs containing other assembled TALENs are assembled in similar fashion. In many cases, expression cassettes for a pair of TALENs, e.g., cTNmir604Fw1-01 (SEQ ID NO:68) and cTNmir604Rv1-01 (SEQ ID NO:71) which recognize and cleave a target sequence MIR604AXA2 (aka. MIR604FR1, 5'-TACAC GTACT AATCG TGCT T CACGC ACAGG CAC AG CACGT AGTAG ACAGG A-3', SEQ ID NO:66, only the upper strand is shown), are placed in the same transformation vector in order to coordinate their simultaneous expression in the target tissue during transformation.

Figure 4:
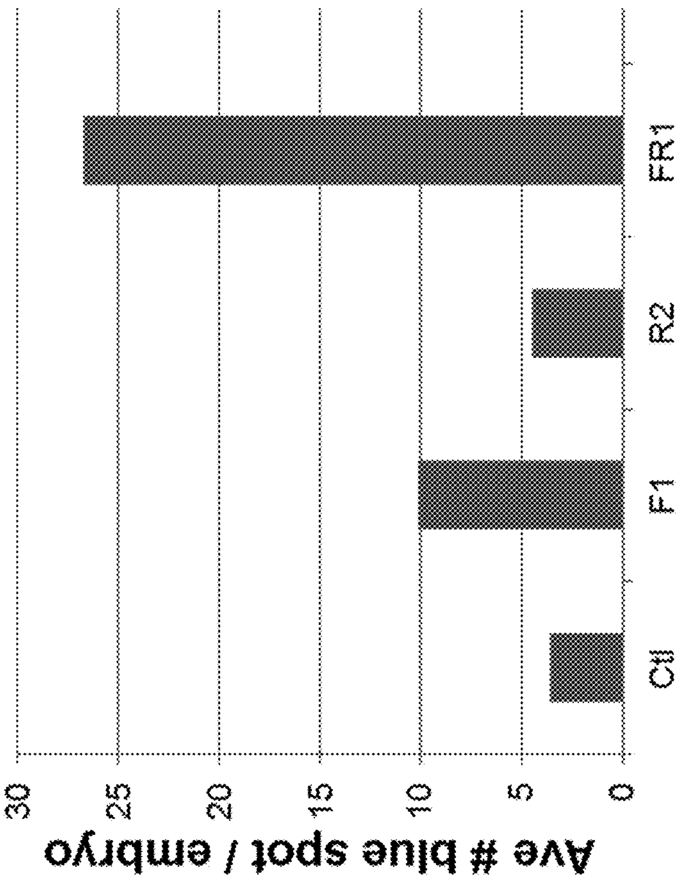
FIG. 4. Number of GUS spots in maize immature embryos bombarded with vectors containing GUUS repeat intra-molecular recombination substrate with MIR604FR1 target sequence (5'-TACAC GTACT AATCG TGCTT CACGC ACAGG CACAG CACGT AGTAG ACAGG A-3', SEQ ID NO:66) along with single TALEN vector (F1, cTNmir604Fw1-01 or R2, cTNmir604Rv2-01) or a pair of TALEN genes (FR1, cTNmir604Fw1-01 and cTNmir604Rv1-01) under the control of maize ubiquitin promoter (prZmUbi1-10) or without TALEN (ctl, blank control). cTNmir604Rv2-01 does not recognize MIR604FR1 sequence and results in background level of GUS activity (R2, negative control).

Example 5.4. Transient Assay for TALEN Activity Against AX_MIR604 DNA Sequences Assembled construct MIRA2R1FLA-GUUS containing the assembled TALEN sequence (SEQ ID NO:84) encoding for cTNmir604Rv1-01 (SEQ ID NO:71) under the control of maize ubiquitin promoter (prZmUbi1-10) and the nonfunctional GUS recombination assay substrate cassette were bombarded into immature maize embryos. The direct repeat of GUS fragment also contains an inverted repeat of the cTNmir604Rv1-01 TALEN recognition sequence mir604Rv1 (5'-TCCTG TCTAC TACGT GCT-3', SEQ ID. NO:43). Similarly, expression constructs containing DNA sequences encoding for cTNmir604Fw1-01, cTNmir604Fw1-02, cTNmir604Fw1-03, cTNmir604Rv1-02, cTNmir604Rv1-03, or the corresponding pairs of them were bombarded into maize embryos along with their target substrate(s). In many cases, expression cassettes for a pair of TALENs recognizing and cleaving a target sequence, e.g., cTNmir604Fw1-01 and cTNmir604Rv1-01 for MIR604AXA2 (aka. mir604FR1, SEQ ID NO:66), were placed in the same transformation vector in order to coordinate their simultaneous expression in the target tissue. 1 to 4 days after bombardment, transformed maize embryos were placed in X-Gluc solution overnight to detect GUS activity histochemically. GUS activity is only visible when the GUUS repeat undergoes intramolecular recombination. Co-expression of a pair of TALENs (cTNmir604Fw1-01 and cTNmir604Rv1-01) recognizing MIR604FR1 (SEQ ID NO:66) target greatly increases the number of blue spots (FIG. 4, treatment FR1), suggesting the target sequence is cleaved by the pair of heterodimeric TALENs to increase the frequency of homologous recombination.

Example 5.5. Maize Chromosomal Locus Containing the Target Recognition Sites is Cleaved at High Frequency by Artificial TALENs To test cleavage of chromosomal target sequence mir604FR2 (SEQ ID NO:67) by TALENs expressed in maize cells, two different pairs of TALENs were used. The first pair of TALENs were in a single expression vector (21321) comprising nucleic acid sequences encoding for the expression of cTNmir604Fw2-03 and cTNmir604Rv2-03, and the second pair of TALENs were in a single expression vector (21998) comprising nucleic acid sequences encoding for the expression of cTNmir604Fw2-05 and cTNmir604Rv2-04. The expression vectors (21321 and 21998) were each co-delivered by biolistic transformation into maize embryos along with the donor vector 21942 described in Example 4.4.1. Transformed embryos were selected on mannose to recover stable transgenic plants. Stable transgenic plants were analyzed for the presence of mutations in the target region using qPCR Taqman assay and/or sequencing of PCR products. Results in Table 4 show that for both pairs of TALENs for target site MIR6041-R2 (5'-TGCATCCGTGCAGTGCAGTG CAGTG CAGGA CAGGA CCTCC TTTGT TTAGG A-3', SEQ ID NO:67)

resulted in high percentage of mutation in stable transformants when TALEN expression vectors are delivered into plant cells with biolistic method. Both the full length and truncated version of TALENs can mediate targeted mutagenesis at the target loci efficiently.

Interestingly, we also detected mutations of MIR604 insertion site locus mir604FR2 target site (5'-TGCAT CCGTG CAGTG CAGTG CAGTG CAGGA CAGGA CCTCC TTTGT TTAGG A-3', SEQ ID NO:67) in many regenerated mannose selection escape plants. For example, in co-transformation experiments with vector TALEN vector 21321 and donor 21942 (Table 4), 14 of the plants generated, namely MZET130501B017A, MZET130501B038A, MZET130501B027A, MZET130501B031A, MZET130501A012A, MZET130501B041A, MZET130501B096A, MZET130402A030A, MZET130501B044A, MZET130501B057A, MZET130501B084A, MZET130501B130A, MZET130501B045A, MZET130704C003A, contained a mutation in the mir604FR2 target sequence, but they did not harbor any detectable transgenes from either donor or TALEN expression vectors and thus were escapes of mannose selection. In these escape plants, about 5% of them have mutations in the mir604FR2 target site and some of them have both alleles of the mir604FR2 target sequences mutated. Therefore, it is a viable approach to recover plants with mutations in target sites by transiently delivering TALENs and then regenerating untransformed plants directly without selection. Mutant plants can be identified by screening population of regenerants with proper assays such as PCR.

To test cleavage of chromosomal target locus by TALENs expressed in maize cells delivered by *Agrobacterium,* 4 different binary vectors (21631, 21632, 21633 and 21634) containing expression cassettes of different pairs of TALENs were constructed. All four binary vectors comprise the donor nucleic acid sequence comprising expression cassettes for eCry3.1Ab, mCry3A, and PMI. 21631 and 21633 additionally comprise nucleic acid sequences encoding for the expression of cTNmir604Fw1-01 and cTNmir604Rv1-01; 21632 and 21634 additionally comprise nucleic acid sequences encoding for the expression of cTNmir604Fw2-01 and cTNmir604Rv2-01. 21631 and 21632 have the TALEN expression cassettes and the gene targeting donor in one T-DNA, while 21633 and 21634 have these in two separate T-DNAs. Expression of the pair of TALENs in 21631 and 21633 is expected to result in cleavage of the chromosomal target sequence MIR604AXA2 (aka. MIR604FR1, 5'-TACAC GTACT AATCG TGCTT CACGC ACAGG CACAG CACGT AGTAG ACAGG A-3', SEQ ID NO:66) in the maize genome. Similarly, expression of the pair of TALENs in 21632 and 21634 should result in cleavage of the chromosomal target sequence MIR604AXA7 (aka. MIR604FR2, 5'-TGCAT CCGTG CAGTG CAGTG CAGTG CAGGA CAGGA CCTCC TTTGT TTAGG A-3', SEQ ID NO:67) in the maize genome. These vectors transformed into maize embryos by *Agrobacterium*-mediated transformation method. Stable transgenic plants were analyzed for the presence of mutations in the target region using Taqman assay and/or sequencing of PCR products. Results in Table 4 show that for both pairs of TALENs for target site MIR604FR1 (SEQ ID NO:66) and MIR604FR2 (SEQ ID NO:67) resulted in high percentage of mutation in stable transformants when delivered via *Agrobacterium*-mediated transformation (Table 4).

TABLE 4

High rate of mutagenesis of mir604FR1(SEQ ID NO: 66) and mir604FR2 (SEQ ID NO: 67) target sequences at the native chromosomal MIR604 insertion site locus in stable transformants derived from co-transformation of a TALEN expression vector and a donor vector containing PMI selectable marker gene

| Target locus | Delivery method | Nuclease vector | Donor | No. of experiments | Total explants | No. of stable events | No. of events with target site mutation | Mutation frequency (% transformants) |
|---|---|---|---|---|---|---|---|---|
| MIR604 insertion site FR2 target | Biolistic | 21321 | 21942 | 7 | 6279 | 132 | 46 | 34.8% |
| MIR604 insertion site FR2 target | Biolistic | 21998 | 21942 | 2 | 7845 | 519 | 148 | 28.5% |
| MIR604 insertion site FR1 target | *Agrobacterium* | 21631 | 21631 | 3 | 4521 | 492 | 134 | 27.2% |
| MIR604 insertion site FR1 target | *Agrobacterium* | 21633 | 21633 | 3 | 5305 | 1024 | 218 | 21.3% |
| MIR604 insertion site FR2 target | *Agrobacterium* | 21632 | 21632 | 3 | 4633 | 673 | 316 | 47.0% |
| MIR604 insertion site FR2 target | *Agrobacterium* | 21634 | 21634 | 2 | 5764 | 990 | 247 | 24.9% |

Example 5.6. Targeted Insertion of Transgenic Sequences into NP2222 Chromosomal Locus Corresponding to the MIR604 Insertion Site Mediated by Assembled TALENs Cultured immature embryos Maize elite inbred line NP2222 were co-transformed with the targeting donor vector 21942 and TALEN expression vector 21321 or 21998 using particle bombardment (Table 4 and Table 5). Targeting donor vector 21942 contains trait gene expression cassettes flanked by regions of homology (xJHAX-03 and xJHAX-04) flanking the TALEN cleavage site (SEQ ID NO:67) at the MIR604 insertion site. Table 5 shows the analysis results for potential targeted insertion at the MIR604FR2 cleavage site (SEQ ID NO:67). Four events showing PCR products as expected for double-stranded homologous recombination are obtained out of 519 PMI positive stable events (Table 5). Of these, a single event was identified as a clean event, meaning that it comprises a single copy of the donor nucleic acid sequence described in example 4.4.1, specifically the eCry3.1Ab, mCry3A, and PMI expression cassettes, is backbone free, shows evidence of a double-crossover homologous recombination event, and has no integration of the vector DNA comprising the nuclease.

TABLE 5

Targeted insertion of mCry3A, eCry3.1Ab, and PMI expression cassettes into native safe harbor locus (native MIR604 insertion site locus) mediated by cleavage of FR2 sequence by TALEN

| Delivery method | Nuclease vector | Donor | Number of Expts | Total explants | positive events | Targeted events | Intact Low Copy events |
|---|---|---|---|---|---|---|---|
| Biolistic | 21998: | 21942 | 2 | 7845 | 519 | 4 | 1 |

In the above experiments, transformation was done using particle bombardment of cultured immature embryos. However, immature embryos or calli derived from cultured embryos can also be used as targets. Transformation can also be done using an *Agrobacterium*-mediated gene delivery method as shown in Table 4 using target tissues such as immature embryos, cultured embryos or calli derived from cultured embryos. For example, *Agrobacterium*-mediated transformation and recovery of events as result of targeted insertion mediated by TALEN to target site can be done using mannose selection in a fashion as described in the art (U.S. Pat. No. 7,935,862, for example), where, for example, NP2222 immature embryos are used as transformation targets.

Example 6. Targeted Insertion of Transgenes at the Safe Harbor (MIR604 Insertion Site) Mediated by Engineered Meganucleases

Example 6.1. Maize Chromosomal Target Sequence Selection for Design of Engineered Meganucleases Targeted insertion of transgenic sequences for replacing short stretch of DNA sequences (allele replacement) or inserting large DNA fragment (transgene insertion) can also be mediated by homologous recombination using DNA breaks introduced by engineered meganucleases (Puchta and Fauser, *Plant Journal* 78:727-741 (2014); Chen and Gao, *Plant Cell Rep.* 33:575-583 (2014)). The present example shows if breaks induced by engineered meganucleases can be used to mediate the insertion of large DNA molecules into the desired chromosomal safe harbor target in corn plants. To compare its effectiveness against TALEN and CRISPR-Cas9, the safe harbor locus #1 (MIR604 event insertion site) was chosen as the transgene insertion site. Therefore, although not to be limited by methodology, the present application teaches transgene insertion mediated by 3 nucleases platforms, namely TALEN, meganuclease and sgRNA-Cas9. Maize safe harbor locus #1 (aka. M1R604 event insertion site) sequences (SEQ ID NO: 1 or SEQ ID NO: 2) were scanned for optimal targets for designing engineered meganucleases using technologies in the art, e.g., by using rational protein design methodology to design engineered meganucleases with altered cleavage specificity based on LAGLIDADG family meganuclease I-CreI (U.S. Pat. No. 8,021,867). The rationally designed engineered I-CreI meganuclease variants that cleave the target sequence at high efficiency and with minimal off target cleavage are selected to mediate targeted insertion of transgenes at the safe harbor locus. DNA sequences encoding novel meganuclease variants are placed under the control of maize ubiquitin-1 promoter (prUbi1-10) followed by the NOS terminator and the expression cassette is sub-cloned into a biolistic transformation vector backbone.

To test the in planta activity of engineered I-CreI meganuclease variant in cleaving maize chromosomal target sequence and its ability to mediate targeted insertion through homologous recombination, meganuclease expression vector is co-bombarded with targeting donor vector 21942 into immature maize embryos. Briefly, plasmid DNA vector carrying expression cassette for the engineered meganuclease is mixed with a fragment of vector 21942 which encodes the donor nucleic acid sequence and precipitated onto gold particles. The donor nucleic acid sequence of vector 21942 contains regions from xJHAX-03 to xJHAX-04, including PMI marker gene and two gene cassettes as described in Example 4.4.1. Immature embryos are isolated from harvested immature ears at about 9-11 days after pollination and pre-cultured for 1 to 3 days on osmoticum media. Pre-cultured embryos are then bombarded with gold particles with co-precipitated DNA vectors (21942 fragment and the meganuclease expression plasmid) using BioRad PDS-1000 Biolistic particle delivery system. Methods for maize immature embryo bombardment, callus induction tissue regeneration and rooting methods are known in the art (for example, Wright et al. 2001, *Plant Cell* Reports 20:429-436 (2001)). Bombarded embryos are then incubated in callus induction media and then moved onto mannose selection media. Mannose resistant calli are transferred to regeneration media to induce shoot formation. Shoots are then sub-cultured onto rooting media. Samples are then harvested from rooted plants for PCR and Taqman assays to identify potential plants containing the targeted insertion. Identified putative targeted insertion events are further characterized by more detailed PCR, sequencing and Southern analysis for confirmation. In addition to the stably transformed events, we also assay for the presence of mutations in regenerated plants that escaped the mannose selection, i.e., transformation escapes that do not contain any transgene from the targeted insertion donor or the meganuclease vector. Escape plants that are negative for any transgene but have mutations at the safe harbor locus #1 (MIR604 insertion site) target sequence are identified. Transient expression of the meganuclease in the maize cells is sufficient for generating mutations at the chromosome targets. Also, selection is optional to obtain mutant plants. If a sufficient number of regenerated plants is screened, targeted mutants can be easily identified through transient delivery and expression of meganuclease in plant cells.

Example 6.2. Generation of Targeted Insertion Events at the MIR604 Insertion Site Safe Harbor Locus Mediated by Engineered Meganucleases The two homology arms, namely xJHAX-03 (SEQ ID NO: 38) and xJHAX-04 (SEQ ID NO: 39), of donor vector 21942 have sequences identical to the safe harbor #1 (MIR604 insertion site SEQ ID NO: 1 and SEQ ID NO: 2) and are used to guide targeted insertion of donor vector sequences to the cleavage site of engineered meganuclease at the target locus using homologous recombination. PCR reactions are also performed in a subset of events that are likely to targeted insertion based on Taqman analysis. Events identified to have a targeted insertion at the target locus using PCR primer pairs spanning the recombination junctions are analyzed by detailed DNA sequencing and Southern blot analysis to confirm that targeted insertion has happened.

Example 6.3. Generation of Targeted Insertion Events at the Safe Harbor Locus #1 (MIR604 Insertion Site) with *Agrobacterium*-Mediated Transformation Mediated by Engineered Meganucleases Targeted insertion of transgenes into the safe harbor locus can also be generated with DNA donor and expression vectors for meganuclease delivered via *Agrobacterium. Agrobacterium*-mediated transformation methods are well-known in the art (for example, Ishida et al., *Nat. Biotechnol.* 14:745-750 (1996)). Meganuclease expression cassette and donor DNA can be placed either into separate binary vectors or in the same binary vector and then co-transformed in plant cells. Donor DNA and meganuclease can be co-delivered by using separate binary vectors. Binary vector 22445 is constructed by inserting the donor nucleic acid sequence from vector 21942 (namely, the three expression cassettes operably linked to xJHAX-03 (SEQ ID NO: 38) and xJHAX-04 (SEQ ID NO: 39), as described in Example 4.4.1), into a binary vector useful for *Agrobacterium*-mediated transformation. A binary vector is also constructed for co-delivery of both the donor nucleic acid sequence and the meganuclease expression cassette from a single binary vector, where the donor nucleic acid sequence and the meganuclease expression cassette are each operably linked to right and left border sequences, so that they comprise two separate T-DNA's in a single binary vector. These binary vectors are transformed into *Agrobacterium* strain LBA4404 (pVGW7) via electroporation and then used for transformation of maize immature embryos. For *Agrobacterium*-mediated transformation, the *Agrobacterium* strain comprising the binary vector comprising 2 T-DNA's is used to infect maize immature embryos. Alternatively, *Agrobacterium* strains containing two binary vectors are mixed and then used to co-infect maize immature embryos. Infected embryos are co-cultivated with *Agrobacterium* cells for 2-4 days and then used to induce calli. Calli are selected with mannose—containing media and mannose-resistant calli are regenerated into plantlets. Samples are taken from rooted plantlets for Taqman and PCR analysis for identifying targeted insertion events as described above for biolistic transformation. PCR reactions are also performed in a subset of events that are likely to have targeted insertion based on Taqman analysis. Events identified to have targeted insertion at the target locus using PCR primer pairs spanning the recombination junctions are analyzed by detailed DNA sequencing and Southern blot analysis to confirm that targeted insertion has occurred.

Example 7. Molecular Characterization of Targeted Insertion of Transgenic Sequences into Genomic AX MIR604 Locus Targeted insertion events identified by PCR assays were further characterized by more detailed sequencing and Southern blot analysis for confirmation. For example, events positive for junction PCRs (FIG. 2 and FIG. 3) as expected from homologous recombination occurring at one or both homologous arms were obtained from screening PMI positive stable events (as shown in Table 1 and Table 5). Detailed overlapping PCR analyses were done using primers spanning targeted insertion junctions comprising the AX_MIR604 (SEQ ID NO:2) flanking genomic regions (xJHAX-03 and xJHAX-04) and part of the transformation donor vector. Presence of positive PCR signal suggests that site-directed nucleases indeed mediate targeted insertion into the MIR604 safe harbor locus (SEQ ID NO:2) at the DNA cleavage site of MIR604FR2 (5'-TGCAT CCGTG CAGTG CAGTG CAGTG CAGGA CAGGA CCTCC TTTGT TTAGG A-3', SEQ ID NO:67). Detailed Southern blot analysis showed that indeed insertion of gene stacks happened at the MIR604 insertion site safe harbor target locus through double crossover homologous recombination as shown by the presence of expected size (FIG. 5, lanes 4, 5, 6 and 8). Lanes 4, 5, 6 and 8 have a ~28 Kb band as expected for double recombination product of donor vector with ~18 Kb chromosomal target fragment. Another event from the same experiment in lane 7 (FIG. 5) has a copy of insertion that is probably from a single crossover recombination and has additional rearrangements since the size of the recombinant band is much larger than expected size of ~28 Kb.

Example 8. Gene Expression and Insect Resistance of Transgenic Events Obtained by Targeted Insertion Technologies Targeted insertion events (MZET130403A067A, MZET134406B450A, MZET134504B010A, MZET134505A104A, MZET134711A236A, MZET140508A344A, MZET140807A856A, MZET140913A741A, MZET140913A594A, MZET130403A067A, MZET131500A128A) are evaluated for transgene expression by qPCR and ELISA assays. As a control, random integration events derived from donor vector (21942 or 22445) are also assayed for trait gene expression. Expression level is also compared with a maize line (AX5707DW) with the introgressed MIR604 locus. Since the inserted transgene contains Western corn rootworm resistance genes mCry3Aa and eCry3.1Ab, transgenic events and their progeny are evaluated in respect to the performance of insect resistance by growing them in pots infected by corn rootworm.

Example 9. High Throughput Assay for Identifying Plants with Targeted Mutations at Desirable Sequences Currently, targeted mutants are identified using one of the following methods. The first method is PCR amplification of the target region followed by restriction enzyme digestion and gel electrophoresis if the mutated sequence contains a restriction site (Lloyd et al. 2005, *Proc. Natl. Acad. Sci. USA*

102:2232-37 (2005); Zhang et al, *Proc. Natl. Acad. Sci. USA* 107:12028-33 (2010)). This method is simple, but requires the presence of a suitable restriction site and thus cannot be used for most targets. A second method is PCR amplification of the target region followed by Sanger sequencing or deep sequencing (Gross et al., *Hum. Genet.* 105:72-78 (1999). Shukla et al., *Nature* 459:437-41 (2009); Townsend et al., *Nature* 459:442-45 (2009)). A sequencing approach is definitive and sensitive, but takes a longer time and throughput can be limited by capacity. A third approach is PCR amplification of the target region followed by denaturation, annealing and capillary electrophoresis (Li-Sucholeik et al., *Electrophoresis* 20:1224-1232 (1999); Larsen et al., *Hum. Mutat.* 13:318-327 (1999)) or denaturing high-performance liquid chromatography to detect base pair changes by heteroduplex analysis (McCallum et al., *Nature Biotechnology* 18:455-457). These methods are limited by throughput and the identified mutations need to be further verified by sequencing. A fourth method is PCR amplification of the target region followed by denaturation, heteroduplex formation/strand annealing, digestion with mismatch-specific nuclease (such as CEL1 and T7 endonuclease) and gel electrophoresis (Oleykowski et al., *Nucleic Acids Res.* 26:597-4602 (1998); Colbert et al., *Plant Physiol.* 126:480-484 (2001); Lombardo et al., *Nat. Biotechnol.* 25:1298-306 (2007)), for example using the commercially available Surveyer™ nuclease assay kit (Transgenomic, Gaithersburg, Md., USA; Qiu et al., *BioTechniques* 36:702-707 (2004)). However, the gel-based assays are not as sensitive as high-throughput DNA sequencing and can only detect mutation with frequency of 1% or more. Therefore, there is still a need for a simple and high throughput method for identifying induced mutations of target sequences. Additionally, all of the above approaches of identifying a potential mutant in a target site are based on the presence of a new signal in a qualitative fashion, either a new band in a gel or a new peak in a chromatogram that is different from the wild type reference sequence.

Figure 6:
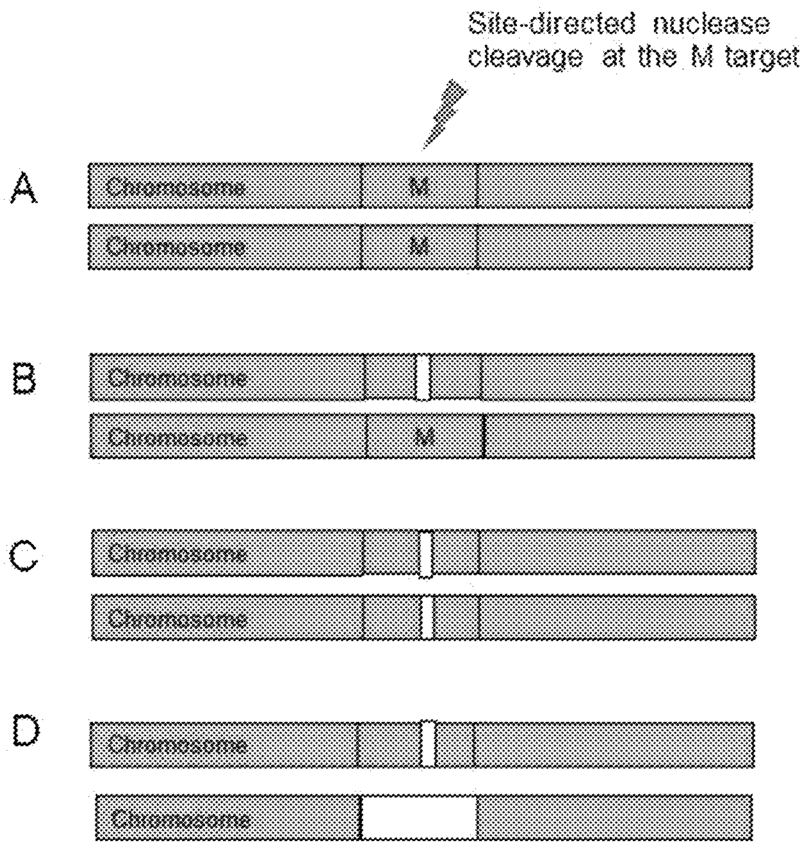
FIG. 6. Schematic diagram showing reduction of target sequence copy number in a plant with a mutation in the target sequence (M) generated by cleavage with a site-directed nuclease.

We developed an alternative approach of identifying potential mutations. The method measures the reduction of the wild type target site sequence in cells or tissues that have been treated with a site-directed nuclease in a quantitative fashion in comparison with a reference sample as shown in FIG. 6. In a DNA sample isolated from wild type (WT) tissues, there is no reduction of the target sequence DNA copy number. Typically, the copy number call in WT tissue is 2 copies for a single copy gene in a diploid organism. For example, ADH gene in WT maize has 2 copies. If one of the copies is mutated, only one copy of the wild type (WT) target site sequence remains. If both copies of the target sequences are mutated, the copy number of the M target sequence becomes zero (FIG. 6). Thus, by performing quantitative polymerase reaction assays to measure changes in the target sequence copy number, it is possible to detect if there is a mutation present in the DNA samples by comparing the result with that of a reference sample such as WT tissue. This quantitative approach significantly differs from previously known methods.

Target gene copy number can be assayed by several quantitative polymerase reaction (qPCR) techniques. Generally, qPCR is performed in such a way in that the amplified DNA is detected and measured quantitatively as the reaction progresses, or in "real time". Therefore, qPCR is also referred to as real-time PCR. There are several potential approaches for the real-time detection of products in qPCR: (1) Measurement of PCR product with non-specific fluorescent dyes (such as SYBR® Green) that intercalate with any double-stranded DNA; this detection method is suitable when a single amplicon is being studied, as the dye will intercalate into any double-stranded DNA generated. (2) Measurement of PCR product based on target sequence-specific binding of oligonucleotide probes covalently labeled with a fluorescent reporter tag, such as in TaqMan® probes, Molecular Beacons™, or Scorpion primers. The oligonucleotide itself has no significant fluorescence, but it fluoresces either when annealed to the template (as in Molecular Beacons™) or when the dye is clipped from the oligonucleotide during extension (as in TagMan® probes). The advantage of fluorescent probes is that they can be used in multiplex assays for detection of several target sequences in the same reaction. With TaqMan® probes, a target sequence-specific oligonucleotide probe is constructed with a fluorescent reporter at one end and a fluorescence quencher at the opposite end. The close proximity of the reporter to the quencher prevents detection of its fluorescence. The fluorescent oligonucleotide probe is broken down by the 5'- to 3'-exonuclease activity of the Taq polymerase so the fluorescent tag is no longer in proximity with the quencher and thus allows unquenched emission of fluorescence, which can be detected after excitation with a laser (Groves, *J Biomol. Tech.* 10:11-16 (1999)). An increase in the number of copies of PCR product at each PCR cycle results in a proportional increase in fluorescence due to the breakdown of the probe and release of the reporter.

Figure 7:
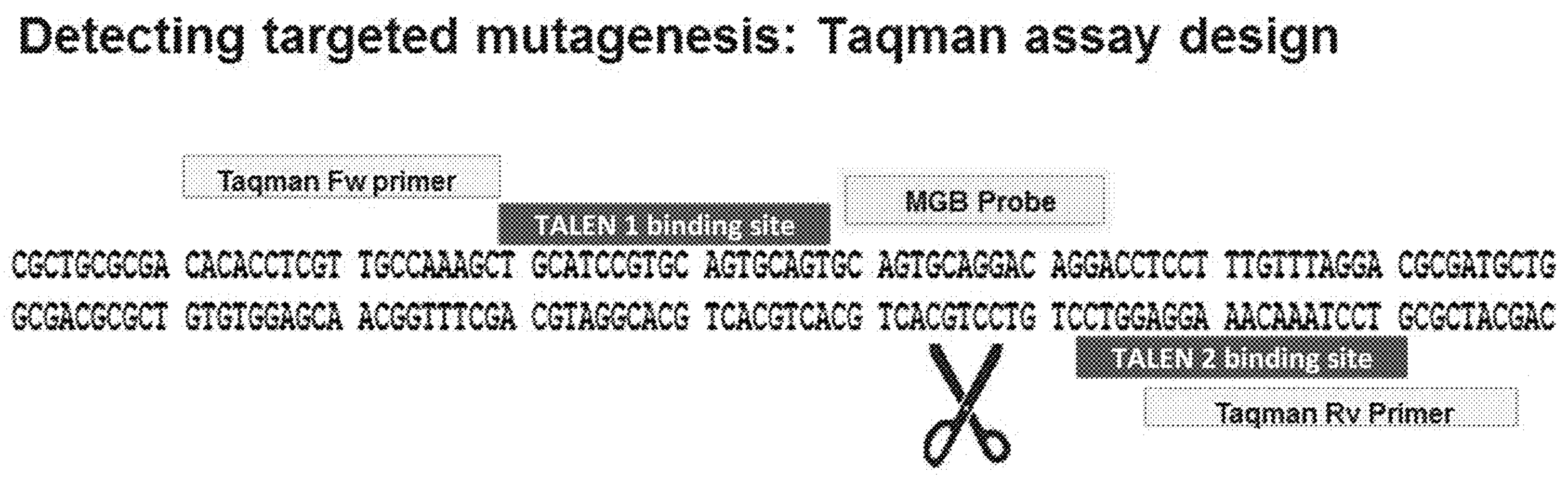
FIG. 7. Schematic representation of Taqman assay probe design for a target sequence in the MIR604 insertion site and interpretation of Taqman assay results in regard to targeted mutation.

As an example, we have designed a Taqman® probe-based method to specifically detect targeted mutation at the maize genomic MIR604 insertion site sequence that contains the cleavage site of CRISPR-Cas9 nuclease gRNA targeting SEQ ID NO:3 (5'-AGTGC AGTGC AGTGC AGGAC AGG-3') and the pair of TALENs (cTNmir604Fw2-01/cTNmir604Rv2-01) cleaving target sequence (SEQ ID NO:67, 5'-TGCAT CCGTG CAGTG CAGTG CAGTG CAGGA CAGGA CCTCC TTTGT TTAGG A-3'). As shown in FIG. 7, a real-time qPCR Taqman assay for detecting mutations within SEQ ID NO:67 target sequence consists of two primers, a FW primer, 5'-CACAC CTCGT TGCCA AAGC-3' (SEQ ID NO:92) and a RV primer, 5'-CATCG CGTCC TAAAC AAAGG A-3' (SEQ ID NO:93), and a fluorescently labeled Taqman® probe (5'-CCTGT CCTGC ACTGC-3', SEQ ID NO:94) which hybridizes to the nuclease cleavage target site sequence (5'-GCAGT GCAGG ACAGG-3', SEQ ID NO:95, the target site M as shown in FIG. 6).

Example 10. Generation of Plants with Targeted Mutations at Desirable Sequences without Transgene Insertion Using the target specific assay as outlined above and in FIG. 6 and FIG. 7 and qPCR Taqman assays for other target sequences, maize plants regenerated from immature embryos treated with engineered TALE nucleases or gRNA-Cas9 as described previously in Example 4 and Example 5 were assayed for copy number of different target sequences. Table 6 shows the results.

Fluorescently labeled MGB Taqman® probe comprising of sequence 5'-CCTGT CCTGC ACTGC-3' (SEQ ID NO.94) for assay 4 (Mir604 JHAX Fw2/Rv2_MGB) is for detecting the copy number of intact nuclease cleavage site sequence (5'-GCAGT GCAGG ACAGG-3', SEQ ID NO:95) corresponding to the target sequence M in FIG. 6. A "low" copy number call has 1 copy. A "med" copy number call has 2 copies. A "high" copy number call has 3 or more copies. In WT maize plants and regenerated plants with no target site mutation, the copy number call with Assay 4 (the last column in Table 6, Mir604 JHAXFw2/Rv2_MGB) is "Med" (2 copies). In this set of 20 plants, 11 plants (55%) have no mutation at the genomic target sequence (SEQ ID NO:95, 5'-GCAGT GCAGG ACAGG-3'), but 6 plants (30%) have mutations in one copy of the target sequences (Low copy call), and 3 plants (15%) have both copies of the target sequences are mutated (copy call is 0). Since the qPCR assays can be multiplexed, several other assays for detecting transgene sequences are performed at the same time. In this set of plants, 7 of the 20 plants contain detectable transgene insertions (positive for Assays 1 to 3). Of the 9 plants with target sequence mutations, 5 (MZET130501B027A, MZET130501B031A, MZET130501B038A, MZET130501B044A and MZET130501B045A) of them do not contain any detectable transgene insertions, including 1 plant (MZET130501B027A) that has both copies of the target sequence mutated (biallelic or homozygous mutations). This experiment clearly demonstrated that targeted mutations at desirable sequences can be efficiently generated without transgene insertion by transiently expressing a site-directed nuclease. Additionally, the mutants can be efficiently identified using high throughput real-time qPCR assays containing at least one assay probe hybridizing to the nuclease cleavage site.

TABLE 6

Copy number determination of target sequence (SEQ ID NO: 67) in regenerated maize plants from a Biolistic transformation experiment using qPCR Taqman assays

| Plant ID | Construct ID | Assay 1[1]: cTNmir604Fw2-03 | Assay 2[2]: cPMI-09 | Assay 3[3]: mCry3A | Assay 4[4]: Mir604 JHAX Fw2/Rv2_MGB |
|---|---|---|---|---|---|
| MZET130501B026A | 21321 21942 | 0 | 0 | 0 | Med |
| MZET130501B027A | 21321 21942 | 0 | 0 | 0 | 0 |
| MZET130501B028A | 21321 21942 | 0 | High | High | Low |
| MZET130501B029A | 21321 21942 | 0 | 0 | 0 | Med |
| MZET130501B030A | 21321 21942 | 0 | 0 | 0 | Med |
| MZET130501B031A | 21321 21942 | 0 | 0 | 0 | Low |
| MZET130501B032A | 21321 21942 | 0 | Low | Low | 0 |
| MZET130501B033A | 21321 21942 | 0 | High | High | 0 |
| MZET130501B034A | 21321 21942 | 0 | Low | Low | Med |
| MZET130501B035A | 21321 21942 | 0 | 0 | 0 | Med |
| MZET130501B036A | 21321 21942 | 0 | 0 | 0 | Med |
| MZET130501B037A | 21321 21942 | 0 | 0 | 0 | Med |
| MZET130501B038A | 21321 21942 | 0 | 0 | 0 | Low |
| MZET130501B039A | 21321 21942 | 0 | Low | Low | Med |
| MZET130501B040A | 21321 21942 | Low | High | 0 | Med |
| MZET130501B041A | 21321 21942 | 0 | 0 | 0 | Med |
| MZET130501B042A | 21321 21942 | 0 | High | High | Low |
| MZET130501B043A | 21321 21942 | 0 | 0 | 0 | Med |
| MZET130501B044A | 21321 21942 | 0 | 0 | 0 | Low |
| MZET130501B045A | 21321 21942 | 0 | 0 | 0 | Low |

[1]Assay 1 (cTNmir604Fw2-03) is for detecting insertion of site-directed TALE nuclease expression vector (21321)
[2]Assay 2 for detecting inserted selectable marker gene cPMI-09 present in the donor vector (21942)
[3] Assay 3 for detecting inserted insect control gene mCry3A present in the donor vector (21942)
[4]Assay 4 (Mir604 JHAX Fw2/Rv2_MGB) is for detecting the copy number of intact target sequence (5'-GCAGT GCAGG ACAGG-3', SEQ ID NO: 95) that is hybridizing to Taqman probe comprising of sequences 5'-CCTGT CCTGC ACTGC-3', (SEQ ID NO: 94)

Figure 8A:
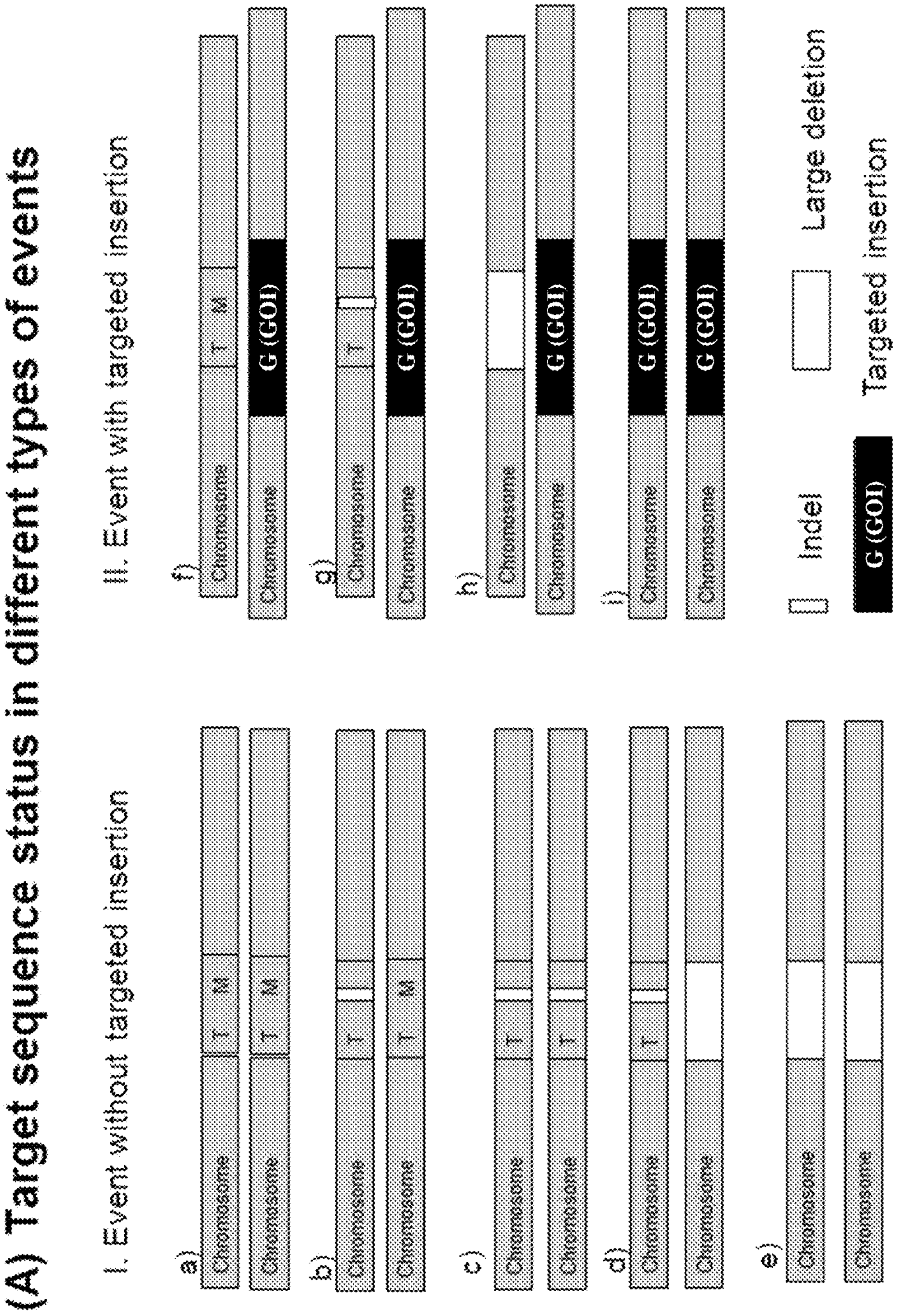

Example 11. High Throughput Assays and Strategies for Enriching Plants with Potential Targeted Insertion at Desirable Genomic Loci For identifying potential transgenic events containing targeted insertion at the MIR604 insertion site safe harbor locus, we developed a high throughput approach of enriching for potential mutations. The method involves the use of one assay (Assay T in FIG. 8A) to identify a plant that has a reduction in the copy number of the target sequence (Target T). The fluorescent probe for assay target T is located away from the fluorescent probe of assay target M (FIG. 8A) which detects the copy number of the site-directed nuclease cleavage site M (also in FIG. 6) by at least 5 nucleotides in the region of the target locus. It should be noted that assay T probe can sit within the same amplicon as assay M probe. However, it should be as far away from M as possible as long as it is still within the region replaced by targeted insertion of transgenic sequences (as shown in FIG. 8A, region containing gene of interest (GOI). Since targeted insertion usually replaces certain sequences at the target locus other than the nuclease cleavage site (M), whereas non-targeted events that are mostly likely modified at the nuclease cleavage site by NHEJ usually would have smaller target site deletions. If a plant has reduced copy number at the nuclease cleavage site (Target M), but not having a reduced copy number call (i.e., wild type) at target region further away (Target T), this plant is very likely to have only small deletion and no targeted insertion at the target locus (Event types a, b and c in FIG. 8A and FIG. 8B) and can be discarded irrespective of the Target M or Target G copy number call. Events can be further enriched by looking at the Assay G results. Any plants negative for GOI (Assay G), i.e., event types d and e in FIG. 8A without transgene can be further discarded. The rest of the plants, i.e., event types from d to i in FIG. 8B with positive GOI signal are chosen as candidate plants with potential targeted insertion at the target locus and these events are characterized further by PCR reactions specific for recombination junctions as shown in FIG. 2.

Example 12. Use of High Throughput qPCR Assays for Enrichment of Candidate Transgenic Events with Targeted Insertion at the Genomic Safe Harbor Locus MIR604 Insertion Site Results of copy number call of different target sequences were obtained using target-specific Assay 1 (Table 7, corresponding to assay T in FIG. 8), Assay 2 for nuclease cleavage site (Table 7, corresponding to target M in FIG. 8) and other transgene sequences (Assays 3 to 7 in Table 7, corresponding to assay G in FIG. 8) from maize plants regenerated from immature embryos treated with engineered TALEN as described previously in Example 5.

Table 7 shows assay results of some representative maize plants obtained from targeting experiments with co-delivery of the TALE nuclease expression vector 21321 and donor vector 21942. In this experiment, Assay 1 which is corresponding to the assay T of FIG. 8 has a Taqman probe sequence of 5'-CTCGT TGCCA AAGCT GCATC CGT-3' (SEQ ID NO:97) which is located 18 bases away from the nuclease cleavage site (SEQ ID NO:67, 5'-TGCAT CCGTG CAGTG CAGTG CAGTG CA/GGA CAGGA CCTCC TTTGT TTAGG A-3' where "/" indicates potential cleavage position). All plants that have "Med" copy number call for target (Assay 1) can be discarded irrespective of other assay results since there is no homologous recombination-mediated replacement of the target sequences (SEQ ID NO:67). In some events (MZET130501A012A and MZET130501B033A) Assay 1 has higher copy number call than Assay 2, it means that the deletion around the nuclease cleavage site is relatively small at the target region. By using results from other assays (Assay 3 to Assay 7), further enrichment can be obtained by discarding plants that do not have genes of interest (GOI). If high quality targeted insertion events are desired, any plants positive for nuclease expression vector (Assay 6), and/or vector backbone (Assay 7), and having more than one copy of the donor vector (Assay 3 to 5) can be discarded. By using this enrichment method, only a subset of the total transgenic plants from a targeted insertion experiment will need to be analyzed further by other assays such as junction PCR (FIG. 2 and FIG. 3) and DNA blot analysis (FIG. 5) to identify truly targeted insertion events. For example, events MZET131500A118A and MZET131500A128A (FIG. 5) were identified by following the above enrichment process from a set of 334 plants in targeted insertion experiment MZET131500A.

TABLE 7

Taqman assays of transgenic events and use of assay results to enrich for potential targeted insertion events from regenerated maize plants derived from a Biolistic transformation experiment using qPCR Taqman assays.

| Plant ID | Assay 1 MIR604 Fw2/Rv2 insertion site | Assay 2 Mir604 JHAX Fw2/Rv2_MGB | Assay 3 prCMP-04 | Assay 4 cPMI-09 | Assay 5 cWrangr-01 | Assay 6 cTNmir604Fw2-03 | Assay 7 xprLacZ-01-01 | Note |
|---|---|---|---|---|---|---|---|---|
| MZET130402A039A | Med | Med | 0 | 0 | 0 | 0 | 0 | Discard#* |
| MZET130402A040A | 0 | 0 | High | Med | High | 0 | 0 | Keep& |
| MZET130402A055A | Med | Med | Low | Low | Low | Low | 0 | Discard# |
| MZET130402A056A | Med | Med | 0 | 0 | 0 | 0 | 0 | Discard#* |
| MZET130501A012A | Low | 0 | 0 | 0 | 0 | 0 | 0 | Discard* |
| MZET130501A013A | Med | Med | 0 | 0 | 0 | 0 | 0 | Discard#* |
| MZET130501B031A | Low | Low | 0 | 0 | 0 | 0 | 0 | Discard* |
| MZET130501B032A | 0 | 0 | Low | Low | Low | 0 | 0 | Keep& |
| MZET130501B033A | Low | 0 | High | High | High | 0 | 0 | Keep& |
| MZET130501B034A | Med | Med | Low | Low | Low | 0 | 0 | Discard#* |
| MZET130501B050A | Low | Low | Low | Low | Med | 0 | 0 | Keep& |
| MZET130501B061A | Med | Med | 0 | 0 | 0 | 0 | 0 | Discard#* |
| MZET130501B062A | 0 | 0 | Low | Low | Med | 0 | 0 | Keep& |
| MZET130501B063A | Med | Med | 0 | 0 | 0 | 0 | 0 | Discard* |
| MZET130501B064A | 0 | 0 | Low | Low | Low | 0 | 0 | Keep& |
| MZET130501B065A | Med | Med | Low | Low | Low | 0 | 0 | Discard# |
| MZET130501B066A | Med | Med | 0 | 0 | 0 | 0 | 0 | Discard# |
| MZET130501B135A | 0 | 0 | Low | Low | Med | Low | 0 | Keep& |
| MZET130501B136A | Med | Med | 0 | 0 | 0 | 0 | 0 | Discard* |
| MZET130704B006A | Med | Med | 0 | 0 | 0 | 0 | 0 | Discard* |
| MZET130704B007A | 0 | 0 | High | High | High | 0 | 0 | Keep& |
| MZET130704B008A | 0 | 0 | Low | Low | Low | 0 | 0 | Keep& |
| MZET130704B009A | Med | Med | 0 | Med | Med | 0 | 0 | Discard#* |
| MZET130704B030A | 0 | 0 | 0 | Low | Low | 0 | 0 | Discard* |
| MZET130704B031A | Med | Med | 0 | 0 | 0 | 0 | 0 | Discard# |

TABLE 7-continued

Taqman assays of transgenic events and use of assay results to enrich for potential targeted insertion events from regenerated maize plants derived from a Biolistic transformation experiment using qPCR Taqman assays.

| Plant ID | Assay 1 MIR604 Fw2/Rv2 insertion site | Assay 2 Mir604 JHAX Fw2/Rv2_MGB | Assay 3 prCMP-04 | Assay 4 cPMI-09 | Assay 5 cWrangr-01 | Assay 6 cTNmir604Fw2-03 | Assay 7 xprLacZ-01-01 | Note |
|---|---|---|---|---|---|---|---|---|
| MZET130704B032A | Med | Med | 0 | 0 | 0 | 0 | 0 | Discard# |
| MZET130704B033A | 0 | 0 | Low | Low | Low | 0 | 0 | Keep& |
| MZET130704B036A | Med | Med | 0 | Low | 0 | 0 | 0 | Discard# |
| Assay purpose | Target region status | Nuclease cleavage site | Donor vector GOI cassette 1 | Donor vector GOI cassette 2 | Donor vector GOI cassette 3 | Nuclease expression vector | Vector backbone | |

#For no target change;
*For no (intact) GOI insertion;
&For further junction PCR assays to identify targeted insertion events

Example 13 Targeted Gene Stacking and Replacement of Transgene Sequences at the MIR604 Transgene Locus

Example 13.1 T-DNA Insert Sequences of Maize Commercial Event MIR604

Maize event MIR604 contains a single copy insertion of pNOV2130 T-DNA in a maize genome. The T-DNA insertion and its flanking genomic sequences were cloned and shown FIG. 9. The PMI marker gene sequence (cPMI-01, Seq. ID No. 98) is present in the transgene T-DNA insert located next to the flanking maize genomic region MIR604LBFS1.

Example 13.2 Selection of TALEN Target Site Sequences in MIR604 Event Transgene Locus In order to stack additional trait gene cassettes to the MIR604 transgene locus, we concentrated our effort on the unique regions of the transgene. The PMI gene (cPMI-01, SEQ ID No. 98) is a desirable target since it is a selectable marker gene and is no longer needed after transgenic plant generation is completed. A new selectable marker gene cassette can be used to replace the PMI cassette using MIR604_RBFS1 or the mCry3A gene expression cassette and MIR604_LBFS1 as regions of homology. We have chosen 3 target sequences (Seq. ID No. 99 to 101) in the PMI gene to design and assemble TALENs for demonstrating feasibility of gene insertion into the MIR604 transgenic locus. PMI_Target_Sequence #1 contains the following sequences, 5'-TTAAC TCAGT GCAAA ACTAT GCCTG GGGCA GCAAA ACGGC GTTGA CTGAA-3' (SEQ ID No.99), PMI_Target_Sequence #2 has the following sequences, 5'-TCTCC ATTCA GGTTC ATCCA AACAA ACACA ATTCT GAAAT CGGTT TTGCC AAA-3', SEQ ID No. 100) and PMI_Target_Sequence #3 contains the following sequences, 5'-TGCAC ATCCG GCGAT TGCTC ACTTT TTACA ACAGC CTGAT GCCGA ACGTT TAA-3' (SEQ ID No. 101).

Example 13.3 Design and Assembly of TALEN Fusion Nuclease Genes Against the PMI Gene Sequences TALENs were designed for targeted cleavage of PMI transgene at sequence targets #1 and #3 (SEQ ID No. 99 and 101). For example, a pair of TALENs for cleaving PMI target sequence #1 (SEQ ID No. 99) were designed for TsPMIFW1 (5'-TTA ACT CAG TGC AAA ACT-3', SEQ ID No.102) and TsPMIRV1 (5'-TTC ACT CAA CGC CGT TTT-3', SEQ ID No.103). TALEN molecule TLN_PMIFW1a (SEQ ID No. 108) was designed to bind the TsPMIFW1 sequence target (5'-TTA ACT CAG TGC AAA ACT-3', SEQ ID No. 102) and TALEN molecule TLN_PMIRV1a (5'-TTC AGT CAA CGC CGT TTT-3', SEQ ID No.109) was designed to recognize TsPMIRV1 sequence target (SEQ ID No. 103). Similarly, another pair of TALENs was designed against TsPMIFW3 (5'-TGC ACA TCC GGC GAT TGC T-3', SEQ ID No.106) and TsPMIRV3 (5'-TTA AAC GTT CGG CAT CAG-3', SEQ ID No.107) for cleavage of PMI Target Sequence #3 (SEQ ID No. 101). TALEN molecule TLN_PMIFW3 (SEQ ID No.110) was designed to bind the TsPMIFW3 sequence (5'-TGC ACA TCC GGC GAT TGC T-3', SEQ ID No. 106) and TALEN molecule TLN_PMIRV3 (SEQ ID No.111) was designed to bind the TsPMIRV3 sequence (5'-TTA AAC GTT CGG CAT CAG-3', SEQ ID No. 107). The protein coding sequences of designed TALEN proteins TLN_PMIFW1a (SEQ ID No. 108), TLN_PMIRV1a (SEQ ID No. 109), TLN_PMIFW3 (SEQ ID No.110) and TLN_PMIRV3 (SEQ ID No.111) were back-translated into DNA sequences. DNA molecules encoding these TALENs were assembled as described in previous examples. The TALEN gene DNA sequences cTNPMIFW1a (SEQ ID No. 112), cTNPMIRV1a (SEQ ID No. 113), cTNPMIFW3-02 (SEQ ID No. 114) and cTNPMIRV3-02 (SEQ ID No.115) encode TLN_PMIFW1a (SEQ ID No.108), TLN_PMIRV1a (SEQ ID No. 109), TLN_PMIFW3 (SEQ ID No.110) and TLN_PMIRV3 (SEQ ID No.111), respectively.

Example 13.4 TALEN Expression Vector and Targeting Donor Vector Construction DNA sequences, cTNPMIFW3-02 (SEQ ID No. 114) and cTNPMIRV3-02 (SEQ ID No. 115) were introduced into expression cassettes, each driven by a constitutive promoter. The two TALEN gene expression cassettes were then introduced into a binary vector backbone to form binary vector 22840. Donor vector 22842 comprises the donor nucleic acid sequence, which comprises an insecticidal gene expression cassette and a glyphosate tolerance gene cassette between two homology sequences (xMIR604-01 and xMIR604-02). The glyphosate tolerance gene cassette comprises the gene ZmEPSPS, whose presence can be used to identify a successful insertion of the donor nucleic acid sequence. The two homology sequences (xMIR604-01 and xMIR604-02) are identical to sequences flanking the TALEN target sequence, i.e. PMI_Target_Sequence #3 (SEQ ID No. 101). Targeted insertion of donor sequences from vector 22872 via homologous recombination into the MIR604 transgenic locus mediated by TALEN cleavage is illustrated in FIG. 10.

Example 13.5 Stacking of Additional Trait Genes into a Transgenic Locus of a Commercial Event (MIR604) and Inactivation of an Unneeded Transgene Maize MIR604 event is widely cultivated for controlling Western corn rootworm (WCR) (Que et al., 2010, *GM Crops.* 1, 220-229). MIR604 transgene contains a PMI selectable marker gene for the generation of the transgenic event (FIG. 9). PMI gene doesn't offer any agronomic benefit and is no longer needed after event generation. However, it can be used as a landing pad for insertion of other trait gene cassettes into the MIR604 locus. To demonstrate such utility, MIR604 transgene locus was introgressed into an elite corn transformation line (NP2222) to form a new transgene receptor line NP2222DW. Line NP2222DW was used as transformation host for generation of targeted insertion events through site-directed nuclease mediated insertion into the PMI gene via homologous recombination. Immature embryos derived from selfed or sib-crossed NP2222DW plants were co-infected with recA-minus *Agrobacterium* strain LBA4404 (carrying helper plasmid pVGW7) containing binary vector 22840 (comprising TALEN expression cassettes) or 22872 (comprising donor nucleic acid sequence, which comprises two expression cassettes). Generation of transgenic events from infected immature embryos was as described except glyphosate was used as selection (Negrotto et al. (2000), *Plant Cell Rep.* 19, 798-803). Calli derived from infected immature embryos were selected on 2 mM of glyphosate. Plants were regenerated on media containing 0.2 mM glyphosate. Glyphosate selected plants were sampled determining for transgene copy number and target site cleavage with Taqman assays.

Figure 10:
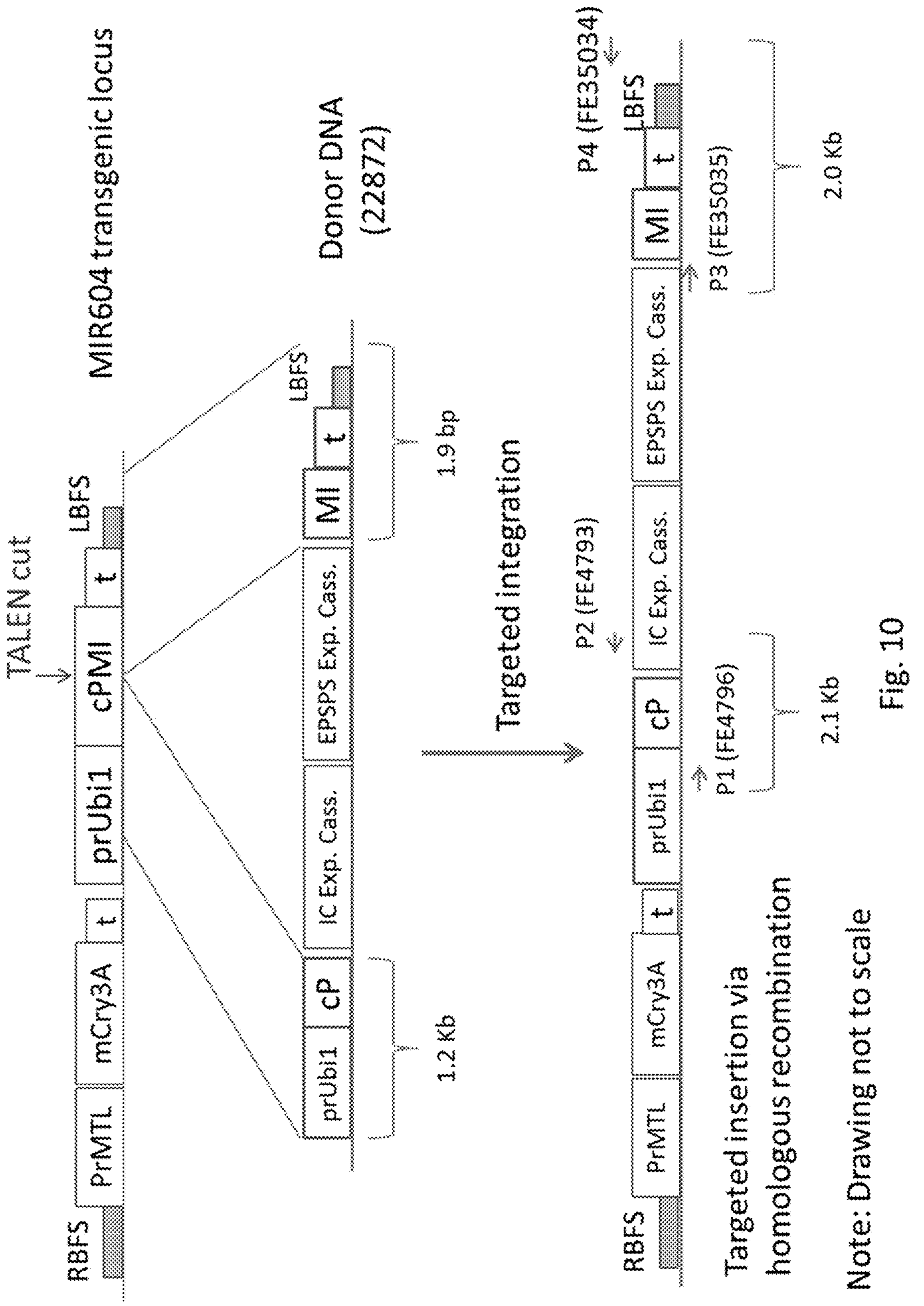
FIG. 10. Targeted insertion of an insecticidal gene (IC) expression cassette (Exp. Cass.) and an expression cassette comprising the selectable marker ZmEPSPS (EPSPS Exp. Cass.) from donor vector 22872 the into MIR604 transgene locus (FIG. 9) mediated by TALENs expressed from vector 22840. A pair of TALENs is expressed from 22840 and cleaves the cPMI target sequence. t: tNOS-05; LBFS: maize genomic sequences flanking the T-DNA Left Border; RBFS: maize genomic sequences flanking the T-DNA Right Border; P1(FE4796): SEQ ID NO: 127; P2 (FE4793): SEQ ID NO: 128; P3 (FE35035): SEQ ID NO: 132; P4 (14E35034): SEQ ID NO: 131.

Plants with target sequence cleavage were further analyzed by PCR for targeted integration with primers spanning across recombination junctions (FIG. 10). For example, for amplification of recombination junction involving xMIR604-02, the primer pair (P1/P2), FE4796 (SEQ ID NO: 127)/FE4793 (SEQ ID NO: 128) was used and the reaction would produce a PCR product of 2.13 Kb if recombination occurred. Another primer pair, 14E35036 (SEQ ID NO: 129')/FE35037 (SEQ ID NO: 130) with a product of 2.5 kb was also used for identification of potential targeted recombinants involving homology region of xMIR604-02. For amplification of recombination junction involving xMIR604-01, a pair of primers (P3/P4), FE35034 (SEQ ID NO: 131)/FE35035 (SEQ ID NO: 132) was used and the PCR reaction is expected to produce a product of 2 Kb if there is homologous recombination. Table 8 shows several experiments of targeted insertion that targeted events were recovered using glyphosate selection ("ZmEPSPS positive events"). These experiments demonstrated DNA sequences containing additional trait genes can be efficiently inserted into the existing commercial event MIR604 locus through homologous recombination mediated by TALEN. It should be pointed out that other site-directed nucleases including engineered meganuclease, zinc finger nuclease or CRISPR-Cas9 can be used to substitute for TALEN in the above mentioned vector 22840 for cleaving the PMI gene sequences to mediate targeted insertion. Similarly, other methods of gene delivery including biolistic particle bombardment, whisker-mediated transformation, electroporation and PEG-mediated protoplast transformation can be used to introduce the site-directed nuclease expression vector and donor DNA molecules.

TABLE 8

Targeted insertion of expression cassettes flanked by homologous sequences in donor vector 22872 into MIR604 transgenic locus mediated by TALEN expressed from vector 22840 delivered by *Agrobacterium* infection

| Experiment | Target Sequence | Nuclease vector ID | Donor vector ID | Total explants | ZmEPSPS positive events | Events with cPMI-01 target site mutations* | No. of targeted events** |
|---|---|---|---|---|---|---|---|
| MZET144515 | cPMI-01 | 22840 | 22872 | 1682 | 53 | 10 | 2 |
| MZET151723 | cPMI-01 | 22840 | 22872 | 2676 | 252 | ND | 9 |
| MZET151818 | cPMI-01 | 22840 | 22872 | 4500 | 307 | ND | 4 |
| MZET152212 | cPMI-01 | 22840 | 22872 | 3680 | 628 | 236 | 8 |
| MZET152311 | cPMI-01 | 22840 | 22872 | 4150 | 808 | 277 | 12 |

*Based on target sequence (cPMI-01) copy number call as determined by qPCR Taqman assay.

**As identified by PCR reactions with primers spanning across recombination junctions (FIG. 10)

Figure 11:
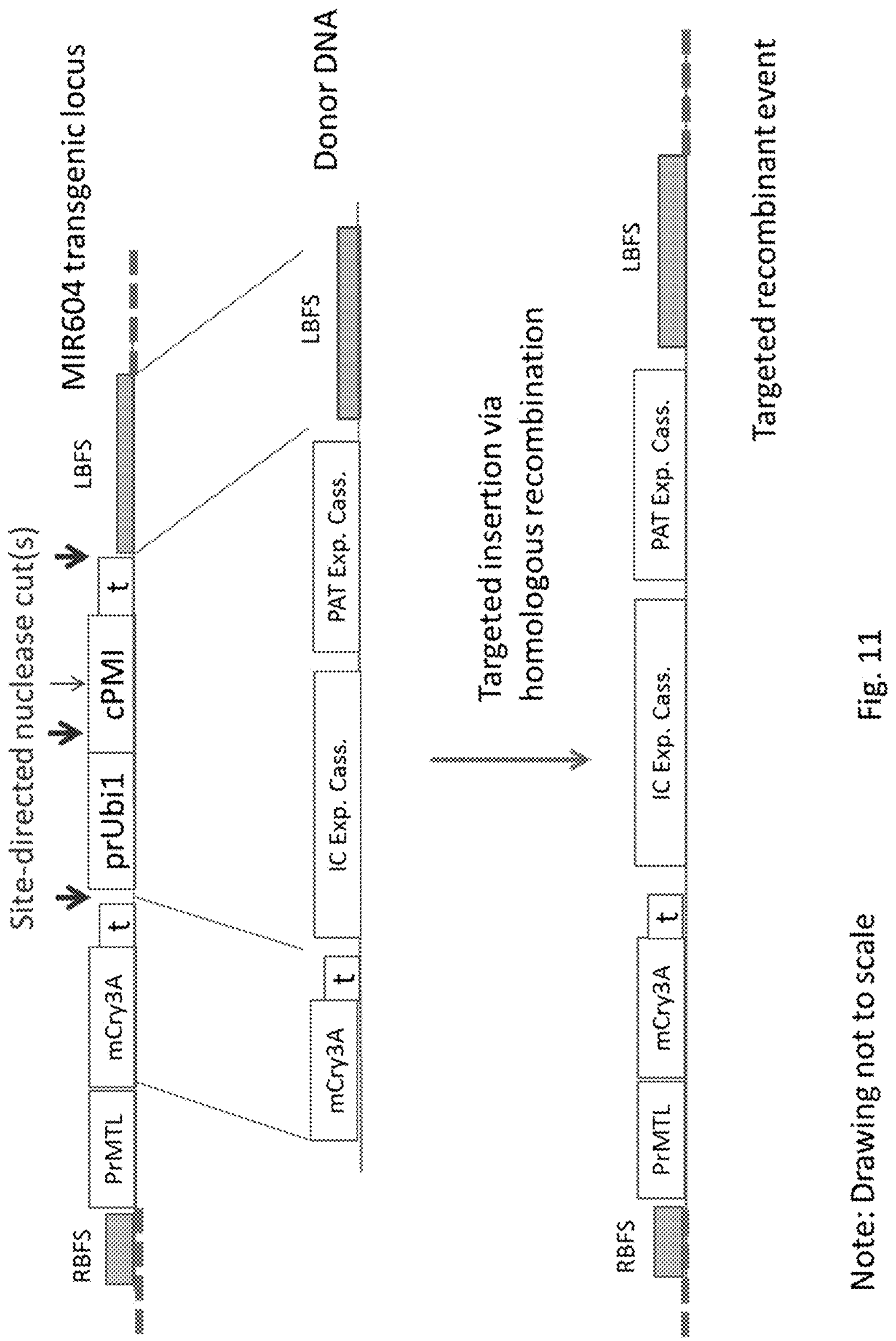
FIG. 11. Targeted insertion of transgene expression cassettes into MIR604 transgene locus (FIG. 9) mediated by site-directed nuclease to replace the whole PMI marker gene cassette.

Example 13.6 Stacking of Additional Trait Genes into MIR604 Transgenic Locus by Replacing the PMI Gene Cassette or the Whole Transgene The genomic region harboring MIR604 transgene is a preferred location for trait gene expression. In addition to inserting additional transgenes into the PMI gene, the whole MIR604 transgene locus can be used as a landing pad for insertion of other trait gene cassettes by replacing part of the transgene sequences or the whole T-DNA insert. Similar to targeted insertion into PMI gene above (Example 13.5), line NP2222DW was used as transformation host for generation of targeted insertion events through site-directed nuclease mediated insertion into the MIR604 locus via homologous recombination. For replacing only the PMI cassette, the mCry3A gene and the LBFS region were used as homology sequences in the donor vector (FIG. 11). The same TALEN expression vector (22840) can be delivered into the NP2222DW maize cells along with the donor containing an insecticidal (IC) expression cassette and a selectable marker (such as PMI, ZmEPSPS, or PAT) expression cassettes (FIG. 11). Furthermore, one or more site-directed nucleases can be used to introduce chromosomal breaks in the PMI cassette sequences. For example, two or more single-guide RNAs (sgRNAs) can be used in conjunction with the Cas9 protein to cleave PMI cassette sequence simultaneously to remove the whole PMI expression cassette (FIG. 11). Immature embryos are placed on callus induction media and then calli are selected on bialaphos-containing media. Generation of transgenic events from infected immature embryos, is, for example, as described above for mannose or glyphosate, where bialaphos may also be used as selection agent. Selected plants are sampled for transgene copy number and target site cleavage with Taqman assays. Plants with target sequence cleavage are further analyzed by PCR for targeted integration with primers spanning across the recombination junctions (FIG. 11).

Figure 12:
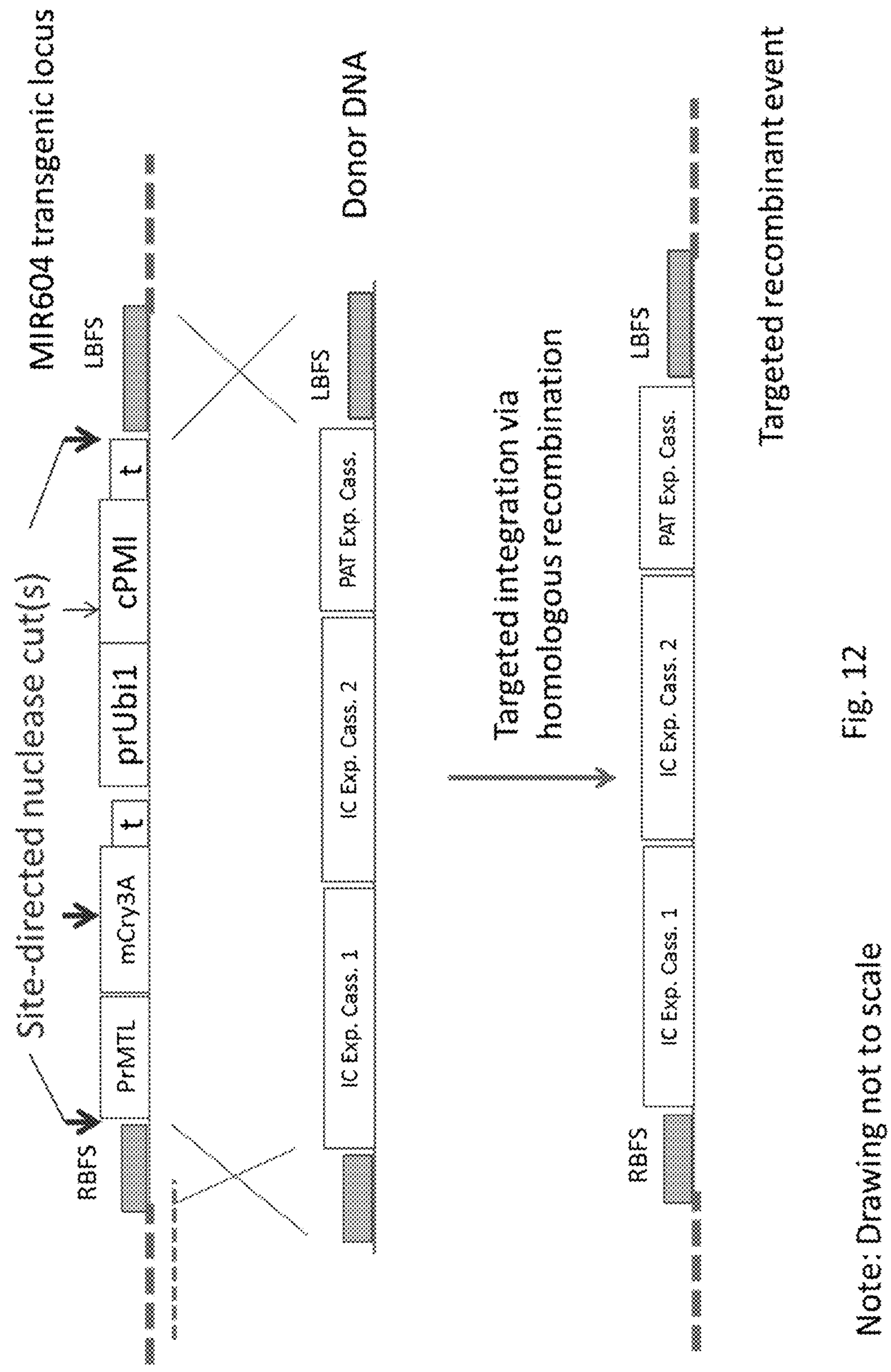
FIG. 12. Targeted insertion of the donor transgene expression cassettes into MIR604 transgene locus (FIG. 9) mediated by site-directed nuclease to replace the whole MIR604 T-DNA insert.

For replacing the whole MIR604 T-DNA insert, both RBFS and LBFS are inserted into the donor molecule to serve as homology sequences to mediate insertion of novel trait gene cassettes (for example, insecticidal (IC) gene expression cassettes 1, 2, and a selectable marker (PAT, for example) expression cassette as the third cassette via homologous recombination (FIG. 12). Immature embryos isolated from selfed or sib-crossed NP2222DW ears are co-infected with recA-minus *Agrobacterium* strain LBA4404 (carrying helper plasmid pVGW7) containing binary vector 22840 and the donor DNA vector comprising IC expression cassettes 1, 2, and the PAT expression cassette. Similarly, more than one site-directed nuclease can be used simultaneously to cleave more than one MIR604 transgene sequence. For example, two or more single-guide RNAs (sgRNAs) can be used in conjunction with the Cas9 protein to cleave T-DNA sequence within the MIR604 transgene (for example, LB- and RB-proximal sequences and/or PMI and mCry3A cassettes) simultaneously to remove at least one expression cassette of the MIR604 T-DNA insert (FIG. 12). Infected immature embryos are placed on callus induction media and then calli are selected on bialaphos-containing media. Generation of transgenic events from infected immature embryos, is, for example, as described above for mannose or glyphosate, where bialaphos may also be used as selection agent. Selected plants are sampled for transgene copy number and target site cleavage with Taqman assays. Plants with target sequence cleavage are further analyzed by PCR for targeted integration with primers spanning across the recombination junctions (FIG. 12). It should be obvious to those skilled in the art that other methods of gene delivery including biolistic particle bombardment, whisker-mediated transformation, electroporation and PEG-mediated protoplast transformation can be used to introduce site-directed nuclease expression vector and donor DNA molecules.

Example 14 Targeted Gene Stacking and Replacement of Transgenic Loci Containing a Nonfunctional Selectable Marker Gene

Example 14.1 Design and Assembly of TALENs for Making Chromosomal Breaks in Transgenic Loci Containing a Nonfunctional Selectable Marker Gene It is known in the art that transgene sequences can be inserted into transgenic maize and rice loci containing a truncated non-functional selectable marker gene PMI, by using *Agrobacterium*-mediated transformation and taking advantage of dsDNA breaks created by expression of native meganuclease I-CeuI (U.S. Pat. No. 7,935,862, incorporated by reference herein). However, targeted insertion mediated by native meganucleases is limited by the fact that a previously engineered nuclease cleavage site has to be inserted first in the transgene locus. Here, we want to test if novel designer site-directed nucleases such as TALEN can be designed against randomly chosen sequences within the existing transgenic locus to mediate targeted insertion of additional transgene sequences, to overcome this limitation. To achieve this, two pairs of TALENs were designed against a randomly selected target sequence (5'-ATAGA GATCC TCTAG AGTCG ACCAT GGTGA TCACT GCAGG CATGC AAGCT TGT-3', SEQ ID. No. 116, only the upper strand is shown) within the transgene locus of pNOV5025 transgenic events. Two sequences within this stretch of DNA were chosen as TALEN binding sites, 5'-ATAGA GATCC TCTAG AGT-3' (aka. rPMIFw1, SEQ ID No. 117, only the upper strand is shown) and 5'-ACAAG CTTGC ATGCC TGC-3' (aka. rPMIRv1, SEQ ID No. 118, only the lower strand is shown). One pair of TALENs consists of one full-length TALEN (cTNrPMIFw1-01, SEQ ID No. 119) designed against target sequence rPMIFw15'-ATAGA GATCC TCTAG AGT-3' (SEQ. ID. No.117) and another full-length TALEN (cTNrPMIRv1-01, SEQ ID No. 120) designed against target sequence rPMIRv1 5'-ACAAG CTTGC ATGCC TGC-3' (SEQ ID No.118). The second pair of TALENs consists of one truncated TALEN (cTNrPMIFw1-02, SEQ. ID. No. 121) designed against target sequence rPMIFw1, 5'-ATAGA GATCC TCTAG AGT-3' (SEQ. ID. No. 117) and another truncated TALEN (cTNrPMIRv1-02, SEQ. ID. No. 122) designed against target sequence rPMIRv1, 5'-ACAAG CTTGC ATGCC TGC-3' (SEQ ID No.118).

Example 14.2 Expression and Transformation Vectors of TALENs for Truncated PMI Target Locus Sequences Artificial fusion nuclease DNA sequences were then assembled from library of fragments containing different RVD repeats, promoter and terminator to form TALEN expression cassettes directly after Type IIs enzyme digestion and ligation as described (Cermak et al, 2011, Nucleic Acid Research 39(12):e82; Zhang et al., 2011, *Nature Biotech* 29:149-154). Several expression vectors (21438, 21792 and 21793) for TALENs against truncated PMI target sequences were made. Vector 21438 comprises expression cassettes for TALENs cTNrPMIFw1-01 and cTNrPMIRv1-01. Vector 21792 comprises expression cassettes for TALENS cTNrPMIRv1-01 and cTNrPMIFw1-01. Vector 21793 comprises expression cassettes for TALENs cTNrPMIRv1-02 and cTNrPMIFw1-02. Initially, an existing targeting donor vector pNOV5045 (U.S. Pat. No. 7,935,862) was used for testing targeted insertion. Later, additional targeting donor vectors 21779 and 22173 were also constructed and used for targeted insertion experiments (Table 9). Donor vectors pNOV5025, 21779, and 22713 contain the complementing 5'-region of the PMIintron cassette for restoring the PMI function and also other sequences of interest and regions of homology. Upon cleavage of the chromosomal target sequences by TALENs, donor vector sequence can be integrated into the target site via homologous recombination.

Example 14.3 Targeted Insertion of Transgenes into Transgenic Loci Containing a Nonfunctional Truncated PMI Gene Mediated by TALEN Selectable transgenic loci were generated from target vector pNOV5025 (described in U.S. Pat. No. 7,935,862) using *Agrobacterium*-mediated transformation in maize line NP2222 as described using PPO as selectable marker. To test the effect of TALEN-mediated targeted insertion into these pNOV5025 loci, a donor vector (pNOV5045, 21779 or 22173) was co-delivered into immature maize embryo tissues along with a TALEN expression vector (21438, 21792 or 21793). After gene delivery and tissue recovery, transformed target tissues were placed on culture media containing mannose selection agent to recover events with targeted insertion, i.e. cells with reconstituted functional PMI gene as described (U.S. Pat. No. 7,935,862). Targeted insertion events through homologous recombination should be resistant to mannose. To differentiate truly targeted events from selection escapes, tissues (callus or leaf) from putative mannose resistant events were first analyzed by PCR using primers spanning a targeted insertion junction. The presence of a positive PCR signal suggests TALEN-mediated targeted insertion into the pNOV5025 transgenic loci. Positive events are further analyzed by Southern blot analysis method to confirm that these events have truly targeted insertion as described (U.S. Pat. No. 7,935,862). Table 9 shows the results of several targeted insertion experiments. The results demonstrate that useful trait genes can be inserted reproducibly into predetermined transgene loci by reconstituting a selectable marker gene at a useful frequency using different TALEN expression vectors and targeting donors. Both the full length and truncated version of TALENs can mediate targeted insertion at the transgenic loci.

TABLE 9

Targeted insertion experiments of pNOV5025 transgenic target loci with different donor vectors mediated by TALEN expression

| Target locus | Nuclease vector | Donor | # Experiments | Total explants | Targeted events | Intact LC events |
|---|---|---|---|---|---|---|
| pNOV5025 transgenic loci with truncated PMI, F1 embryos | 21438: FL TALEN | pNOV5045: GUS + tPMI | 8 | 6536 | 0 | 0 |
| pNOV5025 transgenic lines with truncated PMI, F2 embryos | 21438: FL TALEN | 21779: tPMI | 7 | 11521 | 4 | 4 |
| pNOV5025 transgenic lines with truncated PMI, F2 embryos | 21792: FL TALEN | 21779: tPMI | 3 | 8590 | 1 | 1 |
| pNOV5025 transgenic lines with truncated PMI, F2 embryos | 21793; dNC TALEN | 21779: tPMI | 5 | 10180 | 1 | 1 |

Although the foregoing invention has been described in some detail by way of illustration and example for purposes of clarity of understanding, it will be apparent that certain changes and modifications may be practiced with the scope of the present invention.

What is claimed is:

1. A method of integrating a transgene into a genomic nuclease cleavage site in an event MIR604 transgenic maize genome, comprising introducing into an event MIR604 maize cell:

a) a first nucleic acid molecule comprising at least 100 contiguous nucleotides, wherein said at least 100 contiguous nucleotides have at least 90% identity with a target site in a nucleotide sequence comprising SEQ ID NO: 135, and further comprising a transgene; and b) a second nucleic acid molecule comprising a nucleotide sequence encoding a nuclease for site-directed cleavage at a genomic nuclease cleavage site adjacent to a nucleotide sequence with at least 90% identity to a nucleotide sequence comprising SEQ ID NO: 135, that corresponds to the at least 100 contiguous nucleotides of (a), under conditions wherein expression of the second nucleic acid molecule can occur to produce the nuclease and the nuclease can cleave the nucleotide sequence at the genomic nuclease cleavage site, whereby the transgene is integrated at the genomic nuclease target cleavage site in the event MIR604 maize genome.

2. A method of producing a maize plant, plant part, or progeny thereof comprising a transgene integrated into a genomic nuclease cleavage site in an event MIR604 maize genome, comprising regenerating a maize plant from the maize cell produced by the method of claim 1.

3. A maize plant, plant part, or progeny thereof comprising a transgene integrated into a genomic nuclease cleavage site in an event MIR604 maize genome, produced by the method of claim 2.

* * * * *

SEQUENCE LISTING

```
Sequence total quantity: 140
SEQ ID NO: 1            moltype = DNA  length = 1582
FEATURE                 Location/Qualifiers
source                  1..1582
                        mol_type = genomic DNA
                        organism = Zea mays
SEQUENCE: 1
cgagcagtag aaaaaaaaaa caacgccaag agatggcaga gtcaacaacc gatcacagta  60
cgtatcgcat tcacatcaag attttaagaa cgaccccccg gctggccaat ggccactttc  120
ttgcccgtgc ccgacagcgg acacggcgcc atgccctccg cgccgcacga gcgaggtgtc  180
gtgagaaccg gcaaaaaaaa aaaaaaaaat catcccaagt gcgctgaagt gaagtgcctt  240
cccccgcgtt tccttgcccc tggccggtac ccatttggcg ccgattcttt tcttgccccc  300
ccggccggcc gctcgctcgc ctttggattc ttccaaagcc gctgatggga tcgtggcgaa  360
cacacccacc acccgtcttt gcccaaagcg acccggcaca ggccgcgccg gcttcactaa  420
ccactagcgc ttgtactaat aaaatggttt ctagcgtttg ttgctctcct ttttcctttt  480
ttcgccggtt cttcggagcc gtgtggacag cgtccagtcc agcaggcata gggtggtctc  540
ggcggcggcc gtccgacgac gatcgatctc catgagattc cgcgacaggc caggacggaa  600
agctgggccc ttctcaccaa ttcgcgtcgg agccggaaca agattccctc ccccaatcat  660
ttcgacgcgc cctttcttcg ccacccctcg tggccgtgtt tcgcggccct tatctctttc  720
ccgtgacgcg ttcttttgta gcttagcggc cggcacgttg ctaaccaggc tagcttcgtt  780
cgtttttaat ctgcctatcg agaagagaag aaaaattcgt ccatggggcc acggcctctt  840
ctgcaggcat ttggcagaac cagtgaatgg agatggacgg atgctgctca gatacgcagt  900
caaacctgcc ggcgaaatta cggggggagc tggctggctg gctggacgcc agagcacaca  960
tggatgacgc ggcacggcag ctagccgagc aggcgctctg cgcacgcaag tgtcgtgccg  1020
atctcgcacc agcagcatcg cgtcctaaac aaaggaggtc ctgtcctgca ctgcactgca  1080
cggatgcagc tttggcaacg aggtgtgtcg cgcagcgctc ctgcacggat gtagctttgg  1140
attgctggat aatatctcgc gcaagcatcg tatttattta tttaatttat tatttattta  1200
tttattacga cgtccaccgc tgtgcgtgct ccgtttcgga ttataataaa actaatatta  1260
```

-continued

```
aataaaaaaa tcggattaaa ggatgtttcc gaaataaaga tctccaccac aggagcgaaa  1320
gaaaagagaa acgaaatggt gttgcgatta tacggcggct ccgtcgtcgt cggatcgaca  1380
tgtaaaaagt acgtgcacaa aaggcaaagc aaaatcacct catcaaagac caaaagcgga  1440
gcaaagaata gatactaaat ccacatattt ttttttgttc ctgtctacta tgtgctgtgc  1500
ctgtgcgtga agcacgatta gtacgtgtag tcacttgtca tattcttttt agtgtcttgt  1560
cactagtcac atggagtagc aa                                            1582

SEQ ID NO: 2           moltype = DNA  length = 17176
FEATURE                Location/Qualifiers
source                 1..17176
                       mol_type = other DNA
                       organism = Zea mays
SEQUENCE: 2
ccattaaatc gacgaaagca actagatcct gattttgatt acgattacga ttgacgagta  60
tggatcatga ttttattgca tattttatga ttttattgca tattttatta ttttattgtc  120
gatttatgta ctaacttgtt tttgttaaaa taggatgtca aagaaaatga agtctttagc  180
tcgtagtttg cttgggtcga ggaggagctc gaggagcagc tcgaggggtg aggattcagt  240
ttttcagggc acaggttcta ccatgagcag acggagagcg ctggcagaac atttgcctcc  300
acaagatgta agttagttgt taaattacat tatttgagtt acttaatatt gtatgatgta  360
agttatttgt ttcataggat gctgaaattg aggaaccagt ggtagaggat catgcaagag  420
atgatgttga agatgatggt ggagataatg tgggagatga tgctggagac gacgctggtg  480
gggattctgg ggctggggat tctggggctg gtggagattc tgcagctggg tctggaactt  540
ctcgagttaa gagaacgagg aagctgcatt ttgttggacc acctccagag cttccacccg  600
aatctcgggt tgtaataaag cctagtggaa agtgagtgac atatctttgc ttaaatgtta  660
ttgaaagtta tgttttaatt tctacattga tttctgtttg caggacttgg atcgacgact  720
cgttcacagg cacaggacac tacaggcagg tgaacatggt tcttggtaat cttgttcgtc  780
tgcactggcc tggtcttgtg actttgccta ctggcgagtc tgtccccgcc accacttggg  840
agcattatcg ctatggtgtc tgtagaacgt ttggcaacac acaggcacta gtttgggatg  900
cattctgggt atgacttgtt tatactattt tagttattcc atatatgttt gcttttatga  960
taacactatg gtttttgcag aaacggtaca agttgccgga cgatggatca tatgatatga  1020
acgctcgtta cgtgtttgag tttaacgcga acgatgtcgt tgcagatgca atgtactatg  1080
cacgaattca ggctataaag gcatggtaca gagcaaatgc tgatgatcga ccgatgccaa  1140
atacaaaggc cgagtggtca tcaatttact tgacggagga gcaataccta gaggtaaaca  1200
ggttgttgcc tctcatatcg cacaaagcca tgtatttgct tgctttattt aaaaattttg  1260
atgtaggtgt cggtgccgtg gatggccacc cgaccagacg gttatcgggc attgtgcaga  1320
tggtgggctt cccctgactt tcgtgccatt tccgaaagga acaggggaaa ccgtgggact  1380
gagtcgttcc acaactacgg cggtgatggt catgtgcgct tggctaagcg aatggtaagt  1440
cacagtttgt cgtaactttg aatcacatag caaatgtgtc attataactt ttatgtacag  1500
gaagtcaaat ccggccgtac gcccacggat gtggaggtgt atatgcaagg gcatagggcc  1560
ataggggttc tgatcctcag aatcctgatg tgttatgcac tcagacggcc accgaccgtc  1620
tagtgagttt ttgatactct attatgtgtg ttgatattgt ttgcaagggc ataggggtta  1680
tgcacttata tttgatattg tttgcctcca ggcttcgtat gggcaggaga tggttcaacg  1740
ccatggggag gagtacgatt ggaggagcca gccaatcgac cctcagacag catatgctag  1800
cgcaggagga caagctcatg gacggtgaga ttatttgatt tggttttcaa aattgtcatc  1860
atatgcttgc gattcaactg agccatgagt tactatacta agtgcatggt tcactcttgt  1920
aggttgggta tttttgattc tacgattgat tccagagagc tgagacgccg tggacgacaa  1980
tccacatcgt cgtcttcaca gtcgtcccgt tcacgatcag cagcccatga gatagagctt  2040
gcagtgttgc gtcaacaggc agagtaccat caatcagtct tgagggaaca attggagtac  2100
cagaggcaac aatctgaata ccagagacaa caagccgagt accagaagaa gagggacgag  2160
tattatgcaa gcctccaggc ccaaaatcaa gctcttctct cggtaagttg aagtaacatt  2220
ttgtagctta ttttgcaaaa cacttgatgt gtatcttgtt tgttcaacaa tgacttgtat  2280
ataatttgta gcaactagcc caacaagcgg gcgtcccgat gccgacatat gggatgccgc  2340
ctccggactt tgcactgcca atgccaatgt tggcgcctcc acctccacct ccgcctccgc  2400
ctacgtcaca attccctatg gtatgtacac atatgcgtgt gtgacatgtt catagatgtc  2460
ttatgtgttt aaatgaacaa ctgagtggtt actatttcat gtgcttgtgt tatagggatt  2520
tcagacacca cccgcttcag ttgccgcacc tggagatggg tctgggcaag acgacacaac  2580
acattcgtgg gtcaacaacc tattcaacac gcagagtcca gccggaggag gtggctactt  2640
gaaccatcca gacgatggat atgattgatg tgtcgtgatg tttatttatg aaacactttg  2700
caacacttgt ttgtgagaca caatttcagt ttgcaacaac cgtcgaacct atatgttgat  2760
gttaaatttg tgaatgttat tatttatgtg agaatatttg tgattgtgaa tacttattag  2820
aatgtgtata tttgtgattg tgaatgtgaa tgtgtatatg tgcatgaatc tgttttcgtt  2880
ttgtaaatgt cagatttttt aaaaaacaga attttgtgta aattctgtaa tttgttatgt  2940
ccgacggcct agtggtagcc gtcggacata acacatggtt atgtccgacg gcattaacta  3000
ccgtcggaca taagggatgc ttatgtccga cggcctagtg gtagccgtcg gacttaatcc  3060
tgtggggccc acattccgac cggtaaaacg gttgggattt gttatctccg acgggcacac  3120
gcagccgtcg gagatagctt atgtccgacg gctgccgtcg gacattgcac tatttccgac  3180
gagttatctc cgacggctta aagccgtcgg agataaggct ttgccgtcgg aaataatcta  3240
tttccgacgg tttattcctt atgtccgacg gttttggcca tcggacgttt ctccgtttac  3300
tgtagtggaa gggagtgcag tagaagtgca atggcctaat gtccttcacc ataaaaaaaa  3360
caaagttcaa atctttcaga tttatttact cttggagtag catagcatag gtgtacaagg  3420
gaagtgctta taataatggt aacaagatac tcatcctctc atacctgccg tctcactgac  3480
aggaaacggt aggtggcaag ttggtaagct tttcggtttt agccatgtcc gatcccatgt  3540
gtggatcctg tactgtacat cgacatgcga catcttggtt ggcctatctg atctttaatg  3600
tcgccgcgca cagagaggag atccggtctc atgaagtggc tccgcagatt cctcaagggg  3660
ccgaagcccg gcgaaccgag ccgccggcgg ccccaggtgg cggccgggga agaggaggac  3720
gcgctttggc accaacgacc agctagacca aaggtactac tactaccact gtactagtga  3780
ctgagttcct cccttcttct tctacagttc gtctctgtct ctccaaatgg ctctttgatc  3840
tatccaaaca tgccgtttca cagcttcaca tccgattcaa ctcgcatcca ttgcagtgcc  3900
atcttaaact cttagctccg aaaaaggaag ttgctaaaga ctagtacaat atctttcttc  3960
```

-continued

```
gctgtttcca gatcgatcca cctaggaacg agaatgagga actagtggac cgtgccattg  4020
ccgagcctct tgcagaggct gtcaaaccgc ccagaggtag taccgtagat ggacgaatcc  4080
agatacacat tccatgtcag catggtataa atttctctga aaccgtttca tccctgcatc  4140
ccgttgctgt aaattgctgc gccagagaaa acccataggg gagaagacag caacgacgac  4200
gaagatctgg caagagccgt acaggacagt ctgaatatga acccttacac gccttacaac  4260
ccctatccac cctctcaggc ccaacctaga gggcacaggt caaccgctat cacaatcacc  4320
atttactggc accctaagat attctctaac gcgccaaagc agctcaatgc cgtcagtgtc  4380
cgtgctgcag ggtatgcgga ggctgcaagc atgagatagg gcgtggccat tacttgagct  4440
gcatgggcat ttactggcac cctcagtgct tccgctgcag gtcctgcggt caccttatcc  4500
gtgagaccga ggtaattaag ctcttgcatt ttctttcacc gtggaagtgt gttacagtgt  4560
taccagagat gagatcatat ccgttattct tttcgtcgtg ccttccagtt caccttgctg  4620
ggtgcggatt cgtaccacaa gctgtgctac aaggagctgc atcatccaaa atgcgacgtc  4680
tgccttcagt ttgtaaggcc tcgtgtcctc ggaaaacctg agcgatctgc actacagact  4740
gataaactgc gtacgcgtta gcatttctac accgtgccgt ctcgtcagtg taatgagagg  4800
ctcattcttt gtagatgtgt ttctgcagat cccaacgaac gggagtggct tgatagagta  4860
cagagcccac ccgttctggg gccagaagta ttgcccttcg catgagcgcg acaggacgcc  4920
acgttgctgc agctgtgaga aaatggaggt acaggtacag atactagata gaaaatgtgg  4980
tcgcagtccg atcactcgtt ttcaaactag gttgtacatt gcctgatcat attcaagggc  5040
atcacttttc ggttgtgatt gtgcagccaa ggaacacgaa gtacatgtcg ctgggagacg  5100
gacgcggcct gtgcatggaa tgcctgggat ctgcagtgat ggacacgagc gagtgccagc  5160
ctctgtacca ttctatcaga gactactacg aggggatgga catgagactg gaccagcaga  5220
tacccgtgct cttggttgag cggcaagcgc tcaacgaagc catggaaggg gagagtaaag  5280
tgagtgtttc ttctggttct gccccttttt tttgtgtgtg tttctgcaaa acgtacagcc  5340
ttcggaaaca ctaacgctga ccgcatctgc gaaatccagg gcccacgcca catgcctgag  5400
actaggggcc tatgtctgtc cgaggagcgg actgtgagca gtgtaagtgt tcaacaactc  5460
aagctgtggc ggttactgct gggatgctta gcccacaatg cgacagtttc tgctcttctg  5520
actgtgtgtt acttctgcag atacttagga ggcccagaat tggtggaaac aaccggttac  5580
tagacatgag aactcggcca cagaagctga ctaggagatg tgaagttact gcaatacttg  5640
tcctgtatgg cctccccagg tctggcaatt tttttttat ctctggagtc tggaggacat  5700
cacttttttg tacctaccgg attcaaatac tgcggttctt ctcacgttct gtgaccggtg  5760
gtgtcgtcgt ttgtgtcaca acgctattgc aggctactga caggttccat cctcgcccat  5820
gagctgatgc acgggtggct gcgtctcaaa ggtacatccg tatatggatg gatggacaaa  5880
acatttcata cacccattta tcatctttat ttatgaattt tcttggaaag ctctaccgga  5940
tcgtactttt cattcaggtt accgaaacct aaacgcggag gtggaagaag gcatatgcca  6000
ggtcatgtct tacttgtggc tggaatcaga gattcttccg tcatcctcga ggcacgcgca  6060
gccttcatca tcctatccag caacatcatc cgagaaaggt ggaatatctc ataccgggaa  6120
gaagctgggc gagttcttca tgcaccagat tgccaatgac acgtcgacgg cctatggtga  6180
cgggttcaga actgcgtacg ctgccgtcaa caagtatggc cttcgccaaa cactgagcca  6240
tatacgccta acaggaggtt tccctgtata ataagagtga aaaaaacata aaatgtccat  6300
gcatgatcat atcgatatca aaaggttata tacatattgg gatgaagttg gctatggaac  6360
actggatgca tagtgattca atttcggtga cctttgagtt ttcaaagagg taatgtcgga  6420
gtaaatcaga aagtaaaccc gtataaagca tggttgagac gattgtttac tctatagtga  6480
tgcatgctac atgcatggcc aagaagagag caacgggcca taggaccatc gttattaccc  6540
atcgttgtta atcaaattta gggctagata aatagtaaac catctatagg aacatccaga  6600
gtcaatctac tctatgtatc ataccgacca ggggcggatc taggtaaaat aaccattgat  6660
gtcatctcca ttaaattata gtatcatcaa cctatttaag tgctaacaat catacatttt  6720
aatgaagatt attaaaatcc attggtgtca catgacacca caaaaatggc ctagatccgc  6780
ccctgatacc gacaaaccta gaaaaatttg taactgagaa ctgatgacca tacacatgaa  6840
catgaattag gactttcaaa gagtccaatc aaagtaaaca attagactaa gcatgtaaga  6900
tagggtgcca gatgttgtat caggcttttg agcacatgtg caacttgtat gtcgtggaac  6960
gtgacaaccg gtcaaggaat gcgcatgtga cggtgtaaaa tcaatataac aacatgaaga  7020
acaatcataa gtataggttg aaactacaca tgataactag tatatctttc taacaacaat  7080
gattagtaca atatgtaccg tggtaaagtg gtgacaccat tagagatcgc attagaacgg  7140
catggcgctt actttaaaaa atgttagaga agcggttatg gtcaaacaga atattatgtg  7200
aatatgcggg aagatgaaca aatctataac acagaaacga aggaaccaaa taggatcagc  7260
ggagagtaca gtgccaacgc gcgacgaaac gaggaagcca gaaaggcacc gccgcatgcc  7320
cgcaccgcgt gactgtcgaa ggcggccgtg agcgctccga catcgaagga gtttatttca  7380
aaaatgggac gaccaacatt gcgcttttca catttgtttc ctaacgttgc actctttcac  7440
atatggcacc gagacacgca atcttgttga caccgctcgt agtccggtcc gggcagtgag  7500
gtcttacctg tcgtggtttc agaaaccggg gataataaga tttgtgttcg gtaaggacgc  7560
agcgcggact cactctgaat ggtcagagga ctcaatgatg gatctgagac aaggggttat  7620
actggtttag gcttgcgccc tagtccaatg ttgatcatag tattgcttag agcgtgttac  7680
agttgagtgc tcgtatctag aagatggggg ttgtcttgct cttttatagc tcaaggatag  7740
atcttacaat gagacttgta ttctgttggg gtcgagctca gcttcctact tctgggtgac  7800
gtagctcctc cggtatcgtc tgctgggtcg tgcgccatcg tatccctggt atggcgtcgc  7860
gtcttatccg ttcgccgtat gagttcttgt agctattctg atgcaaacgt agtggtgcct  7920
ggtgggtctc gcagagtcgg tttgtggtga ggtttagggg cgtctttagt acaacttcat  7980
cttccatcat tccctatgcg tcaccttcca gcatgcgtag gcgtacgctt cgtacagcgt  8040
attaccgcgt cccttctgga cttctggtat gtaggtcact gtagagaccc aatgctgggt  8100
tgattggtcc caccggtcag cgaggatgct ctctagaatg tatctggcgt cgtgattggc  8160
agaggccttc ggtactgctc ccatggttca gacgtggctt ggtggtgatc tgtctcatcg  8220
tgctgacgtg acttgatagt actaggtcgg ctcttacctc ctatagatgt gctcgctaga  8280
aagtccattg tcatcttgct gggttgctcg gcatgtaggt tgatcggtaa atccgcctcg  8340
tcgagttgct cgataatgtt gctcggcggg cgggtatgta ggtagtccga cctcaccggg  8400
ttgttcggca atcccgcctc gccgagttgc tcggtgaacg ggttggtcgg cagccccacc  8460
tcgccaggtt gtttggcaca cgtgttggtc tgttggtggg tcgtcgagag cccttttggg  8520
ctttttttggg cacccggttt ctggtacccc acaataccca agctagagtt ccacatttgc  8580
ccctaccttc cttcccggct ccggcgacaa gcccaggatc ctggtgtaat ggggcgagga  8640
gaagcagttc ttgacggagg agaccagctc catgatcccc aacaaaatga aggagacaac  8700
```

-continued

```
cgaggcctac ctcggcgtca ccatcaataa cactgttgtc accgtcccag tctatttcaa  8760
tgagtcccag cgccagacta ccaaaaacgt cgccgtcatc tccggccttc accgtcatgc  8820
gcatcatcaa cgagcccacc actgtcgcca tcacctacgg gctcgacaag aaatcgagca  8880
gcaacaacga gaataatgtc gtcatcttcg acctcgacgg cggtaccttt gacgtcgcgc  8940
tccggcggct aaggaccgca ctgccgacga gggcatgagt ggcgccgaga tggaagagaa  9000
gaggagcaca aatggcggtc gtcggcaaag acaaagagaa ctcgagcgtg agtggaggaa  9060
ggggcaaatg tgtaactcca gcttggatat gactccactg accagattac gagcgacatc  9120
aactagattg tgtgtctcag tggctcagtg ccatttttg aggtttgggt gccaatattt  9180
tttcgtagtg gaaggcaccg cgcccatcgg gttttgggag ccaaacgcca aacccgctcg  9240
cctcatattc cgcaacgtac agcggtttca tgggctggtt gaaggcccgg gccgcaaacc  9300
aaccgagtcg ggccgacgcc ctgggagatc cgcacggctg gtctggccca agcaacctgg  9360
tgggttggtg ccaggttaca gcctgggctg atctgtggac ggtggaccat gcaaggttgt  9420
actgggcttg caaggttgta ctgggcctac tggaacagtc atagcccgtg ccgtcgtggt  9480
gaccgtcgta cgcggccgat ctggcagact gggcaggtcg ctgctccgtg ctgtttgtgg  9540
atgcaatgca actatgcaag agtgatcacg gaaaacggac ggagcctgtc tgtcctgttg  9600
cgacgtagta caagcgcctg aacagtgacg ctacgctatg ccacgagcct acgagtggta  9660
ggtagtagta cactggtcag aatccagcag tgcacccacg ccgctgctga ctttgctgat  9720
gagagggagg ggtcgagcga gtctgtgtga aaccgtgaac cccgccgggg ccttcagtac  9780
gtacgatacc acgagcagta gaaaaaacaa cgccaagatg gcagagtcaa caaccgatca  9840
cagtacgtat cgcattcaca tcaagatttt aagaacgacc cccggctggc caatggcagg  9900
ccacttggtt gcccgtgccc gacagaggga cacggcgcca tgccctccgc gccgcacgga  9960
cgaggtgtcg tgagaaccgg caaaaaaaaa aatcatcgca agtgcgctga agtgaagtgc  10020
cttcccccgc gtttccttgc ccctggccgg tacccatttg gcgccgattc ttttcttgcc  10080
ccccggccgg ccgctcgctc gcctttggat tcttccaaag ccgctgatgg gatggtggcg  10140
aacacaccca ccacccgtct ttgcccaaag cgacccggca caggccgcgc cggcttcact  10200
aaccactagc gcttgtacta ataaaatggt ttctagcgtt tgttgctctc ctttttcttt  10260
tttcgccggt tcttcggagc cgtgtggaca ctggacagcg tccagtccag caggcatagg  10320
gtggtctcgg cggcggtcgt ccgacgacga tcgatctcca tgagattccg cgacaggcca  10380
ggacggaaag ctgggccctt ctcaccaatt cgcgtcggag ccggaacaag attccctccc  10440
ccaatcattt cgacgcgccc tttcttcgcc acccctcgtg gccgtgtttc gcggccggcc  10500
cttatctcct tcccgtgacg cgttcttttg tagcttagcg gccggcacgt tgctaaccag  10560
gctagcttcg ttcgttttta atctgcctat cgagaagaga agaaaaattc gtccatgggg  10620
ccacggcctc ttctgcaggc atttggcatg tgaaggaacc cgaaccagtg aatggagatg  10680
gacggatgct gctcagatac gcagtcaaac ctgccggcga aattacgggg ggagctggct  10740
ggctggctgg ctggacgcca gatcacacat ggatgacgcg gcacggcagc tagccgagca  10800
ggcgctctgc gcacgcaagt gtcgtgccga tctcgcacca gcagcatcgc gtcctaaaca  10860
aaggaggtcc tgtcctgcac tgcactgcac tgcacggatg cagctttggc aacgaggtgt  10920
gtcgcgcagc gctcctgcac ggatgtagct ttggattgct ggataatgtc tcgcgcaagc  10980
gtcgtattta tttatttatt tattacagcc tccaccgccg tgcgtgctcc gtttcggatt  11040
ataataaaac taatattaaa taaaaaaatc ggattaaagg atgtttccga aataaagatc  11100
tccaccacag gagcgaaaga aaaaaaaaga gaaacgggct atggagaaat ggtgttgcga  11160
gtatacggcg gctccgtcgt cgtcggatcg acatgtacaa agtaggtgca caaaaggcaa  11220
agcaaaatca cctcatcaaa gaccaaaagc ggagcaaaga atcgatacta aatccacatg  11280
tttttttgt tcctgtctac tacgtgctgt gcctgtgcgt gaagcacgat tagtacgtgt  11340
actcactctt gtcatattct ttttagtgtc ttgtcactag tcacatggag tagcaaccat  11400
ggctggcgat acccgcgata aataaaaaaa agagagaggg agtaatatat tagatactca  11460
cccattataa attataaaat attttagagt ttgaataggt agttcttgta tatttattta  11520
tagaccttca agtttgtccg cctctcgaga gccgaacttt gttgcccatg cttccccggc  11580
tcaggtcatg ccacctcctt caccaagggc acacggaaga tctggtggag cttgtcatca  11640
ccccgcgccc ttcaaacatg tgaggatgcg tcgtcgctgg cactagtagc actcattgta  11700
ggcactacat tgacagtttc ctccagatat gtagtgagga aacacttgaa caacacgttt  11760
gggattacat atgatgtttt gtttgttcat caatgataat tccttcttct tgcttaatga  11820
ttggctctag aaccgataca tggcacattt catcaggaag ggcgcatgca cgaaattaaa  11880
ctgttatcga tgtttcggtt tctaagttga agaaaacaat ggctaacaac tagcccatgt  11940
gagcataacg acaaggccta caaacaaaac ccaagaaata gctaaatcat ggtctggatc  12000
cactctgcta tgatagatca ccttttctaa catagttcat cctcccattt gctctcgctc  12060
acctagtgcc tccatcgctg agatcaatga taagtaccaa gtgtacgatg aatcccattt  12120
gtcatgcgtc ttgcaagaat ggttggtccg cttgcagtgc cggtccagct atggacccag  12180
gggcctatgt cataactcaa gcaagaccat acccccatat gctaccaaga tgccttttaa  12240
gaatcctggt aaaagaaatc ggtggaagac gactcaacga ctatcaggcc ccatttttg  12300
ggaccatgct caaggatttg gctttagcaa aagtagataa cactattttg gggagcttga  12360
tctcaaggac acatgaagga ataaagctat tttagtcaag acgtccttaa ggaacacaat  12420
aagaccctag gtccctaatg actagtgtgt tatatgtttc gagacgctcc tacacctaag  12480
ttcttttagc tatttccatt cacaatgatg gtatatgacc taggtaccaa tgccccacgg  12540
agtttctaac attaagaatg atctaaaaca taaggaccct agagccaggg cactcctggt  12600
attaaaacat ttaaacccta ttgccttagt gctgattttt gtttttgtt tgtaggagga  12660
gaaacgagca cttgttgcct ctcgcgacaa tcttgatagg ctgtaccgtg atgccagtaa  12720
ctccttgacc atcctagaga ggagccaccg cttcaccatg tctgacctag atcatcacca  12780
ccatgagctg caggcgtctc aagatgaagt cttgcaactt ggacgattgt tgtcgactaa  12840
ggattccacc atcaaggatc tgcgcttcta aaaagctcgt cccgcaggag ctagaggcgg  12900
cccagcttgc tattaagact ctaaaggaca actgcaccgt cctgaagacc cagcgcgata  12960
aagctatgga taaagttgtt cgcgctggac ggatcctgat gaggaggcac ggcgttgtgg  13020
tgcctgacga tattgttgtc gatgtcaagg ccgcgcctga tgctacaagt cgtccctctt  13080
tttctgttgc tcctgcgaag gataccgtct gcaaggatgt ttcgatgcag tgatgtcctg  13140
taaaacactt tacttattga gttagtatct ccttggagga tggatgtaat atggattcaa  13200
tgtgcatgcg acaattgtgt tagaactcga atattctacg aacagggtgc cggaaaacgg  13260
ccctagcact ggcaagtaag atgttctctt ttcctgaagt gttttcaatt ttagccggtt  13320
gttatgctat tagggtatag tggtcaccct aaacagcgca aatgcaagta taccgcgttg  13380
gcttaaggtg tgttccgact taagtcagtt gccttgctgg tagggcatag tggtcaccct  13440
```

-continued

```
gagtaaagta agtcagagta tattgcaccg acctaagtcg attgcactac tagcagggta  13500
tagtgatcac cctaagtcaa gtaagcatga gcatatcgca ccgacttagg tcatcaccga  13560
cttaagccga ttgttctgtt agcagggtat aatggtcacc ctaagtcaga taagcatgag  13620
catgtcacac cggcttaagt cgttgccgac ttaagccgat tgctccgtca gcagggtata  13680
gtggtcaccc taataagtca ggtaagcatg agcatatcgc actggcttaa gtcgttgccg  13740
acttaagccg attgctccgt cagtagggta tagtggtcac cctaagtcaa gtaagcgtga  13800
gcatgtcgca ctggcttaag tcgattgctc cgtcagcagg gtataatggt cactttaagt  13860
caagtaagtg tgagcatgtc gcaccagctt aagtcatcgc cgacttaagc tgattgctcc  13920
attagcaggg tatagtggtc accctaagtt aggtaatcgt gctgatttca agtctagccc  13980
aatcaaagtc agttgtaagt caagagtatg aatgcctttg gagaatgaaa actttattga  14040
tgatgaaatt ctcggattta cagagtacaa tgttccttca agaattttga ggccttgcta  14100
aggatagaat tttctgaggt gttctatgtt ccatgagttc ccttctgtgc cgtccatttg  14160
agtaagccgg tatggtcccg gccgagtgac cgcctctaat atgatgaacg atccttccca  14220
cagtggtgat agcttgtgcc gcccttcccc cgttagaatt cggcgaagga ccaagtctcc  14280
cactgcaaag gatcggtgcc gcatagcttt atcatggtag cacctcaagg tctgctggta  14340
cctagccgac tgaattactg tgttcaatag ttcttcttcc agtacatcaa tatcttccag  14400
tctggtcgct tctgcttcag ctatgctttc gaaagttaat cttggtgccc tgaagattag  14460
gtcagcgggc agcactgcct ctaacccata aaccatgaaa aacggggtat ttctatgcag  14520
agctcgactg ggttgagttc tcaggctcta gaccacgtat ggcagctctc tgatccattt  14580
tcctgcaagc ttttcactct tgtcaaatat tttcttcctg agtgcttcta gtatcattcc  14640
gttggttctt tctacctggc cattggctct tgggtgtgct actgatgcat acttaacctg  14700
gaagctccgt tgctcgcaga aatcgagttc agagctggtg aagttggatc ccagatcggt  14760
gatgatgttg tttggtatcc caaacctgaa tattatgtct tgtataaact ccaccacttt  14820
ggctgaggtc aaggaagcaa ttggcttgta ctttatccat tttgtgaatt tgttaatggc  14880
aaccagtaca tgagtatagc ctccctgagc cttcttaaaa ggtccgatca tgtccagccc  14940
acagcatgcg aacggccatg ttacaggaat ggtctgcagc tgctgcgcgg gtaagtgttg  15000
ttgctttgat aggaattggc atgcttcaca cttctggact aactcggcaa catcgttctt  15060
tattgttggc caatagaaac cggatctaaa agccttcccg accagagtcc ttgacgctgc  15120
atgtattcca cactgcccgg cgtggatttc atccaacaat tgtttctcgg tagtcgagtg  15180
aatacatttc atgaggactc ttgctgcacc tctcctgtac agtaagcccc atatgatggt  15240
gtagtgggcc aactgcctcg cgatgcattc cactgcagcc ttgtcatctg gctcttcttc  15300
atttttatat acctgatgat aggctctctc cagtcgttgg ggtccgactc tggttggctc  15360
aaggtattgc acacttccac ctgatccaag atgatgcttg gttgtgatat ttcttggacg  15420
aagatcccag gtggagcctg ggcccgactg gatcccagct tcgacaacgc gtctgctgct  15480
gcgttgcggt ctcgttccac atgatggaac tctaatcctt caaatttgtc ctctagtttt  15540
cgcacaaccg cgcagtattt gcccatggag tcagtcgagc agtcctagtc tttgcttatc  15600
tggattatga ccactagcga atcaccatat accatcagtt tcttgatgcc gagtgataca  15660
acaatgctta aaccatggat cagttcttca tactttgctg cattatttga cgctggaaat  15720
agtagctgga gtgcataatt gtgttgctca cctccaggag caataaagag aatccctgca  15780
cccgctccct atagtttcaa cgagccatca aagtacattt tccacacctc gataacctct  15840
gggctatctg ggacctgatg ttcagtccac tctgatacga agtcaaccag cgcctgagtc  15900
ttgattgccg tgcggggcca gaactctatg ttgtgagctc caagctcaca cgcccacttg  15960
gcgatccttc caatagcttc tttgttgtgg agaatgtccc ctattgggaa tcctatgacc  16020
actatgactt tgtggtcgtc aaagtagtgt cggagtttgc gtgcggttag aagtactgca  16080
tacaacaact tctgtacttg aggatacctt atctttgagg gcccgaggac ttcactgatg  16140
aagtagactg gatgttgcac cgggtacaca tgtccttcct ccacccgctt gactactaac  16200
gtggtgctta ccacgtgagt cgtgctggag atgtataaca tcaaatcttc caccaactga  16260
ttcagcgtag ctcgtcgtgg cggcttgagc actggtggtg tagtcaaaaa attttagttc  16320
ctctagagct tcctgcgcct ctgtggtcca ctgaaacttg tccacctttt tgagcaattt  16380
gtagaaggcc atgccttgct cccctagtct tgatatgaac ctgctcaggg ctgccatgca  16440
tccagtaagc ctctgtacct ttttctatga tcgcaacact tccattctca tgatggcctt  16500
gaccttttcc gggttagctt caatcccttg gtgactgaca atgaatctga gtaacttccc  16560
tgcctgtact ctgaaaacac acttttctgg gttgagcttc caccggtaat gcctcaggct  16620
attgaagact agctgcaaat cttcaatgaa gttttctgtt ttgatcacca catcatcaac  16680
ataggcttcc acccgcttgc cccagtggtc ggctaagcat gtctgaatgg ctctctggta  16740
agttgctccc gtgttcttga ggtcgaatga catgaaggtg taatagaaag ctccaaatgg  16800
ggtgatgaaa gcattcttct cctcatcttc ttttgctaag cagatatgat ggtatctaga  16860
atagcagtct aggaaggaca acatagaaca gccagcggtc gaatcaacca cctgatctat  16920
tctagggagc ccgaagggat ctttggtgtc tcagacctgg gggaccctca accaaatcga  16980
caagtgaatt ttgtgtcgcg tgtccctgcc cagatggatt agtgcaagat gaaacacaag  17040
aggaggggtg aggtttatat tatcttgcac cagggtgctt gcagtagggg atacaatctt  17100
tgcgagagag ggaacggatc ccaggtctct tgagagatct agtgttgtga aggggagttc  17160
gatgtttgag caagcc                                                  17176

SEQ ID NO: 3           moltype = DNA  length = 23
FEATURE                Location/Qualifiers
source                 1..23
                       mol_type = genomic DNA
                       organism = Zea mays
SEQUENCE: 3
agtgcagtgc agtgcaggac agg                                          23

SEQ ID NO: 4           moltype = DNA  length = 23
FEATURE                Location/Qualifiers
source                 1..23
                       mol_type = genomic DNA
                       organism = Zea mays
SEQUENCE: 4
actaatcgtg cttcacgcac agg                                          23
```

```
SEQ ID NO: 5            moltype = DNA  length = 23
FEATURE                 Location/Qualifiers
source                  1..23
                        mol_type = genomic DNA
                        organism = Zea mays
SEQUENCE: 5
aggcacagca cgtagtagac agg                                           23

SEQ ID NO: 6            moltype = DNA  length = 23
FEATURE                 Location/Qualifiers
source                  1..23
                        mol_type = genomic DNA
                        organism = Zea mays
SEQUENCE: 6
acatgtcgat ccgacgacga cgg                                           23

SEQ ID NO: 7            moltype = DNA  length = 23
FEATURE                 Location/Qualifiers
source                  1..23
                        mol_type = genomic DNA
                        organism = Zea mays
SEQUENCE: 7
agttttatta taatccgaaa cgg                                           23

SEQ ID NO: 8            moltype = DNA  length = 23
FEATURE                 Location/Qualifiers
source                  1..23
                        mol_type = genomic DNA
                        organism = Zea mays
SEQUENCE: 8
aatccgaaac ggagcacgca cgg                                           23

SEQ ID NO: 9            moltype = DNA  length = 23
FEATURE                 Location/Qualifiers
source                  1..23
                        mol_type = genomic DNA
                        organism = Zea mays
SEQUENCE: 9
aaacggagca cgcacggcgg tgg                                           23

SEQ ID NO: 10           moltype = DNA  length = 22
FEATURE                 Location/Qualifiers
source                  1..22
                        mol_type = genomic DNA
                        organism = Zea mays
SEQUENCE: 10
ggagcacgca cggcggtgga gg                                            22

SEQ ID NO: 11           moltype = DNA  length = 23
FEATURE                 Location/Qualifiers
source                  1..23
                        mol_type = genomic DNA
                        organism = Zea mays
SEQUENCE: 11
atccaaagct acatccgtgc agg                                           23

SEQ ID NO: 12           moltype = DNA  length = 22
FEATURE                 Location/Qualifiers
source                  1..22
                        mol_type = genomic DNA
                        organism = Zea mays
SEQUENCE: 12
gtgcagtgca gtgcagtgca gg                                            22

SEQ ID NO: 13           moltype = DNA  length = 23
FEATURE                 Location/Qualifiers
source                  1..23
                        mol_type = genomic DNA
                        organism = Zea mays
SEQUENCE: 13
ggacaggacc tcctttgttt agg                                           23

SEQ ID NO: 14           moltype = DNA  length = 23
FEATURE                 Location/Qualifiers
source                  1..23
                        mol_type = genomic DNA
                        organism = Zea mays
SEQUENCE: 14
```

-continued

```
gcgtgcgcag agcgcctgct cgg                                    23

SEQ ID NO: 15          moltype = DNA  length = 22
FEATURE                Location/Qualifiers
source                 1..22
                       mol_type = genomic DNA
                       organism = Zea mays
SEQUENCE: 15
gcgtcatcca tgtgtgatct gg                                     22

SEQ ID NO: 16          moltype = DNA  length = 24
FEATURE                Location/Qualifiers
source                 1..24
                       mol_type = genomic DNA
                       organism = Zea mays
SEQUENCE: 16
gtccatctcc attcactggt tcgg                                   24

SEQ ID NO: 17          moltype = DNA  length = 23
FEATURE                Location/Qualifiers
source                 1..23
                       mol_type = genomic DNA
                       organism = Zea mays
SEQUENCE: 17
aatgcctgca gaagaggccg tgg                                    23

SEQ ID NO: 18          moltype = DNA  length = 24
FEATURE                Location/Qualifiers
source                 1..24
                       mol_type = genomic DNA
                       organism = Zea mays
SEQUENCE: 18
gcggccggca cgttgctaac cagg                                   24

SEQ ID NO: 19          moltype = DNA  length = 23
FEATURE                Location/Qualifiers
source                 1..23
                       mol_type = genomic DNA
                       organism = Zea mays
SEQUENCE: 19
agagaagaaa aattcgtcca tgg                                    23

SEQ ID NO: 20          moltype = DNA  length = 22
FEATURE                Location/Qualifiers
source                 1..22
                       mol_type = genomic DNA
                       organism = Zea mays
SEQUENCE: 20
ggcctcttct gcaggcattt gg                                     22

SEQ ID NO: 21          moltype = DNA  length = 23
FEATURE                Location/Qualifiers
source                 1..23
                       mol_type = genomic DNA
                       organism = Zea mays
SEQUENCE: 21
aaggaacccg aaccagtgaa tgg                                    23

SEQ ID NO: 22          moltype = DNA  length = 21
FEATURE                Location/Qualifiers
source                 1..21
                       mol_type = genomic DNA
                       organism = Zea mays
SEQUENCE: 22
atcggtccta aacaaaggag g                                      21

SEQ ID NO: 23          moltype = DNA  length = 22
FEATURE                Location/Qualifiers
source                 1..22
                       mol_type = genomic DNA
                       organism = Zea mays
SEQUENCE: 23
ggatgcagct ttggcaacga gg                                     22

SEQ ID NO: 24          moltype = DNA  length = 22
FEATURE                Location/Qualifiers
source                 1..22
                       mol_type = genomic DNA
                       organism = Zea mays
```

```
SEQUENCE: 24
gtcgcgcagc gctcctgcac gg                                               22

SEQ ID NO: 25          moltype = DNA  length = 24
FEATURE                Location/Qualifiers
source                 1..24
                       mol_type = genomic DNA
                       organism = Zea mays
SEQUENCE: 25
gctcctgcac ggatgtagct ttgg                                             24

SEQ ID NO: 26          moltype = DNA  length = 22
FEATURE                Location/Qualifiers
source                 1..22
                       mol_type = genomic DNA
                       organism = Zea mays
SEQUENCE: 26
ggatgtagct ttggattgct gg                                               22

SEQ ID NO: 27          moltype = DNA  length = 23
FEATURE                Location/Qualifiers
source                 1..23
                       mol_type = genomic DNA
                       organism = Zea mays
SEQUENCE: 27
aaataaaaaa atcggattaa agg                                              23

SEQ ID NO: 28          moltype = DNA  length = 20
FEATURE                Location/Qualifiers
source                 1..20
                       mol_type = other DNA
                       organism = Zea mays
SEQUENCE: 28
agtgcagtgc agtgcaggac                                                  20

SEQ ID NO: 29          moltype = DNA  length = 4170
FEATURE                Location/Qualifiers
misc_feature           1..4170
                       note = Streptococcus pyogenes, Zea mays
source                 1..4170
                       mol_type = other DNA
                       organism = synthetic construct
SEQUENCE: 29
atggacaaga agtacagcat cggcctggac atcggcacca acagcgtggg ctgggccgtg  60
atcaccgacg agtacaaggt gccgagcaag aagttcaagg tgctgggcaa caccgacagg  120
cacagcatca agaagaacct gatcggcgcc ctgctgttcg acagcggcga gaccgccgag  180
gccaccaggc tgaagaggac cgccaggagg aggtacacca ggaggaagaa caggatctgc  240
tacctgcagg agatcttcag caacgagatg gccaaggtgg acgacagctt cttccacagg  300
ctggaggaga gcttcctggt ggaggaggac aagaagcacg agaggcaccc gatcttcggc  360
aacatcgtgg acgaggtggc ctaccacgag aagtacccga ccatctacca cctgaggaag  420
aagctggtgg acagcaccga caaggccgac ctgaggctga tctacctggc cctggcccac  480
atgatcaagt tcaggggcca cttcctgatc gagggcgacc tgaacccgga caacagcgac  540
gtggacaagc tgttcatcca gctggtgcag acctacaacc agctgttcga ggagaacccg  600
atcaacgcca gcggcgtgga cgccaaggcc atcctgagcg ccaggctgag caagagcagg  660
aggctggaga acctgatcgc ccagctgccg ggcgagaaga agaacggcct gttcggcaac  720
ctgatcgccc tgagcctggg cctgaccccg aacttcaaga gcaacttcga cctggccgag  780
gacgccaagc tgcagctgag caaggacacc tacgacgacg acctggacaa cctgctggcc  840
cagatcggcg accagtacgc cgacctgttc ctggccgcca agaacctgag cgacgccatc  900
ctgctgagcg acatcctgag ggtgaacacc gagatcacca aggccccgct gagcgccagc  960
atgatcaaga ggtacgacga gcaccaccag gacctgaccc tgctgaaggc cctggtgagg  1020
cagcagctgc cggagaagta caaggagatc ttcttcgacc agagcaagaa cggctacgcc  1080
ggctacatcg acggcggcgc cagccaggag gagttctaca agttcatcaa gccgatcctg  1140
gagaagatgg acggcaccga ggagctgctg gtgaagctga acagggagga cctgctgagg  1200
aagcagagga ccttcgacaa cggcagcatc ccgcaccaga tccacctggg cgagctgcac  1260
gccatcctga ggaggcagga ggacttctac ccgttcctga aggacaacag ggagaagatc  1320
gagaagatcc tgaccttccg catcccgtac tacgtgggcc cgctggccag gggcaacagc  1380
aggttcgcct ggatgaccag gaagagcgag gagaccatca ccccgtggaa cttcgaggag  1440
gtggtggaca agggcgccag cgcccagagc ttcatcgaga ggatgaccaa cttcgacaag  1500
aacctgccga acgagaaggt gctgccgaag cacagcctgc tgtacgagta cttcaccgtg  1560
tacaacgagc tgaccaaggt gaagtacgtg accgagggca tgaggaagcc ggccttcctg  1620
agcggcgagc agaagaaggc catcgtggac ctgctgttca agaccaacag gaaggtgacc  1680
gtgaagcagc tgaaggagga ctacttcaag aagatcgagt gcttcgacag cgtggagatc  1740
agcggcgtgg aggacaggtt caacgccagc ctgggcacct accacgacct gctgaagatc  1800
atcaaggaca aggacttcct ggacaacgag gagaacgagg acatcctgga ggacatcgtg  1860
ctgaccctga ccctgttcga ggacagggag atgatcgagg agaggctgaa gacctacgcc  1920
cacctgttcg acgacaaggt gatgaagcag ctgaagagga ggaggtacac cggctggggc  1980
aggctgagca ggaagctgat caacggcatc agggacaagc agagcggcaa gaccatcctg  2040
gacttcctga agagcgacgg cttcgccaac aggaacttca tgcagctgat ccacgacgac  2100
agcctgacct tcaaggagga catccagaag gcccaggtga gcggccaggg cgacagcctg  2160
```

-continued

```
cacgagcaca tcgccaacct ggccggcagc ccggccatca agaagggcat cctgcagacc  2220
gtgaaggtgg tggacgagct ggtgaaggtg atgggcaggc acaagccgga gaacatcgtg  2280
atcgagatgg ccagggagaa ccagaccacc cagaagggcc agaagaacag cagggagagg  2340
atgaagagga tcgaggaggg catcaaggag ctgggcagcc agatcctgaa ggagcacccg  2400
gtggagaaca cccagctgca gaacgagaag ctgtacctgt actacctgca gaacggcagg  2460
gacatgtacg tggaccagga gctggacatc aacaggctga gcgactacga cgtggaccac  2520
atcgtgccgc agagcttcct gaaggacgac agcatcgaca acaaggtgct gaccaggagc  2580
gacaagaaca ggggcaagag cgacaacgtg ccgagcgagg aggtggtgaa gaagatgaaa  2640
aactactgga ggcagctgct gaacgccaag ctgatcaccc agaggaagtt cgacaacctg  2700
accaaggccg agaggggcgg cctgagcgag ctggacaagg ccggcttcat taaaaggcag  2760
ctggtggaga ccaggcagat caccaagcac gtggcccaga tcctggacag caggatgaac  2820
accaagtacg acgagaacga caagctgatc agggaggtga aggtgatcac cctgaagagc  2880
aagctggtga gcgacttcag gaaggacttc cagttctaca aggtgaggga gatcaataat  2940
taccaccacg cccacgacgc ctacctgaac gccgtggtgg gcaccgccct gattaaaaag  3000
tacccgaagc tggagagcga gttcgtgtac ggcgactaca aggtgtacga cgtgaggaag  3060
atgatcgcca agagcgagca ggagatcggc aaggccaccg ccaagtactt cttctacagc  3120
aacatcatga acttcttcaa gaccgagatc accctggcca acggcgagat caggaagagg  3180
ccgctgatcg agaccaacgg cgagaccggc gagatcgtgt gggacaaggg cagggacttc  3240
gccaccgtga ggaaggtgct gtccatgccg caggtgaaca tcgtgaagaa gaccgaggtg  3300
cagaccggcg gcttcagcaa ggagagcatc ctgccgaaga ggaacagcga caagctgatc  3360
gccaggaaga aggactggga cccgaagaag tacggcggct tcgacagccc gaccgtggcc  3420
tacagcgtgc tggtggtggc caaggtggag aagggcaaga gcaagaagct gaagagcgtg  3480
aaggagctgg tgggcatcac catcatggag aggagcagct tcgagaagaa cccagtggac  3540
ttcctggagg ccaagggcta caaggaggtg aagaaggacc tgatcattaa actgccgaag  3600
tacagcctgt tcgagctgga gaacggcagg aagaggatgc tggccagcgc cggcgagctg  3660
cagaagggca acgagctggc cctgccgagc aagtacgtga acttcctgta cctggccagc  3720
cactacgaga agctgaaggg cagcccggag gacaacgagc agaagcagct gttcgtggag  3780
cagcacaagc actacctgga cgagatcatc gagcagatca gcgagttcag caagagggtg  3840
atcctggccg acgccaacct ggacaaggtg ctgagcgcct acaacaagca cagggacaag  3900
ccgatcaggg agcaggccga gaacatcatc cacctgttca ccctgaccaa cctgggcgcc  3960
ccggccgcct tcaagtactt cgacaccacc atcgacagga agaggtacac cagcaccaag  4020
gaggtgctgg acgccaccct gatccaccag agcatcaccg gcctgtacga gaccaggatc  4080
gacctgagcc agctgggcgg cgacagcagc ccgccgaaga agaagaggaa ggtgagctgg  4140
aaggacgcca gcggctggag caggatgtga                                    4170

SEQ ID NO: 30          moltype = AA  length = 1389
FEATURE                Location/Qualifiers
REGION                 1..1389
                       note = Streptococcus pyogenes, Zea mays
source                 1..1389
                       mol_type = protein
                       organism = synthetic construct
SEQUENCE: 30
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELVGITIME RSSFEKNPVD FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDSS PPKKKRKVSW  1380
KDASGWSRM                                                           1389

SEQ ID NO: 31          moltype = DNA  length = 17
FEATURE                Location/Qualifiers
source                 1..17
                       mol_type = other DNA
                       organism = Zea mays
SEQUENCE: 31
gcagtgcagt gcaggac                                                  17

SEQ ID NO: 32          moltype = DNA  length = 18
FEATURE                Location/Qualifiers
source                 1..18
```

```
                        mol_type = other DNA
                        organism = Zea mays
SEQUENCE: 32
tgcagtgcag tgcaggac                                                18

SEQ ID NO: 33           moltype = DNA  length = 19
FEATURE                 Location/Qualifiers
source                  1..19
                        mol_type = other DNA
                        organism = Zea mays
SEQUENCE: 33
gtgcagtgca gtgcaggac                                               19

SEQ ID NO: 34           moltype = DNA  length = 21
FEATURE                 Location/Qualifiers
source                  1..21
                        mol_type = other DNA
                        organism = Zea mays
SEQUENCE: 34
cagtgcagtg cagtgcagga c                                            21

SEQ ID NO: 35           moltype = DNA  length = 85
FEATURE                 Location/Qualifiers
misc_feature            1..85
                        note = Streptococcus pyogenes, Oryzae sativa
source                  1..85
                        mol_type = other DNA
                        organism = synthetic construct
SEQUENCE: 35
gttttagagc tagaaatagc aagttaaaat aaggctagtc cgttatcaac ttgaaaaagt  60
ggcaccgagt cggtgctttt ttttt                                        85

SEQ ID NO: 36           moltype = DNA  length = 105
FEATURE                 Location/Qualifiers
misc_feature            1..105
                        note = Streptococcus pyogenes, Zea mays, Oryza sativa
source                  1..105
                        mol_type = other DNA
                        organism = synthetic construct
SEQUENCE: 36
agtgcagtgc agtgcaggac gttttagagc tagaaatagc aagttaaaat aaggctagtc  60
cgttatcaac ttgaaaaagt ggcaccgagt cggtgctttt ttttt                  105

SEQ ID NO: 37           moltype = DNA  length = 480
FEATURE                 Location/Qualifiers
misc_feature            1..480
                        note = Streptococcus pyogenes, Zea mays, Oryza sativa
source                  1..480
                        mol_type = other DNA
                        organism = synthetic construct
SEQUENCE: 37
gggatcttta aacatacgaa cagatcactt aaagttcttc tgaagcaact taaagttatc  60
aggcatgcat ggatcttgga ggaatcagat gtgcagtcag ggaccatagc acaggacagg  120
cgtcttctac tggtgctacc agcaaatgct ggaagccggg aacactgggt acgttggaaa  180
ccacgtgatg tggagtaaga taaactgtag gagaaaagca tttcgtagtg ggccatgaag  240
cctttcagga catgtattgc agtatgggcc ggcccattac gcaattggac gacaacaaag  300
actagtatta gtaccacctc ggctatccac atagatcaaa gctggtttaa aagagttgtg  360
cagatgatcc gtggcagtgc agtgcagtgc aggacgtttt agagctagaa atagcaagtt  420
aaaataaggc tagtccgtta tcaacttgaa aaagtggcac cgagtcggtg cttttttttt  480

SEQ ID NO: 38           moltype = DNA  length = 1995
FEATURE                 Location/Qualifiers
source                  1..1995
                        mol_type = genomic DNA
                        organism = Zea mays
SEQUENCE: 38
aacgagaata atgtcgtcat cttcgacctc gacggcggta cctttgacgt cgcgctccgg  60
cggctaagga ccgcactgcc gacgagggca tgagtggcgc cgagatggaa gagaagagga  120
gcacaaatgg cggtcgtcgg caaagacaaa gagaactcga gcgtgagtgg aggaaggggc  180
aaatgtgtaa ctccagcttg gatatgactc cactgaccag attacgagcg acatcaacta  240
gattgtgtgt ctcagtggct cagtgccatt ttttgaggtt tgggtgccaa tattttttcg  300
tagtggaagg caccgcgccc atcgggtttt gggagccaaa cgccaaaccc gctcgcctca  360
tattccgcaa cgtacagcgg tttcatgggc tggttgaagg cccgggccgc aaaccaaccg  420
agtcgggccg acgccctggg agatccgcac ggctggtctg gcccaagcaa cctggtgggt  480
tggtgccagg ttacagcctg ggctgatctg tggacggtgg accatgcaag gttgtactgg  540
gcttgcaagg ttgtactggg cctactggaa cagtcatagc ccgtgccgtc gtggtgaccg  600
tcgtacgcgg ccgatctggc agactgggca ggtcgctgct ccgtgctgtt tgtggatgca  660
atgcaactat gcaagagtga tcacggaaaa cggacggagc ctgtctgtcc tgttgcgacg  720
tagtacaagc gcctgaacag tgacgctacg ctatgccacg agcctacgag tggtaggtag  780
```

-continued

```
tagtacactg gtcagaatcc agcagtgcac ccacgccgct gctgactttg ctgatgagag  840
ggaggggtcg agcgagtctg tgtgaaaccg tgaaccccgc cggggccttc agtacgtacg  900
ataccacgag cagtagaaaa aacaacgcca agatggcaga gtcaacaacc gatcacagta  960
cgtatcgcat tcacatcaag attttaagaa cgaccccccgg ctggccaatg gcaggcccact  1020
tggttgcccg tgcccgacag agggacacgg cgccatgccc tccgcgccgc acggacgagg  1080
tgtcgtgaga accggcaaaa aaaaaaatca tcgcaagtgc gctgaagtga agtgccttcc  1140
cccgcgtttc cttgcccctg gccggtaccc atttggcgcc gattcttttc ttgccccccg  1200
gccggccgct cgctcgcctt tggattcttc caaagccgct gatgggatgg tggcgaacac  1260
acccaccacc cgtctttgcc caaagcgacc cggcacaggc cgcgccggct tcactaacca  1320
ctagcgcttg tactaataaa atggtttcta gcgtttgttg ctctcctttt tctttttcg  1380
ccggttcttc ggagccgtgt ggacactgga cagcgtccag tccagcaggc atagggtggt  1440
ctcggcggcg gtcgtccgac gacgatcgat ctccatgaga ttccgcgaca ggccaggacg  1500
gaaagctggg cccttctcac caattcgcgt cggagccgga acaagattcc ctcccccaat  1560
catttcgacg cgcccttct tcgccacccc tcgtggccgt gtttcgcggc cggcccttat  1620
ctccttcccg tgacgcgttc ttttgtagct tagcggccgg cacgttgcta accaggctag  1680
cttcgttcgt ttttaatctg cctatcgaga agagaagaaa aattcgtcca tggggccacg  1740
gcctcttctg caggcatttg gcatgtgaag gaacccgaac cagtgaatgg agatggacgg  1800
atgctgctca gatacgcagt caaacctgcc ggcgaaatta cggggggagc tggctggctg  1860
gctggctgga cgccagatca cacatggatg acgcggcacg gcagctagcc gagcaggcgc  1920
tctgcgcacg caagtgtcgt gccgatctcg caccagcagc atcgcgtcct aaacaaagga  1980
ggtcctgtcc tgcac                                                    1995

SEQ ID NO: 39          moltype = DNA  length = 942
FEATURE                Location/Qualifiers
source                 1..942
                       mol_type = genomic DNA
                       organism = Zea mays
SEQUENCE: 39
gcactgcact gcactgcacg gatgcagctt tggcaacgag gtgtgtcgcg cagcgctcct  60
gcacggatgt agctttggat tgctggataa tgtctcgcgc aagcgtcgta tttatttatt  120
tatttattac agcctccacc gccgtgcgtg ctccgtttcg gattataata aaactaatat  180
taaataaaaa aatcggatta aaggatgttt ccgaaataaa gatctccacc acaggagcga  240
aagaaaaaaa aagagaaacg ggctatggag aaatggtgtt gcgagtatac ggcggctccg  300
tcgtcgtcgg atcgacatgt acaaagtagg tgcacaaaag gcaaagcaaa atcacctcat  360
caaagaccaa aagcggagca aagaatcgat actaaatcca catgtttttt ttgttcctgt  420
ctactacgtg ctgtgcctgt gcgtgaagca cgattagtac gtgtactcac tcttgtcata  480
ttctttttag tgtcttgtca ctagtcacat ggagtagcaa ccatggctgg cgatacccgc  540
gataaataaa aaaaagagag agggagtaat atattagata ctcacccatt ataaattata  600
aaatatttta gagtttgaat aggtagttct tgtatattta tttatagacc ttcaagtttg  660
tccgcctctc gagagccgaa ctttgttgcc catgcttccc cggctcaggt catgccacct  720
ccttcaccaa gggcacacgg aagatctggt ggagcttgtc atcaccccgc gcccttcaaa  780
catgtgagga tgcgtcgtcg ctggcactag tagcactcat tgtaggcact acattgacag  840
tttcctccag atatgtagtg aggaaacact tgaacaacac gtttgggatt acatatgatg  900
ttttgtttgt tcatcaatga taattccttc ttcttgctta at                    942

SEQ ID NO: 40          moltype = DNA  length = 18
FEATURE                Location/Qualifiers
source                 1..18
                       mol_type = genomic DNA
                       organism = Zea mays
SEQUENCE: 40
ttgctactcc atgtgact                                                 18

SEQ ID NO: 41          moltype = DNA  length = 16
FEATURE                Location/Qualifiers
source                 1..16
                       mol_type = genomic DNA
                       organism = Zea mays
SEQUENCE: 41
ttgtcatatt cttttt                                                   16

SEQ ID NO: 42          moltype = DNA  length = 19
FEATURE                Location/Qualifiers
source                 1..19
                       mol_type = genomic DNA
                       organism = Zea mays
SEQUENCE: 42
tacacgtact aatcgtgct                                                19

SEQ ID NO: 43          moltype = DNA  length = 18
FEATURE                Location/Qualifiers
source                 1..18
                       mol_type = genomic DNA
                       organism = Zea mays
SEQUENCE: 43
tcctgtctac tacgtgct                                                 18

SEQ ID NO: 44          moltype = DNA  length = 19
FEATURE                Location/Qualifiers
```

-continued

```
source                  1..19
                        mol_type = genomic DNA
                        organism = Zea mays
SEQUENCE: 44
ttgttcctgt ctactacgt                                                 19

SEQ ID NO: 45           moltype = DNA  length = 20
FEATURE                 Location/Qualifiers
source                  1..20
                        mol_type = genomic DNA
                        organism = Zea mays
SEQUENCE: 45
ttggtctttg atgaggtgat                                                20

SEQ ID NO: 46           moltype = DNA  length = 20
FEATURE                 Location/Qualifiers
source                  1..20
                        mol_type = genomic DNA
                        organism = Zea mays
SEQUENCE: 46
tcgacatgta caaagtaggt                                                20

SEQ ID NO: 47           moltype = DNA  length = 19
FEATURE                 Location/Qualifiers
source                  1..19
                        mol_type = genomic DNA
                        organism = Zea mays
SEQUENCE: 47
ttcggaaaca tcctttaat                                                 19

SEQ ID NO: 48           moltype = DNA  length = 19
FEATURE                 Location/Qualifiers
source                  1..19
                        mol_type = genomic DNA
                        organism = Zea mays
SEQUENCE: 48
ttataataaa actaatatt                                                 19

SEQ ID NO: 49           moltype = DNA  length = 20
FEATURE                 Location/Qualifiers
source                  1..20
                        mol_type = genomic DNA
                        organism = Zea mays
SEQUENCE: 49
taataaataa ataaataaat                                                20

SEQ ID NO: 50           moltype = DNA  length = 19
FEATURE                 Location/Qualifiers
source                  1..19
                        mol_type = genomic DNA
                        organism = Zea mays
SEQUENCE: 50
ttggattgct ggataatgt                                                 19

SEQ ID NO: 51           moltype = DNA  length = 18
FEATURE                 Location/Qualifiers
source                  1..18
                        mol_type = genomic DNA
                        organism = Zea mays
SEQUENCE: 51
tcgttgccaa agctgcat                                                  18

SEQ ID NO: 52           moltype = DNA  length = 19
FEATURE                 Location/Qualifiers
source                  1..19
                        mol_type = genomic DNA
                        organism = Zea mays
SEQUENCE: 52
tcctgtcctg cactgcact                                                 19

SEQ ID NO: 53           moltype = DNA  length = 19
FEATURE                 Location/Qualifiers
source                  1..19
                        mol_type = genomic DNA
                        organism = Zea mays
SEQUENCE: 53
tgcatccgtg cagtgcagt                                                 19

SEQ ID NO: 54           moltype = DNA  length = 17
```

-continued

```
FEATURE                 Location/Qualifiers
source                  1..17
                        mol_type = genomic DNA
                        organism = Zea mays
SEQUENCE: 54
tcctaaacaa aggaggt                                                17

SEQ ID NO: 55           moltype = DNA  length = 17
FEATURE                 Location/Qualifiers
source                  1..17
                        mol_type = genomic DNA
                        organism = Zea mays
SEQUENCE: 55
taggacgcga tgctgct                                                17

SEQ ID NO: 56           moltype = DNA  length = 18
FEATURE                 Location/Qualifiers
source                  1..18
                        mol_type = genomic DNA
                        organism = Zea mays
SEQUENCE: 56
tgcgcacgca agtgtcgt                                               18

SEQ ID NO: 57           moltype = DNA  length = 19
FEATURE                 Location/Qualifiers
source                  1..19
                        mol_type = genomic DNA
                        organism = Zea mays
SEQUENCE: 57
tccatctcca ttcactggt                                              19

SEQ ID NO: 58           moltype = DNA  length = 19
FEATURE                 Location/Qualifiers
source                  1..19
                        mol_type = genomic DNA
                        organism = Zea mays
SEQUENCE: 58
ttctgcaggc atttggcat                                              19

SEQ ID NO: 59           moltype = DNA  length = 18
FEATURE                 Location/Qualifiers
source                  1..18
                        mol_type = genomic DNA
                        organism = Zea mays
SEQUENCE: 59
ttttcttctc ttctcgat                                               18

SEQ ID NO: 60           moltype = DNA  length = 19
FEATURE                 Location/Qualifiers
source                  1..19
                        mol_type = genomic DNA
                        organism = Zea mays
SEQUENCE: 60
taaccaggct agcttcgtt                                              19

SEQ ID NO: 61           moltype = DNA  length = 18
FEATURE                 Location/Qualifiers
source                  1..18
                        mol_type = genomic DNA
                        organism = Zea mays
SEQUENCE: 61
taagctacaa aagaacgc                                               18

SEQ ID NO: 62           moltype = DNA  length = 18
FEATURE                 Location/Qualifiers
source                  1..18
                        mol_type = genomic DNA
                        organism = Zea mays
SEQUENCE: 62
tgtttcgcgg ccggccct                                               18

SEQ ID NO: 63           moltype = DNA  length = 18
FEATURE                 Location/Qualifiers
source                  1..18
                        mol_type = genomic DNA
                        organism = Zea mays
SEQUENCE: 63
tttccgtcct ggcctgtc                                               18
```

-continued

```
SEQ ID NO: 64           moltype = DNA  length = 19
FEATURE                 Location/Qualifiers
source                  1..19
                        mol_type = genomic DNA
                        organism = Zea mays
SEQUENCE: 64
tcgtccgacg acgatcgat                                               19

SEQ ID NO: 65           moltype = DNA  length = 19
FEATURE                 Location/Qualifiers
source                  1..19
                        mol_type = genomic DNA
                        organism = Zea mays
SEQUENCE: 65
tcctaaacaa aggaggtcc                                               19

SEQ ID NO: 66           moltype = DNA  length = 51
FEATURE                 Location/Qualifiers
source                  1..51
                        mol_type = other DNA
                        organism = Zea mays
SEQUENCE: 66
tacacgtact aatcgtgctt cacgcacagg cacagcacgt agtagacagg a           51

SEQ ID NO: 67           moltype = DNA  length = 51
FEATURE                 Location/Qualifiers
source                  1..51
                        mol_type = other DNA
                        organism = Zea mays
SEQUENCE: 67
tgcatccgtg cagtgcagtg cagtgcagga caggacctcc tttgtttagg a           51

SEQ ID NO: 68           moltype = AA  length = 1343
FEATURE                 Location/Qualifiers
REGION                  1..1343
                        note = Xanthomonas spp, Zea mays
source                  1..1343
                        mol_type = protein
                        organism = synthetic construct
SEQUENCE: 68
MASSPPKKKR KVSWKDASGW SRMHADPIRP RRPSPARELL PGPQPDRVQP TADRGVSAPA  60
GSPLDGLPAR RTVSRTRLPS PPAPSPAFSA GSFSDLLRPF DPSLLDTSLL DSMPAVGTPH  120
TAAAPAEWDE MQSALRAADD PPPTVRVAVT AARPPRAKPA PRRRAAQPSD ASPAAQVDLR  180
TLGYSQQQQE KIKPKVRSTV AQHHEALVGH GFTHAHIVAL SQHPAALGTV AVTYQHIITA  240
LPEATHEDIV GVGKQWSGAR ALEALLTDAG ELRGPPLQLD TGQLVKIAKR GGVTAMEAVH  300
ASRNALTGAP LNLTPDQVVA IASNIGGKQA LETVQRLLPV LCQAHGLTPD QVVAIASHDG  360
GKQALETVQR LLPVLCQDHG LTPEQVVAIA SNIGGKQALE TVQRLLPVLC QDHGLTPDQV  420
VAIASHDGGK QALETVQRLL PVLCQAHGLT PDQVVAIASN NGGKQALETV QRLLPVLCQA  480
HGLTPDQVVA IASNGGGKQA LETVQRLLPV LCQAHGLTPE QVVAIASNIG GKQALETVQR  540
LLPVLCQAHG LTPEQVVAIA SHDGGKQALE TVQRLLPVLC QDHGLTPEQV VAIASNGGGK  600
QALETVQRLL PVLCQAHGLT PDQVVAIASN IGGKQALETV QRLLPVLCQA HGLTPDQVVA  660
IASNIGGKQA LETVQRLLPV LCQDHGLTPE QVVAIASNGG GKQALETVQR LLPVLCQDHG  720
LTPDQVVAIA SHDGGKQALE TVQRLLPVLC QAHGLTPDQV VAIASNNGGK QALETVQRLL  780
PVLCQAHGLT PDQVVAIASN GGGKQALETV QRLLPVLCQA HGLTPEQVVA IASNNGGKQA  840
LETVQRLLPV LCQAHGLTPE QVVAIASHDG GKQALETVQR LLPVLCQDHG LTPDQVVAIA  900
SNGGKQALES IVAQLSRPDP ALAALTNDHL VALACLGGRP AMDAVKKGLP HAPELIRRVN  960
RRIGERTSHR VADYAQVVRV LEFFQCHSHP AYAFDEAMTQ FGMSRNGLVQ LFRRVGVTEL  1020
EARGGTLPPA SQRWDRILQA SGMKRAKPSP TSAQTPDQAS LHAFADSLER DLDAPSPMHE  1080
GDQTRASSRK RSRSDRAVTG PSAQQAVEVR VPEQRDALHL PLSWRVKRPR TRIWGGLPDP  1140
GTPTAADQLV KSELEEKKSE LRHKLKYVPH EYIELIEIAR NSTQDRILEM KVMEFFMKVY  1200
GYRGKHLGGS RKPDGAIYTV GSPIDYGVIV DTKAYSGGYN LPIGQADEMQ RYVEENQTRN  1260
KHINPNEWWK VYPSSVTEFK FLFVSGHFKG NYKAQLTRLN HITNCNGAVL SVEELLIGGE  1320
MIKAGTLTLE EVRRKFNNGE INF                                          1343

SEQ ID NO: 69           moltype = AA  length = 1211
FEATURE                 Location/Qualifiers
REGION                  1..1211
                        note = Xanthomonas spp, Zea mays
source                  1..1211
                        mol_type = protein
                        organism = synthetic construct
SEQUENCE: 69
MASSPPKKKR KVSWKDASGW SRMHADPWPR RRAAQPSDAS PAAQVDLRTL GYSQQQQEKI  60
KPKVRSTVAQ HHEALVGHGF THAHIVALSQ HPAALGTVAV TYQHIITALP EATHEDIVGV  120
GKQWSGARAL EALLTDAGEL RGPPLQLDTG QLVKIAKRGG VTAMEAVHAS RNALTGAPLN  180
LTPDQVVAIA SNIGGKQALE TVQRLLPVLC QAHGLTPDQV VAIASHDGGK QALETVQRLL  240
PVLCQDHGLT PEQVVAIASN IGGKQALETV QRLLPVLCQD HGLTPDQVVA IASHDGGKQA  300
LETVQRLLPV LCQAHGLTPD QVVAIASNNG GKQALETVQR LLPVLCQAHG LTPDQVVAIA  360
SNGGGKQALE TVQRLLPVLC QAHGLTPEQV VAIASNIGGK QALETVQRLL PVLCQAHGLT  420
```

-continued

```
PEQVVAIASH DGGKQALETV QRLLPVLCQD HGLTPEQVVA IASNGGGKQA LETVQRLLPV  480
LCQAHGLTPD QVVAIASNIG GKQALETVQR LLPVLCQAHG LTPDQVVAIA SNIGGKQALE  540
TVQRLLPVLC QDHGLTPEQV VAIASNGGGK QALETVQRLL PVLCQDHGLT PDQVVAIASH  600
DGGKQALETV QRLLPVLCQA HGLTPDQVVA IASNNGGKQA LETVQRLLPV LCQAHGLTPD  660
QVVAIASNGG GKQALETVQR LLPVLCQAHG LTPEQVVAIA SNNGGKQALE TVQRLLPVLC  720
QAHGLTPEQV VAIASHDGGK QALETVQRLL PVLCQDHGLT PDQVVAIASN GGKQALESIV  780
AQLSRPDPAL AALTNDHLVA LACLGGRPAM DAVKKGLPHA PELIRRVNRR IGERTSHRVA  840
DYAQVVRVLE FFQCHSHPAY AFDEAMTQFG MSRNGLVQLF RRVGVTELEA RGGTLPPASQ  900
RWDRILQASG MKRAKPSPTS AQTPDQASLH AFADSLERDL DAPSPMHEGD QTRASSRKRS  960
RSDRAVTGPS AQQAVEVRVP EQRDALHLPL SWRVKRPRTR IWGGLPDPGT PTAADQLVKS  1020
ELEEKKSELR HKLKYVPHEY IELIEIARNS TQDRILEMKV MEFFMKVYGY RGKHLGGSRK  1080
PDGAIYTVGS PIDYGVIVDT KAYSGGYNLP IGQADEMQRY VEENQTRNKH INPNEWWKVY  1140
PSSVTEFKFL FVSGHFKGNY KAQLTRLNHI TNCNGAVLSV EELLIGGEMI KAGTLTLEEV  1200
RRKFNNGEIN F                                                       1211

SEQ ID NO: 70          moltype = AA  length = 1037
FEATURE                Location/Qualifiers
REGION                 1..1037
                       note = Xanthomonas spp, Zea mays
source                 1..1037
                       mol_type = protein
                       organism = synthetic construct
SEQUENCE: 70
MASSPPKKKR KVSWKDASGW SRMHADPWPR RRAAQPSDAS PAAQVDLRTL GYSQQQQEKI  60
KPKVRSTVAQ HHEALVGHGF THAHIVALSQ HPAALGTVAV TYQHIITALP EATHEDIVGV  120
GKQWSGARAL EALLTDAGEL RGPPLQLDTG QLVKIAKRGG VTAMEAVHAS RNALTGAPLN  180
LTPDQVVAIA SNIGGKQALE TVQRLLPVLC QAHGLTPDQV VAIASHDGGK QALETVQRLL  240
PVLCQDHGLT PEQVVAIASN IGGKQALETV QRLLPVLCQD HGLTPDQVVA IASHDGGKQA  300
LETVQRLLPV LCQAHGLTPD QVVAIASNNG GKQALETVQR LLPVLCQAHG LTPDQVVAIA  360
SNGGGKQALE TVQRLLPVLC QAHGLTPEQV VAIASNIGGK QALETVQRLL PVLCQAHGLT  420
PEQVVAIASH DGGKQALETV QRLLPVLCQD HGLTPEQVVA IASNGGGKQA LETVQRLLPV  480
LCQAHGLTPD QVVAIASNIG GKQALETVQR LLPVLCQAHG LTPDQVVAIA SNIGGKQALE  540
TVQRLLPVLC QDHGLTPEQV VAIASNGGGK QALETVQRLL PVLCQDHGLT PDQVVAIASH  600
DGGKQALETV QRLLPVLCQA HGLTPDQVVA IASNNGGKQA LETVQRLLPV LCQAHGLTPD  660
QVVAIASNGG GKQALETVQR LLPVLCQAHG LTPEQVVAIA SNNGGKQALE TVQRLLPVLC  720
QAHGLTPEQV VAIASHDGGK QALETVQRLL PVLCQDHGLT PDQVVAIASN GGKQALESIV  780
AQLSRPDPAL AALTNDHLVA LACLGGRPAM DAVKKGLPHA PELIRRVNRR IGERTSHRVA  840
LQLVKSELEE KKSELRHKLK YVPHEYIELI EIARNSTQDR ILEMKVMEFF MKVYGYRGKH  900
LGGSRKPDGA IYTVGSPIDY GVIVDTKAYS GGYNLPIGQA DEMQRYVEEN QTRNKHINPN  960
EWWKVYPSSV TEFKFLFVSG HFKGNYKAQL TRLNHITNCN GAVLSVEELL IGGEMIKAGT  1020
LTLEEVRRKF NNGEINF                                                 1037

SEQ ID NO: 71          moltype = AA  length = 1309
FEATURE                Location/Qualifiers
REGION                 1..1309
                       note = Xanthomonas spp, Zea mays
source                 1..1309
                       mol_type = protein
                       organism = synthetic construct
SEQUENCE: 71
MASSPPKKKR KVSWKDASGW SRMHADPIRP RRPSPARELL PGPQPDRVQP TADRGVSAPA  60
GSPLDGLPAR RTVSRTRLPS PPAPSPAFSA GSFSDLLRPF DPSLLDTSLL DSMPAVGTPH  120
TAAAPAEWDE MQSALRAADD PPPTVRVAVT AARPPRAKPA PRRRAAQPSD ASPAAQVDLR  180
TLGYSQQQQE KIKPKVRSTV AQHHEALVGH GFTHAHIVAL SQHPAALGTV AVTYQHIITA  240
LPEATHEDIV GVGKQWSGAR ALEALLTDAG ELRGPPLQLD TGQLVKIAKR GGVTAMEAVH  300
ASRNALTGAP LNLTPDQVVA IASHDGGKQA LETVQRLLPV LCQAHGLTPD QVVAIASHDG  360
GKQALETVQR LLPVLCQDHG LTPEQVVAIA SNGGGKQALE TVQRLLPVLC QDHGLTPDQV  420
VAIASNNGGK QALETVQRLL PVLCQAHGLT PDQVVAIASN GGGKQALETV QRLLPVLCQA  480
HGLTPDQVVA IASHDGGKQA LETVQRLLPV LCQAHGLTPE QVVAIASNGG GKQALETVQR  540
LLPVLCQAHG LTPEQVVAIA SNIGGKQALE TVQRLLPVLC QDHGLTPEQV VAIASHDGGK  600
QALETVQRLL PVLCQAHGLT PDQVVAIASN GGGKQALETV QRLLPVLCQA HGLTPDQVVA  660
IASNIGGKQA LETVQRLLPV LCQDHGLTPE QVVAIASHDG GKQALETVQR LLPVLCQDHG  720
LTPDQVVAIA SNNGGKQALE TVQRLLPVLC QAHGLTPDQV VAIASNGGGK QALETVQRLL  780
PVLCQAHGLT PDQVVAIASN NGGKQALETV QRLLPVLCQA HGLTPEQVVA IASHDGGKQA  840
LETVQRLLPV LCQDHGLTPD QVVAIASNGG KQALESIVAQ LSRPDPALAA LTNDHLVALA  900
CLGGRPAMDA VKKGLPHAPE LIRRVNRRIG ERTSHRVADY AQVVRVLEFF QCHSHPAYAF  960
DEAMTQFGMS RNGLVQLFRR VGVTELEARG GTLPPASQRW DRILQASGMK RAKPSPTSAQ  1020
TPDQASLHAF ADSLERDLDA PSPMHEGDQT RASSRKRSRS DRAVTGPSAQ QAVEVRVPEQ  1080
RDALHLPLSW RVKRPRTRIW GGLPDPGTPT AADQLVKSEL EEKKSELRHK LKYVPHEYIE  1140
LIEIARNSTQ DRILEMKVME FFMKVYGYRG KHLGGSRKPD GAIYTVGSPI DYGVIVDTKA  1200
YSGGYNLPIG QADEMQRYVE ENQTRNKHIN PNEWWKVYPS SVTEFKFLFV SGHFKGNYKA  1260
QLTRLNHITN CNGAVLSVEE LLIGGEMIKA GTLTLEEVRR KFNNGEINF              1309

SEQ ID NO: 72          moltype = AA  length = 1177
FEATURE                Location/Qualifiers
REGION                 1..1177
                       note = Xanthomonas spp, Zea mays
source                 1..1177
                       mol_type = protein
```

```
                        organism = synthetic construct
SEQUENCE: 72
MASSPPKKKR KVSWKDASGW SRMHADPWPR RRAAQPSDAS PAAQVDLRTL GYSQQQQEKI  60
KPKVRSTVAQ HHEALVGHGF THAHIVALSQ HPAALGTVAV TYQHIITALP EATHEDIVGV  120
GKQWSGARAL EALLTDAGEL RGPPLQLDTG QLVKIAKRGG VTAMEAVHAS RNALTGAPLN  180
LTPDQVVAIA SHDGGKQALE TVQRLLPVLC QAHGLTPDQV VAIASHDGGK QALETVQRLL  240
PVLCQDHGLT PEQVVAIASN GGGKQALETV QRLLPVLCQD HGLTPDQVVA IASNNGGKQA  300
LETVQRLLPV LCQAHGLTPD QVVAIASNGG GKQALETVQR LLPVLCQAHG LTPDQVVAIA  360
SHDGGKQALE TVQRLLPVLC QAHGLTPEQV VAIASNGGGK QALETVQRLL PVLCQAHGLT  420
PEQVVAIASN IGGKQALETV QRLLPVLCQD HGLTPEQVVA IASHDGGKQA LETVQRLLPV  480
LCQAHGLTPD QVVAIASNGG GKQALETVQR LLPVLCQAHG LTPDQVVAIA SNIGGKQALE  540
TVQRLLPVLC QDHGLTPEQV VAIASHDGGK QALETVQRLL PVLCQDHGLT PDQVVAIASN  600
NGGKQALETV QRLLPVLCQA HGLTPDQVVA IASNGGGKQA LETVQRLLPV LCQAHGLTPD  660
QVVAIASNNG GKQALETVQR LLPVLCQAHG LTPEQVVAIA SHDGGKQALE TVQRLLPVLC  720
QDHGLTPDQV VAIASNGGKQ ALESIVAQLS RPDPALAALT NDHLVALACL GGRPAMDAVK  780
KGLPHAPELI RRVNRRIGER TSHRVADYAQ VVRVLEFFQC HSHPAYAFDE AMTQFGMSRN  840
GLVQLFRRVG VTELEARGGT LPPASQRWDR ILQASGMKRA KPSPTSAQTP DQASLHAFAD  900
SLERDLDAPS PMHEGDQTRA SSRKRSRSDR AVTGPSAQQA VEVRVPEQRD ALHLPLSWRV  960
KRPRTRIWGG LPDPGTPTAA DQLVKSELEE KKSELRHKLK YVPHEYIELI EIARNSTQDR  1020
ILEMKVMEFF MKVYGYRGKH LGGSRKPDGA IYTVGSPIDY GVIVDTKAYS GGYNLPIGQA  1080
DEMQRYVEEN QTRNKHINPN EWWKVYPSSV TEFKFLPVSG HFKGNYKAQL TRLNHITNCN  1140
GAVLSVEELL IGGEMIKAGT LTLEEVRRKF NNGEINF                         1177

SEQ ID NO: 73           moltype = AA  length = 1003
FEATURE                 Location/Qualifiers
REGION                  1..1003
                        note = Xanthomonas spp, Zea mays
source                  1..1003
                        mol_type = protein
                        organism = synthetic construct
SEQUENCE: 73
MASSPPKKKR KVSWKDASGW SRMHADPWPR RRAAQPSDAS PAAQVDLRTL GYSQQQQEKI  60
KPKVRSTVAQ HHEALVGHGF THAHIVALSQ HPAALGTVAV TYQHIITALP EATHEDIVGV  120
GKQWSGARAL EALLTDAGEL RGPPLQLDTG QLVKIAKRGG VTAMEAVHAS RNALTGAPLN  180
LTPDQVVAIA SHDGGKQALE TVQRLLPVLC QAHGLTPDQV VAIASHDGGK QALETVQRLL  240
PVLCQDHGLT PEQVVAIASN GGGKQALETV QRLLPVLCQD HGLTPDQVVA IASNNGGKQA  300
LETVQRLLPV LCQAHGLTPD QVVAIASNGG GKQALETVQR LLPVLCQAHG LTPDQVVAIA  360
SHDGGKQALE TVQRLLPVLC QAHGLTPEQV VAIASNGGGK QALETVQRLL PVLCQAHGLT  420
PEQVVAIASN IGGKQALETV QRLLPVLCQD HGLTPEQVVA IASHDGGKQA LETVQRLLPV  480
LCQAHGLTPD QVVAIASNGG GKQALETVQR LLPVLCQAHG LTPDQVVAIA SNIGGKQALE  540
TVQRLLPVLC QDHGLTPEQV VAIASHDGGK QALETVQRLL PVLCQDHGLT PDQVVAIASN  600
NGGKQALETV QRLLPVLCQA HGLTPDQVVA IASNGGGKQA LETVQRLLPV LCQAHGLTPD  660
QVVAIASNNG GKQALETVQR LLPVLCQAHG LTPEQVVAIA SHDGGKQALE TVQRLLPVLC  720
QDHGLTPDQV VAIASNGGKQ ALESIVAQLS RPDPALAALT NDHLVALACL GGRPAMDAVK  780
KGLPHAPELI RRVNRRIGER TSHRVALQLV KSELEEKKSE LRHKLKYVPH EYIELIEIAR  840
NSTQDRILEM KVMEFFMKVY GYRGKHLGGS RKPDGAIYTV GSPIDYGVIV DTKAYSGGYN  900
LPIGQADEMQ RYVEENQTRN KHINPNEWWK VYPSSVTEFK FLFVSGHFKG NYKAQLTRLN  960
HITNCNGAVL SVEELLIGGE MIKAGTLTLE EVRRKFNNGE INF                   1003

SEQ ID NO: 74           moltype = AA  length = 1343
FEATURE                 Location/Qualifiers
REGION                  1..1343
                        note = Xanthomonas spp, Zea mays
source                  1..1343
                        mol_type = protein
                        organism = synthetic construct
SEQUENCE: 74
MASSPPKKKR KVSWKDASGW SRMHADPIRP RRPSPARELL PGPQPDRVQP TADRGVSAPA  60
GSPLDGLPAR RTVSRTRLPS PPAPSPAFSA GSFSDLLRPF DPSLLDTSLL DSMPAVGTPH  120
TAAAPAEWDE MQSALRAADD PPPTVRVAVT AARPPRAKPA PRRRAAQPSD ASPAAQVDLR  180
TLGYSQQQQE KIKPKVRSTV AQHHEALVGH GFTHAHIVAL SQHPAALGTV AVTYQHIITA  240
LPEATHEDIV GVGKQWSGAR ALEALLTDAG ELRGPPLQLD TGQLVKIAKR GGVTAMEAVH  300
ASRNALTGAP LNLTPDQVVA IASNNGGKQA LETVQRLLPV LCQAHGLTPD QVVAIASHDG  360
GKQALETVQR LLPVLCQDHG LTPEQVVAIA SNIGGKQALE TVQRLLPVLC QDHGLTPDQV  420
VAIASNGGGK QALETVQRLL PVLCQAHGLT PDQVVAIASH DGGKQALETV QRLLPVLCQA  480
HGLTPDQVVA IASHDGGKQA LETVQRLLPV LCQAHGLTPE QVVAIASNNG GKQALETVQR  540
LLPVLCQAHG LTPEQVVAIA SNGGGKQALE TVQRLLPVLC QDHGLTPEQV VAIASNNGGK  600
QALETVQRLL PVLCQAHGLT PDQVVAIASH DGGKQALETV QRLLPVLCQA HGLTPDQVVA  660
IASNIGGKQA LETVQRLLPV LCQDHGLTPE QVVAIASNNG GKQALETVQR LLPVLCQDHG  720
LTPDQVVAIA SNGGGKQALE TVQRLLPVLC QAHGLTPDQV VAIASNNGGK QALETVQRLL  780
PVLCQAHGLT PDQVVAIASH DGGKQALETV QRLLPVLCQA HGLTPEQVVA IASNIGGKQA  840
LETVQRLLPV LCQAHGLTPE QVVAIASNNG GKQALETVQR LLPVLCQDHG LTPDQVVAIA  900
SNGGKQALES IVAQLSRPDP ALAALTNDHL VALACLGGRP AMDAVKKGLP HAPELIRRVN  960
RRIGERTSHR VADYAQVVRV LEFFQCHSHP AYAFDEAMTQ FGMSRNGLVQ LFRRVGVTEL  1020
EARGGTLPPA SQRWDRILQA SGMKRAKPSP TSAQTPDQAS LHAFADSLER DLDAPSPMHE  1080
GDQTRASSRK RSRSDRAVTG PSAQQAVEVR VPEQRDALHL PLSWRVKRPR TRIWGGLPDP  1140
GTPTAADQLV KSELEEKKSE LRHKLKYVPH EYIELIEIAR NSTQDRILEM KVMEFFMKVY  1200
GYRGKHLGGS RKPDGAIYTV GSPIDYGVIV DTKAYSGGYN LPIGQADEMQ RYVEENQTRN  1260
KHINPNEWWK VYPSSVTEFK FLFVSGHFKG NYKAQLTRLN HITNCNGAVL SVEELLIGGE  1320
```

-continued

```
MIKAGTLTLE EVRRKFNNGE INF                                    1343

SEQ ID NO: 75          moltype = AA  length = 1211
FEATURE                Location/Qualifiers
REGION                 1..1211
                       note = Xanthomonas spp, Zea mays
source                 1..1211
                       mol_type = protein
                       organism = synthetic construct
SEQUENCE: 75
MASSPPKKKR KVSWKDASGW SRMHADPWPR RRAAQPSDAS PAAQVDLRTL GYSQQQQEKI  60
KPKVRSTVAQ HHEALVGHGF THAHIVALSQ HPAALGTVAV TYQHIITALP EATHEDIVGV  120
GKQWSGARAL EALLTDAGEL RGPPLQLDTG QLVKIAKRGG VTAMEAVHAS RNALTGAPLN  180
LTPDQVVAIA SNNGGKQALE TVQRLLPVLC QAHGLTPDQV VAIASHDGGK QALETVQRLL  240
PVLCQDHGLT PEQVVAIASN IGGKQALETV QRLLPVLCQD HGLTPDQVVA IASNGGGKQA  300
LETVQRLLPV LCQAHGLTPD QVVAIASHDG GKQALETVQR LLPVLCQAHG LTPDQVVAIA  360
SHDGGKQALE TVQRLLPVLC QAHGLTPEQV VAIASNNGGK QALETVQRLL PVLCQAHGLT  420
PEQVVAIASN GGGKQALETV QRLLPVLCQD HGLTPEQVVA IASNNGGKQA LETVQRLLPV  480
LCQAHGLTPD QVVAIASHDG GKQALETVQR LLPVLCQAHG LTPDQVVAIA SNIGGKQALE  540
TVQRLLPVLC QDHGLTPEQV VAIASNNGGK QALETVQRLL PVLCQDHGLT PDQVVAIASN  600
GGGKQALETV QRLLPVLCQA HGLTPDQVVA IASNNGGKQA LETVQRLLPV LCQAHGLTPD  660
QVVAIASHDG GKQALETVQR LLPVLCQAHG LTPEQVVAIA SNIGGKQALE TVQRLLPVLC  720
QAHGLTPEQV VAIASNNGGK QALETVQRLL PVLCQDHGLT PDQVVAIASN GGKQALESIV  780
AQLSRPDPAL AALTNDHLVA LACLGGRPAM DAVKKGLPHA PELIRRVNRR IGERTSHRVA  840
DYAQVVRVLE FFQCHSHPAY AFDEAMTQFG MSRNGLVQLF RRVGVTELEA RGGTLPPASQ  900
RWDRILQASG MKRAKPSPTS AQTPDQASLH AFADSLERDL DAPSPMHEGD QTRASSRKRS  960
RSDRAVTGPS AQQAVEVRVP EQRDALHLPL SWRVKRPRTR IWGGLPDPGT PTAADQLVKS  1020
ELEEKKSELR HKLKYVPHEY IELIEIARNS TQDRILEMKV MEFFMKVYGY RGKHLGGSRK  1080
PDGAIYTVGS PIDYGVIVDT KAYSGGYNLP IGQADEMQRY VEENQTRNKH INPNEWWKVY  1140
PSSVTEFKFL FVSGHFKGNY KAQLTRLNHI TNCNGAVLSV EELLIGGEMI KAGTLTLEEV  1200
RRKFNNGEIN F                                                 1211

SEQ ID NO: 76          moltype = AA  length = 1037
FEATURE                Location/Qualifiers
REGION                 1..1037
                       note = Xanthomonas spp, Zea mays
source                 1..1037
                       mol_type = protein
                       organism = synthetic construct
SEQUENCE: 76
MASSPPKKKR KVSWKDASGW SRMHADPWPR RRAAQPSDAS PAAQVDLRTL GYSQQQQEKI  60
KPKVRSTVAQ HHEALVGHGF THAHIVALSQ HPAALGTVAV TYQHIITALP EATHEDIVGV  120
GKQWSGARAL EALLTDAGEL RGPPLQLDTG QLVKIAKRGG VTAMEAVHAS RNALTGAPLN  180
LTPDQVVAIA SNNGGKQALE TVQRLLPVLC QAHGLTPDQV VAIASHDGGK QALETVQRLL  240
PVLCQDHGLT PEQVVAIASN IGGKQALETV QRLLPVLCQD HGLTPDQVVA IASNGGGKQA  300
LETVQRLLPV LCQAHGLTPD QVVAIASHDG GKQALETVQR LLPVLCQAHG LTPDQVVAIA  360
SHDGGKQALE TVQRLLPVLC QAHGLTPEQV VAIASNNGGK QALETVQRLL PVLCQAHGLT  420
PEQVVAIASN GGGKQALETV QRLLPVLCQD HGLTPEQVVA IASNNGGKQA LETVQRLLPV  480
LCQAHGLTPD QVVAIASHDG GKQALETVQR LLPVLCQAHG LTPDQVVAIA SNIGGKQALE  540
TVQRLLPVLC QDHGLTPEQV VAIASNNGGK QALETVQRLL PVLCQDHGLT PDQVVAIASN  600
GGGKQALETV QRLLPVLCQA HGLTPDQVVA IASNNGGKQA LETVQRLLPV LCQAHGLTPD  660
QVVAIASHDG GKQALETVQR LLPVLCQAHG LTPEQVVAIA SNIGGKQALE TVQRLLPVLC  720
QAHGLTPEQV VAIASNNGGK QALETVQRLL PVLCQDHGLT PDQVVAIASN GGKQALESIV  780
AQLSRPDPAL AALTNDHLVA LACLGGRPAM DAVKKGLPHA PELIRRVNRR IGERTSHRVA  840
LQLVKSELEE KKSELRHKLK YVPHEYIELI EIARNSTQDR ILEMKVMEFF MKVYGYRGKH  900
LGGSRKPDGA IYTVGSPIDY GVIVDTKAYS GGYNLPIGQA DEMQRYVEEN QTRNKHINPN  960
EWWKVYPSSV TEFKFLFVSG HFKGNYKAQL TRLNHITNCN GAVLSVEELL IGGEMIKAGT  1020
LTLEEVRRKF NNGEINF                                           1037

SEQ ID NO: 77          moltype = AA  length = 1275
FEATURE                Location/Qualifiers
REGION                 1..1275
                       note = Xanthomonas ssp, Zea mays
source                 1..1275
                       mol_type = protein
                       organism = synthetic construct
SEQUENCE: 77
MASSPPKKKR KVSWKDASGW SRMHADPIRP RRPSPARELL PGPQPDRVQP TADRGVSAPA  60
GSPLDGLPAR RTVSRTRLPS PPAPSPAFSA GSFSDLLRPF DPSLLDTSLL DSMPAVGTPH  120
TAAAPAEWDE MQSALRAADD PPPTVRVAVT AARPPRAKPA PRRRAAQPSD ASPAAQVDLR  180
TLGYSQQQQE KIKPKVRSTV AQHHEALVGH GFTHAHIVAL SQHPAALGTV AVTYQHIITA  240
LPEATHEDIV GVGKQWSGAR ALEALLTDAG ELRGPPLQLD TGQLVKIAKR GGVTAMEAVH  300
ASRNALTGAP LNLTPDQVVA IASHDGGKQA LETVQRLLPV LCQAHGLTPD QVVAIASHDG  360
GKQALETVQR LLPVLCQDHG LTPEQVVAIA SNGGGKQALE TVQRLLPVLC QDHGLTPDQV  420
VAIASNIGGK QALETVQRLL PVLCQAHGLT PDQVVAIASN IGGKQALETV QRLLPVLCQA  480
HGLTPDQVVA IASNIGGKQA LETVQRLLPV LCQAHGLTPE QVVAIASHDG GKQALETVQR  540
LLPVLCQDHG LTPEQVVAIA SNIGGKQALE TVQRLLPVLC QAHGLTPDQV VAIASNIGGK  600
QALETVQRLL PVLCQAHGLT PDQVVAIASN IGGKQALETV QRLLPVLCQD HGLTPEQVVA  660
IASNNGGKQA LETVQRLLPV LCQDHGLTPD QVVAIASNNG GKQALETVQR LLPVLCQAHG  720
```

-continued

```
LTPDQVVAIA SNIGGKQALE TVQRLLPVLC QAHGLTPDQV VAIASNNGGK QALETVQRLL  780
PVLCQAHGLT PEQVVAIASN NGGKQALETV QRLLPVLCQD HGLTPDQVVA IASNGGKQAL  840
ESIVAQLSRP DPALAALTND HLVALACLGG RPAMDAVKKG LPHAPELIRR VNRRIGERTS  900
HRVADYAQVV RVLEFFQCHS HPAYAFDEAM TQFGMSRNGL VQLFRRVGVT ELEARGGTLP  960
PASQRWDRIL QASGMKRAKP SPTSAQTPDQ ASLHAFADSL ERDLDAPSPM HEGDQTRASS  1020
RKRSRSDRAV TGPSAQQAVE VRVPEQRDAL HLPLSWRVKR PRTRIWGGLP DPGTPTAADQ  1080
LVKSELEEKK SELRHKLKYV PHEYIELIEI ARNSTQDRIL EMKVMEFFMK VYGYRGKHLG  1140
GSRKPDGAIY TVGSPIDYGV IVDTKAYSGG YNLPIGQADE MQRYVEENQT RNKHINPNEW  1200
WKVYPSSVTE FKFLFVSGHF KGNYKAQLTR LNHITNCNGA VLSVEELLIG GEMIKAGTLT  1260
LEEVRRKFNN GEINF                                                  1275

SEQ ID NO: 78          moltype = AA  length = 1143
FEATURE                Location/Qualifiers
REGION                 1..1143
                       note = Xanthomonas ssp, Zea mays
source                 1..1143
                       mol_type = protein
                       organism = synthetic construct
SEQUENCE: 78
MASSPPKKKR KVSWKDASGW SRMHADPWPR RRAAQPSDAS PAAQVDLRTL GYSQQQQEKI  60
KPKVRSTVAQ HHEALVGHGF THAHIVALSQ HPAALGTVAV TYQHIITALP EATHEDIVGV  120
GKQWSGARAL EALLTDAGEL RGPPLQLDTG QLVKIAKRGG VTAMEAVHAS RNALTGAPLN  180
LTPDQVVAIA SHDGGKQALE TVQRLLPVLC QAHGLTPDQV VAIASHDGGK QALETVQRLL  240
PVLCQDHGLT PEQVVAIASN GGGKQALETV QRLLPVLCQD HGLTPDQVVA IASNIGGKQA  300
LETVQRLLPV LCQAHGLTPD QVVAIASNIG GKQALETVQR LLPVLCQAHG LTPDQVVAIA  360
SNIGGKQALE TVQRLLPVLC QAHGLTPEQV VAIASHDGGK QALETVQRLL PVLCQDHGLT  420
PEQVVAIASN IGGKQALETV QRLLPVLCQA HGLTPDQVVA IASNIGGKQA LETVQRLLPV  480
LCQAHGLTPD QVVAIASNIG GKQALETVQR LLPVLCQDHG LTPEQVVAIA SNNGGKQALE  540
TVQRLLPVLC QDHGLTPDQV VAIASNNGGK QALETVQRLL PVLCQAHGLT PDQVVAIASN  600
IGGKQALETV QRLLPVLCQA HGLTPDQVVA IASNNGGKQA LETVQRLLPV LCQAHGLTPE  660
QVVAIASNNG GKQALETVQR LLPVLCQDHG LTPDQVVAIA SNGGKQALES IVAQLSRPDP  720
ALAALTNDHL VALACLGGRP AMDAVKKGLP HAPELIRRVN RRIGERTSHR VADYAQVVRV  780
LEFFQCHSHP AYAFDEAMTQ FGMSRNGLVQ LFRRVGVTEL EARGGTLPPA SQRWDRILQA  840
SGMKRAKPSP TSAQTPDQAS LHAFADSLER DLDAPSPMHE GDQTRASSRK RSRSDRAVTG  900
PSAQQAVEVR VPEQRDALHL PLSWRVKRPR TRIWGGLPDP GTPTAADQLV KSELEEKKSE  960
LRHKLKYVPH EYIELIEIAR NSTQDRILEM KVMEFFMKVY GYRGKHLGGS RKPDGAIYTV  1020
GSPIDYGVIV DTKAYSGGYN LPIGQADEMQ RYVEENQTRN KHINPNEWWK VYPSSVTEFK  1080
FLFVSGHFKG NYKAQLTRLN HITNCNGAVL SVEELLIGGE MIKAGTLTLE EVRRKFNNGE  1140
INF                                                               1143

SEQ ID NO: 79          moltype = AA  length = 969
FEATURE                Location/Qualifiers
REGION                 1..969
                       note = Xanthomonas ssp, Zea mays
source                 1..969
                       mol_type = protein
                       organism = synthetic construct
SEQUENCE: 79
MASSPPKKKR KVSWKDASGW SRMHADPWPR RRAAQPSDAS PAAQVDLRTL GYSQQQQEKI  60
KPKVRSTVAQ HHEALVGHGF THAHIVALSQ HPAALGTVAV TYQHIITALP EATHEDIVGV  120
GKQWSGARAL EALLTDAGEL RGPPLQLDTG QLVKIAKRGG VTAMEAVHAS RNALTGAPLN  180
LTPDQVVAIA SHDGGKQALE TVQRLLPVLC QAHGLTPDQV VAIASHDGGK QALETVQRLL  240
PVLCQDHGLT PEQVVAIASN GGGKQALETV QRLLPVLCQD HGLTPDQVVA IASNIGGKQA  300
LETVQRLLPV LCQAHGLTPD QVVAIASNIG GKQALETVQR LLPVLCQAHG LTPDQVVAIA  360
SNIGGKQALE TVQRLLPVLC QAHGLTPEQV VAIASHDGGK QALETVQRLL PVLCQDHGLT  420
PEQVVAIASN IGGKQALETV QRLLPVLCQA HGLTPDQVVA IASNIGGKQA LETVQRLLPV  480
LCQAHGLTPD QVVAIASNIG GKQALETVQR LLPVLCQDHG LTPEQVVAIA SNNGGKQALE  540
TVQRLLPVLC QDHGLTPDQV VAIASNNGGK QALETVQRLL PVLCQAHGLT PDQVVAIASN  600
IGGKQALETV QRLLPVLCQA HGLTPDQVVA IASNNGGKQA LETVQRLLPV LCQAHGLTPE  660
QVVAIASNNG GKQALETVQR LLPVLCQDHG LTPDQVVAIA SNGGKQALES IVAQLSRPDP  720
ALAALTNDHL VALACLGGRP AMDAVKKGLP HAPELIRRVN RRIGERTSHR VALQLVKSEL  780
EEKKSELRHK LKYVPHEYIE LIEIARNSTQ DRILEMKVME FFMKVYGYRG KHLGGSRKPD  840
GAIYTVGSPI DYGVIVDTKA YSGGYNLPIG QADEMQRYVE ENQTRNKHIN PNEWWKVYPS  900
SVTEFKFLFV SGHFKGNYKA QLTRLNHITN CNGAVLSVEE LLIGGEMIKA GTLTLEEVRR  960
KFNNGEINF                                                         969

SEQ ID NO: 80          moltype = AA  length = 1024
FEATURE                Location/Qualifiers
REGION                 1..1024
                       note = Xanthomonas ssp, Zea mays
source                 1..1024
                       mol_type = protein
                       organism = synthetic construct
SEQUENCE: 80
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPEQ VVAIASNNGG  180
KQALETVQRL LPVLCQAHGL TPEQVVAIAS HDGGKQALET VQRLLPVLCQ AHGLTPEQVV  240
AIASNIGGKQ ALETVQRLLP VLCQAHGLTP EQVVAIASNG GGKQALETVQ RLLPVLCQAH  300
```

-continued

```
GLTPEQVVAI ASHDGGKQAL ETVQRLLPVL CQAHGLTPEQ VVAIASHDGG KQALETVQRL  360
LPVLCQAHGL TPEQVVAIAS NNGGKQALET VQRLLPVLCQ AHGLTPEQVV AIASNGGGKQ  420
ALETVQRLLP VLCQAHGLTP EQVVAIASNN GGKQALETVQ RLLPVLCQAH GLTPEQVVAI  480
ASHDGGKQAL ETVQRLLPVL CQAHGLTPEQ VVAIASNIGG KQALETVQRL LPVLCQAHGL  540
TPEQVVAIAS NNGGKQALET VQRLLPVLCQ AHGLTPEQVV AIASNGGGKQ ALETVQRLLP  600
VLCQAHGLTP EQVVAIASNN GGKQALETVQ RLLPVLCQAH GLTPEQVVAI ASHDGGKQAL  660
ETVQRLLPVL CQAHGLTPEQ VVAIASNIGG KQALETVQRL LPVLCQAHGL TPEQVVAIAS  720
NNGGKQALET VQRLLPVLCQ AHGLTPQQVV AIASNGGGRP ALESIVAQLS RPDPALAALT  780
NDHLVALACL GGRPALDAVK KGLPHAPALI KRTNRRIPER TSHRVAGSQL VKSELEEKKS  840
ELRHKLKYVP HEYIELIEIA RNSTQDRILE MKVMEFFMKV YGYRGKHLGG SRKPDGAIYT  900
VGSPIDYGVI VDTKAYSGGY NLPIGQADEM QRYVEENQTR NKHINPNEWW KVYPSSVTEF  960
KFLFVSGHFK GNYKAQLTRL NHITNCNGAV LSVEELLIGG EMIKAGTLTL EEVRRKFNNG  1020
EINF                                                             1024

SEQ ID NO: 81          moltype = AA  length = 1024
FEATURE                Location/Qualifiers
REGION                 1..1024
                       note = Xanthomonas ssp, Zea mays
source                 1..1024
                       mol_type = protein
                       organism = synthetic construct
SEQUENCE: 81
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPEQ VVAIASHDGG  180
KQALETVQRL LPVLCQAHGL TPEQVVAIAS HDGGKQALET VQRLLPVLCQ AHGLTPEQVV  240
AIASNGGGKQ ALETVQRLLP VLCQAHGLTP EQVVAIASNI GGKQALETVQ RLLPVLCQAH  300
GLTPEQVVAI ASNIGGKQAL ETVQRLLPVL CQAHGLTPEQ VVAIASNIGG KQALETVQRL  360
LPVLCQAHGL TPEQVVAIAS HDGGKQALET VQRLLPVLCQ AHGLTPEQVV AIASNIGGKQ  420
ALETVQRLLP VLCQAHGLTP EQVVAIASNI GGKQALETVQ RLLPVLCQAH GLTPEQVVAI  480
ASNIGGKQAL ETVQRLLPVL CQAHGLTPEQ VVAIASNNGG KQALETVQRL LPVLCQAHGL  540
TPEQVVAIAS NNGGKQALET VQRLLPVLCQ AHGLTPEQVV AIASNIGGKQ ALETVQRLLP  600
VLCQAHGLTP EQVVAIASNN GGKQALETVQ RLLPVLCQAH GLTPEQVVAI ASNNGGKQAL  660
ETVQRLLPVL CQAHGLTPEQ VVAIASNGGG KQALETVQRL LPVLCQAHGL TPEQVVAIAS  720
HDGGKQALET VQRLLPVLCQ AHGLTPQQVV AIASHDGGRP ALESIVAQLS RPDPALAALT  780
NDHLVALACL GGRPALDAVK KGLPHAPALI KRTNRRIPER TSHRVAGSQL VKSELEEKKS  840
ELRHKLKYVP HEYIELIEIA RNSTQDRILE MKVMEFFMKV YGYRGKHLGG SRKPDGAIYT  900
VGSPIDYGVI VDTKAYSGGY NLPIGQADEM QRYVEENQTR NKHINPNEWW KVYPSSVTEF  960
KFLFVSGHFK GNYKAQLTRL NHITNCNGAV LSVEELLIGG EMIKAGTLTL EEVRRKFNNG  1020
EINF                                                             1024

SEQ ID NO: 82          moltype = DNA  length = 4032
FEATURE                Location/Qualifiers
misc_feature           1..4032
                       note = Xanthomonas ssp, Zea mays
source                 1..4032
                       mol_type = other DNA
                       organism = synthetic construct
SEQUENCE: 82
atggctagct cccccccgaa gaagaagagg aaggtcagct ggaaggatgc tagcggctgg  60
agcaggatgc acgctgatcc aatcaggccg aggaggccaa gcccagcaag ggagctgctg  120
ccaggcccac agccagatag ggtgcagcca accgccgata ggggcgtgag cgctccagct  180
ggcagcccgc tggatggcct gccagctagg aggaccgtga gcaggaccag gctgccgagc  240
ccaccagctc cgagcccagc cttcagcgct ggcagcttca gcgatctgct gaggccattc  300
gatccgagcc tgctggatac atcgctgctg gatagcatgc cagctgtggg caccccacac  360
accgctgctg ctccagctga gtgggatgag atgcagtccg ccctccgcgc cgccgacgac  420
ccgccgccaa ccgtgagggt ggccgtgacc gctgctaggc cgccaagggc taagccagct  480
ccaaggagga gggccgctca gccaagcgat gctagccccg ccgcgcaggt cgacctcagg  540
accctgggct acagccagca gcagcaggag aagatcaagc cgaaggtgag gagcaccgtg  600
gcccagcacc acgaggctct ggtgggccac ggcttcaccc acgctcacat cgtggccctg  660
agccagcacc cagctgctct gggcaccgtg gctgtgacct accagcacat catcaccgcc  720
ctgccagagg ctacccacga ggacatcgtg ggcgtgggca agcagtggag cggcgctagg  780
gccctggagg ctctgctgac cgatgctggc gagctgaggg gcccaccgct ccagctggat  840
accggccagc tggtgaagat cgccaagagg ggcggcgtga ccgctatgga ggctgtgcac  900
gccagcagga acgctctgac cggcgctcca ctgaacctga cccccgacca ggtggtggcc  960
atcgcgagca acatcggcgg caagcaggct ctcgaaaccg tgcagaggct gctcccggtg  1020
ctgtgccagg cccacggcct caccccagac caggtcgtcg cgatcgcctc ccacgatggc  1080
ggcaagcagg ccctggagac tgtgcagcgc ctgctgcccg tcctgtgcca ggaccacggc  1140
ctcaccccgg agcaggtcgt cgctatcgct agcaacatcg gcggcaagca ggcgctcgaa  1200
accgtccaga ggctcctccc agtcctctgc caggatcacg gcctgacccc ggatcaggtg  1260
gtcgccatcg cttcccacga tggcggcaag caggcgctgg agactgtcca gcgcctcctc  1320
ccagtcctct gccaggcgca cggcctcacc cccgatcagg tcgtggcgat cgcgagcaac  1380
aacggcggca agcaggctct cgaaaccgtg cagaggctgc tgccggtgct ctgccaggct  1440
cacggcctga ccccagacca ggtggtggct atcgcctcca acggcggcgg caagcaggcc  1500
ctggagactg tgcagaggct cctcccggtc ctgtgccagg cccacggcct cacccccgag  1560
caggtcgtcg cgatcgctag caacatcggc ggcaagcagg ccctggagac tgtgcagagg  1620
ctgctcccag tcctgtgcca ggcccacggc ctgacccccg agcaggtggt cgcgatcgcg  1680
agccacgacg gcggcaagca ggcgctcgaa accgtccaga ggctcctccc cgtgctctgc  1740
caggatcacg gcctgacccc agagcaggtg gtggctatcg cgagcaacgg cggcggcaag  1800
```

```
caggctctcg aaaccgtcca gaggctcctc ccagtgctct gccaggctca cggcctcacc  1860
ccggaccagg tcgtcgccat cgcttccaac atcggcggca agcaggctct cgaaaccgtg  1920
cagaggctgc tcccggtgct gtgccaggcc cacggcctca ccccagacca ggtcgtcgcg  1980
atcgcctcca acatcggcgg caagcaggcc ctggagactg tgcagcgcct gctgcccgtc  2040
ctgtgccagg accacggcct caccccggag caggtcgtcg ctatcgctag caacggcggc  2100
ggcaagcagg cgctcgaaac cgtccagagg ctcctcccag tcctctgcca ggatcacggc  2160
ctgaccccgg atcaggtggt cgccatcgct tcccacgatg gcggcaagca ggcgctggag  2220
actgtccagc gcctcctccc agtcctctgc caggcgcacg gcctcacccc cgatcaggtc  2280
gtggcgatcg cgagcaacaa cggcggcaag caggctctcg aaaccgtgca gaggctgctg  2340
ccggtgctct gccaggctca cggcctgacc ccagaccagg tggtggctat cgcctccaac  2400
ggcggcggca agcaggccct ggagactgtg cagaggctcc tcccggtcct gtgccaggcc  2460
cacggcctca cccccgagca ggtcgtcgcg atcgctagca acaacggcgg caagcaggcc  2520
ctggagactg tgcagaggct gctcccagtc ctgtgccagg cccacggcct gacccccgag  2580
caggtggtcg cgatcgcgag ccacgacggc ggcaagcagg cgctcgaaac cgtccagagg  2640
ctcctccccg tgctctgcca ggatcacggc ctcacccccg accaggtcgt ggctatcgcg  2700
tccaacggcg gcaagcaggc tctcgagagc atcgtggccc agctgagcag gccggacccg  2760
gccctggccg ccctgaccaa cgatcacctg gtggctctgg cctgcctggg cggcaggcca  2820
gccatggacg ctgtgaagaa gggcctgccg cacgctccag agctgatccg cagggtgaac  2880
aggaggatcg gcgagaggac cagccacagg gtggccgact acgctcaggt ggtgagggtg  2940
ctggagttct tccagtgcca cagccacccg gcctacgcct tcgacgaggc tatgacccag  3000
ttcggcatga gcaggaacgg cctggtgcag ctgttcagga gggtgggcgt gaccgagctg  3060
gaggctaggg gcggcaccct gccgccagct agccagaggt gggaccgcat cctccaggcc  3120
agcggcatga aaagggctaa gccaagcccg accagcgctc agaccccaga tcaggctagc  3180
ctgcacgctt tcgccgacag cctggagagg gatctggatg ctccgagccc aatgcacgag  3240
ggcgaccaga ccagggccag cagcaggaag aggagcagga gcgacagggc tgtgaccggc  3300
ccgagcgccc agcaggctgt ggaggtgagg gtgccagagc agagggatgc cctgcacctg  3360
ccgctgagct ggagggtgaa gaggccaagg accaggatct ggggcggcct gccagatccg  3420
ggcaccccaa ccgctgctga tcagctcgtg aagagcgagc tggaggagaa gaagagcgag  3480
ctgaggcata aactgaagta cgtgccacac gagtacatcg agctgatcga gatcgccagg  3540
aacagcaccc aggatcgcat cctggagatg aaggtgatgg agttcttcat gaaagtgtac  3600
ggctacaggg gcaagcacct gggcggcagc aggaagccag atggcgccat ctacaccgtg  3660
ggcagcccaa tcgactacgg cgtgatcgtg gataccaagg cttacagcgg cggctacaac  3720
ctgccgatcg gccaggctga tgagatgcag aggtacgtgg aggagaatca aaccaggaac  3780
aagcacatca acccaaacga gtggtggaag gtgtacccga gcagcgtgac cgagttcaag  3840
ttcctgttcg tgagcggcca cttcaagggc aactacaagg ctcagctcac caggctgaac  3900
cacatcacca actgcaacgg cgccgtgctg agcgtggagg agctgctgat cggcggcgag  3960
atgatcaagg ctggcaccct gaccctggag gaggtgagga ggaagttcaa caacggcgag  4020
atcaacttct ga                                                     4032
```

```
SEQ ID NO: 83            moltype = DNA  length = 3114
FEATURE                  Location/Qualifiers
misc_feature             1..3114
                         note = Xanthomonas ssp, Zea mays
source                   1..3114
                         mol_type = other DNA
                         organism = synthetic construct
SEQUENCE: 83
atggctagct cccccccgaa gaagaagagg aaggtcagct ggaaggatgc tagcggctgg  60
agcaggatgc acgctgatcc atggccaagg aggagggccg ctcagccaag cgatgctagc  120
cccgccgcgc aggtcgacct caggaccctg ggctacagcc agcagcagca ggagaagatc  180
aagccgaagg tgaggagcac cgtggcccag caccacgagg ctctggtggg ccacggcttc  240
acccacgctc acatcgtggc cctgagccag cacccagctg ctctgggcac cgtggctgtg  300
acctaccagc acatcatcac cgccctgcca gaggctaccc acgaggacat cgtgggcgtg  360
ggcaagcagt ggagcggcgc tagggccctg gaggctctgc tgaccgatgc tggcgagctg  420
aggggcccac cgctccagct ggataccggc cagctggtga agatcgccaa gaggggcggc  480
gtgaccgcta tggaggctgt gcacgccagc aggaacgctc tgaccggcgc tccactgaac  540
ctgacccccg accaggtggt ggccatcgcg agcaacatcg gcggcaagca ggctctcgaa  600
accgtgcaga ggctgctccc ggtgctgtgc caggcccacg gcctcacccc agaccaggtc  660
gtcgcgatcg cctcccacga tggcggcaag caggccctgg agactgtgca gcgcctgctg  720
cccgtcctgt gccaggacca cggcctcacc ccggagcagg tcgtcgctat cgctagcaac  780
atcggcggca agcaggcgct cgaaaccgtc cagaggctcc tcccagtcct ctgccaggat  840
cacggcctga ccccggatca ggtggtcgcc atcgcttccc acgatggcgg caagcaggcg  900
ctggagactg tccagcgcct cctcccagtc ctctgccagg cgcacggcct cacccccgat  960
caggtcgtgg cgatcgcgag caacaacggc ggcaagcagg ctctcgaaac cgtgcagagg  1020
ctgctgccgg tgctctgcca ggctcacggc ctgaccccag accaggtggt ggctatcgcc  1080
tccaacggcg gcggcaagca ggccctggag actgtgcaga ggctcctccc ggtcctgtgc  1140
caggcccacg gcctcacccc cgagcaggtc gtcgcgatcg ctagcaacat cggcggcaag  1200
caggccctgg agactgtgca gaggctgctc ccagtcctgt gccaggccca cggcctgacc  1260
cccgagcagg tggtcgcgat cgcgagccac gacggcggca agcaggcgct cgaaaccgtc  1320
cagaggctcc tccccgtgct ctgccaggat cacggcctga ccccagagca ggtggtggct  1380
atcgcgagca acggcggcgg caagcaggct ctcgaaaccg tccagaggct cctcccagtg  1440
ctctgccagg ctcacggcct caccccggac caggtcgtcg ccatcgcttc caacatcggc  1500
ggcaagcagg ctctcgaaac cgtgcagagg ctgctcccgg tgctgtgcca ggcccacggc  1560
ctcaccccag accaggtcgt cgcgatcgcc tccaacatcg gcggcaagca ggccctggag  1620
actgtgcagc gcctgctgcc cgtcctgtgc caggaccacg gcctcacccc ggagcaggtc  1680
gtcgctatcg ctagcaacgg cggcggcaag caggcgctcg aaaccgtcca gaggctcctc  1740
ccagtcctct gccaggatca cggcctgacc ccggatcagg tggtcgccat cgcttcccac  1800
gatggcggca agcaggcgct ggagactgtc cagcgcctcc tcccagtcct ctgccaggcg  1860
cacggcctca cccccgatca ggtcgtggcg atcgcgagca acaacggcgg caagcaggct  1920
```

```
ctcgaaaccg tgcagaggct gctgccggtg ctctgccagg ctcacggcct gaccccagac  1980
caggtggtgg ctatcgcctc caacggcggc ggcaagcagg ccctggagac tgtgcagagg  2040
ctcctcccgg tcctgtgcca ggcccacggc ctcacccccg agcaggtcgt cgcgatcgct  2100
agcaacaacg gcggcaagca ggccctggag actgtgcaga ggctgctccc agtcctgtgc  2160
caggcccacg gcctgacccc cgagcaggtg gtcgcgatcg cgagccacga cggcggcaag  2220
caggcgctcg aaaccgtcca gaggctcctc cccgtgctct gccaggatca cggcctcacc  2280
cccgaccagg tcgtggctat cgcgtccaac ggcggcaagc aggctctcga gagcatcgtg  2340
gcccagctga gcaggccgga cccggccctg gccgccctga ccaacgatca cctggtggct  2400
ctggcctgcc tgggcggcag gccagccatg gacgctgtga agaagggcct gccgcacgct  2460
ccagagctga tccgcagggt gaacaggagg atcggcgaga ggaccagcca cagggtggcc  2520
ctgcagctcg tgaagagcga gctggaggag aagaagagcg agctgaggca taaactgaag  2580
tacgtgccac acgagtacat cgagctgatc gagatcgcca ggaacagcac ccaggatcgc  2640
atcctggaga tgaaggtgat ggagttcttc atgaaagtgt acggctacag gggcaagcac  2700
ctgggcggca gcaggaagcc agatggcgcc atctacaccg tgggcagccc aatcgactac  2760
ggcgtgatcg tggataccaa ggcttacagc ggcggctaca acctgccgat cggccaggct  2820
gatgagatgc agaggtacgt ggaggagaat caaaccagga acaagcacat caacccaaac  2880
gagtggtgga aggtgtaccc gagcagcgtg accgagttca agttcctgtt cgtgagcggc  2940
cacttcaagg gcaactacaa ggctcagctc accaggctga accacatcac caactgcaac  3000
ggcgccgtgc tgagcgtgga ggagctgctg atcggcggcg agatgatcaa ggctggcacc  3060
ctgaccctgg aggaggtgag gaggaagttc aacaacggcg agatcaactt ctga        3114

SEQ ID NO: 84           moltype = DNA  length = 3930
FEATURE                 Location/Qualifiers
misc_feature            1..3930
                        note = Xanthomonas ssp, Zea mays
source                  1..3930
                        mol_type = other DNA
                        organism = synthetic construct
SEQUENCE: 84
atggctagct cccccccgaa gaagaagagg aaggtcagct ggaaggatgc tagcggctgg  60
agcaggatgc acgctgatcc aatcaggccg aggaggccaa gcccagcaag ggagctgctg  120
ccaggcccac agccagatag ggtgcagcca accgccgata ggggcgtgag cgctccagct  180
ggcagcccgc tggatggcct gccagctagg aggaccgtga gcaggaccag gctgccgagc  240
ccaccagctc cgagcccagc cttcagcgct ggcagcttca gcgatctgct gaggccattc  300
gatccgagcc tgctggatac atcgctgctg gatagcatgc cagctgtggg caccccacac  360
accgctgctg ctccagctga gtgggatgag atgcagtccg ccctccgcgc cgccgacgac  420
ccgccgccaa ccgtgagggt ggccgtgacc gctgctaggc cgccaagggc taagccagct  480
ccaaggagga gggccgctca gccaagcgat gctagccccg ccgcgcaggt cgacctcagg  540
accctgggct acagccagca gcagcaggag aagatcaagc cgaaggtgag gagcaccgtg  600
gcccagcacc acgaggctct ggtgggccac ggcttcaccc acgctcacat cgtggccctg  660
agccagcacc cagctgctct gggcaccgtg gctgtgacct accagcacat catcaccgcc  720
ctgccagagg ctacccacga ggacatcgtg ggcgtgggca agcagtggag cggcgctagg  780
gccctggagg ctctgctgac cgatgctggc gagctgaggg gcccaccgct ccagctggat  840
accggccagc tggtgaagat cgccaagagg ggcggcgtga ccgctatgga ggctgtgcac  900
gccagcagga acgctctgac cggcgctcca ctgaacctga cccccgacca ggtggtggcc  960
atcgcgagcc acgacggcgg caagcaggct ctcgaaaccg tgcagaggct gctcccggtg  1020
ctgtgccagg cccacggcct caccccagac caggtcgtcg cgatcgcctc ccacgatggc  1080
ggcaagcagg ccctggagac tgtgcagcgc ctgctgcccg tcctgtgcca ggaccacggc  1140
ctcaccccgg agcaggtcgt cgctatcgct agcaacggcg gcggcaagca ggcgctcgaa  1200
accgtccaga ggctcctccc agtcctctgc caggatcacg gcctgacccc ggatcaggtg  1260
gtcgccatcg cttccaacaa cggcggcaag caggcgctgg agactgtcca gcgcctcctc  1320
ccagtcctct gccaggcgca cggcctcacc cccgatcagg tcgtggcgat cgcgagcaac  1380
ggcggcggca agcaggctct cgaaaccgtg cagaggctgc tgccggtgct ctgccaggct  1440
cacggcctga ccccagacca ggtggtggct atcgcctccc acgatggcgg caagcaggcc  1500
ctggagactg tgcagaggct cctcccggtc ctgtgccagg cccacggcct cacccccgag  1560
caggtcgtcg cgatcgctag caacggcggc ggcaagcagg ccctggagac tgtgcagagg  1620
ctgctcccag tcctgtgcca ggcccacggc ctgacccccg agcaggtggt cgcgatcgcg  1680
agcaacatcg gcggcaagca ggcgctcgaa accgtccaga ggctcctccc cgtgctctgc  1740
caggatcacg gcctgacccc agagcaggtg gtggctatcg cgagccacga cggcggcaag  1800
caggctctcg aaaccgtcca gaggctcctc ccagtgctct gccaggctca cggcctcacc  1860
ccggaccagg tcgtcgccat cgcttccaac ggcggcggca agcaggctct cgaaaccgtg  1920
cagaggctgc tcccggtgct gtgccaggcc cacggcctca ccccagacca ggtcgtcgcg  1980
atcgcctcca acatcggcgg caagcaggcc ctggagactg tgcagcgcct gctgcccgtc  2040
ctgtgccagg accacggcct caccccggag caggtcgtcg ctatcgctag ccacgacggc  2100
ggcaagcagg cgctcgaaac cgtccagagg ctcctcccag tcctctgcca ggatcacggc  2160
ctgaccccgg atcaggtggt cgccatcgct tccaacaacg gcggcaagca ggcgctggag  2220
actgtccagc gcctcctccc agtcctctgc caggcgcacg gcctcacccc cgatcaggtc  2280
gtggcgatcg cgagcaacgg cggcggcaag caggctctcg aaaccgtgca gaggctgctg  2340
ccggtgctct gccaggctca cggcctgacc ccagaccagg tggtggctat cgcctccaac  2400
aacggcggca agcaggccct ggagactgtg cagaggctcc tcccagtcct gtgccaggcc  2460
cacggcctga cccccgagca ggtggtcgcg atcgcgagcc acgacggcgg caagcaggcg  2520
ctcgaaaccg tccagaggct cctccccgtg ctctgccagg atcacggcct cacccccgac  2580
caggtcgtgg ctatcgcgtc caacggcggc aagcaggctc tcgagagcat cgtggcccag  2640
ctgagcaggc cggacccggc cctggccgcc ctgaccaacg atcacctggt ggctctggcc  2700
tgcctgggcg gcaggccagc catggacgct gtgaagaagg gcctgccgca cgctccagag  2760
ctgatccgca gggtgaacag gaggatcggc gagaggacca gccacagggt ggccgactac  2820
gctcaggtgg tgagggtgct ggagttcttc cagtgccaca gccacccggc ctacgccttc  2880
gacgaggcta tgacccagtt cggcatgagc aggaacggcc tggtgcagct gttcaggagg  2940
gtgggcgtga ccgagctgga ggctaggggc ggcaccctgc cgccagctag ccagaggtgg  3000
```

-continued

```
gaccgcatcc tccaggccag cggcatgaaa agggctaagc caagcccgac cagcgctcag  3060
accccagatc aggctagcct gcacgctttc gccgacagcc tggagaggga tctggatgct  3120
ccgagcccaa tgcacgaggg cgaccagacc agggccagca gcaggaagag gagcaggagc  3180
gacagggctg tgaccggccc gagcgcccag caggctgtgg aggtgagggt gccagagcag  3240
agggatgccc tgcacctgcc gctgagctgg agggtgaaga ggccaaggac caggatctgg  3300
ggcggcctgc cagatccggg caccccaacc gctgctgatc agctcgtgaa gagcgagctg  3360
gaggagaaga agagcgagct gaggcataaa ctgaagtacg tgccacacga gtacatcgag  3420
ctgatcgaga tcgccaggaa cagcacccag gatcgcatcc tggagatgaa ggtgatggag  3480
ttcttcatga aagtgtacgg ctacaggggc aagcacctgg gcggcagcag gaagccagat  3540
ggcgccatct acaccgtggg cagcccaatc gactacggcg tgatcgtgga taccaaggct  3600
tacagcggcg gctacaacct gccgatcggc caggctgatg agatgcagag gtacgtggag  3660
gagaatcaaa ccaggaacaa gcacatcaac ccaaacgagt ggtggaaggt gtacccgagc  3720
agcgtgaccg agttcaagtt cctgttcgtg agcggccact tcaagggcaa ctacaaggct  3780
cagctcacca ggctgaacca catcaccaac tgcaacggcg ccgtgctgag cgtggaggag  3840
ctgctgatcg gcggcgagat gatcaaggct ggcaccctga ccctggagga ggtgaggagg  3900
aagttcaaca acggcgagat caacttctga                                  3930

SEQ ID NO: 85          moltype = DNA  length = 3012
FEATURE                Location/Qualifiers
misc_feature           1..3012
                       note = Xanthomonas ssp, Zea mays
source                 1..3012
                       mol_type = other DNA
                       organism = synthetic construct
SEQUENCE: 85
atggctagct ccccccgaa gaagaagagg aaggtcagct ggaaggatgc tagcggctgg  60
agcaggatgc acgctgatcc atggccaagg aggagggccg ctcagccaag cgatgctagc  120
cccgccgcgc aggtcgacct caggaccctg ggctacagcc agcagcagca ggagaagatc  180
aagccgaagg tgaggagcac cgtggcccag caccacgagg ctctggtggg ccacggcttc  240
acccacgctc acatcgtggc cctgagccag cacccagctg ctctgggcac cgtggctgtg  300
acctaccagc acatcatcac cgccctgcca gaggctaccc acgaggacat cgtgggcgtg  360
ggcaagcagt ggagcggcgc tagggccctg gaggctctgc tgaccgatgc tggcgagctg  420
aggggcccac cgctccagct ggataccggc cagctggtga agatcgccaa gaggggcggc  480
gtgaccgcta tggaggctgt gcacgccagc aggaacgctc tgaccggcgc tccactgaac  540
ctgaccccg accaggtggt ggccatcgcg agccacgacg gcggcaagca ggctctcgaa  600
accgtgcaga ggctgctccc ggtgctgtgc caggcccacg gcctcacccc agaccaggtc  660
gtcgcgatcg cctcccacga tggcggcaag caggccctgg agactgtgca gcgcctgctg  720
cccgtcctgt gccaggacca cggcctcacc ccggagcagg tcgtcgctat cgctagcaac  780
ggcggcggca agcaggcgct cgaaaccgtc cagaggctcc tcccagtcct ctgccaggat  840
cacggcctga ccccggatca ggtggtcgcc atcgcttcca acaacggcgg caagcaggcg  900
ctggagactg tccagcgcct cctcccagtc ctctgccagg cgcacggcct cacccccgat  960
caggtcgtgg cgatcgcgag caacggcggc ggcaagcagg ctctcgaaac cgtgcagagg  1020
ctgctgccgg tgctctgcca ggctcacggc ctgaccccag accaggtggt ggctatcgcc  1080
tcccacgatg gcggcaagca ggccctggag actgtgcaga ggctcctccc ggtcctgtgc  1140
caggcccacg gcctcacccc cgagcaggtc gtcgcgatcg ctagcaacgg cggcggcaag  1200
caggccctgg agactgtgca gaggctgctc ccagtcctgt gccaggccca cggcctgacc  1260
cccgagcagg tggtcgcgat cgcgagcaac atcggcggca agcaggcgct cgaaaccgtc  1320
cagaggctcc tccccgtgct ctgccaggat cacggcctga ccccagagca ggtggtggct  1380
atcgcgagcc acgacggcgg caagcaggct ctcgaaaccg tccagaggct cctcccagtg  1440
ctctgccagg ctcacggcct caccccggac caggtcgtcg ccatcgcttc caacggcggc  1500
ggcaagcagg ctctcgaaac cgtgcagagg ctgctcccgg tgctgtgcca ggcccacggc  1560
ctcaccccag accaggtcgt cgcgatcgcc tccaacatcg gcggcaagca ggccctggag  1620
actgtgcagc gcctgctgcc cgtcctgtgc caggaccacg gcctcacccc ggagcaggtc  1680
gtcgctatcg ctagccacga cggcggcaag caggcgctcg aaaccgtcca gaggctcctc  1740
ccagtcctct gccaggatca cggcctgacc ccggatcagg tggtcgccat cgcttccaac  1800
aacggcggca agcaggcgct ggagactgtc cagcgcctcc tcccagtcct ctgccaggcg  1860
cacggcctca cccccgatca ggtcgtggcg atcgcgagca acggcggcgg caagcaggct  1920
ctcgaaaccg tgcagaggct gctgccggtg ctctgccagg ctcacggcct gaccccagac  1980
caggtggtgg ctatcgcctc caacaacggc ggcaagcagg ccctggagac tgtgcagagg  2040
ctcctcccag tcctgtgcca ggcccacggc ctgacccccg agcaggtggt cgcgatcgcg  2100
agccacgacg gcggcaagca ggcgctcgaa accgtccaga ggctcctccc cgtgctctgc  2160
caggatcacg gcctcacccc cgaccaggtc gtggctatcg cgtccaacgg cggcaagcag  2220
gctctcgaga gcatcgtggc ccagctgagc aggccggacc cggccctggc cgccctgacc  2280
aacgatcacc tggtggctct ggcctgcctg ggcggcaggc cagccatgga cgctgtgaag  2340
aagggcctgc cgcacgctcc agagctgatc cgcagggtga acaggaggat cggcgagagg  2400
accagccaca gggtggccct gcagctcgtg aagagcgagc tggaggagaa gaagagcgag  2460
ctgaggcata aactgaagta cgtgccacac gagtacatcg agctgatcga gatcgccagg  2520
aacagcaccc aggatcgcat cctggagatg aaggtgatgg agttcttcat gaaagtgtac  2580
ggctacaggg gcaagcacct gggcggcagc aggaagccag atggcgccat ctacaccgtg  2640
ggcagcccaa tcgactacgg cgtgatcgtg gataccaagg cttacagcgg cggctacaac  2700
ctgccgatcg gccaggctga tgagatgcag aggtacgtgg aggagaatca aaccaggaac  2760
aagcacatca acccaaacga gtggtggaag gtgtacccga gcagcgtgac cgagttcaag  2820
ttcctgttcg tgagcggcca cttcaagggc aactacaagg ctcagctcac caggctgaac  2880
cacatcacca actgcaacgg cgccgtgctg agcgtggagg agctgctgat cggcggcgag  2940
atgatcaagg ctggcaccct gaccctggag gaggtgagga ggaagttcaa caacggcgag  3000
atcaacttct ga                                                    3012

SEQ ID NO: 86          moltype = DNA  length = 4032
FEATURE                Location/Qualifiers
```

-continued

```
misc_feature          1..4032
                      note = Xanthomonas ssp, Zea mays
source                1..4032
                      mol_type = other DNA
                      organism = synthetic construct
SEQUENCE: 86
atggctagct cccccccgaa gaagaagagg aaggtcagct ggaaggatgc tagcggctgg  60
agcaggatgc acgctgatcc aatcaggccg aggaggccaa gcccagcaag ggagctgctg  120
ccaggcccac agccagatag ggtgcagcca accgccgata ggggcgtgag cgctccagct  180
ggcagcccgc tggatggcct gccagctagg aggaccgtga gcaggaccag gctgccgagc  240
ccaccagctc cgagcccagc cttcagcgct ggcagcttca gcgatctgct gaggccattc  300
gatccgagcc tgctggatac atcgctgctg gatagcatgc cagctgtggg caccccacac  360
accgctgctg ctccagctga gtgggatgag atgcagtccg ccctccgcgc cgccgacgac  420
ccgccgccaa ccgtgagggt ggccgtgacc gctgctaggc cgccaagggc taagccagct  480
ccaaggagga gggccgctca gccaagcgat gctagccccg ccgcgcaggt cgacctcagg  540
accctgggct acagccagca gcagcaggag aagatcaagc cgaaggtgag gagcaccgtg  600
gcccagcacc acgaggctct ggtgggccac ggcttcaccc acgctcacat cgtggccctg  660
agccagcacc cagctgctct gggcaccgtg gctgtgacct accagcacat catcaccgcc  720
ctgccagagg ctacccacga ggacatcgtg ggcgtgggca agcagtggag cggcgctagg  780
gccctggagg ctctgctgac cgatgctggc gagctgaggg gcccaccgct ccagctggat  840
accggccagc tggtgaagat cgccaagagg ggcggcgtga ccgctatgga ggctgtgcac  900
gccagcagga acgctctgac cggcgctcca ctgaacctga cccccgacca ggtggtggcc  960
atcgcgagca acaacggcgg caagcaggct ctcgaaaccg tgcagaggct gctcccggtg  1020
ctgtgccagg cccacggcct caccccagac caggtcgtcg cgatcgcctc ccacgatggc  1080
ggcaagcagg ccctggagac tgtgcagcgc ctgctgcccg tcctgtgcca ggaccacggc  1140
ctcaccccgg agcaggtcgt cgctatcgct agcaacatcg gcggcaagca ggcgctcgaa  1200
accgtccaga ggctcctccc agtcctctgc caggatcacg gcctgacccc ggatcaggtg  1260
gtcgccatcg cttccaacgg cggcggcaag caggcgctgg agactgtcca gcgcctcctc  1320
ccagtcctct gccaggcgca cggcctcacc cccgatcagg tcgtggcgat cgcgagccac  1380
gacggcggca agcaggctct cgaaaccgtg cagaggctgc tgccggtgct ctgccaggct  1440
cacggcctga ccccagacca ggtggtggct atcgcctccc acgatggcgg caagcaggcc  1500
ctggagactg tgcagaggct cctcccggtc ctgtgccagg cccacggcct cacccccgag  1560
caggtcgtcg cgatcgctag caacaacggc ggcaagcagg ccctggagac tgtgcagagg  1620
ctgctcccag tcctgtgcca ggcccacggc ctgacccccg agcaggtggt cgcgatcgcg  1680
agcaacggcg gcggcaagca ggcgctcgaa accgtccaga ggctcctccc cgtgctctgc  1740
caggatcacg gcctgacccc agagcaggtg gtggctatcg cgagcaacaa cggcggcaag  1800
caggctctcg aaaccgtcca gaggctcctc ccagtgctct gccaggctca cggcctcacc  1860
ccggaccagg tcgtcgccat cgcttcccac gatggcggca agcaggctct cgaaaccgtg  1920
cagaggctgc tcccggtgct gtgccaggcc cacggcctca ccccagacca ggtcgtcgcg  1980
atcgcctcca acatcggcgg caagcaggcc ctggagactg tgcagcgcct gctgcccgtc  2040
ctgtgccagg accacggcct caccccggag caggtcgtcg ctatcgctag caacaacggc  2100
ggcaagcagg cgctcgaaac cgtccagagg ctcctcccag tcctctgcca ggatcacggc  2160
ctgaccccgg atcaggtggt cgccatcgct tccaacggcg gcggcaagca ggcgctggag  2220
actgtccagc gcctcctccc agtcctctgc caggcgcacg gcctcacccc cgatcaggtc  2280
gtggcgatcg cgagcaacaa cggcggcaag caggctctcg aaaccgtgca gaggctgctg  2340
ccggtgctct gccaggctca cggcctgacc ccagaccagg tggtggctat cgcctcccac  2400
gatggcggca agcaggccct ggagactgtg cagaggctcc tcccggtcct gtgccaggcc  2460
cacggcctca cccccgagca ggtcgtcgcg atcgctagca acatcggcgg caagcaggcc  2520
ctggagactg tgcagaggct gctcccagtc ctgtgccagg cccacggcct gacccccgag  2580
caggtggtcg cgatcgcgag caacaacggc ggcaagcagg cgctcgaaac cgtccagagg  2640
ctcctccccg tgctctgcca ggatcacggc ctcacccccg accaggtcgt ggctatcgcg  2700
tccaacggcg gcaagcaggc tctcgagagc atcgtggccc agctgagcag gccggacccg  2760
gccctggccg ccctgaccaa cgatcacctg gtggctctgg cctgcctggg cggcaggcca  2820
gccatggacg ctgtgaagaa gggcctgccg cacgctccag agctgatccg cagggtgaac  2880
aggaggatcg gcgagaggac cagccacagg gtggccgact acgctcaggt ggtgagggtg  2940
ctggagttct tccagtgcca cagccacccg gcctacgcct tcgacgaggc tatgacccag  3000
ttcggcatga gcaggaacgg cctggtgcag ctgttcagga gggtgggcgt gaccgagctg  3060
gaggctaggg gcggcaccct gccgccagct agccagaggt gggaccgcat cctccaggcc  3120
agcggcatga aaagggctaa gccaagcccg accagcgctc agaccccaga tcaggctagc  3180
ctgcacgctt tcgccgacag cctggagagg gatctggatg ctccgagccc aatgcacgag  3240
ggcgaccaga ccagggccag cagcaggaag aggagcagga gcgacagggc tgtgaccggc  3300
ccgagcgccc agcaggctgt ggaggtgagg gtgccagagc agagggatgc cctgcacctg  3360
ccgctgagct ggagggtgaa gaggccaagg accaggatct ggggcggcct gccagatccg  3420
ggcaccccaa ccgctgctga tcagctcgtg aagagcgagc tggaggagaa gaagagcgag  3480
ctgaggcata aactgaagta cgtgccacac gagtacatcg agctgatcga gatcgccagg  3540
aacagcaccc aggatcgcat cctggagatg aaggtgatgg agttcttcat gaaagtgtac  3600
ggctacaggg gcaagcacct gggcggcagc aggaagccag atggcgccat ctacaccgtg  3660
ggcagcccaa tcgactacgg cgtgatcgtg gataccaagg cttacagcgg cggctacaac  3720
ctgccgatcg gccaggctga tgagatgcag aggtacgtgg aggagaatca aaccaggaac  3780
aagcacatca acccaaacga gtggtggaag gtgtacccga gcagcgtgac cgagttcaag  3840
ttcctgttcg tgagcggcca cttcaagggc aactacaagg ctcagctcac caggctgaac  3900
cacatcacca actgcaacgg cgccgtgctg agcgtggagg agctgctgat cggcggcgag  3960
atgatcaagg ctggcaccct gaccctggag gaggtgagga ggaagttcaa caacggcgag  4020
atcaacttct ga                                                    4032

SEQ ID NO: 87         moltype = DNA  length = 3114
FEATURE               Location/Qualifiers
misc_feature          1..3114
                      note = Xanthomonas ssp, Zea mays
```

-continued

```
source                  1..3114
                        mol_type = other DNA
                        organism = synthetic construct
SEQUENCE: 87
atggctagct cccccccgaa gaagaagagg aaggtcagct ggaaggatgc tagcggctgg  60
agcaggatgc acgctgatcc atggccaagg aggagggccg ctcagccaag cgatgctagc  120
cccgccgcgc aggtcgacct caggaccctg ggctacagcc agcagcagca ggagaagatc  180
aagccgaagg tgaggagcac cgtggcccag caccacgagg ctctggtggg ccacggcttc  240
acccacgctc acatcgtggc cctgagccag cacccagctg ctctgggcac cgtggctgtg  300
acctaccagc acatcatcac cgccctgcca gaggctaccc acgaggacat cgtgggcgtg  360
ggcaagcagt ggagcggcgc tagggccctg gaggctctgc tgaccgatgc tggcgagctg  420
aggggcccac cgctccagct ggataccggc cagctggtga agatcgccaa gaggggcggc  480
gtgaccgcta tggaggctgt gcacgccagc aggaacgctc tgaccggcgc tccactgaac  540
ctgacccccg accaggtggt ggccatcgcg agcaacaacg gcggcaagca ggctctcgaa  600
accgtgcaga ggctgctccc ggtgctgtgc caggcccacg gcctcacccc agaccaggtc  660
gtcgcgatcg cctcccacga tggcggcaag caggccctgg agactgtgca gcgcctgctg  720
cccgtcctgt gccaggacca cggcctcacc ccggagcagg tcgtcgctat cgctagcaac  780
atcggcggca agcaggcgct cgaaaccgtc cagaggctcc tcccagtcct ctgccaggat  840
cacggcctga ccccggatca ggtggtcgcc atcgcttcca acggcggcgg caagcaggcg  900
ctggagactg tccagcgcct cctcccagtc ctctgccagg cgcacggcct cacccccgat  960
caggtcgtgg cgatcgcgag ccacgacggc ggcaagcagg ctctcgaaac cgtgcagagg  1020
ctgctgccgg tgctctgcca ggctcacggc ctgaccccag accaggtggt ggctatcgcc  1080
tcccacgatg gcggcaagca ggccctggag actgtgcaga ggctcctccc ggtcctgtgc  1140
caggcccacg gcctcacccc cgagcaggtc gtcgcgatcg ctagcaacaa cggcggcaag  1200
caggccctgg agactgtgca gaggctgctc ccagtcctgt gccaggccca cggcctgacc  1260
cccgagcagg tggtcgcgat cgcgagcaac ggcggcggca agcaggcgct cgaaaccgtc  1320
cagaggctcc tccccgtgct ctgccaggat cacggcctga ccccagagca ggtggtggct  1380
atcgcgagca acaacggcgg caagcaggct ctcgaaaccg tccagaggct cctcccagtg  1440
ctctgccagg ctcacggcct caccccggac caggtcgtcg ccatcgcttc ccacgatggc  1500
ggcaagcagg ctctcgaaac cgtgcagagg ctgctcccgg tgctgtgcca ggcccacggc  1560
ctcaccccag accaggtcgt cgcgatcgcc tccaacatcg gcggcaagca ggccctggag  1620
actgtgcagc gcctgctgcc cgtcctgtgc caggaccacg gcctcacccc ggagcaggtc  1680
gtcgctatcg ctagcaacaa cggcggcaag caggcgctcg aaaccgtcca gaggctcctc  1740
ccagtcctct gccaggatca cggcctgacc ccggatcagg tggtcgccat cgcttccaac  1800
ggcggcggca agcaggcgct ggagactgtc cagcgcctcc tcccagtcct ctgccaggcg  1860
cacggcctca cccccgatca ggtcgtggcg atcgcgagca acaacggcgg caagcaggct  1920
ctcgaaaccg tgcagaggct gctgccggtg ctctgccagg ctcacggcct gaccccagac  1980
caggtggtgg ctatcgcctc ccacgatggc ggcaagcagg ccctggagac tgtgcagagg  2040
ctcctcccgg tcctgtgcca ggcccacggc ctcacccccg agcaggtcgt cgcgatcgct  2100
agcaacatcg gcggcaagca ggccctggag actgtgcaga ggctgctccc agtcctgtgc  2160
caggcccacg gcctgacccc cgagcaggtg gtcgcgatcg cgagcaacaa cggcggcaag  2220
caggcgctcg aaaccgtcca gaggctcctc cccgtgctct gccaggatca cggcctcacc  2280
cccgaccagg tcgtggctat cgcgtccaac ggcggcaagc aggctctcga gagcatcgtg  2340
gcccagctga gcaggccgga cccggccctg gccgccctga ccaacgatca cctggtggct  2400
ctggcctgcc tgggcggcag gccagccatg gacgctgtga agaagggcct gccgcacgct  2460
ccagagctga tccgcagggt gaacaggagg atcggcgaga ggaccagcca cagggtggcc  2520
ctgcagctcg tgaagagcga gctggaggag aagaagagcg agctgaggca taaactgaag  2580
tacgtgccac acgagtacat cgagctgatc gagatcgcca ggaacagcac ccaggatcgc  2640
atcctggaga tgaaggtgat ggagttcttc atgaaagtgt acggctacag gggcaagcac  2700
ctgggcggca gcaggaagcc agatggcgcc atctacaccg tgggcagccc aatcgactac  2760
ggcgtgatcg tggataccaa ggcttacagc ggcggctaca acctgccgat cggccaggct  2820
gatgagatgc agaggtacgt ggaggagaat caaaccagga acaagcacat caaccccaac  2880
gagtggtgga aggtgtaccc gagcagcgtg accgagttca agttcctgtt cgtgagcggc  2940
cacttcaagg gcaactacaa ggctcagctc accaggctga accacatcac caactgcaac  3000
ggcgccgtgc tgagcgtgga ggagctgctg atcggcggcg agatgatcaa ggctggcacc  3060
ctgaccctgg aggaggtgag gaggaagttc aacaacggcg agatcaactt ctga        3114

SEQ ID NO: 88           moltype = DNA  length = 3075
FEATURE                 Location/Qualifiers
misc_feature            1..3075
                        note = Xanthomonas ssp, Zea mays
source                  1..3075
                        mol_type = other DNA
                        organism = synthetic construct
SEQUENCE: 88
atgggaaaac ctattcctaa tcctctgctg ggcctggatt ctaccggagg catggcccct  60
aagaaaaagc ggaaggtgga cggcggagtg gacctgagaa cactgggata ttctcagcag  120
cagcaggaga agatcaagcc caaggtgaga tctacagtgg cccagcacca cgaagccctg  180
gtgggacacg gatttacaca cgcccacatt gtggccctgt ctcagcaccc tgccgccctg  240
ggaacagtgg ccgtgaaata tcaggatatg attgccgccc tgcctgaggc cacacacgaa  300
gccattgtgg gagtgggaaa acagtggtct ggagccagag ccctggaagc cctgctgaca  360
gtggccggag aactgagagg acctcctctg cagctggata caggacagct gctgaagatt  420
gccaaaaggg gcggagtgac cgcggtggaa gccgtgcacg cctggagaaa tgccctgaca  480
ggagcccctc tgaacctgac ccccgaacag gtggtggcca ttgccagcaa caacggcggc  540
aagcaggccc tggaaaccgt gcagagactg ctgcccgtgc tgtgccaggc ccatggcctg  600
acacctgaac aggtggtggc tatcgcctct cacgacggag gaaaacaggc tctggaaaca  660
gtgcagcggc tgctgcctgt gctgtgtcag gctcacggct tgactccaga acaggtggtg  720
gctattgctt ccaatattgg ggggaaacag gccctggaaa ctgtgcagcg cctgctgcca  780
gtgctgtgcc aggctcacgg actgaccccc gaacaggtgg tggccattgc cagcaacggc  840
```

```
ggcggcaagc aggccctgga aaccgtgcag agactgctgc ccgtgctgtg ccaggcccat  900
ggcctgacac ctgaacaggt ggtggctatc gcctctcacg acggaggaaa acaggctctg  960
gaaacagtgc agcggctgct gcctgtgctg tgtcaggctc acggcttgac tccagaacag  1020
gtggtggcta ttgcttccca cgacgggggg aaacaggccc tggaaactgt gcagcgcctg  1080
ctgccagtgc tgtgccaggc tcacgggctg acccccgaac aggtggtggc cattgccagc  1140
aacaacggcg gcaagcaggc cctggaaacc gtgcagagac tgctgcccgt gctgtgccag  1200
gcccatggcc tgacacctga acaggtggtg gctatcgcct ctaacggcgg aggaaaacag  1260
gctctggaaa cagtgcagcg gctgctgcct gtgctgtgtc aggctcacgg cttgactcca  1320
gaacaggtgg tggctattgc ttccaacaac ggggggaaac aggccctgga aactgtgcag  1380
cgcctgctgc cagtgctgtg ccaggctcac ggcctcactc ccgaacaggt ggtggccatt  1440
gccagccacg acggcggcaa gcaggccctg gaaaccgtgc agagactgct gcccgtgctg  1500
tgccaggccc atggcctgac acctgaacag gtggtggcta tcgcctctaa tatcggagga  1560
aaacaggctc tggaaacagt gcagcggctg ctgcctgtgc tgtgtcaggc tcacggcttg  1620
actccagaac aggtggtggc tattgcttcc aacaacgggg ggaaacaggc cctggaaact  1680
gtgcagcgcc tgctgccagt gctgtgccag gctcacggac tgacccccga acaggtggtg  1740
gccattgcca gcaacggcgg cggcaagcag gccctggaaa ccgtgcagag actgctgccc  1800
gtgctgtgcc aggcccatgg cctgacacct gaacaggtgg tggctatcgc ctctaacaac  1860
ggaggaaaac aggctctgga aacagtgcag cggctgctgc ctgtgctgtg tcaggctcac  1920
ggcttgactc cagaacaggt ggtggctatt gcttcccacg acggggggaa acaggccctg  1980
gaaactgtgc agcgcctgct gccagtgctg tgccaggctc acgggctgac ccccgaacag  2040
gtggtggcca ttgccagcaa catcggcggc aagcaggccc tggaaaccgt gcagagactg  2100
ctgcccgtgc tgtgccaggc ccatggcctg acacctgaac aggtggtggc tatcgcctct  2160
aacaacggag gaaaacaggc tctggaaaca gtgcagcggc tgctgcctgt gctgtgtcag  2220
gctcacggct tgactccaca gcaggtcgtg gcaattgcta gcaacggcgg cggacggccc  2280
gccctggaga gcattgtggc ccagctgtct agacctgatc ctgccctggc cgccctgaca  2340
aatgatcacc tggtggccct ggcctgtctg ggaggcagac ctgccctgga tgccgtgaaa  2400
aaaggactgc ctcacgcccc tgccctgatt aaaagaacaa atagaagaat ccccgagcgg  2460
acctctcaca gagtggccgg atcccagctg gtgaaatctg agctggagga gaagaagtct  2520
gagctgagac acaagctgaa gtacgtgcct cacgagtaca tcgagctgat cgagatcgcc  2580
agaaatagca cccaggatag aatcctggag atgaaggtga tggagttctt catgaaagtg  2640
tacggctaca gaggaaagca tctgggagga agcagaaaac ctgacggagc catttataca  2700
gtgggcagcc ctatcgatta tggcgtgatc gtggatacaa aggcctacag cggaggctac  2760
aatctgccta ttggacaggc cgatgagatg cagagatacg tggaggagaa ccaaaccagg  2820
aacaagcata tcaaccctaa cgagtggtgg aaggtgtacc cttctagcgt gaccgagttc  2880
aagttcctgt ttgtgagcgg ccacttcaag ggcaattata aggcccagct gaccaggctg  2940
aaccacatca caaattgtaa tggcgccgtg ctgtctgtgg aggaactgct gattggagga  3000
gagatgatta aggccggaac actgacactg gaggaggtga gaagaaagtt caacaacggc  3060
gagatcaact tctga                                                   3075
```

```
SEQ ID NO: 89           moltype = DNA  length = 3828
FEATURE                 Location/Qualifiers
misc_feature            1..3828
                        note = Xanthomonas ssp, Zea mays
source                  1..3828
                        mol_type = other DNA
                        organism = synthetic construct
SEQUENCE: 89
atggctagct ccccccccgaa gaagaagagg aaggtcagct ggaaggatgc tagcggctgg  60
agcaggatgc acgctgatcc aatcaggccg aggaggccaa gcccagcaag ggagctgctg  120
ccaggcccac agccagatag ggtgcagcca accgccgata ggggcgtgag cgctccagct  180
ggcagcccgc tggatggcct gccagctagg aggaccgtga gcaggaccag gctgccgagc  240
ccaccagctc cgagcccagc cttcagcgct ggcagcttca gcgatctgct gaggccattc  300
gatccgagcc tgctggatac atcgctgctg gatagcatgc cagctgtggg caccccacac  360
accgctgctg ctccagctga gtgggatgag atgcagtccg ccctccgcgc cgccgacgac  420
ccgccgccaa ccgtgagggt ggccgtgacc gctgctaggc cgccaagggc taagccagct  480
ccaaggagga gggccgctca gccaagcgat gctagccccg ccgcgcaggt cgacctcagg  540
accctgggct acagccagca gcagcaggag aagatcaagc cgaaggtgag gagcaccgtg  600
gcccagcacc acgaggctct ggtgggccac ggcttcaccc acgctcacat cgtggccctg  660
agccagcacc cagctgctct gggcaccgtg gctgtgacct accagcacat catcaccgcc  720
ctgccagagg ctacccacga ggacatcgtg ggcgtgggca agcagtggag cggcgctagg  780
gccctggagg ctctgctgac cgatgctggc gagctgaggg gcccaccgct ccagctggat  840
accggccagc tggtgaagat cgccaagagg ggcggcgtga ccgctatgga ggctgtgcac  900
gccagcagga acgctctgac cggcgctcca ctgaacctga cccccgacca ggtggtggcc  960
atcgcgagcc acgacggcgg caagcaggct ctcgaaaccg tgcagaggct gctcccggtg  1020
ctgtgccagg cccacggcct caccccagac caggtcgtcg cgatcgcctc ccacgatggc  1080
ggcaagcagg ccctggagac tgtgcagcgc ctgctgcccg tcctgtgcca ggaccacggc  1140
ctcaccccgg agcaggtcgt cgctatcgct agcaacggcg gcggcaagca ggcgctcgaa  1200
accgtccaga ggctcctccc agtcctctgc caggatcacg gcctgacccc ggatcaggtg  1260
gtcgccatcg cttccaacat cggcggcaag caggcgctgg agactgtcca gcgcctcctc  1320
ccagtcctct gccaggcgca cggcctcacc cccgatcagg tcgtggcgat cgcgagcaac  1380
atcggcggca agcaggctct cgaaaccgtg cagaggctgc tgccggtgct ctgccaggct  1440
cacggcctga ccccagacca ggtggtggct atcgcctcca acatcggcgg caagcaggcc  1500
ctggagactg tgcagaggct cctcccagtc ctgtgccagg cccacggcct gacccccgag  1560
caggtggtcg cgatcgcgag ccacgacggc ggcaagcagg cgctcgaaac cgtccagagg  1620
ctcctccccg tgctctgcca ggatcacggc ctgaccccag agcaggtggt ggctatcgcg  1680
agcaacatcg gcggcaagca ggctctcgaa accgtccaga ggctcctccc agtgctctgc  1740
caggctcacg gcctcacccc ggaccaggtc gtcgccatcg cttccaacat cggcggcaag  1800
caggctctcg aaaccgtgca gaggctgctc ccggtgctgt gccaggccca cggcctcacc  1860
ccagaccagg tcgtcgcgat cgcctccaac atcggcggca agcaggccct ggagactgtg  1920
```

```
cagcgcctgc tgcccgtcct gtgccaggac cacggcctca ccccggagca ggtcgtcgct  1980
atcgctagca acaacggcgg caagcaggcg ctcgaaaccg tccagaggct cctcccagtc  2040
ctctgccagg atcacggcct gaccccggat caggtggtcg ccatcgcttc caacaacggc  2100
ggcaagcagg cgctggagac tgtccagcgc ctcctcccag tcctctgcca ggcgcacggc  2160
ctcacccccg atcaggtcgt ggcgatcgcg agcaacatcg gcggcaagca ggctctcgaa  2220
accgtgcaga ggctgctgcc ggtgctctgc caggctcacg gcctgacccc agaccaggtg  2280
gtggctatcg cctccaacaa cggcggcaag caggccctgg agactgtgca gaggctcctc  2340
ccagtcctgt gccaggccca cggcctgacc cccgagcagg tggtcgcgat cgcgagcaac  2400
aacggcggca agcaggcgct cgaaaccgtc cagaggctcc tccccgtgct ctgccaggat  2460
cacggcctca cccccgacca ggtcgtggct atcgcgtcca acggcggcaa gcaggctctc  2520
gagagcatcg tggcccagct gagcaggccg gacccggccc tggccgccct gaccaacgat  2580
cacctggtgg ctctggcctg cctgggcggc aggccagcca tggacgctgt gaagaagggc  2640
ctgccgcacg ctccagagct gatccgcagg gtgaacagga ggatcggcga gaggaccagc  2700
cacagggtgg ccgactacgc tcaggtggtg agggtgctgg agttcttcca gtgccacagc  2760
cacccggcct acgccttcga cgaggctatg acccagttcg gcatgagcag gaacggcctg  2820
gtgcagctgt tcaggagggt gggcgtgacc gagctggagg ctaggggcgg caccctgccg  2880
ccagctagcc agaggtggga ccgcatcctc caggccagcg gcatgaaaag ggctaagcca  2940
agcccgacca gcgctcagac cccagatcag gctagcctgc acgctttcgc cgacagcctg  3000
gagagggatc tggatgctcc gagcccaatg cacgagggcg accagaccag ggccagcagc  3060
aggaagagga gcaggagcga cagggctgtg accggcccga gcgcccagca ggctgtggag  3120
gtgagggtgc cagagcagag ggatgccctg cacctgccgc tgagctggag ggtgaagagg  3180
ccaaggacca ggatctgggg cggcctgcca gatccgggca ccccaaccgc tgctgatcag  3240
ctcgtgaaga gcgagctgga ggagaagaag agcgagctga ggcataaact gaagtacgtg  3300
ccacacgagt acatcgagct gatcgagatc gccaggaaca gcacccagga tcgcatcctg  3360
gagatgaagg tgatggagtt cttcatgaaa gtgtacggct acaggggcaa gcacctgggc  3420
ggcagcagga agccagatgg cgccatctac accgtgggca gcccaatcga ctacggcgtg  3480
atcgtggata ccaaggctta cagcggcggc tacaacctgc cgatcggcca ggctgatgag  3540
atgcagaggt acgtggagga gaatcaaacc aggaacaagc acatcaaccc aaacgagtgg  3600
tggaaggtgt acccgagcag cgtgaccgag ttcaagttcc tgttcgtgag cggccacttc  3660
aagggcaact acaaggctca gctcaccagg ctgaaccaca tcaccaactg caacggcgcc  3720
gtgctgagcg tggaggagct gctgatcggc ggcgagatga tcaaggctgg caccctgacc  3780
ctggaggagg tgaggaggaa gttcaacaac ggcgagatca acttctga              3828
```

```
SEQ ID NO: 90          moltype = DNA  length = 2910
FEATURE                Location/Qualifiers
misc_feature           1..2910
                       note = Xanthomonas ssp, Zea mays
source                 1..2910
                       mol_type = other DNA
                       organism = synthetic construct
SEQUENCE: 90
atggctagct cccccccgaa gaagaagagg aaggtcagct ggaaggatgc tagcggctgg  60
agcaggatgc acgctgatcc atggccaagg aggagggccg ctcagccaag cgatgctagc  120
cccgccgcgc aggtcgacct caggaccctg ggctacagcc agcagcagca ggagaagatc  180
aagccgaagg tgaggagcac cgtggcccag caccacgagg ctctggtggg ccacggcttc  240
acccacgctc acatcgtggc cctgagccag cacccagctg ctctgggcac cgtggctgtg  300
acctaccagc acatcatcac cgccctgcca gaggctaccc acgaggacat cgtgggcgtg  360
ggcaagcagt ggagcggcgc tagggccctg gaggctctgc tgaccgatgc tggcgagctg  420
aggggcccac cgctccagct ggataccggc cagctggtga agatcgccaa gagggggcggc  480
gtgaccgcta tggaggctgt gcacgccagc aggaacgctc tgaccggcgc tccactgaac  540
ctgacccccg accaggtggt ggccatcgcg agccacgacg gcggcaagca ggctctcgaa  600
accgtgcaga ggctgctccc ggtgctgtgc caggcccacg gcctcacccc agaccaggtc  660
gtcgcgatcg cctcccacga tggcggcaag caggccctgg agactgtgca gcgcctgctg  720
cccgtcctgt gccaggacca cggcctcacc ccggagcagg tcgtcgctat cgctagcaac  780
ggcggcggca agcaggcgct cgaaaccgtc cagaggctcc tcccagtcct ctgccaggat  840
cacggcctga ccccggatca ggtggtcgcc atcgcttcca acatcggcgg caagcaggcg  900
ctggagactg tccagcgcct cctcccagtc ctctgccagg cgcacggcct cacccccgat  960
caggtcgtgg cgatcgcgag caacatcggc ggcaagcagg ctctcgaaac cgtgcagagg  1020
ctgctgccgg tgctctgcca ggctcacggc ctgaccccag accaggtggt ggctatcgcc  1080
tccaacatcg gcggcaagca ggccctggag actgtgcaga ggctcctccc agtcctgtgc  1140
caggcccacg gcctgacccc cgagcaggtg gtcgcgatcg cgagccacga cggcggcaag  1200
caggcgctcg aaaccgtcca gaggctcctc cccgtgctct gccaggatca cggcctgacc  1260
ccagagcagg tggtggctat cgcgagcaac atcggcggca agcaggctct cgaaaccgtc  1320
cagaggctcc tcccagtgct ctgccaggct cacggcctca ccccggacca ggtcgtcgcc  1380
atcgcttcca acatcggcgg caagcaggct ctcgaaaccg tgcagaggct gctcccggtg  1440
ctgtgccagg cccacggcct caccccagac caggtcgtcg cgatcgcctc caacatcggc  1500
ggcaagcagg ccctggagac tgtgcagcgc ctgctgcccg tcctgtgcca ggaccacggc  1560
ctcaccccgg agcaggtcgt cgctatcgct agcaacaacg gcggcaagca ggcgctcgaa  1620
accgtccaga ggctcctccc agtcctctgc caggatcacg gcctgacccc ggatcaggtg  1680
gtcgccatcg cttccaacaa cggcggcaag caggcgctgg agactgtcca gcgcctcctc  1740
ccagtcctct gccaggcgca cggcctcacc cccgatcagg tcgtggcgat cgcgagcaac  1800
atcggcggca agcaggctct cgaaaccgtg cagaggctgc tgccggtgct ctgccaggct  1860
cacggcctga ccccagacca ggtggtggct atcgcctcca acaacggcgg caagcaggcc  1920
ctggagactg tgcagaggct cctcccagtc ctgtgccagg cccacggcct gacccccgag  1980
caggtggtcg cgatcgcgag caacaacggc ggcaagcagg cgctcgaaac cgtccagagg  2040
ctcctccccg tgctctgcca ggatcacggc ctcacccccg accaggtcgt ggctatcgcg  2100
tccaacggcg gcaagcaggc tctcgagagc atcgtggccc agctgagcag gccggacccg  2160
gccctggccg ccctgaccaa cgatcacctg gtggctctgg cctgcctggg cggcaggcca  2220
gccatggacg ctgtgaagaa gggcctgccg cacgctccag agctgatccg cagggtgaac  2280
```

-continued

```
aggaggatcg gcgagaggac cagccacagg gtggccctgc agctcgtgaa gagcgagctg  2340
gaggagaaga agagcgagct gaggcataaa ctgaagtacg tgccacacga gtacatcgag  2400
ctgatcgaga tcgccaggaa cagcacccag gatcgcatcc tggagatgaa ggtgatggag  2460
ttcttcatga aagtgtacgg ctacaggggc aagcacctgg gcggcagcag gaagccagat  2520
ggcgccatct acaccgtggg cagcccaatc gactacggcg tgatcgtgga taccaaggct  2580
tacagcggcg gctacaacct gccgatcggc caggctgatg agatgcagag gtacgtggag  2640
gagaatcaaa ccaggaacaa gcacatcaac ccaaacgagt ggtggaaggt gtacccgagc  2700
agcgtgaccg agttcaagtt cctgttcgtg agcggccact tcaagggcaa ctacaaggct  2760
cagctcacca ggctgaacca catcaccaac tgcaacggcg ccgtgctgag cgtggaggag  2820
ctgctgatcg gcggcgagat gatcaaggct ggcaccctga ccctggagga ggtgaggagg  2880
aagttcaaca acggcgagat caacttctga                                  2910
```

```
SEQ ID NO: 91          moltype = DNA  length = 3075
FEATURE                Location/Qualifiers
misc_feature           1..3075
                       note = Xanthomonas ssp, Zea mays
source                 1..3075
                       mol_type = other DNA
                       organism = synthetic construct
SEQUENCE: 91
atgggaaaac ctattcctaa tcctctgctg ggcctggatt ctaccggagg catggcccct  60
aagaaaaagc ggaaggtgga cggcggagtg gacctgagaa cactgggata ttctcagcag  120
cagcaggaga agatcaagcc caaggtgaga tctacagtgg cccagcacca cgaagccctg  180
gtgggacacg gatttacaca cgcccacatt gtggccctgt ctcagcaccc tgccgccctg  240
ggaacagtgg ccgtgaaata tcaggatatg attgccgccc tgcctgaggc cacacacgaa  300
gccattgtgg gagtgggaaa acagtggtct ggagccagag ccctggaagc cctgctgaca  360
gtggccggag aactgagagg acctcctctg cagctggata caggacagct gctgaagatt  420
gccaaaaggg gcggagtgac cgcggtggaa gccgtgcacg cctggagaaa tgccctgaca  480
ggagcccctc tgaacctgac cccgaacag gtggtggcca ttgccagcca cgacggcggc  540
aagcaggccc tggaaaccgt gcagagactg ctgcccgtgc tgtgccaggc ccatggcctg  600
acacctgaac aggtggtggc tatcgcctct cacgacggag gaaaacaggc tctggaaaca  660
gtgcagcggc tgctgcctgt gctgtgtcag gctcacggct tgactccaga acaggtggtg  720
gctattgctt ccaacggcgg ggggaaacag gccctggaaa ctgtgcagcg cctgctgcca  780
gtgctgtgcc aggctcacgg actgaccccc gaacaggtgg tggccattgc cagcaacatc  840
ggcggcaagc aggccctgga aaccgtgcag agactgctgc ccgtgctgtg ccaggcccat  900
ggcctgacac ctgaacaggt ggtggctatc gcctctaata tcggaggaaa acaggctctg  960
gaaacagtgc agcggctgct gcctgtgctg tgtcaggctc acggcttgac tccagaacag  1020
gtggtggcta ttgcttccaa tattgggggg aaacaggccc tggaaactgt gcagcgcctg  1080
ctgccagtgc tgtgccaggc tcacgggctg acccccgaac aggtggtggc cattgccagc  1140
cacgacggcg gcaagcaggc cctggaaacc gtgcagagac tgctgcccgt gctgtgccag  1200
gcccatggcc tgacacctga acaggtggtg gctatcgcct ctaatatcgg aggaaaacag  1260
gctctggaaa cagtgcagcg gctgctgcct gtgctgtgtc aggctcacgg cttgactcca  1320
gaacaggtgg tggctattgc ttccaatatt ggggggaaac aggccctgga aactgtgcag  1380
cgcctgctgc cagtgctgtg ccaggctcac ggcctcactc ccgaacaggt ggtggccatt  1440
gccagcaaca tcggcggcaa gcaggccctg gaaaccgtgc agagactgct gcccgtgctg  1500
tgccaggccc atggcctgac acctgaacag gtggtggcta tcgcctctaa caacggagga  1560
aaacaggctc tggaaacagt gcagcggctg ctgcctgtgc tgtgtcaggc tcacggcttg  1620
actccagaac aggtggtggc tattgcttcc aacaacgggg ggaaacaggc cctggaaact  1680
gtgcagcgcc tgctgccagt gctgtgccag gctcacggac tgacccccga acaggtggtg  1740
gccattgcca gcaacatcgg cggcaagcag gccctggaaa ccgtgcagag actgctgccc  1800
gtgctgtgcc aggcccatgg cctgacacct gaacaggtgg tggctatcgc ctctaacaac  1860
ggaggaaaac aggctctgga aacagtgcag cggctgctgc ctgtgctgtg tcaggctcac  1920
ggcttgactc cagaacaggt ggtggctatt gcttccaaca acggggggaa acaggccctg  1980
gaaactgtgc agcgcctgct gccagtgctg tgccaggctc acgggctgac ccccgaacag  2040
gtggtggcca ttgccagcaa cggcggcggc aagcaggccc tggaaaccgt gcagagactg  2100
ctgcccgtgc tgtgccaggc ccatggcctg acacctgaac aggtggtggc tatcgcctct  2160
cacgacggag gaaaacaggc tctggaaaca gtgcagcggc tgctgcctgt gctgtgtcag  2220
gctcacggct tgactccaca gcaggtcgtg gcaattgcta gccacgacgg cggacggccc  2280
gccctggaga gcattgtggc ccagctgtct agacctgatc ctgccctggc cgccctgaca  2340
aatgatcacc tggtggccct ggcctgtctg ggaggcagac ctgccctgga tgccgtgaaa  2400
aaaggactgc ctcacgcccc tgccctgatt aaaagaacaa atagaagaat ccccgagcgg  2460
acctctcaca gagtggccgg atcccagctg gtgaaatctg agctggagga gaagaagtct  2520
gagctgagac acaagctgaa gtacgtgcct cacgagtaca tcgagctgat cgagatcgcc  2580
agaaatagca cccaggatag aatcctggag atgaaggtga tggagttctt catgaaagtg  2640
tacggctaca gaggaaagca tctgggagga agcagaaaac ctgacggagc catttataca  2700
gtgggcagcc ctatcgatta tggcgtgatc gtggatacaa aggcctacag cggaggctac  2760
aatctgccta ttggacaggc cgatgagatg cagagatacg tggaggagaa ccaaaccagg  2820
aacaagcata tcaaccctaa cgagtggtgg aaggtgtacc cttctagcgt gaccgagttc  2880
aagttcctgt ttgtgagcgg ccacttcaag ggcaattata aggcccagct gaccaggctg  2940
aaccacatca caaattgtaa tggcgccgtg ctgtctgtgg aggaactgct gattggagga  3000
gagatgatta aggccggaac actgacactg gaggaggtga gaagaaagtt caacaacggc  3060
gagatcaact tctga                                                  3075
```

```
SEQ ID NO: 92          moltype = DNA  length = 19
FEATURE                Location/Qualifiers
source                 1..19
                       mol_type = other DNA
                       organism = Zea mays
SEQUENCE: 92
```

```
cacacctcgt tgccaaagc                                         19

SEQ ID NO: 93          moltype = DNA  length = 21
FEATURE                Location/Qualifiers
source                 1..21
                       mol_type = other DNA
                       organism = Zea mays
SEQUENCE: 93
catcgcgtcc taaacaaagg a                                      21

SEQ ID NO: 94          moltype = DNA  length = 15
FEATURE                Location/Qualifiers
source                 1..15
                       mol_type = other DNA
                       organism = Zea mays
SEQUENCE: 94
cctgtcctgc actgc                                             15

SEQ ID NO: 95          moltype = DNA  length = 15
FEATURE                Location/Qualifiers
source                 1..15
                       mol_type = other DNA
                       organism = Zea mays
SEQUENCE: 95
gcagtgcagg acagg                                             15

SEQ ID NO: 96          moltype = DNA  length = 22
FEATURE                Location/Qualifiers
source                 1..22
                       mol_type = other DNA
                       organism = Zea mays
SEQUENCE: 96
tgcagtgcag tgcaggacag ga                                     22

SEQ ID NO: 97          moltype = DNA  length = 23
FEATURE                Location/Qualifiers
source                 1..23
                       mol_type = other DNA
                       organism = Zea mays
SEQUENCE: 97
ctcgttgcca aagctgcatc cgt                                    23

SEQ ID NO: 98          moltype = DNA  length = 1176
FEATURE                Location/Qualifiers
misc_feature           1..1176
                       note = Escherichia coli
source                 1..1176
                       mol_type = other DNA
                       organism = synthetic construct
SEQUENCE: 98
atgcaaaaac tcattaactc agtgcaaaac tatgcctggg gcagcaaaac ggcgttgact  60
gaactttatg gtatggaaaa tccgtccagc cagccgatgg ccgagctgtg gatgggcgca  120
catccgaaaa gcagttcacg agtgcagaat gccgccggag atatcgtttc actgcgtgat  180
gtgattgaga gtgataaatc gactctgctc ggagaggccg ttgccaaacg ctttggcgaa  240
ctgcctttcc tgttcaaagt attatgcgca gcacagccac tctccattca ggttcatcca  300
aacaaacaca attctgaaat cggttttgcc aaagaaaatg ccgcaggtat cccgatggat  360
gccgccgagc gtaactataa agatcctaac cacaagccgg agctggtttt tgcgctgacg  420
cctttccttg cgatgaacgc gtttcgtgaa ttttccgaga ttgtctccct actccagccg  480
gtcgcaggtg cacatccggc gattgctcac tttttacaac agcctgatgc cgaacgttta  540
agcgaactgt tcgccagcct gttgaatatg cagggtgaag aaaaatcccg cgcgctggcg  600
attttaaaat cggccctcga tagccagcag ggtgaaccgt ggcaaacgat tcgtttaatt  660
tctgaatttt acccggaaga cagcggtctg ttctccccgc tattgctgaa tgtggtgaaa  720
ttgaaccctg gcgaagcgat gttcctgttc gctgaaacac cgcacgctta cctgcaaggc  780
gtggcgctgg aagtgatggc aaactccgat aacgtgctgc gtgcgggtct gacgcctaaa  840
tacattgata ttccggaact ggttgccaat gtgaaattcg aagccaaacc ggctaaccag  900
ttgttgaccc agccggtgaa acaaggtgca gaactggact tcccgattcc agtggatgat  960
tttgccttct cgctgcatga ccttagtgat aaagaaacca ccattagcca gcagagtgcc  1020
gccattttgt tctgcgtcga aggcgatgca acgttgtgga aaggttctca gcagttacag  1080
cttaaaccgg gtgaatcagc gtttattgcc gccaacgaat caccggtgac tgtcaaaggc  1140
cacggccgtt tagcgcgtgt ttacaacaag ctgtaa                      1176

SEQ ID NO: 99          moltype = DNA  length = 50
FEATURE                Location/Qualifiers
misc_feature           1..50
                       note = Escherichia coli
source                 1..50
                       mol_type = other DNA
                       organism = synthetic construct
SEQUENCE: 99
```

-continued

```
ttaactcagt gcaaaactat gcctggggca gcaaaacggc gttgactgaa            50

SEQ ID NO: 100         moltype = DNA  length = 53
FEATURE                Location/Qualifiers
misc_feature           1..53
                       note = Escherichia coli
source                 1..53
                       mol_type = other DNA
                       organism = synthetic construct
SEQUENCE: 100
tctccattca ggttcatcca aacaaacaca attctgaaat cggttttgcc aaa        53

SEQ ID NO: 101         moltype = DNA  length = 53
FEATURE                Location/Qualifiers
misc_feature           1..53
                       note = Escherichia coli
source                 1..53
                       mol_type = other DNA
                       organism = synthetic construct
SEQUENCE: 101
tgcacatccg gcgattgctc actttttaca acagcctgat gccgaacgtt taa        53

SEQ ID NO: 102         moltype = DNA  length = 18
FEATURE                Location/Qualifiers
misc_feature           1..18
                       note = Escherichia coli
source                 1..18
                       mol_type = other DNA
                       organism = synthetic construct
SEQUENCE: 102
ttaactcagt gcaaaact                                               18

SEQ ID NO: 103         moltype = DNA  length = 18
FEATURE                Location/Qualifiers
misc_feature           1..18
                       note = Escherichia coli
source                 1..18
                       mol_type = other DNA
                       organism = synthetic construct
SEQUENCE: 103
ttcagtcaac gccgtttt                                               18

SEQ ID NO: 104         moltype = DNA  length = 19
FEATURE                Location/Qualifiers
misc_feature           1..19
                       note = Escherichia coli
source                 1..19
                       mol_type = other DNA
                       organism = synthetic construct
SEQUENCE: 104
tctccattca ggttcatcc                                              19

SEQ ID NO: 105         moltype = DNA  length = 19
FEATURE                Location/Qualifiers
misc_feature           1..19
                       note = Escherichia coli
source                 1..19
                       mol_type = other DNA
                       organism = synthetic construct
SEQUENCE: 105
tttggcaaaa ccgatttca                                              19

SEQ ID NO: 106         moltype = DNA  length = 19
FEATURE                Location/Qualifiers
misc_feature           1..19
                       note = Escherichia coli
source                 1..19
                       mol_type = other DNA
                       organism = synthetic construct
SEQUENCE: 106
tgcacatccg gcgattgct                                              19

SEQ ID NO: 107         moltype = DNA  length = 18
FEATURE                Location/Qualifiers
misc_feature           1..18
                       note = Escherichia coli
source                 1..18
                       mol_type = other DNA
                       organism = synthetic construct
```

-continued

```
SEQUENCE: 107
ttaaacgttc ggcatcag                                                    18

SEQ ID NO: 108          moltype = AA  length = 1000
FEATURE                 Location/Qualifiers
REGION                  1..1000
                        note = Xanthomonas ssp, Escherichia coli
source                  1..1000
                        mol_type = protein
                        organism = synthetic construct
SEQUENCE: 108
MEQKLISEED LVDLRTLGYS QQQQEKIKPK VRSTVAQHHE ALVGHGFTHA HIVALSQHPA  60
ALGTVAVTYQ HIITALPEAT HEDIVGVGKQ WSGARALEAL LTDAGELRGP PLQLDTGQLV  120
KIAKRGGVTA MEAVHASRNA LTGAPLNLTP DQVVAIASNG GGKQALETVQ RLLPVLCQAH  180
GLTPDQVVAI ASNIGGKQAL ETVQRLLPVL CQDHGLTPEQ VVAIARNIGG KQALETVQRL  240
LPVLCQDHGL TPDQVVAIAS HDGGKQALET VQRLLPVLCQ AHGLTPDQVV AIARNGGGKQ  300
ALETVQRLLP VLCQAHGLTP DQVVAIASHD GGKQALETVQ RLLPVLCQAH GLTPEQVVAI  360
ARNIGGKQAL ETVQRLLPVL CQDHGLTPDQ VVAIASNKGG KQALETVQRL LPVLCQDHGL  420
TPEQVVAIAS NGGGKQALET VQRLLPVLCQ AHGLTPDQVV AIASNKGGKQ ALETVQRLLP  480
VLCQDHGLTP DQVVAIASHD GGKQALETVQ RLLPVLCQDH GLTPDQVVAI ASNIGGKQAL  540
ETVQRLLPVL CQDHGLTPDQ VVAIASNIGG KQALETVQRL LPVLCQAHGL TPEQVVAIAR  600
NIGGKQALET VQRLLPVLCQ AHGLTPEQVV AIASNIGGKQ ALETVQRLLP VLCQAHGLTP  660
DQVVAIARHD GGKQALETVQ RLLPVLCQDH GLTPDQVVAI ASNGGGKQAL ESIVAQLSRP  720
DPALAALTND HLVALACLGG RPAMDAVKKG LPHAPELIRR VNRRIGERTS HRVADYAQVV  780
RVLEFFQCHS HPAYAFDEAM TQFGQLVKSE LEEKKSELRH KLKYVPHEYI ELIEIARNST  840
QDRILEMKVM EFFMKVYGYR GKHLGGSRKP DGAIYTVGSP IDYGVIVDTK AYSGGYNLPI  900
GQADEMQRYV EENQTRNKHI NPNEWWKVYP SSVTEFKFLF VSGHFKGNYK AQLTRLNHIT  960
NCNGAVLSVE ELLIGGEMIK AGTLTLEEVR RKFNNGEINF                        1000

SEQ ID NO: 109          moltype = AA  length = 1000
FEATURE                 Location/Qualifiers
REGION                  1..1000
                        note = Xanthomonas ssp, Escherichia coli
source                  1..1000
                        mol_type = protein
                        organism = synthetic construct
SEQUENCE: 109
MEQKLISEED LVDLRTLGYS QQQQEKIKPK VRSTVAQHHE ALVGHGFTHA HIVALSQHPA  60
ALGTVAVTYQ HIITALPEAT HEDIVGVGKQ WSGARALEAL LTDAGELRGP PLQLDTGQLV  120
KIAKRGGVTA MEAVHASRNA LTGAPLNLTP DQVVAIASNG GGKQALETVQ RLLPVLCQAH  180
GLTPDQVVAI ASHDGGKQAL ETVQRLLPVL CQDHGLTPEQ VVAIARNIGG KQALETVQRL  240
LPVLCQDHGL TPDQVVAIAS NKGGKQALET VQRLLPVLCQ AHGLTPDQVV AIARNGGGKQ  300
ALETVQRLLP VLCQAHGLTP DQVVAIASHD GGKQALETVQ RLLPVLCQAH GLTPEQVVAI  360
ARNIGGKQAL ETVQRLLPVL CQDHGLTPDQ VVAIASNIGG KQALETVQRL LPVLCQDHGL  420
TPEQVVAIAS HDGGKQALET VQRLLPVLCQ AHGLTPDQVV AIASNKGGKQ ALETVQRLLP  480
VLCQDHGLTP DQVVAIASHD GGKQALETVQ RLLPVLCQDH GLTPDQVVAI ASHDGGKQAL  540
ETVQRLLPVL CQDHGLTPDQ VVAIASNKGG KQALETVQRL LPVLCQAHGL TPEQVVAIAR  600
NGGGKQALET VQRLLPVLCQ AHGLTPEQVV AIASNGGGKQ ALETVQRLLP VLCQAHGLTP  660
DQVVAIARNG GGKQALETVQ RLLPVLCQDH GLTPDQVVAI ASNGGGKQAL ESIVAQLSRP  720
DPALAALTND HLVALACLGG RPAMDAVKKG LPHAPELIRR VNRRIGERTS HRVADYAQVV  780
RVLEFFQCHS HPAYAFDEAM TQFGQLVKSE LEEKKSELRH KLKYVPHEYI ELIEIARNST  840
QDRILEMKVM EFFMKVYGYR GKHLGGSRKP DGAIYTVGSP IDYGVIVDTK AYSGGYNLPI  900
GQADEMQRYV EENQTRNKHI NPNEWWKVYP SSVTEFKFLF VSGHFKGNYK AQLTRLNHIT  960
NCNGAVLSVE ELLIGGEMIK AGTLTLEEVR RKFNNGEINF                        1000

SEQ ID NO: 110          moltype = AA  length = 1001
FEATURE                 Location/Qualifiers
REGION                  1..1001
                        note = Xanthomonas ssp, Escherichia coli
source                  1..1001
                        mol_type = protein
                        organism = synthetic construct
SEQUENCE: 110
MGDPKKKRKV IDYPYDVPDY AIDIADLRTL GYSQQQQEKI KPKVRSTVAQ HHEALVGHGF  60
THAHIVALSQ HPAALGTVAV KYQDMIAALP EATHEAIVGV GKQWSGARAL EALLTVAGEL  120
RGPPLQLDTG QLLKIAKRGG VTAVEAVHAW RNALTGAPLN LTPQQVVAIA SNNGGKQALE  180
TVQRLLPVLC QAHGLTPEQV VAIASHDGGK QALETVQRLL PVLCQAHGLT PEQVVAIASN  240
IGGKQALETV QALLPVLCQA HGLTPEQVVA IASHDGGKQA LETVQRLLPV LCQAHGLTPE  300
QVVAIASNIG GKQALETVQA LLPVLCQAHG LTPQQVVAIA SNGGGKQALE TVQRLLPVLC  360
QAHGLTPEQV VAIASHDGGK QALETVQRLL PVLCQAHGLT PEQVVAIASH DGGKQALETV  420
QRLLPVLCQA HGLTPQQVVA IASNNGGKQA LETVQRLLPV LCQAHGLTPQ QVVAIASNNG  480
GKQALETVQR LLPVLCQAHG LTPEQVVAIA SHDGGKQALE TVQRLLPVLC QAHGLTPQQV  540
VAIASNNGGK QALETVQRLL PVLCQAHGLT PEQVVAIASN IGGKQALETV QALLPVLCQA  600
HGLTPQQVVA IASNGGGKQA LETVQRLLPV LCQAHGLTPQ QVVAIASNGG GKQALETVQR  660
LLPVLCQAHG LTPQQVVAIA SNNGGKQALE TVQRLLPVLC QAHGLTPEQV VAIASHDGGK  720
QALETVQRLL PVLCQAHGLT PQQVVAIASN GGGRPALESI VAQLSRPDPA LAALTNDHLV  780
ALACLGGRPA LDAVKKGLGD PISRSQLVKS ELEEKKSELR HKLKYVPHEY IELIEIARNS  840
TQDRILEMKV MEFFMKVYGY RGKHLGGSRK PDGAIYTVGS PIDYGVIVDT KAYSGGYNLP  900
IGQADEMQRY VEENQTRNKH INPNEWWKVY PSSVTEFKFL FVSGHFKGNY KAQLTRLNHI  960
```

```
TNCNGAVLSV EELLIGGEMI KAGTLTLEEV RRKFNNGEIN F                    1001

SEQ ID NO: 111          moltype = AA  length = 1007
FEATURE                 Location/Qualifiers
REGION                  1..1007
                        note = Xanthomonas ssp, Escherichia coli
source                  1..1007
                        mol_type = protein
                        organism = synthetic construct
SEQUENCE: 111
MGDPKKKRKV IDKETAAAKF ERQHMDSIDI ADLRTLGYSQ QQQEKIKPKV RSTVAQHHEA  60
LVGHGFTHAH IVALSQHPAA LGTVAVKYQD MIAALPEATH EAIVGVGKQW SGARALEALL  120
TVAGELRGPP LQLDTGQLLK IAKRGGVTAV EAVHAWRNAL TGAPLNLTPQ QVVAIASNGG  180
GKQALETVQR LLPVLCQAHG LTPEQVVAIA SNIGGKQALE TVQALLPVLC QAHGLTPEQV  240
VAIASNIGGK QALETVQALL PVLCQAHGLT PEQVVAIASN IGGKQALETV QALLPVLCQA  300
HGLTPEQVVA IASHDGGKQA LETVQRLLPV LCQAHGLTPQ QVVAIASNNG GKQALETVQR  360
LLPVLCQAHG LTPQQVVAIA SNGGGKQALE TVQRLLPVLC QAHGLTPQQV VAIASNGGGK  420
QALETVQRLL PVLCQAHGLT PEQVVAIASH DGGKQALETV QRLLPVLCQA HGLTPQQVVA  480
IASNNGGKQA LETVQRLLPV LCQAHGLTPQ QVVAIASNNG GKQALETVQR LLPVLCQAHG  540
LTPEQVVAIA SHDGGKQALE TVQRLLPVLC QAHGLTPEQV VAIASNIGGK QALETVQALL  600
PVLCQAHGLT PQQVVAIASN GGGKQALETV QRLLPVLCQA HGLTPEQVVA IASHDGGKQA  660
LETVQRLLPV LCQAHGLTPE QVVAIASNIG GKQALETVQA LLPVLCQAHG LTPQQVVAIA  720
SNNGGKQALE TVQRLLPVLC QAHGLTPQQV VAIASNGGGR PALESIVAQL SRPDPALAAL  780
TNDHLVALAC LGGRPALDAV KKGLGDPISR SQLVKSELEE KKSELRHKLK YVPHEYIELI  840
EIARNSTQDR ILEMKVMEFF MKVYGYRGKH LGGSRKPDGA IYTVGSPIDY GVIVDTKAYS  900
GGYNLPIGQA DEMQRYVEEN QTRNKHINPN EWWKVYPSSV TEFKFLFVSG HFKGNYKAQL  960
TRLNHITNCN GAVLSVEELL IGGEMIKAGT LTLEEVRRKF NNGEINF              1007

SEQ ID NO: 112          moltype = DNA  length = 3003
FEATURE                 Location/Qualifiers
misc_feature            1..3003
                        note = Xanthomonas ssp, Escherichia coli
source                  1..3003
                        mol_type = other DNA
                        organism = synthetic construct
SEQUENCE: 112
atggagcaga agctgatcag cgaggaggac ctcgtcgacc tcaggaccct gggctacagc  60
cagcagcagc aggagaagat caagccgaag gtgaggagca ccgtggccca gcaccacgag  120
gctctggtgg gccacggctt cacccacgct cacatcgtgg ccctgagcca gcacccagct  180
gctctgggca ccgtggctgt gacctaccag cacatcatca ccgccctgcc agaggctacc  240
cacgaggaca tcgtgggcgt gggcaagcag tggagcggcg ctagggccct ggaggctctg  300
ctgaccgatg ctggcgagct gaggggccca ccgctccagc tggataccgg ccagctggtg  360
aagatcgcca agaggggcgg cgtgaccgct atggaggctg tgcacgccag caggaacgct  420
ctgaccggcg ctccactgaa cctgaccccc gaccaggtgg tggccatcgc gagcaacggc  480
ggcggcaagc aggctctcga aaccgtgcag aggctgctcc cggtgctgtg ccaggcccac  540
ggcctcaccc cagaccaggt cgtcgcgatc gcctccaaca tcggcggcaa gcaggccctg  600
gagactgtgc agcgcctgct gcccgtcctg tgccaggacc acggcctcac cccggagcag  660
gtcgtcgcta tcgctagaaa catcggcggc aagcaggcgc tcgaaaccgt ccagaggctc  720
ctcccagtcc tctgccagga tcacggcctg accccggatc aggtggtcgc catcgcttca  780
cacgacggcg gcaagcaggc gctggagact gtccagcgcc tcctcccagt cctctgccag  840
gcgcacggcc tcacccccga tcaggtcgtg gcgatcgcga gaaacggcgg cggcaagcag  900
gctctcgaaa ccgtgcagag gctgctgccg gtgctctgcc aggctcacgg cctgacccca  960
gaccaggtgg tggctatcgc ctcccacgac ggcggcaagc aggccctgga gactgtgcag  1020
aggctgctgc cggtcctgtg ccaggcccac ggcctcaccc ccgagcaggt cgtcgcgatc  1080
gctagaaaca tcggcggcaa gcaggccctg gagactgtcc agaggctcct cccggtcctg  1140
tgccaggacc acggcctgac cccggaccag gtggtcgcca tcgcctccaa caagggcggc  1200
aagcaggcgc tcgaaaccgt gcagaggctc ctgccggtgc tctgccagga tcacggcctg  1260
accccagagc aggtggtggc tatcgcgagc aacggcggcg gcaagcaggc tctcgaaacc  1320
gtccagaggc tcctcccagt gctctgccag gctcacggcc tcaccccgga ccaggtcgtc  1380
gccatcgctt caaacaaggg cggcaagcag gccctggaga ctgtgcagag gctgctgccc  1440
gtgctgtgcc aggaccacgg cctgacccca gatcaggtgg tggctatcgc tagccacgac  1500
ggcggcaagc aggcgctgga gactgtccag aggctcctcc cagtcctgtg ccaggatcac  1560
ggcctcaccc cggaccaggt cgtcgccatc gcttcaaaca tcggcggcaa gcaggccctg  1620
gagactgtgc agaggctgct gcccgtgctg tgccaggacc acggcctcac cccggatcag  1680
gtcgtggcca tcgcgtccaa catcggcggc aagcaggcgc tggagactgt ccagaggctg  1740
ctgcccgtcc tgtgccaggc gcacggcctc accccagagc aggtcgtcgc catcgccaga  1800
aacatcggcg gcaagcaggc tctcgaaacc gtgcagaggc tgctgcccgt gctctgccag  1860
gcccacggcc tgaccccgga gcaggtggtg gcgatcgcct ccaacatcgg cggcaagcag  1920
gctctcgaaa ccgtgcagag gctcctcccc gtgctctgcc aggctcacgg cctgaccccc  1980
gatcaggtgg tcgcgatcgc tagacacgac ggcggcaagc aggccctgga gactgtccag  2040
cgcctgctgc cagtcctgtg ccaggaccac ggcctcaccc ccgaccaggt cgtggctatc  2100
gcgtccaacg gcggcggcaa gcaggctctc gagagcatcg tggcccagct gagcaggccg  2160
gacccggccc tggccgccct gaccaacgat cacctggtgg ctctggcctg cctgggcggc  2220
aggccagcca tggacgctgt gaagaagggc ctgccgcacg ctccagagct gatccgcagg  2280
gtgaacagga ggatcggcga gaggaccagc cacagggtgg ccgactacgc tcaggtggtg  2340
agggtgctgg agttcttcca gtgccacagc cacccggcct acgccttcga cgaggctatg  2400
acccagttcg gccagctcgt gaagagcgag ctggaggaga agaagagcga gctgaggcac  2460
aagctgaagt acgtgccaca cgagtacatc gagctgatcg agatcgccag gaacagcacc  2520
caggatcgca tcctggagat gaaggtgatg gagttcttca tgaaggtgta cggctacagg  2580
```

```
ggcaagcacc tgggcggcag caggaagcca gatggcgcca tctacaccgt gggcagccca  2640
atcgactacg gcgtgatcgt ggataccaag gcttacagcg gcggctacaa cctgccgatc  2700
ggccaggctg atgagatgca gaggtacgtg gaggagaacc agaccaggaa caagcacatc  2760
aacccaaacg agtggtggaa ggtgtacccg agcagcgtga ccgagttcaa gttcctgttc  2820
gtgagcggcc acttcaaggg caactacaag gctcagctca ccaggctgaa ccacatcacc  2880
aactgcaacg gcgccgtgct gagcgtggag gagctgctga tcggcggcga gatgatcaag  2940
gctggcaccc tgaccctgga ggaggtgagg aggaagttca acaacggcga gatcaacttc  3000
tga                                                                3003
```

```
SEQ ID NO: 113         moltype = DNA  length = 3003
FEATURE                Location/Qualifiers
misc_feature           1..3003
                       note = Xanthomonas ssp, Escherichia coli
source                 1..3003
                       mol_type = other DNA
                       organism = synthetic construct
SEQUENCE: 113
atggagcaga agctgatcag cgaggaggac ctcgtcgacc tcaggaccct gggctacagc  60
cagcagcagc aggagaagat caagccgaag gtgaggagca ccgtggccca gcaccacgag  120
gctctggtgg gccacggctt cacccacgct cacatcgtgg ccctgagcca gcacccagct  180
gctctgggca ccgtggctgt gacctaccag cacatcatca ccgccctgcc agaggctacc  240
cacgaggaca tcgtgggcgt gggcaagcag tggagcggcg ctagggccct ggaggctctg  300
ctgaccgatg ctggcgagct gaggggccca ccgctccagc tggataccgg ccagctggtg  360
aagatcgcca agaggggcgg cgtgaccgct atggaggctg tgcacgccag caggaacgct  420
ctgaccggcg ctccactgaa cctgaccccc gaccaggtgg tggccatcgc gagcaacggc  480
ggcggcaagc aggctctcga aaccgtgcag aggctgctcc cggtgctgtg ccaggcccac  540
ggcctcaccc cagaccaggt cgtcgcgatc gcctcccacg acggcggcaa gcaggccctg  600
gagactgtgc agcgcctgct gcccgtcctg tgccaggacc acggcctcac cccggagcag  660
gtcgtcgcta tcgctagaaa catcggcggc aagcaggcgc tcgaaaccgt ccagaggctc  720
ctcccagtcc tctgccagga tcacggcctg accccggatc aggtggtcgc catcgcttca  780
aacaagggcg gcaagcaggc gctggagact gtccagcgcc tcctcccagt cctctgccag  840
gcgcacggcc tcacccccga tcaggtcgtg gcgatcgcga gaaacggcgg cggcaagcag  900
gctctcgaaa ccgtgcagag gctgctgccg gtgctctgcc aggctcacgg cctgacccca  960
gaccaggtgg tggctatcgc ctcccacgac ggcggcaagc aggccctgga gactgtgcag  1020
aggctgctgc cggtcctgtg ccaggcccac ggcctcaccc ccgagcaggt cgtcgcgatc  1080
gctagaaaca tcggcggcaa gcaggccctg gagactgtcc agaggctcct cccggtcctg  1140
tgccaggacc acggcctgac cccggaccag gtggtcgcca tcgcctccaa catcggcggc  1200
aagcaggcgc tcgaaaccgt gcagaggctc ctgccggtgc tctgccagga tcacggcctg  1260
accccagagc aggtggtggc tatcgcgagc cacgacggcg gcaagcaggc tctcgaaacc  1320
gtccagaggc tcctcccagt gctctgccag gctcacggcc tcaccccgga ccaggtcgtc  1380
gccatcgctt caaacaaggg cggcaagcag gccctggaga ctgtgcagag gctgctgccc  1440
gtgctgtgcc aggaccacgg cctgacccca gatcaggtgg tggctatcgc tagccacgac  1500
ggcggcaagc aggcgctgga gactgtccag aggctcctcc cagtcctgtg ccaggatcac  1560
ggcctcaccc cggaccaggt cgtcgccatc gcttcacacg acggcggcaa gcaggccctg  1620
gagactgtgc agaggctgct gcccgtgctg tgccaggacc acggcctcac cccggatcag  1680
gtcgtggcca tcgcgtccaa caagggcggc aagcaggcgc tggagactgt ccagaggctg  1740
ctgcccgtcc tgtgccaggc gcacggcctc accccagagc aggtcgtcgc catcgccaga  1800
aacggcggcg gcaagcaggc tctcgaaacc gtgcagaggc tgctgcccgt gctctgccag  1860
gcccacggcc tgaccccgga gcaggtggtg gcgatcgcct ccaacggcgg cggcaagcag  1920
gctctcgaaa ccgtgcagag gctcctcccc gtgctctgcc aggctcacgg cctgaccccc  1980
gatcaggtgg tcgcgatcgc tagaaacggc ggcggcaagc aggccctgga gactgtccag  2040
cgcctgctgc cagtcctgtg ccaggaccac ggcctcaccc ccgaccaggt cgtggctatc  2100
gcgtccaacg gcggcggcaa gcaggctctc gagagcatcg tggcccagct gagcaggccg  2160
gacccggccc tggccgccct gaccaacgat cacctggtgg ctctggcctg cctgggcggc  2220
aggccagcca tggacgctgt gaagaagggc ctgccgcacg ctccagagct gatccgcagg  2280
gtgaacagga ggatcggcga gaggaccagc cacagggtgg ccgactacgc tcaggtggtg  2340
agggtgctgg agttcttcca gtgccacagc cacccggcct acgccttcga cgaggctatg  2400
acccagttcg gccagctcgt gaagagcgag ctggaggaga agaagagcga gctgaggcac  2460
aagctgaagt acgtgccaca cgagtacatc gagctgatcg agatcgccag gaacagcacc  2520
caggatcgca tcctggagat gaaggtgatg gagttcttca tgaaggtgta cggctacagg  2580
ggcaagcacc tgggcggcag caggaagcca gatggcgcca tctacaccgt gggcagccca  2640
atcgactacg gcgtgatcgt ggataccaag gcttacagcg gcggctacaa cctgccgatc  2700
ggccaggctg atgagatgca gaggtacgtg gaggagaacc agaccaggaa caagcacatc  2760
aacccaaacg agtggtggaa ggtgtacccg agcagcgtga ccgagttcaa gttcctgttc  2820
gtgagcggcc acttcaaggg caactacaag gctcagctca ccaggctgaa ccacatcacc  2880
aactgcaacg gcgccgtgct gagcgtggag gagctgctga tcggcggcga gatgatcaag  2940
gctggcaccc tgaccctgga ggaggtgagg aggaagttca acaacggcga gatcaacttc  3000
tga                                                                3003
```

```
SEQ ID NO: 114         moltype = DNA  length = 3006
FEATURE                Location/Qualifiers
misc_feature           1..3006
                       note = Xanthomonas ssp, Escherichia coli
source                 1..3006
                       mol_type = other DNA
                       organism = synthetic construct
SEQUENCE: 114
atgggcgatc ctaaaaagaa acgtaaggtc atcgattacc catacgatgt tccagattac  60
gctatcgata tcgccgatct acgcacgctc ggctacagcc agcagcaaca ggagaagatc  120
```

-continued

```
aaaccgaagg ttcgttcgac agtggcgcag caccacgagg cactggtcgg ccacgggttt  180
acacacgcgc acatcgttgc gttaagccaa cacccggcag cgttagggac cgtcgctgtc  240
aagtatcagg acatgatcgc agcgttgcca gaggcgacac acgaagcgat cgttggcgtc  300
ggcaaacagt ggtccggcgc acgcgctctg gaggccttgc tcacggtggc gggagagttg  360
agaggtccac cgttacagtt ggacacaggc caacttctca agattgcaaa acgtggcggc  420
gtgaccgcag tggaggcagt gcatgcatgg cgcaatgcac tgacgggtgc cccgctcaac  480
ttgaccccccc agcaggtggt ggccatcgcc agcaataatg gtggcaagca ggcgctggag  540
acggtccagc ggctgttgcc ggtgctgtgc caggcccacg gcttgacccc ggagcaggtg  600
gtggccatcg ccagccacga tggcggcaag caggcgctgg agacggtcca gcggctgttg  660
ccggtgctgt gccaggccca cggcttgacc ccggagcagg tggtggccat cgccagcaat  720
attggtggca agcaggcgct ggagacggtg caggcgctgt tgccggtgct gtgccaggcc  780
cacggcttga ccccggagca ggtggtggcc atcgccagcc acgatggcgg caagcaggcg  840
ctggagacgg tccagcggct gttgccggtg ctgtgccagg cccacggctt gaccccggag  900
caggtggtgg ccatcgccag caatattggt ggcaagcagg cgctggagac ggtgcaggcg  960
ctgttgccgg tgctgtgcca ggcccacggc ttgaccccccc agcaggtggt ggccatcgcc  1020
agcaatggcg gtggcaagca ggcgctggag acggtccagc ggctgttgcc ggtgctgtgc  1080
caggcccacg gcttgacccc ggagcaggtg gtggccatcg ccagccacga tggcggcaag  1140
caggcgctgg agacggtcca gcggctgttg ccggtgctgt gccaggccca cggcttgacc  1200
ccggagcagg tggtggccat cgccagccac gatggcggca agcaggcgct ggagacggtc  1260
cagcggctgt tgccggtgct gtgccaggcc cacggcttga ccccccagca ggtggtggcc  1320
atcgccagca ataatggtgg caagcaggcg ctggagacgg tccagcggct gttgccggtg  1380
ctgtgccagg cccacggctt gaccccccag caggtggtgg ccatcgccag caataatggt  1440
ggcaagcagg cgctggagac ggtccagcgg ctgttgccgg tgctgtgcca ggcccacggc  1500
ttgaccccgg agcaggtggt ggccatcgcc agccacgatg gcggcaagca ggcgctggag  1560
acggtccagc ggctgttgcc ggtgctgtgc caggcccacg gcttgacccc ccagcaggtg  1620
gtggccatcg ccagcaataa tggtggcaag caggcgctgg agacggtcca gcggctgttg  1680
ccggtgctgt gccaggccca cggcttgacc ccggagcagg tggtggccat cgccagcaat  1740
attggtggca agcaggcgct ggagacggtg caggcgctgt tgccggtgct gtgccaggcc  1800
cacggcttga ccccccagca ggtggtggcc atcgccagca atggcggtgg caagcaggcg  1860
ctggagacgg tccagcggct gttgccggtg ctgtgccagg cccacggctt gacccccccag  1920
caggtggtgg ccatcgccag caatggcggt ggcaagcagg cgctggagac ggtccagcgg  1980
ctgttgccgg tgctgtgcca ggcccacggc ttgaccccccc agcaggtggt ggccatcgcc  2040
agcaataatg gtggcaagca ggcgctggag acggtccagc ggctgttgcc ggtgctgtgc  2100
caggcccacg gcttgacccc ggagcaggtg gtggccatcg ccagccacga tggcggcaag  2160
caggcgctgg agacggtcca gcggctgttg ccggtgctgt gccaggccca cggcttgacc  2220
cctcagcagg tggtggccat cgccagcaat ggcggcggca ggccggcgct ggagagcatt  2280
gttgcccagt tatctcgccc tgatccggcg ttggccgcgt tgaccaacga ccacctcgtc  2340
gccttggcct gcctcggcgg gcgtcctgcg ctggatgcag tgaaaaaggg attgggggat  2400
cctatcagcc gttcccagct ggtgaaatct gagctggagg agaagaagtc tgagctgaga  2460
cacaagctga agtacgtgcc tcacgagtac atcgagctga tcgagatcgc cagaaatagc  2520
acccaggata gaatcctgga gatgaaggtg atggagttct tcatgaaagt gtacggctac  2580
agaggaaagc atctgggagg aagcagaaaa cctgacggag ccatttatac agtgggcagc  2640
cctatcgatt atggcgtgat cgtggataca aaggcctaca gcggaggcta caatctgcct  2700
attggacagg ccgatgagat gcagagatac gtggaggaga accaaaccag gaacaagcat  2760
atcaacccta acgagtggtg gaaggtgtac ccttctagcg tgaccgagtt caagttcctg  2820
tttgtgagcg gccacttcaa gggcaattat aaggcccagc tgaccaggct gaaccacatc  2880
acaaattgta atggcgccgt gctgtctgtg gaggaactgc tgattggagg agagatgatt  2940
aaggccggaa cactgacact ggaggaggtg agaagaaagt tcaacaacgg cgagatcaac  3000
ttctga                                                             3006
```

```
SEQ ID NO: 115          moltype = DNA  length = 3024
FEATURE                 Location/Qualifiers
misc_feature            1..3024
                        note = Xanthomonas ssp, Escherichia coli
source                  1..3024
                        mol_type = other DNA
                        organism = synthetic construct
SEQUENCE: 115
atgggcgatc ctaaaaagaa acgtaaggtc atcgataagg agaccgccgc tgccaagttc  60
gagagacagc acatggacag catcgatatc gccgatctac gcacgctcgg ctacagccag  120
cagcaacagg agaagatcaa accgaaggtt cgttcgacag tggcgcagca ccacgaggca  180
ctggtcggcc acgggtttac acacgcgcac atcgttgcgt taagccaaca cccggcagcg  240
ttagggaccg tcgctgtcaa gtatcaggac atgatcgcag cgttgccaga ggcgacacac  300
gaagcgatcg ttggcgtcgg caaacagtgg tccggcgcac gcgctctgga ggccttgctc  360
acggtggcgg gagagttgag aggtccaccg ttacagttgg acacaggcca acttctcaag  420
attgcaaaac gtggcggcgt gaccgcagtg gaggcagtgc atgcatggcg caatgcactg  480
acgggtgccc cgctcaactt gaccccccag caggtggtgg ccatcgccag caatggcggt  540
ggcaagcagg cgctggagac ggtccagcgg ctgttgccgg tgctgtgcca ggcccacggc  600
ttgaccccgg agcaggtggt ggccatcgcc agcaatattg gtggcaagca ggcgctggag  660
acggtgcagg cgctgttgcc ggtgctgtgc caggcccacg gcttgacccc ggagcaggtg  720
gtggccatcg ccagcaatat tggtggcaag caggcgctgg agacggtgca ggcgctgttg  780
ccggtgctgt gccaggccca cggcttgacc ccggagcagg tggtggccat cgccagcaat  840
attggtggca agcaggcgct ggagacggtg caggcgctgt tgccggtgct gtgccaggcc  900
cacggcttga ccccggagca ggtggtggcc atcgccagcc acgatggcgg caagcaggcg  960
ctggagacgg tccagcggct gttgccggtg ctgtgccagg cccacggctt gaccccccag  1020
caggtggtgg ccatcgccag caataatggt ggcaagcagg cgctggagac ggtccagcgg  1080
ctgttgccgg tgctgtgcca ggcccacggc ttgacccccc agcaggtggt ggccatcgcc  1140
agcaatggcg gtggcaagca ggcgctggag acggtccagc ggctgttgcc ggtgctgtgc  1200
caggcccacg gcttgacccc ccagcaggtg gtggccatcg ccagcaatgg cggtggcaag  1260
```

-continued

```
caggcgctgg agacggtcca gcggctgttg ccggtgctgt gccaggccca cggcttgacc  1320
ccggagcagg tggtggccat cgccagccac gatggcggca agcaggcgct ggagacggtc  1380
cagcggctgt tgccggtgct gtgccaggcc cacggcttga ccccccagca ggtggtggcc  1440
atcgccagca ataatggtgg caagcaggcg ctggagacgg tccagcggct gttgccggtg  1500
ctgtgccagg cccacggctt gacccccccag caggtggtgg ccatcgccag caataatggt  1560
ggcaagcagg cgctggagac ggtccagcgg ctgttgccgg tgctgtgcca ggcccacggc  1620
ttgaccccgg agcaggtggt ggccatcgcc agccacgatg gcggcaagca ggcgctggag  1680
acggtccagc ggctgttgcc ggtgctgtgc caggcccacg gcttgacccc ggagcaggtg  1740
gtggccatcg ccagcaatat tggtggcaag caggcgctgg agacggtgca ggcgctgttg  1800
ccggtgctgt gccaggccca cggcttgacc ccccagcagg tggtggccat cgccagcaat  1860
ggcggtggca agcaggcgct ggagacggtc cagcggctgt tgccggtgct gtgccaggcc  1920
cacggcttga ccccggagca ggtggtggcc atcgccagcc acgatggcgg caagcaggcg  1980
ctggagacgg tccagcggct gttgccggtg ctgtgccagg cccacggctt gaccccggag  2040
caggtggtgg ccatcgccag caatattggt ggcaagcagg cgctggagac ggtgcaggcg  2100
ctgttgccgg tgctgtgcca ggcccacggc ttgacccccc agcaggtggt ggccatcgcc  2160
agcaataatg gtggcaagca ggcgctggag acggtccagc ggctgttgcc ggtgctgtgc  2220
caggcccacg gcttgacccc tcagcaggtg gtggccatcg ccagcaatgg cggcggcagg  2280
ccggcgctgg agagcattgt tgcccagtta tctcgccctg atccggcgtt ggccgcgttg  2340
accaacgacc acctcgtcgc cttggcctgc ctcggcgggc gtcctgcgct ggatgcagtg  2400
aaaaagggat tgggggatcc tatcagccgt tcccagctgg tgaaatctga gctggaggag  2460
aagaagtctg agctgagaca caagctgaag tacgtgcctc acgagtacat cgagctgatc  2520
gagatcgcca gaaatagcac ccaggataga atcctggaga tgaaggtgat ggagttcttc  2580
atgaaagtgt acggctacag aggaaagcat ctgggaggaa gcagaaaacc tgacggagcc  2640
atttatacag tgggcagccc tatcgattat ggcgtgatcg tggatacaaa ggcctacagc  2700
ggaggctaca atctgcctat tggacaggcc gatgagatgc agagatacgt ggaggagaac  2760
caaaccagga acaagcatat caaccctaac gagtggtgga aggtgtaccc ttctagcgtg  2820
accgagttca agttcctgtt tgtgagcggc cacttcaagg gcaattataa ggcccagctg  2880
accaggctga accacatcac aaattgtaat ggcgccgtgc tgtctgtgga ggaactgctg  2940
attggaggag agatgattaa ggccggaaca ctgacactgg aggaggtgag aagaaagttc  3000
aacaacggcg agatcaactt ctga                                        3024
```

```
SEQ ID NO: 116          moltype = DNA  length = 53
FEATURE                 Location/Qualifiers
misc_feature            1..53
                        note = Escherichia coli
source                  1..53
                        mol_type = other DNA
                        organism = synthetic construct
SEQUENCE: 116
atagagatcc tctagagtcg accatggtga tcactgcagg catgcaagct tgt         53

SEQ ID NO: 117          moltype = DNA  length = 18
FEATURE                 Location/Qualifiers
misc_feature            1..18
                        note = Escherichia coli
source                  1..18
                        mol_type = other DNA
                        organism = synthetic construct
SEQUENCE: 117
atagagatcc tctagagt                                                18

SEQ ID NO: 118          moltype = DNA  length = 18
FEATURE                 Location/Qualifiers
misc_feature            1..18
                        note = Escherichia coli
source                  1..18
                        mol_type = other DNA
                        organism = synthetic construct
SEQUENCE: 118
acaagcttgc atgcctgc                                                18

SEQ ID NO: 119          moltype = AA  length = 1344
FEATURE                 Location/Qualifiers
REGION                  1..1344
                        note = Xanthomonas ssp, Escherichia coli
source                  1..1344
                        mol_type = protein
                        organism = synthetic construct
SEQUENCE: 119
MASSPPKKKR KVSWKDASGW SRMHADPIRP RRPSPARELL PGPQPDRVQP TADRGVSAPA  60
GSPLDGLPAR RTVSRTRLPS PPAPSPAFSA GSFSDLLRPF DPSLLDTSLL DSMPAVGTPH  120
TAAAPAEWDE MQSALRAADD PPPTVRVAVT AARPPRAKPA PRRRAAQPSD ASPAAQVDLR  180
TLGYSQQQQE KIKPKVRSTV AQHHEALVGH GFTHAHIVAL SQHPAALGTV AVTYQHIITA  240
LPEATHEDIV GVGKQWSGAR ALEALLTDAG ELRGPPLQLD TGQLVKIAKR GGVTAMEAVH  300
ASRNALTGAP LNLTPDQVVA IASNIGGKQA LETVQRLLPV LCQAHGLTPD QVVAIASNGG  360
GKQALETVQR LLPVLCQDHG LTPEQVVAIA SNIGGKQALE TVQRLLPVLC QDHGLTPDQV  420
VAIASNNGGK QALETVQRLL PVLCQAHGLT PDQVVAIASN IGGKQALETV QRLLPVLCQA  480
HGLTPDQVVA IASNNGGKQA LETVQRLLPV LCQAHGLTPE QVVAIASNIG GKQALETVQR  540
LLPVLCQAHG LTPEQVVAIA SNGGGKQALE TVQRLLPVLC QDHGLTPEQV VAIASHDGGK  600
```

-continued

QALETVQRLL PVLCQAHGLT PDQVVAIASH DGGKQALETV QRLLPVLCQA HGLTPDQVVA 660
IASNGGGKQA LETVQRLLPV LCQDHGLTPE QVVAIASHDG GKQALETVQR LLPVLCQDHG 720
LTPDQVVAIA SNGGGKQALE TVQRLLPVLC QAHGLTPDQV VAIASNIGGK QALETVQRLL 780
PVLCQAHGLT PDQVVAIASN NGGKQALETV QRLLPVLCQA HGLTPEQVVA IASNIGGKQA 840
LETVQRLLPV LCQAHGLTPE QVVAIASNNG GKQALETVQR LLPVLCQDHG LTPDQVVAIA 900
SNGGGKQALE SIVAQLSRPD PALAALTNDH LVALACLGGR PAMDAVKKGL PHAPELIRRV 960
NRRIGERTSH RVADYAQVVR VLEFFQCHSH PAYAFDEAMT QFGMSRNGLV QLFRRVGVTE 1020
LEARGGTLPP ASQRWDRILQ ASGMKRAKPS PTSAQTPDQA SLHAFADSLE RDLDAPSPMH 1080
EGDQTRASSR KRSRSDRAVT GPSAQQAVEV RVPEQRDALH LPLSWRVKRP RTRIWGGLPD 1140
PGTPTAADQL VKSELEEKKS ELRHKLKYVP HEYIELIEIA RNSTQDRILE MKVMEFFMKV 1200
YGYRGKHLGG SRKPDGAIYT VGSPIDYGVI VDTKAYSGGY NLPIGQADEM QRYVEENQTR 1260
NKHINPNEWW KVYPSSVTEF KFLFVSGHFK GNYKAQLTRL NHITNCNGAV LSVEELLIGG 1320
EMIKAGTLTL EEVRRKFNNG EINF 1344

SEQ ID NO: 120 moltype = AA length = 1344
FEATURE Location/Qualifiers
REGION 1..1344
note = Xanthomonas ssp, Escherichia coli
source 1..1344
mol_type = protein
organism = synthetic construct
SEQUENCE: 120
MASSPPKKKR KVSWKDASGW SRMHADPIRP RRPSPARELL PGPQPDRVQP TADRGVSAPA 60
GSPLDGLPAR RTVSRTRLPS PPAPSPAFSA GSFSDLLRPF DPSLLDTSLL DSMPAVGTPH 120
TAAAPAEWDE MQSALRAADD PPPTVRVAVT AARPPRAKPA PRRRAAQPSD ASPAAQVDLR 180
TLGYSQQQQE KIKPKVRSTV AQHHEALVGH GFTHAHIVAL SQHPAALGTV AVTYQHIITA 240
LPEATHEDIV GVGKQWSGAR ALEALLTDAG ELRGPPLQLD TGQLVKIAKR GGVTAMEAVH 300
ASRNALTGAP LNLTPDQVVA IASNIGGKQA LETVQRLLPV LCQAHGLTPD QVVAIASHDG 360
GKQALETVQR LLPVLCQDHG LTPEQVVAIA SNIGGKQALE TVQRLLPVLC QDHGLTPDQV 420
VAIASNIGGK QALETVQRLL PVLCQAHGLT PDQVVAIASN NGGKQALETV QRLLPVLCQA 480
HGLTPDQVVA IASHDGGKQA LETVQRLLPV LCQAHGLTPE QVVAIASNGG GKQALETVQR 540
LLPVLCQAHG LTPEQVVAIA SNGGGKQALE TVQRLLPVLC QDHGLTPEQV VAIASNNGGK 600
QALETVQRLL PVLCQAHGLT PDQVVAIASH DGGKQALETV QRLLPVLCQA HGLTPDQVVA 660
IASNIGGKQA LETVQRLLPV LCQDHGLTPE QVVAIASNGG GKQALETVQR LLPVLCQDHG 720
LTPDQVVAIA SNNGGKQALE TVQRLLPVLC QAHGLTPDQV VAIASHDGGK QALETVQRLL 780
PVLCQAHGLT PDQVVAIASH DGGKQALETV QRLLPVLCQA HGLTPEQVVA IASNGGGKQA 840
LETVQRLLPV LCQAHGLTPE QVVAIASNNG GKQALETVQR LLPVLCQDHG LTPDQVVAIA 900
SHDGGKQALE SIVAQLSRPD PALAALTNDH LVALACLGGR PAMDAVKKGL PHAPELIRRV 960
NRRIGERTSH RVADYAQVVR VLEFFQCHSH PAYAFDEAMT QFGMSRNGLV QLFRRVGVTE 1020
LEARGGTLPP ASQRWDRILQ ASGMKRAKPS PTSAQTPDQA SLHAFADSLE RDLDAPSPMH 1080
EGDQTRASSR KRSRSDRAVT GPSAQQAVEV RVPEQRDALH LPLSWRVKRP RTRIWGGLPD 1140
PGTPTAADQL VKSELEEKKS ELRHKLKYVP HEYIELIEIA RNSTQDRILE MKVMEFFMKV 1200
YGYRGKHLGG SRKPDGAIYT VGSPIDYGVI VDTKAYSGGY NLPIGQADEM QRYVEENQTR 1260
NKHINPNEWW KVYPSSVTEF KFLFVSGHFK GNYKAQLTRL NHITNCNGAV LSVEELLIGG 1320
EMIKAGTLTL EEVRRKFNNG EINF 1344

SEQ ID NO: 121 moltype = AA length = 1038
FEATURE Location/Qualifiers
REGION 1..1038
note = Xanthomonas ssp, Escherichia coli
source 1..1038
mol_type = protein
organism = synthetic construct
SEQUENCE: 121
MASSPPKKKR KVSWKDASGW SRMHADPWPR RRAAQPSDAS PAAQVDLRTL GYSQQQQEKI 60
KPKVRSTVAQ HHEALVGHGF THAHIVALSQ HPAALGTVAV TYQHIITALP EATHEDIVGV 120
GKQWSGARAL EALLTDAGEL RGPPLQLDTG QLVKIAKRGG VTAMEAVHAS RNALTGAPLN 180
LTPDQVVAIA SNIGGKQALE TVQRLLPVLC QAHGLTPDQV VAIASNGGGK QALETVQRLL 240
PVLCQDHGLT PEQVVAIASN IGGKQALETV QRLLPVLCQD HGLTPDQVVA IASNNGGKQA 300
LETVQRLLPV LCQAHGLTPD QVVAIASNIG GKQALETVQR LLPVLCQAHG LTPDQVVAIA 360
SNNGGKQALE TVQRLLPVLC QAHGLTPEQV VAIASNIGGK QALETVQRLL PVLCQAHGLT 420
PEQVVAIASN GGGKQALETV QRLLPVLCQD HGLTPEQVVA IASHDGGKQA LETVQRLLPV 480
LCQAHGLTPD QVVAIASHDG GKQALETVQR LLPVLCQAHG LTPDQVVAIA SNGGGKQALE 540
TVQRLLPVLC QDHGLTPEQV VAIASHDGGK QALETVQRLL PVLCQDHGLT PDQVVAIASN 600
GGGKQALETV QRLLPVLCQA HGLTPDQVVA IASNIGGKQA LETVQRLLPV LCQAHGLTPD 660
QVVAIASNNG GKQALETVQR LLPVLCQAHG LTPEQVVAIA SNIGGKQALE TVQRLLPVLC 720
QAHGLTPEQV VAIASNNGGK QALETVQRLL PVLCQDHGLT PDQVVAIASN GGGKQALESI 780
VAQLSRPDPA LAALTNDHLV ALACLGGRPA MDAVKKGLPH APELIRRVNR RIGERTSHRV 840
ALQLVKSELE EKKSELRHKL KYVPHEYIEL IEIARNSTQD RILEMKVMEF FMKVYGYRGK 900
HLGGSRKPDG AIYTVGSPID YGVIVDTKAY SGGYNLPIGQ ADEMQRYVEE NQTRNKHINP 960
NEWWKVYPSS VTEFKFLFVS GHFKGNYKAQ LTRLNHITNC NGAVLSVEEL LIGGEMIKAG 1020
TLTLEEVRRK FNNGEINF 1038

SEQ ID NO: 122 moltype = AA length = 1038
FEATURE Location/Qualifiers
REGION 1..1038
note = Xanthomonas ssp, Escherichia coli
source 1..1038
mol_type = protein -continued

```
                         organism = synthetic construct
SEQUENCE: 122
MASSPPKKKR KVSWKDASGW SRMHADPWPR RRAAQPSDAS PAAQVDLRTL GYSQQQQEKI  60
KPKVRSTVAQ HHEALVGHGF THAHIVALSQ HPAALGTVAV TYQHIITALP EATHEDIVGV  120
GKQWSGARAL EALLTDAGEL RGPPLQLDTG QLVKIAKRGG VTAMEAVHAS RNALTGAPLN  180
LTPDQVVAIA SNIGGKQALE TVQRLLPVLC QAHGLTPDQV VAIASHDGGK QALETVQRLL  240
PVLCQDHGLT PEQVVAIASN IGGKQALETV QRLLPVLCQD HGLTPDQVVA IASNIGGKQA  300
LETVQRLLPV LCQAHGLTPD QVVAIASNNG GKQALETVQR LLPVLCQAHG LTPDQVVAIA  360
SHDGGKQALE TVQRLLPVLC QAHGLTPEQV VAIASNGGGK QALETVQRLL PVLCQAHGLT  420
PEQVVAIASN GGGKQALETV QRLLPVLCQD HGLTPEQVVA IASNNGGKQA LETVQRLLPV  480
LCQAHGLTPD QVVAIASHDG GKQALETVQR LLPVLCQAHG LTPDQVVAIA SNIGGKQALE  540
TVQRLLPVLC QDHGLTPEQV VAIASNGGGK QALETVQRLL PVLCQDHGLT PDQVVAIASN  600
NGGKQALETV QRLLPVLCQA HGLTPDQVVA IASHDGGKQA LETVQRLLPV LCQAHGLTPD  660
QVVAIASHDG GKQALETVQR LLPVLCQAHG LTPEQVVAIA SNGGGKQALE TVQRLLPVLC  720
QAHGLTPEQV VAIASNNGGK QALETVQRLL PVLCQDHGLT PDQVVAIASH DGGKQALESI  780
VAQLSRPDPA LAALTNDHLV ALACLGGRPA MDAVKKGLPH APELIRRVNR RIGERTSHRV  840
ALQLVKSELE EKKSELRHKL KYVPHEYIEL IEIARNSTQD RILEMKVMEF FMKVYGYRGK  900
HLGGSRKPDG AIYTVGSPID YGVIVDTKAY SGGYNLPIGQ ADEMQRYVEE NQTRNKHINP  960
NEWWKVYPSS VTEFKFLFVS GHFKGNYKAQ LTRLNHITNC NGAVLSVEEL LIGGEMIKAG  1020
TLTLEEVRRK FNNGEINF                                               1038

SEQ ID NO: 123           moltype = DNA  length = 4035
FEATURE                  Location/Qualifiers
misc_feature             1..4035
                         note = Xanthomonas ssp, Escherichia coli
source                   1..4035
                         mol_type = other DNA
                         organism = synthetic construct
SEQUENCE: 123
atggctagct cccccccgaa gaagaagagg aaggtcagct ggaaggatgc tagcggctgg  60
agcaggatgc acgctgatcc aatcaggccg aggaggccaa gcccagcaag ggagctgctg  120
ccaggcccac agccagatag ggtgcagcca accgccgata ggggcgtgag cgctccagct  180
ggcagcccgc tggatggcct gccagctagg aggaccgtga gcaggaccag gctgccgagc  240
ccaccagctc cgagcccagc cttcagcgct ggcagcttca gcgatctgct gaggccattc  300
gatccgagcc tgctggatac atcgctgctg gatagcatgc cagctgtggg caccccacac  360
accgctgctg ctccagctga gtgggatgag atgcagtccg ccctccgcgc cgccgacgac  420
ccgccgccaa ccgtgagggt ggccgtgacc gctgctaggc cgccaagggc taagccagct  480
ccaaggagga gggccgctca gccaagcgat gctagccccg ccgcgcaggt cgacctcagg  540
accctgggct acagccagca gcagcaggag aagatcaagc cgaaggtgag gagcaccgtg  600
gcccagcacc acgaggctct ggtgggccac ggcttcaccc acgctcacat cgtggccctg  660
agccagcacc cagctgctct gggcaccgtg gctgtgacct accagcacat catcaccgcc  720
ctgccagagg ctacccacga ggacatcgtg ggcgtgggca agcagtggag cggcgctagg  780
gccctggagg ctctgctgac cgatgctggc gagctgaggg gcccaccgct ccagctggat  840
accggccagc tggtgaagat cgccaagagg ggcggcgtga ccgctatgga ggctgtgcac  900
gccagcagga acgctctgac cggcgctcca ctgaacctga cccccgacca ggtggtggcc  960
atcgcgagca acatcggcgg caagcaggct ctcgaaaccg tgcagaggct gctcccggtg  1020
ctgtgccagg cccacggcct caccccagac caggtcgtcg cgatcgcctc caacggcggc  1080
ggcaagcagg ccctggagac tgtgcagcgc ctgctgcccg tcctgtgcca ggaccacggc  1140
ctcaccccgg agcaggtcgt cgctatcgct agcaacatcg gcggcaagca ggcgctcgaa  1200
accgtccaga ggctcctccc agtcctctgc caggatcacg gcctgacccc ggatcaggtg  1260
gtcgccatcg cttccaacaa cggcggcaag caggcgctgg agactgtcca gcgcctcctc  1320
ccagtcctct gccaggcgca cggcctcacc cccgatcagg tcgtggcgat cgcgagcaac  1380
atcggcggca agcaggctct cgaaaccgtg cagaggctgc tgccggtgct ctgccaggct  1440
cacggcctga ccccagacca ggtggtggct atcgcctcca acaacggcgg caagcaggcc  1500
ctggagactg tgcagaggct cctcccggtc ctgtgccagg cccacggcct cacccccgag  1560
caggtcgtcg cgatcgctag caacatcggc ggcaagcagg ccctggagac tgtgcagagg  1620
ctgctcccag tcctgtgcca ggcccacggc ctgacccccg agcaggtggt cgcgatcgcg  1680
agcaacggcg gcggcaagca ggcgctcgaa accgtccaga ggctcctccc cgtgctctgc  1740
caggatcacg gcctgacccc agagcaggtg gtggctatcg cgagccacga cggcggcaag  1800
caggctctcg aaaccgtcca gaggctcctc ccagtgctct gccaggctca cggcctcacc  1860
ccggaccagg tcgtcgccat cgcttcccac gatggcggca agcaggctct cgaaaccgtg  1920
cagaggctgc tcccggtgct gtgccaggcc cacggcctca ccccagacca ggtcgtcgcg  1980
atcgcctcca acggcggcgg caagcaggcc ctggagactg tgcagcgcct gctgcccgtc  2040
ctgtgccagg accacggcct caccccggag caggtcgtcg ctatcgctag ccacgacggc  2100
ggcaagcagg cgctcgaaac cgtccagagg ctcctcccag tcctctgcca ggatcacggc  2160
ctgaccccgg atcaggtggt cgccatcgct tccaacggcg gcggcaagca ggcgctggag  2220
actgtccagc gcctcctccc agtcctctgc caggcgcacg gcctcacccc cgatcaggtc  2280
gtggcgatcg cgagcaacat cggcggcaag caggctctcg aaaccgtgca gaggctgctg  2340
ccggtgctct gccaggctca cggcctgacc ccagaccagg tggtggctat cgcctccaac  2400
aacggcggca agcaggccct ggagactgtg cagaggctcc tcccggtcct gtgccaggcc  2460
cacggcctca cccccgagca ggtcgtcgcg atcgctagca acatcggcgg caagcaggcc  2520
ctggagactg tgcagaggct gctcccagtc ctgtgccagg cccacggcct gacccccgag  2580
caggtggtcg cgatcgcgag caacaacggc ggcaagcagg cgctcgaaac cgtccagagg  2640
ctcctccccg tgctctgcca ggatcacggc ctcacccccg accaggtcgt ggctatcgcg  2700
tccaacggcg gcggcaagca ggctctcgag agcatcgtgg cccagctgag caggccggac  2760
ccggccctgg ccgccctgac caacgatcac ctggtggctc tggcctgcct gggcggcagg  2820
ccagccatgg acgctgtgaa gaagggcctg ccgcacgctc cagagctgat ccgcagggtg  2880
aacaggagga tcggcgagag gaccagccac agggtggccg actacgctca ggtggtgagg  2940
gtgctggagt tcttccagtg ccacagccac ccggcctacg ccttcgacga ggctatgacc  3000
```

```
cagttcggca tgagcaggaa cggcctggtg cagctgttca ggagggtggg cgtgaccgag  3060
ctggaggcta ggggcggcac cctgccgcca gctagccaga ggtgggaccg catcctccag  3120
gccagcggca tgaaaagggc taagccaagc ccgaccagcg ctcagacccc agatcaggct  3180
agcctgcacg ctttcgccga cagcctggag agggatctgg atgctccgag cccaatgcac  3240
gagggcgacc agaccagggc cagcagcagg aagaggagca ggagcgacag ggctgtgacc  3300
ggcccgagcg cccagcaggc tgtggaggtg agggtgccag agcagaggga tgccctgcac  3360
ctgccgctga gctggagggt gaagaggcca aggaccagga tctggggcgg cctgccagat  3420
ccgggcaccc caaccgctgc tgatcagctc gtgaagagcg agctggagga gaagaagagc  3480
gagctgaggc ataaactgaa gtacgtgcca cacgagtaca tcgagctgat cgagatcgcc  3540
aggaacagca cccaggatcg catcctggag atgaaggtga tggagttctt catgaaagtg  3600
tacggctaca ggggcaagca cctgggcggc agcaggaagc cagatggcgc catctacacc  3660
gtgggcagcc caatcgacta cggcgtgatc gtggatacca aggcttacag cggcggctac  3720
aacctgccga tcggccaggc tgatgagatg cagaggtacg tggaggagaa tcaaaccagg  3780
aacaagcaca tcaacccaaa cgagtggtgg aaggtgtacc cgagcagcgt gaccgagttc  3840
aagttcctgt tcgtgagcgg ccacttcaag ggcaactaca aggctcagct caccaggctg  3900
aaccacatca ccaactgcaa cggcgccgtg ctgagcgtgg aggagctgct gatcggcggc  3960
gagatgatca aggctggcac cctgaccctg gaggaggtga ggaggaagtt caacaacggc  4020
gagatcaact tctga                                                   4035

SEQ ID NO: 124          moltype = DNA  length = 4035
FEATURE                 Location/Qualifiers
misc_feature            1..4035
                        note = Xanthomonas ssp, Escherichia coli
source                  1..4035
                        mol_type = other DNA
                        organism = synthetic construct
SEQUENCE: 124
atggctagct cccccccgaa gaagaagagg aaggtcagct ggaaggatgc tagcggctgg  60
agcaggatgc acgctgatcc aatcaggccg aggaggccaa gcccagcaag ggagctgctg  120
ccaggcccac agccagatag ggtgcagcca accgccgata ggggcgtgag cgctccagct  180
ggcagcccgc tggatggcct gccagctagg aggaccgtga gcaggaccag gctgccgagc  240
ccaccagctc cgagcccagc cttcagcgct ggcagcttca gcgatctgct gaggccattc  300
gatccgagcc tgctggatac atcgctgctg gatagcatgc cagctgtggg cacccccacac  360
accgctgctg ctccagctga gtgggatgag atgcagtccg ccctccgcgc cgccgacgac  420
ccgccgccaa ccgtgagggt ggccgtgacc gctgctaggc cgccaagggc taagccagct  480
ccaaggagga gggccgctca gccaagcgat gctagccccg ccgcgcaggt cgacctcagg  540
accctgggct acagccagca gcagcaggag aagatcaagc cgaaggtgag gagcaccgtg  600
gcccagcacc acgaggctct ggtgggccac ggcttcaccc acgctcacat cgtggccctg  660
agccagcacc cagctgctct gggcaccgtg gctgtgacct accagcacat catcaccgcc  720
ctgccagagg ctacccacga ggacatcgtg ggcgtgggca agcagtggag cggcgctagg  780
gccctggagg ctctgctgac cgatgctggc gagctgaggg gcccaccgct ccagctggat  840
accggccagc tggtgaagat cgccaagagg ggcggcgtga ccgctatgga ggctgtgcac  900
gccagcagga acgctctgac cggcgctcca ctgaacctga cccccgacca ggtggtggcc  960
atcgcgagca acatcggcgg caagcaggct ctcgaaaccg tgcagaggct gctcccggtg  1020
ctgtgccagg cccacggcct caccccagac caggtcgtcg cgatcgcctc ccacgatggc  1080
ggcaagcagg ccctggagac tgtgcagcgc ctgctgcccg tcctgtgcca ggaccacggc  1140
ctcaccccgg agcaggtcgt cgctatcgct agcaacatcg gcggcaagca ggcgctcgaa  1200
accgtccaga ggctcctccc agtcctctgc caggatcacg gcctgacccc ggatcaggtg  1260
gtcgccatcg cttccaacat cggcggcaag caggcgctgg agactgtcca gcgcctcctc  1320
ccagtcctct gccaggcgca cggcctcacc cccgatcagg tcgtggcgat cgcgagcaac  1380
aacggcggca agcaggctct cgaaaccgtg cagaggctgc tgccggtgct ctgccaggct  1440
cacggcctga ccccagacca ggtggtggct atcgcctccc acgatggcgg caagcaggcc  1500
ctggagactg tgcagaggct cctcccggtc ctgtgccagg cccacggcct cacccccgag  1560
caggtcgtcg cgatcgctag caacggcggc ggcaagcagg ccctggagac tgtgcagagg  1620
ctgctcccag tcctgtgcca ggcccacggc ctgacccccg agcaggtggt cgcgatcgcg  1680
agcaacggcg gcggcaagca ggcgctcgaa accgtccaga ggctcctccc cgtgctctgc  1740
caggatcacg gcctgacccc agagcaggtg gtggctatcg cgagcaacaa cggcggcaag  1800
caggctctcg aaaccgtcca gaggctcctc ccagtgctct gccaggctca cggcctcacc  1860
ccggaccagg tcgtcgccat cgcttcccac gatggcggca agcaggctct cgaaaccgtg  1920
cagaggctgc tcccggtgct gtgccaggcc cacggcctca ccccagacca ggtcgtcgcg  1980
atcgcctcca acatcggcgg caagcaggcc ctggagactg tgcagcgcct gctgcccgtc  2040
ctgtgccagg accacggcct caccccggag caggtcgtcg ctatcgctag caacggcggc  2100
ggcaagcagg cgctcgaaac cgtccagagg ctcctcccag tcctctgcca ggatcacggc  2160
ctgaccccgg atcaggtggt cgccatcgct tccaacaacg gcggcaagca ggcgctggag  2220
actgtccagc gcctcctccc agtcctctgc caggcgcacg gcctcacccc cgatcaggtc  2280
gtggcgatcg cgagccacga cggcggcaag caggctctcg aaaccgtgca gaggctgctg  2340
ccggtgctct gccaggctca cggcctgacc ccagaccagg tggtggctat cgcctcccac  2400
gatggcggca agcaggccct ggagactgtg cagaggctcc tcccggtcct gtgccaggcc  2460
cacggcctca cccccgagca ggtcgtcgcg atcgctagca acggcggcgg caagcaggcc  2520
ctggagactg tgcagaggct gctcccagtc ctgtgccagg cccacggcct gacccccgag  2580
caggtggtcg cgatcgcgag caacaacggc ggcaagcagg cgctcgaaac cgtccagagg  2640
ctcctccccg tgctctgcca ggatcacggc ctcacccccg accaggtcgt ggctatcgcg  2700
tcccacgatg gcggcaagca ggctctcgag agcatcgtgg cccagctgag caggccggac  2760
ccggccctgg ccgccctgac caacgatcac ctggtggctc tggcctgcct gggcggcagg  2820
ccagccatgg acgctgtgaa gaagggcctg ccgcacgctc cagagctgat ccgcagggtg  2880
aacaggagga tcggcgagag gaccagccac agggtggccg actacgctca ggtggtgagg  2940
gtgctggagt tcttccagtg ccacagccac ccggcctacg ccttcgacga ggctatgacc  3000
cagttcggca tgagcaggaa cggcctggtg cagctgttca ggagggtggg cgtgaccgag  3060
ctggaggcta ggggcggcac cctgccgcca gctagccaga ggtgggaccg catcctccag  3120
```

-continued

```
gccagcggca tgaaaagggc taagccaagc ccgaccagcg ctcagacccc agatcaggct  3180
agcctgcacg ctttcgccga cagcctggag agggatctgg atgctccgag cccaatgcac  3240
gagggcgacc agaccagggc cagcagcagg aagaggagca ggagcgacag ggctgtgacc  3300
ggcccgagcg cccagcaggc tgtggaggtg agggtgccag agcagaggga tgccctgcac  3360
ctgccgctga gctggagggt gaagaggcca aggaccagga tctggggcgg cctgccagat  3420
ccgggcaccc caaccgctgc tgatcagctc gtgaagagcg agctggagga gaagaagagc  3480
gagctgaggc ataaactgaa gtacgtgcca cacgagtaca tcgagctgat cgagatcgcc  3540
aggaacagca cccaggatcg catcctggag atgaaggtga tggagttctt catgaaagtg  3600
tacggctaca ggggcaagca cctgggcggc agcaggaagc cagatggcgc catctacacc  3660
gtgggcagcc caatcgacta cggcgtgatc gtggatacca aggcttacag cggcggctac  3720
aacctgccga tcggccaggc tgatgagatg cagaggtacg tggaggagaa tcaaaccagg  3780
aacaagcaca tcaacccaaa cgagtggtgg aaggtgtacc cgagcagcgt gaccgagttc  3840
aagttcctgt tcgtgagcgg ccacttcaag ggcaactaca aggctcagct caccaggctg  3900
aaccacatca ccaactgcaa cggcgccgtg ctgagcgtgg aggagctgct gatcggcggc  3960
gagatgatca aggctggcac cctgaccctg gaggaggtga ggaggaagtt caacaacggc  4020
gagatcaact tctga                                                    4035
```

```
SEQ ID NO: 125          moltype = DNA  length = 3114
FEATURE                 Location/Qualifiers
misc_feature            1..3114
                        note = Xanthomonas ssp, Escherichia coli
source                  1..3114
                        mol_type = other DNA
                        organism = synthetic construct
SEQUENCE: 125
atggctagct ccccccgaa gaagaagagg aaggtcagct ggaaggatgc tagcggctgg  60
agcaggatgc acgctgatcc atggccaagg aggagggccg ctcagccaag cgatgctagc  120
cccgccgcgc aggtcgacct caggaccctg ggctacagcc agcagcagca ggagaagatc  180
aagccgaagg tgaggagcac cgtggcccag caccacgagg ctctggtggg ccacggcttc  240
acccacgctc acatcgtggc cctgagccag cacccagctg ctctgggcac cgtggctgtg  300
acctaccagc acatcatcac cgccctgcca gaggctaccc acgaggacat cgtgggcgtg  360
ggcaagcagt ggagcggcgc tagggccctg gaggctctgc tgaccgatgc tggcgagctg  420
aggggcccac cgctccagct ggataccggc cagctggtga agatcgccaa gaggggcggc  480
gtgaccgcta tggaggctgt gcacgccagc aggaacgctc tgaccggcgc tccactgaac  540
ctgaccccccg accaggtggt ggccatcgcg agcaacatcg gcggcaagca ggctctcgaa  600
accgtgcaga ggctgctccc ggtgctgtgc caggcccacg gcctcacccc agaccaggtc  660
gtcgcgatcg cctccaacgg cggcggcaag caggccctgg agactgtgca gcgcctgctg  720
cccgtcctgt gccaggacca cggcctcacc ccggagcagg tcgtcgctat cgctagcaac  780
atcggcggca agcaggcgct cgaaaccgtc cagaggctcc tcccagtcct ctgccaggat  840
cacggcctga ccccggatca ggtggtcgcc atcgcttcca acaacggcgg caagcaggcg  900
ctggagactg tccagcgcct cctcccagtc ctctgccagg cgcacggcct cacccccgat  960
caggtcgtgg cgatcgcgag caacatcggc ggcaagcagg ctctcgaaac cgtgcagagg  1020
ctgctgccgg tgctctgcca ggctcacggc ctgaccccag accaggtggt ggctatcgcc  1080
tccaacaacg gcggcaagca ggccctggag actgtgcaga ggctcctccc ggtcctgtgc  1140
caggcccacg gcctcacccc cgagcaggtc gtcgcgatcg ctagcaacat cggcggcaag  1200
caggccctgg agactgtgca gaggctgctc ccagtcctgt gccaggccca cggcctgacc  1260
cccgagcagg tggtcgcgat cgcgagcaac ggcggcggca agcaggcgct cgaaaccgtc  1320
cagaggctcc tccccgtgct ctgccaggat cacggcctga ccccagagca ggtggtggct  1380
atcgcgagcc acgacggcgg caagcaggct ctcgaaaccg tccagaggct cctcccagtg  1440
ctctgccagg ctcacggcct caccccggac caggtcgtcg ccatcgcttc ccacgatggc  1500
ggcaagcagg ctctcgaaac cgtgcagagg ctgctcccgg tgctgtgcca ggcccacggc  1560
ctcaccccag accaggtcgt cgcgatcgcc tccaacggcg gcggcaagca ggccctggag  1620
actgtgcagc gcctgctgcc cgtcctgtgc caggaccacg gcctcacccc ggagcaggtc  1680
gtcgctatcg ctagccacga cggcggcaag caggcgctcg aaaccgtcca gaggctcctc  1740
ccagtcctct gccaggatca cggcctgacc ccggatcagg tggtcgccat cgcttccaac  1800
ggcggcggca agcaggcgct ggagactgtc cagcgcctcc tcccagtcct ctgccaggcg  1860
cacggcctca cccccgatca ggtcgtggcg atcgcgagca acatcggcgg caagcaggct  1920
ctcgaaaccg tgcagaggct gctgccggtg ctctgccagg ctcacggcct gaccccagac  1980
caggtggtgg ctatcgcctc caacaacggc ggcaagcagg ccctggagac tgtgcagagg  2040
ctcctcccgg tcctgtgcca ggcccacggc ctcacccccg agcaggtcgt cgcgatcgct  2100
agcaacatcg gcggcaagca ggccctggag actgtgcaga ggctgctccc agtcctgtgc  2160
caggcccacg gcctgacccc cgagcaggtg gtcgcgatcg cgagcaacaa cggcggcaag  2220
caggcgctcg aaaccgtcca gaggctcctc cccgtgctct gccaggatca cggcctcacc  2280
cccgaccagg tcgtggctat cgcgtccaac ggcggcggca agcaggctct cgagagcatc  2340
gtggcccagc tgagcaggcc ggacccggcc ctggccgccc tgaccaacga tcacctggtg  2400
gctctggcct gcctgggcgg caggccagcc atggacgctg tgaagaaggg cctgccgcac  2460
gctccagagc tgatccgcag ggtgaacagg aggatcggcg agaggaccag ccacagggtg  2520
gccctgcagc tcgtgaagag cgagctggag gagaagaaga gcgagctgag gcataaactg  2580
aagtacgtgc cacacgagta catcgagctg atcgagatcg ccaggaacag cacccaggat  2640
cgcatcctgg agatgaaggt gatggagttc ttcatgaaag tgtacggcta caggggcaag  2700
cacctgggcg gcagcaggaa gccagatggc gccatctaca ccgtgggcag cccaatcgac  2760
tacggcgtga tcgtggatac caaggcttac agcggcggct acaacctgcc gatcggccag  2820
gctgatgaga tgcagaggta cgtggaggag aatcaaacca ggaacaagca catcaaccca  2880
aacgagtggt ggaaggtgta cccgagcagc gtgaccgagt tcaagttcct gttcgtgagc  2940
ggccacttca agggcaacta caaggctcag ctcaccaggc tgaaccacat caccaactgc  3000
aacggcgccg tgctgagcgt ggaggagctg ctgatcggcg gcgagatgat caaggctggc  3060
accctgaccc tggaggaggt gaggaggaag ttcaacaacg gcgagatcaa cttc        3114

SEQ ID NO: 126          moltype = DNA  length = 3114
```

-continued

```
FEATURE                Location/Qualifiers
misc_feature           1..3114
                       note = Xanthomonas ssp, Escherichia coli
source                 1..3114
                       mol_type = other DNA
                       organism = synthetic construct
SEQUENCE: 126
atggctagct cccccccgaa gaagaagagg aaggtcagct ggaaggatgc tagcggctgg  60
agcaggatgc acgctgatcc atggccaagg aggagggccg ctcagccaag cgatgctagc  120
cccgccgcgc aggtcgacct caggaccctg ggctacagcc agcagcagca ggagaagatc  180
aagccgaagg tgaggagcac cgtggcccag caccacgagg ctctggtggg ccacggcttc  240
acccacgctc acatcgtggc cctgagccag cacccagctg ctctgggcac cgtggctgtg  300
acctaccagc acatcatcac cgccctgcca gaggctaccc acgaggacat cgtgggcgtg  360
ggcaagcagt ggagcggcgc tagggccctg gaggctctgc tgaccgatgc tggcgagctg  420
aggggcccac cgctccagct ggataccggc cagctggtga agatcgccaa gaggggcggc  480
gtgaccgcta tggaggctgt gcacgccagc aggaacgctc tgaccggcgc tccactgaac  540
ctgacccccg accaggtggt ggccatcgcg agcaacatcg gcggcaagca ggctctcgaa  600
accgtgcaga ggctgctccc ggtgctgtgc caggcccacg gcctcacccc agaccaggtc  660
gtcgcgatcg cctcccacga tggcggcaag caggccctgg agactgtgca gcgcctgctg  720
cccgtcctgt gccaggacca cggcctcacc ccggagcagg tcgtcgctat cgctagcaac  780
atcggcggca agcaggcgct cgaaaccgtc cagaggctcc tcccagtcct ctgccaggat  840
cacggcctga ccccggatca ggtggtcgcc atcgcttcca acatcggcgg caagcaggcg  900
ctggagactg tccagcgcct cctcccagtc ctctgccagg cgcacggcct cacccccgat  960
caggtcgtgg cgatcgcgag caacaacggc ggcaagcagg ctctcgaaac cgtgcagagg  1020
ctgctgccgg tgctctgcca ggctcacggc ctgaccccag accaggtggt ggctatcgcc  1080
tcccacgatg gcggcaagca ggccctggag actgtgcaga ggctcctccc ggtcctgtgc  1140
caggcccacg gcctcacccc cgagcaggtc gtcgcgatcg ctagcaacgg cggcggcaag  1200
caggccctgg agactgtgca gaggctgctc ccagtcctgt gccaggccca cggcctgacc  1260
cccgagcagg tggtcgcgat cgcgagcaac ggcggcggca agcaggcgct cgaaaccgtc  1320
cagaggctcc tccccgtgct ctgccaggat cacggcctga ccccagagca ggtggtggct  1380
atcgcgagca acaacggcgg caagcaggct ctcgaaaccg tccagaggct cctcccagtg  1440
ctctgccagg ctcacggcct caccccggac caggtcgtcg ccatcgcttc ccacgatggc  1500
ggcaagcagg ctctcgaaac cgtgcagagg ctgctcccgg tgctgtgcca ggcccacggc  1560
ctcaccccag accaggtcgt cgcgatcgcc tccaacatcg gcggcaagca ggccctggag  1620
actgtgcagc gcctgctgcc cgtcctgtgc caggaccacg gcctcacccc ggagcaggtc  1680
gtcgctatcg ctagcaacgg cggcggcaag caggcgctcg aaaccgtcca gaggctcctc  1740
ccagtcctct gccaggatca cggcctgacc ccggatcagg tggtcgccat cgcttccaac  1800
aacggcggca agcaggcgct ggagactgtc cagcgcctcc tcccagtcct ctgccaggcg  1860
cacggcctca cccccgatca ggtcgtggcg atcgcgagcc acgacggcgg caagcaggct  1920
ctcgaaaccg tgcagaggct gctgccggtg ctctgccagg ctcacggcct gaccccagac  1980
caggtggtgg ctatcgcctc ccacgatggc ggcaagcagg ccctggagac tgtgcagagg  2040
ctcctcccgg tcctgtgcca ggcccacggc ctcacccccg agcaggtcgt cgcgatcgct  2100
agcaacggcg gcggcaagca ggccctggag actgtgcaga ggctgctccc agtcctgtgc  2160
caggcccacg gcctgacccc cgagcaggtg gtcgcgatcg cgagcaacaa cggcggcaag  2220
caggcgctcg aaaccgtcca gaggctcctc cccgtgctct gccaggatca cggcctcacc  2280
cccgaccagg tcgtggctat cgcgtcccac gatggcggca agcaggctct cgagagcatc  2340
gtggcccagc tgagcaggcc ggacccggcc ctggccgccc tgaccaacga tcacctggtg  2400
gctctggcct gcctgggcgg caggccagcc atggacgctg tgaagaaggg cctgccgcac  2460
gctccagagc tgatccgcag ggtgaacagg aggatcggcg agaggaccag ccacagggtg  2520
gccctgcagc tcgtgaagag cgagctggag gagaagaaga gcgagctgag gcataaactg  2580
aagtacgtgc cacacgagta catcgagctg atcgagatcg ccaggaacag cacccaggat  2640
cgcatcctgg agatgaaggt gatggagttc ttcatgaaag tgtacggcta caggggcaag  2700
cacctgggcg gcagcaggaa gccagatggc gccatctaca ccgtgggcag cccaatcgac  2760
tacggcgtga tcgtggatac caaggcttac agcggcggct acaacctgcc gatcggccag  2820
gctgatgaga tgcagaggta cgtggaggag aatcaaacca ggaacaagca catcaaccca  2880
aacgagtggt ggaaggtgta cccgagcagc gtgaccgagt tcaagttcct gttcgtgagc  2940
ggccacttca agggcaacta caaggctcag ctcaccaggc tgaaccacat caccaactgc  3000
aacggcgccg tgctgagcgt ggaggagctg ctgatcggcg gcgagatgat caaggctggc  3060
accctgaccc tggaggaggt gaggaggaag ttcaacaacg gcgagatcaa cttc        3114

SEQ ID NO: 127         moltype = DNA  length = 20
FEATURE                Location/Qualifiers
misc_feature           1..20
                       note = Zea mays
source                 1..20
                       mol_type = other DNA
                       organism = synthetic construct
SEQUENCE: 127
aaccagcgaa ccagcagcgt                                              20

SEQ ID NO: 128         moltype = DNA  length = 21
FEATURE                Location/Qualifiers
misc_feature           1..21
                       note = Zea mays
source                 1..21
                       mol_type = other DNA
                       organism = synthetic construct
SEQUENCE: 128
tttgctacct gcggtaggtg g                                            21
```

```
SEQ ID NO: 129          moltype = DNA  length = 22
FEATURE                 Location/Qualifiers
misc_feature            1..22
                        note = Zea mays
source                  1..22
                        mol_type = other DNA
                        organism = synthetic construct
SEQUENCE: 129
cggccaattc ctgcattcgt ac                                          22

SEQ ID NO: 130          moltype = DNA  length = 23
FEATURE                 Location/Qualifiers
misc_feature            1..23
                        note = Zea mays
source                  1..23
                        mol_type = other DNA
                        organism = synthetic construct
SEQUENCE: 130
gaattgggta ccagcttgca tgc                                         23

SEQ ID NO: 131          moltype = DNA  length = 23
FEATURE                 Location/Qualifiers
misc_feature            1..23
                        note = Zea mays
source                  1..23
                        mol_type = other DNA
                        organism = synthetic construct
SEQUENCE: 131
gtgccatgta tcggttctag agc                                         23

SEQ ID NO: 132          moltype = DNA  length = 27
FEATURE                 Location/Qualifiers
misc_feature            1..27
                        note = Zea mays
source                  1..27
                        mol_type = other DNA
                        organism = synthetic construct
SEQUENCE: 132
cattaaatta cggacccaaa agcttac                                     27

SEQ ID NO: 133          moltype = DNA  length = 3494
FEATURE                 Location/Qualifiers
misc_feature            1..3494
                        note = Escherichia coli, Zea mays, Agrobacterium tumefaciens
source                  1..3494
                        mol_type = other DNA
                        organism = synthetic construct
SEQUENCE: 133
ctgcagtgca gcgtgacccg gtcgtgcccc tctctagaga taatgagcat tgcatgtcta  60
agttataaaa aattaccaca tattttttt gtcacacttg tttgaagtgc agtttatcta  120
tctttataca tatatttaaa ctttactcta cgaataatat aatctatagt actacaataa  180
tatcagtgtt ttagagaatc atataaatga acagttagac atggtctaaa ggacaattga  240
gtattttgac aacaggactc tacagtttta tctttttagt gtgcatgtgt tctccttttt  300
ttttgcaaat agcttcacct atataatact tcatccattt tattagtaca tccatttagg  360
gtttagggtt aatggttttt atagactaat ttttttagta catctatttt attctatttt  420
agcctctaaa ttaagaaaac taaaactcta ttttagtttt tttatttaat aatttagata  480
taaaatagaa taaaataaag tgactaaaaa ttaaacaaat accctttaag aaattaaaaa  540
aactaaggaa acatttttct tgtttcgagt agataatgcc agcctgttaa acgccgtcga  600
cgagtctaac ggacaccaac cagcgaacca gcagcgtcgc gtcgggccaa gcgaagcaga  660
cggcacggca tctctgtcgc tgcctctgga cccctctcga gagttccgct ccaccgttgg  720
acttgctccg ctgtcggcat ccagaaattg cgtggcggag cggcagacgt gagccggcac  780
ggcaggcggc ctcctcctcc tctcacggca ccggcagcta cgggggattc ctttcccacc  840
gctccttcgc tttcccttcc tcgcccgccg taataaatag acaccccctc cacaccctct  900
ttccccaacc tcgtgttgtt cggagcgcac acacacacaa ccagatctcc cccaaatcca  960
cccgtcggca cctccgcttc aaggtacgcc gctcgtcctc cccccccccc cctctctacc  1020
ttctctagat cggcgttccg gtccatggtt agggcccggt agttctactt ctgttcatgt  1080
ttgtgttaga tccgtgtttg tgttagatcc gtgctgctag cgttcgtaca cggatgcgac  1140
ctgtacgtca gacacgttct gattgctaac ttgccagtgt ttctctttgg ggaatcctgg  1200
gatggctcta gccgttccgc agacgggatc gatttcatga ttttttttgt ttcgttgcat  1260
agggtttggt ttgccctttt cctttatttc aatatatgcc gtgcacttgt ttgtcgggtc  1320
atcttttcat gcttttttt gtcttggttg tgatgatgtg gtctggttgg gcggtcgttc  1380
tagatcggag tagaattctg tttcaaacta cctggtggat ttattaattt tggatctgta  1440
tgtgtgtgcc atacatattc atagttacga attgaagatg atggatggaa atatcgatct  1500
aggataggta tacatgttga tgcgggtttt actgatgcat atacagagat gctttttgtt  1560
cgcttggttg tgatgatgtg gtgtggttgg gcggtcgttc attcgttcta gatcggagta  1620
gaatactgtt tcaaactacc tggtgtattt attaattttg gaactgtatg tgtgtgtcat  1680
acatcttcat agttacgagt ttaagatgga tggaaatatc gatctaggat aggtatacat  1740
gttgatgtgg gttttactga tgcatataca tgatggcata tgcagcatct attcatatgc  1800
```

-continued

```
tctaaccttg agtacctatc tattataata aacaagtatg ttttataatt attttgatct  1860
tgatatactt ggatgatggc atatgcagca gctatatgtg gattttttta gccctgcctt  1920
catacgctat ttatttgctt ggtactgttt cttttgtcga tgctcaccct gttgtttggt  1980
gttacttctg cagggatccc cgatcatgca aaaactcatt aactcagtgc aaaactatgc  2040
ctggggcagc aaaacggcgt tgactgaact ttatggtatg gaaaatccgt ccagccagcc  2100
gatggccgag ctgtggatgg gcgcacatcc gaaaagcagt tcacgagtgc agaatgccgc  2160
cggagatatc gtttcactgc gtgatgcgat tgagagtgat aaatcgactc tgctcggaga  2220
ggccgttgcc aaacgctttg gcgaactgcc tttcctgttc aaagtattat gcgcagcaca  2280
gccactctcc attcaggttc atccaaacaa acacaattct gaaatcggtt ttgccaaaga  2340
aaatgccgca ggtatcccga tggatgccgc cgagcgtaac tataaagatc ctaaccacaa  2400
gccggagctg gtttttgcgc tgacgccttt ccttgcgatg aacgcgtttc gtgaattttc  2460
cgagattgtc tccctactcc agccggtcgc aggtgcacat ccggcgattg ctcacttttt  2520
acaacagcct gatgccgaac gtttaagcga actgttcgcc agcctgttga atatgcaggg  2580
tgaagaaaaa tcccgcgcgc tggcgatttt aaaatcggcc ctcgatagcc agcatggtga  2640
accgtggcaa acgattcgtt taatttctga attttacccg gaagacagcg gtctgttctc  2700
cccgctattg ctgaatgtgg tgaaattgaa ccctggcgaa gcgatgttcc tgttcgctga  2760
aacaccgcac gcttacctgc aaggcgtggc gctggaagtg atggcaaact ccgataacgt  2820
gctgcgtgcg ggtctgacgc ctaaatacat tgatattccg gaactggttg ccaatgtgaa  2880
attcgaagcc aaaccggcta accagttgtt gacccagccg gtgaaacaag gtgcagaact  2940
ggacttcccg attccagtgg atgattttgc cttctcgctg catgacctta gtgataaaga  3000
aaccaccatt agccagcaga gtgccgccat tttgttctgc gtcgaaggcg atgcaacgtt  3060
gtggaaaggt tctcagcagt tacagcttaa accgggtgaa tcagcgttta ttgccgccaa  3120
cgaatcaccg gtgactgtca aaggccacgg ccgtttagcg cgtgtttaca acaagctgta  3180
agagcttact gaaaaaatta acatctcttg ctaagctggg agctcgatcc gtcgacctgc  3240
agatcgttca aacatttggc aataaagttt cttaagattg aatcctgttg ccggtcttgc  3300
gatgattatc atataatttc tgttgaatta cgttaagcat gtaataatta acatgtaatg  3360
catgacgtta tttatgagat gggtttttat gattagagtc ccgcaattat acatttaata  3420
cgcgatagaa aacaaaatat agcgcgcaaa ctaggataaa ttatcgcgcg cggtgtcatc  3480
tatgttacta gatc                                                    3494
```

```
SEQ ID NO: 134         moltype = DNA  length = 8415
FEATURE                Location/Qualifiers
misc_feature           1..8415
                       note = Zea mays, Escherichia coli, Bacillus thuringiensis,
                        Agrobacterium tumefaciens
source                 1..8415
                       mol_type = other DNA
                       organism = synthetic construct
SEQUENCE: 134
gaaggcggga aacgacaatc tgatcatgag cggagaatta agggagtcac gttatgaccc  60
ccgccgatga cgcgggacaa gccgttttac gtttggaact gacagaaccg caacgctgca  120
ggaattggcc gcagcggcca tttaaatcaa ttgggcgcgc cgaattcgag ctcggtacaa  180
gcttgcacat gacaacaatt gtaagaggat ggagaccaca acgatccaac aatacttctg  240
cgacgggctg tgaagtatag agaagttaaa cgcccaaaag ccattgtgtt tggaattttt  300
agttattcta tttttcatga tgtatcttcc tctaacatgc cttaatttgc aaatttggta  360
taactactga ttgaaaatat atgtatgtaa aaaaatacta agcatatttt tgaagctaaa  420
catgatgtta tttaagaaaa tatgttgtta acagaataag attaatatcg aaatggaaac  480
atctgtaaat tagaatcatc ttacaagcta agagatgttc acgctttgag aaacttcttc  540
agatcatgac cgtagaagta gctctccaag actcaacgaa ggctgctgca attccacaaa  600
tgcatgacat gcatccttgt aaccgtcgtc gccgctataa acacggataa ctcaattccc  660
tgctccatca atttagaaat gagcaagcaa gcacccgatc gctcacccca tatgcaccaa  720
tctgactccc aagctctgtt tcgcattagt accgccagca ctccacctat agctaccaat  780
tgagaccttt ccagcctaag cagatcgatt gatcgttaga gtcaaagagt tggtggtacg  840
ggtactttaa ctaccatgga atgatggggc gtgatgtaga gcggaaagcg cctccctacg  900
cggaacaaca ccctcgccat gccgctcgac tacagcctcc tcctcgtcgg cgccacaacg  960
agggagcccg tggtcgcagc caccgaccag catgtctctg tgtcctcgtc cgacctcgac  1020
atgtcatggc aaacagtcgg acgccagcac cagactgacg acatgagtct ctgaagagcc  1080
cgccacctag aaagatccga gccctgctgc tggtagtggt aaccattttc gtcgcgctga  1140
cgcggagagc gagaggccag aaatttatag cgactgacgc tgtggcaggc acgctatcgg  1200
aggttacgac gtggcgggtc actcgacgcg gagttcacag gtcctatcct tgcatcgctc  1260
ggcgcggagt ttacggggac ttatccttac gacgtgctct aaggttgcga taacgggcgg  1320
aggaaggcgt gtggcgtgcg gagacggttt atacacgtag tgtgcgggag tgtgtttcgt  1380
agacgcggga aagcacgacg acttacgaag gttagtggag gaggaggaca cactaaaatc  1440
aggacgcaag aaactcttct attatagtag tagagaagag attataggag tgtgggttga  1500
ttctaaagaa aatcgacgca ggacaaccgt caaaacgggt gctttaatat agtagatata  1560
tatatataga gagagagaga aagtacaaag gatgcatttg tgtctgcata tgatcggagt  1620
attactaacg gccgtcgtaa gaaggtccat catgcgtgga gcgagcccat ttggttggtt  1680
gtcaggccgc agttaaggcc tccatatatg attgtcgtcg ggcccataac agcatctcct  1740
ccaccagttt attgtaagaa taaattaagt agagatattt gtcgtcgggc agaagaaact  1800
tggacaagaa gaagaagcaa gctaggccaa tttcttgccg gcaagaggaa gatagtggcc  1860
tctagtttat atatcggcgt gatgatgatg ctcctagcta gaaatgagag aagaaaaacg  1920
gacgcgtgtt tggtgtgtgt caatggcgtc catccttcca tcagatcaga acgatgaaaa  1980
agtcaagcac ggcatgcata gtatatgtat agcttgtttt agtgtggctt tgctgagacg  2040
aatgaaagca acggcgggca tatttttcag tggctgtagc tttcaggctg aaagagacgt  2100
ggcatgcaat aattcaggga attcgtcagc caattgaggt agctagtcaa cttgtacatt  2160
ggtgcgagca attttccgca ctcaggaggg ctagtttgag agtccaaaaa ctataggaga  2220
ttaaagaggc taaaatcctc tccttattta attttaaata agtagtgtat ttgtatttta  2280
actcctccaa cccttccgat tttatggctc tcaaactagc attcagtcta atgcatgcat  2340
gcttggctag aggtcgtatg gggttgttaa tagcatagct agctacaagt taaccgggtc  2400
```

-continued

```
ttttatattt aataaggaca ggcaaagtat tacttacaaa taaagaataa agctaggacg  2460
aactgctgga ttattactaa atcgaaatgg acgtaatatt ccaggcaaga ataattgttc  2520
gatcaggaga caagtggggc attggaccgg ttcttgcaag caagagccta tggcgtggtg  2580
acacggcgcg ttgcccatac atcatgcctc catcgatgat ccatcctcac ttgctataaa  2640
aagaggtgtc catggtgctc aagctcagcc aagcaaataa gacgacttgt ttcattgatt  2700
cttcaagaga tcgagcttct tttgcaccac aaggtcgagg atccaccatg acggccgaca  2760
acaacaccga ggccctggac agcagcacca ccaaggacgt gatccagaag ggcatcagcg  2820
tggtgggcga cctgctgggc gtggtgggct tccccttcgg cggcgccctg gtgagcttct  2880
acaccaactt cctgaacacc atctggccca gcgaggaccc ctggaaggcc ttcatggagc  2940
aggtggaggc cctgatggac cagaagatcg ccgactacgc caagaacaag gcactggccg  3000
agctacaggg cctccagaac aacgtggagg actatgtgag cgccctgagc agctggcaga  3060
agaacccccgc tgcaccgttc cgcaaccccc acagccaggg ccgcatccgc gagctgttca  3120
gccaggccga gagccacttc cgcaacagca tgcccagctt cgccatcagc ggctacgagg  3180
tgctgttcct gaccacctac gcccaggccg ccaacaccca cctgttcctg ctgaaggacg  3240
cccaaatcta cggagaggag tggggctacg agaaggagga catcgccgag ttctacaagc  3300
gccagctgaa gctgacccag gagtacaccg accactgcgt gaagtggtac aacgtgggtc  3360
tagacaagct ccgcggcagc agctacgaga gctgggtgaa cttcaaccgc taccgccgcg  3420
agatgaccct gaccgtgctg gacctgatcg ccctgttccc cctgtacgac gtgcgcctgt  3480
accccaagga ggtgaagacc gagctgaccc gcgacgtgct gaccgacccc atcgtgggcg  3540
tgaacaacct gcgcggctac ggcaccacct tcagcaacat cgagaactac atccgcaagc  3600
cccacctgtt cgactacctg caccgcatcc agttccacac gcgtttccag cccggctact  3660
acggcaacga cagcttcaac tactggagcg gcaactacgt gagcacccgc cccagcatcg  3720
gcagcaacga catcatcacc agccccttct acggcaacaa gagcagcgag cccgtgcaga  3780
accttgagtt caacggcgag aaggtgtacc gcgccgtggc taacaccaac ctggccgtgt  3840
ggccctctgc agtgtacagc ggcgtgacca aggtggagtt cagccagtac aacgaccaga  3900
ccgacgaggc cagcacccag acctacgaca gcaagcgcaa cgtgggcgcc gtgagctggg  3960
acagcatcga ccagctgccc cccgagacca ccgacgagcc cctggagaag ggctacagcc  4020
accagctgaa ctacgtgatg tgcttcctga tgcagggcag ccgcggcacc atccccgtgc  4080
tgacctggac ccacaagagc gtcgacttct tcaacatgat cgacagcaag aagatcaccc  4140
agctgcccct ggtgaaggcc tacaagctcc agagcggcgc cagcgtggtg gcaggccccc  4200
gcttcaccgg cggcgacatc atccagtgca ccgagaacgg cagcgccgcc accatctacg  4260
tgacccccga cgtgagctac agccagaagt accgcgcccg catccactac gccagcacca  4320
gccagatcac cttcaccctg agcctggacg gggccccctt caaccaatac tacttcgaca  4380
agaccatcaa caagggcgac accctgacct acaacagctt caacctggcc agcttcagca  4440
cccctttcga gctgagcggc aacaacctcc agatcggcgt gaccggcctg agcgccggcg  4500
acaaggtgta catcgacaag atcgagttca tccccgtgaa ctagatctga gctctagatc  4560
cccgaatttc cccgatcgtt caaacatttg gcaataaagt ttcttaagat tgaatcctgt  4620
tgccggtctt gcgatgatta tcatataatt tctgttgaat tacgttaagc atgtaataat  4680
taacatgtaa tgcatgacgt tatttatgag atgggttttt atgattagag tcccgcaatt  4740
atacatttaa tacgcgatag aaaacaaaat atagcgcgca aactaggata aattatcgcg  4800
cgcggtgtca tctatgttac tagatcggga attgggtacc agcttgcatg cctgcagtgc  4860
agcgtgaccc ggtcgtgccc ctctctagag ataatgagca ttgcatgtct aagttataaa  4920
aaattaccac atattttttt tgtcacactt gtttgaagtg cagtttatct atctttatac  4980
atatatttaa actttactct acgaataata taatctatag tactacaata atatcagtgt  5040
tttagagaat catataaatg aacagttaga catggtctaa aggacaattg agtattttga  5100
caacaggact ctacagtttt atcttttttag tgtgcatgtg ttctcctttt tttttgcaaa  5160
tagcttcacc tatataatac ttcatccatt ttattagtac atccatttag ggtttagggt  5220
taatggtttt tatagactaa ttttttttagt acatctattt tattctattt tagcctctaa  5280
attaagaaaa ctaaaactct attttagttt ttttatttaa taatttagat ataaaataga  5340
ataaaataaa gtgactaaaa attaaacaaa tacccttttaa gaaattaaaa aaactaagga  5400
aacatttttc ttgtttcgag tagataatgc cagcctgtta aacgccgtcg acgagtctaa  5460
cggacaccaa ccagcgaacc agcagcgtcg cgtcgggcca agcgaagcag acggcacggc  5520
atctctgtcg ctgcctctgg acccctctcg agagttccgc tccaccgttg gacttgctcc  5580
gctgtcggca tccagaaatt gcgtggcgga gcggcagacg tgagccggca cggcaggcgg  5640
cctcctcctc ctctcacggc accggcagct acgggggatt cctttcccac cgctccttcg  5700
ctttcccttc ctcgcccgcc gtaataaata gacacccccct ccacaccctc tttccccaac  5760
ctcgtgttgt tcggagcgca cacacacaca accagatctc ccccaaatcc acccgtcggc  5820
acctccgctt caaggtacgc cgctcgtcct cccccccccc ccctctctac cttctctaga  5880
tcggcgttcc ggtccatggt tagggcccgg tagttctact tctgttcatg tttgtgttag  5940
atccgtgttt gtgttagatc cgtgctgcta gcgttcgtac acggatgcga cctgtacgtc  6000
agacacgttc tgattgctaa cttgccagtg tttctctttg gggaatcctg ggatggctct  6060
agccgttccg cagacgggat cgatttcatg atttttttttg tttcgttgca tagggtttgg  6120
tttgcccttt tcctttattt caatatatgc cgtgcacttg tttgtcgggt catcttttca  6180
tgcttttttt tgtcttggtt gtgatgatgt ggtctggttg ggcggtcgtt ctagatcgga  6240
gtagaattct gtttcaaact acctggtgga tttattaatt ttggatctgt atgtgtgtgc  6300
catacatatt catagttacg aattgaagat gatggatgga aatatcgatc taggataggt  6360
atacatgttg atgcgggttt tactgatgca tatacagaga tgcttttttgt tcgcttggtt  6420
gtgatgatgt ggtgtggttg ggcggtcgtt cattcgttct agatcggagt agaatactgt  6480
ttcaaactac ctggtgtatt tattaatttt ggaactgtat gtgtgtgtca tacatcttca  6540
tagttacgag tttaagatgg atggaaatat cgatctagga taggtataca tgttgatgtg  6600
ggttttactg atgcatatac atgatggcat atgcagcatc tattcatatg ctctaacctt  6660
gagtacctat ctattataat aaacaagtat gttttataat tattttgatc ttgatatact  6720
tggatgatgg catatgcagc agctatatgt ggattttttt agccctgcct tcatacgcta  6780
tttatttgct tggtactgtt tcttttgtcg atgctcaccc tgttgtttgg tgttacttct  6840
gcagggatcc ccgatcatgc aaaaactcat taactcagtg caaaactatg cctggggcag  6900
caaaacggcg ttgactgaac tttatggtat ggaaaatccg tccagccagc cgatggccga  6960
gctgtggatg ggcgcacatc cgaaaagcag ttcacgagtg cagaatgccg ccggagatat  7020
cgtttcactg cgtgatgcga ttgagagtga taaatcgact ctgctcggag aggccgttgc  7080
caaacgcttt ggcgaactgc ctttcctgtt caaagtatta tgcgcagcac agccactctc  7140
```

-continued

```
cattcaggtt catccaaaca aacacaattc tgaaatcggt tttgccaaag aaaatgccgc  7200
aggtatcccg atggatgccg ccgagcgtaa ctataaagat cctaaccaca agccggagct  7260
ggtttttgcg ctgacgcctt tccttgcgat gaacgcgttt cgtgaatttt ccgagattgt  7320
ctccctactc cagccggtcg caggtgcaca tccggcgatt gctcactttt tacaacagcc  7380
tgatgccgaa cgtttaagcg aactgttcgc cagcctgttg aatatgcagg gtgaagaaaa  7440
atcccgcgcg ctggcgattt taaaatcggc cctcgatagc cagcatggtg aaccgtggca  7500
aacgattcgt ttaatttctg aattttaccc ggaagacagc ggtctgttct ccccgctatt  7560
gctgaatgtg gtgaaattga accctggcga agcgatgttc ctgttcgctg aaacaccgca  7620
cgcttacctg caaggcgtgg cgctggaagt gatggcaaac tccgataacg tgctgcgtgc  7680
gggtctgacg cctaaataca ttgatattcc ggaactggtt gccaatgtga aattcgaagc  7740
caaaccggct aaccagttgt tgacccagcc ggtgaaacaa ggtgcagaac tggacttccc  7800
gattccagtg gatgatttg ccttctcgct gcatgacctt agtgataaag aaaccaccat  7860
tagccagcag agtgccgcca ttttgttctg cgtcgaaggc gatgcaacgt tgtggaaagg  7920
ttctcagcag ttacagctta aaccgggtga atcagcgttt attgccgcca acgaatcacc  7980
ggtgactgtc aaaggccacg gccgtttagc gcgtgtttac aacaagctgt aagagcttac  8040
tgaaaaaatt aacatctctt gctaagctgg gagctcgatc cgtcgacctg cagatcgttc  8100
aaacatttgg caataaagtt tcttaagatt gaatcctgtt gccggtcttg cgatgattat  8160
catataattt ctgttgaatt acgttaagca tgtaataatt aacatgtaat gcatgacgtt  8220
atttatgaga tgggttttta tgattagagt cccgcaatta tacatttaat acgcgataga  8280
aaacaaaata tagcgcgcaa actaggataa attatcgcgc gcggtgtcat ctatgttact  8340
agatctgcta gccctgcagg aaatttaccg gtgcccgggc ggccagcatg gccgtatccg  8400
caatgtgtta ttaag                                                   8415

SEQ ID NO: 135          moltype = DNA  length = 11632
FEATURE                 Location/Qualifiers
misc_feature            1..11632
                        note = Zea mays, Escherichia coli, Bacillus thuringiensis,
                         Agrobacterium tumefaciens
source                  1..11632
                        mol_type = other DNA
                        organism = synthetic construct
SEQUENCE: 135
ggttacagcc tgggctgatc tgtggacggt ggaccatgca aggttgtact gggcttgcaa  60
ggttgtactg ggcctactgg aacagtcata gcccgtgccg tcgtggtgac cgtcgtacgc  120
ggccgatctg gcagactggg caggtcgctg ctccgtgctg tttgtggatg caatgcaact  180
atgcaagagt gatcacggaa aacggacgga gcctgtctgt cctgttgcga cgtagtacaa  240
gcgcctgaac agtgacgcta cgctatgcca cgagcctacg agtggtaggt agtagtacac  300
tggtcagaat ccagcagtgc acccacgccg ctgctgactt tgctgatgag agggaggggt  360
cgagcgagtc tgtgtgaaac cgtgaacccc gccggggcct tcagtacgta cgataccacg  420
agcagtagaa aaaacaacgc caagatggca gagtcaacaa ccgatcacag tacgtatcgc  480
attcacatca agattttaag aacgaccccc ggctggccaa tggcaggcca cttggttgcc  540
cgtgcccgac agagggacac ggcgccatgc cctccgcgcc gcacggacga ggtgtcgtga  600
gaaccggcaa aaaaaaaatc atcgcaagtg cgctgaagtg aagtgccttc ccccgcgttt  660
ccttgcccct ggccggtacc catttggcgc cgattctttt cttgcccccc ggccggccgc  720
tcgctcgcct ttggattctt ccaaagccgc tgatgggatg gtggcgaaca cacccaccac  780
ccgtctttgc ccaaagcgac ccggcacagg ccgcgccggc ttcactaacc actagcgctt  840
gtactaataa aatggtttct agcgtttgtt gctctccttt ttctttttc gccggttctt  900
cggagccgtg tggacactgg acagcgtcca gtccagcagg catagggtgg tctcggcggc  960
ggtcgtccga cgacgatcga tctccatgag attccgcgac aggccaggac ggaaagctgg  1020
gcccttctca ccaattcgcg tcggagccgg aacaagattc cctcccccaa tcatttcgac  1080
gcgccctttc ttcgccaccc ctcgtggccg tgtttcgcgg ccggccctta tctccttccc  1140
gtgacgcgtt cttttgtagc ttagcggccg gcacgttgct aaccaggcta gcttcgttcg  1200
tttttaatct gcctatcgag aagagaagaa aaattcgtcc atggggccac ggcctcttct  1260
gcaggcattt ggcatgtgaa ggaacccgaa ccagtgaatg gagatggacg gatgctgctc  1320
agatacgcag tcaaacctgc cggcgaaatt acggggggag ctggctggct ggctggctgg  1380
acgccagatc acacatggat gacgcggcac ggcagctagc cgagcaggcg ctctgcgcac  1440
gcaattcaac agaaggcggg aaacgacaat ctgatcatga gcggagaatt aagggagtca  1500
cgttatgacc cccgccgatg acgcgggaca agccgtttta cgtttggaac tgacagaacc  1560
gcaacgctgc aggaattggc cgcagcggcc atttaaatca attgggcgcg ccgaattcga  1620
gctcggtaca agcttgcaca tgacaacaat tgtaagagga tggagaccac aacgatccaa  1680
caatacttct gcgacgggct gtgaagtata gagaagttaa acgcccaaaa gccattgtgt  1740
ttggaatttt tagttattct atttttcatg atgtatcttc ctctaacatg ccttaatttg  1800
caaatttggt ataactactg attgaaaata tatgtatgta aaaaaatact aagcatattt  1860
ttgaagctaa acatgatgtt atttaagaaa atatgttgtt aacagaataa gattaatatc  1920
gaaatggaaa catctgtaaa ttagaatcat cttacaagct aagagatgtt cacgctttga  1980
gaaacttctt cagatcatga ccgtagaagt agctctccaa gactcaacga aggctgctgc  2040
aattccacaa atgcatgaca tgcatccttg taaccgtcgt cgccgctata aacacggata  2100
actcaattcc ctgctccatc aatttagaaa tgagcaagca agcacccgat cgctcacccc  2160
atatgcacca atctgactcc caagctctgt ttcgcattag taccgccagc actccaccta  2220
tagctaccaa ttgagacctt tccagcctaa gcagatcgat tgatcgttag agtcaaagag  2280
ttggtggtac gggtacttta actaccatgg aatgatgggg cgtgatgtag agcggaaagc  2340
gcctccctac gcggaacaac accctcgcca tgccgctcga ctacagcctc ctcctcgtcg  2400
gcgccacaac gagggagccc gtggtcgcag ccaccgacca gcatgtctct gtgtcctcgt  2460
ccgacctcga catgtcatgg caaacagtcg gacgccagca ccagactgac gacatgagtc  2520
tctgaagagc ccgccaccta gaaagatccg agccctgctg ctggtagtgg taaccatttt  2580
cgtcgcgctg acgcggagag cgagaggcca gaaatttata gcgactgacg ctgtggcagg  2640
cacgctatcg gaggttacga cgtggcgggt cactcgacgc ggagttcaca ggtcctatcc  2700
ttgcatcgct cggcgcggag tttacgggga cttatcctta cgacgtgctc taaggttgcg  2760
ataacgggcg gaggaaggcg tgtggcgtgc ggagacggtt tatacacgta gtgtgcggga  2820
```

-continued

```
gtgtgtttcg tagacgcggg aaagcacgac gacttacgaa ggttagtgga ggaggaggac  2880
acactaaaat caggacgcaa gaaactcttc tattatagta gtagagaaga gattatagga  2940
gtgtgggttg attctaaaga aaatcgacgc aggacaaccg tcaaaacggg tgctttaata  3000
tagtagatat atatatatag agagagagag aaagtacaaa ggatgcattt gtgtctgcat  3060
atgatcggag tattactaac ggccgtcgta agaaggtcca tcatgcgtgg agcgagccca  3120
tttggttggt tgtcaggccg cagttaaggc ctccatatat gattgtcgtc gggcccataa  3180
cagcatctcc tccaccagtt tattgtaaga ataaattaag tagagatatt tgtcgtcggg  3240
cagaagaaac ttggacaaga agaagaagca agctaggcca atttcttgcc ggcaagagga  3300
agatagtggc ctctagttta tatatcggcg tgatgatgat gctcctagct agaaatgaga  3360
gaagaaaaac ggacgcgtgt ttggtgtgtg tcaatggcgt ccatccttcc atcagatcag  3420
aacgatgaaa aagtcaagca cggcatgcat agtatatgta tagcttgttt tagtgtggct  3480
ttgctgagac gaatgaaagc aacggcgggc atatttttca gtggctgtag ctttcaggct  3540
gaaagagacg tggcatgcaa taattcaggg aattcgtcag ccaattgagg tagctagtca  3600
acttgtacat tggtgcgagc aattttccgc actcaggagg gctagtttga gagtccaaaa  3660
actataggag attaaagagg ctaaaatcct ctccttattt aattttaaat aagtagtgta  3720
tttgtatttt aactcctcca acccttccga ttttatggct ctcaaactag cattcagtct  3780
aatgcatgca tgcttggcta gaggtcgtat ggggttgtta atagcatagc tagctacaag  3840
ttaaccgggt cttttatatt taataaggac aggcaaagta ttacttacaa ataaagaata  3900
aagctaggac gaactgctgg attattacta aatcgaaatg gacgtaatat tccaggcaag  3960
aataattgtt cgatcaggag acaagtgggg cattggaccg gttcttgcaa gcaagagcct  4020
atggcgtggt gacacggcgc gttgcccata catcatgcct ccatcgatga tccatcctca  4080
cttgctataa aaagaggtgt ccatggtgct caagctcagc caagcaaata agacgacttg  4140
tttcattgat tcttcaagag atcgagcttc ttttgcacca caaggtcgag gatccaccat  4200
gacggccgac aacaacaccg aggccctgga cagcagcacc accaaggacg tgatccagaa  4260
gggcatcagc gtggtgggcg acctgctggg cgtggtgggc ttccccttcg gcggcgccct  4320
ggtgagcttc tacaccaact tcctgaacac catctggccc agcgaggacc cctggaaggc  4380
cttcatggag caggtggagg ccctgatgga ccagaagatc gccgactacg ccaagaacaa  4440
ggcactggcc gagctacagg gcctccagaa caacgtggag gactatgtga gcgccctgag  4500
cagctggcag aagaaccccg ctgcaccgtt ccgcaacccc cacagccagg gccgcatccg  4560
cgagctgttc agccaggccg agagccactt ccgcaacagc atgcccagct tcgccatcag  4620
cggctacgag gtgctgttcc tgaccaccta cgcccaggcc gccaacaccc acctgttcct  4680
gctgaaggac gcccaaatct acggagagga gtggggctac gagaaggagg acatcgccga  4740
gttctacaag cgccagctga agctgaccca ggagtacacc gaccactgcg tgaagtggta  4800
caacgtgggt ctagacaagc tccgcggcag cagctacgag agctgggtga acttcaaccg  4860
ctaccgccgc gagatgaccc tgaccgtgct ggacctgatc gccctgttcc ccctgtacga  4920
cgtgcgcctg taccccaagg aggtgaagac cgagctgacc cgcgacgtgc tgaccgaccc  4980
catcgtgggc gtgaacaacc tgcgcggcta cggcaccacc ttcagcaaca tcgagaacta  5040
catccgcaag ccccacctgt tcgactacct gcaccgcatc cagttccaca cgcgtttcca  5100
gcccggctac tacggcaacg acagcttcaa ctactggagc ggcaactacg tgagcacccg  5160
ccccagcatc ggcagcaacg acatcatcac cagccccttc tacggcaaca agagcagcga  5220
gcccgtgcag aaccttgagt tcaacggcga gaaggtgtac cgcgccgtgg ctaacaccaa  5280
cctggccgtg tggccctctg cagtgtacag cggcgtgacc aaggtggagt tcagccagta  5340
caacgaccag accgacgagg ccagcaccca gacctacgac agcaagcgca acgtgggcgc  5400
cgtgagctgg gacagcatcg accagctgcc ccccgagacc accgacgagc ccctggagaa  5460
gggctacagc caccagctga actacgtgat gtgcttcctg atgcagggca gccgcggcac  5520
catccccgtg ctgacctgga cccacaagag cgtcgacttc ttcaacatga tcgacagcaa  5580
gaagatcacc cagctgcccc tggtgaaggc ctacaagctc cagagcggcg ccagcgtggt  5640
ggcaggcccc cgcttcaccg gcggcgacat catccagtgc accgagaacg gcagcgccgc  5700
caccatctac gtgacccccg acgtgagcta cagccagaag taccgcgccc gcatccacta  5760
cgccagcacc agccagatca ccttcaccct gagcctggac ggggcccccct tcaaccaata  5820
ctacttcgac aagaccatca acaagggcga caccctgacc tacaacagct tcaacctggc  5880
cagcttcagc accccctttcg agctgagcgg caacaacctc cagatcggcg tgaccggcct  5940
gagcgccggc gacaaggtgt acatcgacaa gatcgagttc atccccgtga actagatctg  6000
agctctagat ccccgaattt ccccgatcgt tcaaacattt ggcaataaag tttcttaaga  6060
ttgaatcctg ttgccggtct tgcgatgatt atcatataat ttctgttgaa ttacgttaag  6120
catgtaataa ttaacatgta atgcatgacg ttatttatga gatgggtttt tatgattaga  6180
gtcccgcaat tatacattta atacgcgata gaaaacaaaa tatagcgcgc aaactaggat  6240
aaattatcgc gcgcggtgtc atctatgtta ctagatcggg aattgggtac cagcttgcat  6300
gcctgcagtg cagcgtgacc cggtcgtgcc cctctctaga gataatgagc attgcatgtc  6360
taagttataa aaaattacca catatttttt ttgtcacact tgtttgaagt gcagtttatc  6420
tatctttata catatattta aactttactc tacgaataat ataatctata gtactacaat  6480
aatatcagtg ttttagagaa tcatataaat gaacagttag acatggtcta aaggacaatt  6540
gagtattttg acaacaggac tctacagttt tatcttttta gtgtgcatgt gttctccttt  6600
ttttttgcaa atagcttcac ctatataata cttcatccat tttattagta catccattta  6660
gggtttaggg ttaatggttt ttatagacta atttttttag tacatctatt ttattctatt  6720
ttagcctcta aattaagaaa actaaaactc tattttagtt tttttattta ataatttaga  6780
tataaaatag aataaaataa agtgactaaa aattaaacaa atacccttta agaaattaaa  6840
aaaactaagg aaacattttt cttgtttcga gtagataatg ccagcctgtt aaacgccgtc  6900
gacgagtcta acggacacca accagcgaac cagcagcgtc gcgtcgggcc aagcgaagca  6960
gacggcacgg catctctgtc gctgcctctg gacccctctc gagagttccg ctccaccgtt  7020
ggacttgctc cgctgtcggc atccagaaat tgcgtggcgg agcggcagac gtgagccggc  7080
acggcaggcg gcctcctcct cctctcacgg caccggcagc tacgggggat tcctttccca  7140
ccgctccttc gctttccctt cctcgcccgc cgtaataaat agacaccccc tccacaccct  7200
ctttccccaa cctcgtgttg ttcggagcgc acacacacac aaccagatct cccccaaatc  7260
cacccgtcgg cacctccgct tcaaggtacg ccgctcgtcc tccccccccc cccctctcta  7320
ccttctctag atcggcgttc cggtccatgg ttagggcccg gtagttctac ttctgttcat  7380
gtttgtgtta gatccgtgtt tgtgttagat ccgtgctgct agcgttcgta cacggatgcg  7440
acctgtacgt cagacacgtt ctgattgcta acttgccagt gtttctcttt ggggaatcct  7500
gggatggctc tagccgttcc gcagacggga tcgatttcat gatttttttt gtttcgttgc  7560
```

-continued

```
atagggtttg gtttgccctt ttcctttatt tcaatatatg ccgtgcactt gtttgtcggg  7620
tcatcttttc atgctttttt ttgtcttggt tgtgatgatg tggtctggtt gggcggtcgt  7680
tctagatcgg agtagaattc tgtttcaaac tacctggtgg atttattaat tttggatctg  7740
tatgtgtgtg ccatacatat tcatagttac gaattgaaga tgatggatgg aaatatcgat  7800
ctaggatagg tatacatgtt gatgcgggtt ttactgatgc atatacagag atgctttttg  7860
ttcgcttggt tgtgatgatg tggtgtggtt gggcggtcgt tcattcgttc tagatcggag  7920
tagaatactg tttcaaacta cctggtgtat ttattaattt tggaactgta tgtgtgtgtc  7980
atacatcttc atagttacga gtttaagatg gatggaaata tcgatctagg ataggtatac  8040
atgttgatgt gggttttact gatgcatata catgatggca tatgcagcat ctattcatat  8100
gctctaacct tgagtaccta tctattataa taaacaagta tgttttataa ttattttgat  8160
cttgatatac ttggatgatg gcatatgcag cagctatatg tggatttttt tagccctgcc  8220
ttcatacgct atttatttgc ttggtactgt ttcttttgtc gatgctcacc ctgttgtttg  8280
gtgttacttc tgcagggatc cccgatcatg caaaaactca ttaactcagt gcaaaactat  8340
gcctggggca gcaaaacggc gttgactgaa ctttatggta tggaaaatcc gtccagccag  8400
ccgatggccg agctgtggat gggcgcacat ccgaaaagca gttcacgagt gcagaatgcc  8460
gccggagata tcgtttcact gcgtgatgcg attgagagtg ataaatcgac tctgctcgga  8520
gaggccgttg ccaaacgctt tggcgaactg cctttcctgt tcaaagtatt atgcgcagca  8580
cagccactct ccattcaggt tcatccaaac aaacacaatt ctgaaatcgg ttttgccaaa  8640
gaaaatgccg caggtatccc gatggatgcc gccgagcgta actataaaga tcctaaccac  8700
aagccggagc tggtttttgc gctgacgcct ttccttgcga tgaacgcgtt tcgtgaattt  8760
tccgagattg tctccctact ccagccggtc gcaggtgcac atccggcgat tgctcacttt  8820
ttacaacagc ctgatgccga acgtttaagc gaactgttcg ccagcctgtt gaatatgcag  8880
ggtgaagaaa aatcccgcgc gctggcgatt ttaaaatcgg ccctcgatag ccagcatggt  8940
gaaccgtggc aaacgattcg tttaatttct gaattttacc cggaagacag cggtctgttc  9000
tccccgctat tgctgaatgt ggtgaaattg aaccctggcg aagcgatgtt cctgttcgct  9060
gaaacaccgc acgcttacct gcaaggcgtg gcgctggaag tgatggcaaa ctccgataac  9120
gtgctgcgtg cgggtctgac gcctaaatac attgatattc cggaactggt tgccaatgtg  9180
aaattcgaag ccaaaccggc taaccagttg ttgacccagc cggtgaaaca aggtgcagaa  9240
ctggacttcc cgattccagt ggatgatttt gccttctcgc tgcatgacct tagtgataaa  9300
gaaaccacca ttagccagca gagtgccgcc attttgttct gcgtcgaagg cgatgcaacg  9360
ttgtggaaag gttctcagca gttacagctt aaaccgggtg aatcagcgtt tattgccgcc  9420
aacgaatcac cggtgactgt caaaggccac ggccgtttag cgcgtgttta caacaagctg  9480
taagagctta ctgaaaaaat taacatctct tgctaagctg ggagctcgat ccgtcgacct  9540
gcagatcgtt caaacatttg gcaataaagt ttcttaagat tgaatcctgt tgccggtctt  9600
gcgatgatta tcatataatt tctgttgaat tacgttaagc atgtaataat taacatgtaa  9660
tgcatgacgt tatttatgag atgggttttt atgattagag tcccgcaatt atacatttaa  9720
tacgcgatag aaaacaaaat atagcgcgca aactaggata aattatcgcg cgcggtgtca  9780
tctatgttac tagatctgct agccctgcag gaaatttacc ggtgcccggg cggccagcat  9840
ggccgtatcc gcaatgtgtt attaagagtt ggtggtacgg gtactttaac taacgaggtg  9900
tgtcgcgcag cgctcctgca cggatgtagc tttggattgc tggataatgt ctcgcgcaag  9960
cgtcgtattt atttatttat ttattacagc ctccaccgcc gtgcgtgctc cgtttcggat  10020
tataataaaa ctaatattaa ataaaaaaat cggattaaag gatgtttccg aaataaagat  10080
ctccaccaca ggagcgaaag aaaaaaaaag agaaacgggc tatggagaaa tggtgttgcg  10140
agtatacggc ggctccgtcg tcgtcggatc gacatgtaca aagtaggtgc acaaaaggca  10200
aagcaaaatc acctcatcaa agaccaaaag cggagcaaag aatcgatact aaatccacat  10260
gttttttttg ttcctgtcta ctacgtgctg tgcctgtgcg tgaagcacga ttagtacgtg  10320
tactcactct tgtcatattc tttttagtgt cttgtcacta gtcacatgga gtagcaacca  10380
tggctggcga tacccgcgat aaataaaaaa aagagagagg gagtaatata ttagatactc  10440
acccattata aattataaaa tattttagag tttgaatagg tagttcttgt atatttattt  10500
atagaccttc aagtttgtcc gcctctcgag agccgaactt tgttgcccat gcttccccgg  10560
ctcaggtcat gccacctcct tcaccaaggg cacacggaag atctggtgga gcttgtcatc  10620
accccgcgcc cttcaaacat gtgaggatgc gtcgtcgctg gcactagtag cactcattgt  10680
aggcactaca ttgacagttt cctccagata tgtagtgagg aaacacttga acaacacgtt  10740
tgggattaca tatgatgttt tgtttgttca tcaatgataa ttccttcttc ttgcttaatg  10800
attggctcta gaaccgatac atggcacatt tcatcaggaa gggcgcatgc acgaaattaa  10860
actgttatcg atgtttcggt ttctaagttg aagaaaacaa tggctaacaa ctagcccatg  10920
tgagcataac gacaaggcct acaaacaaaa cccaagaaat agctaaatca tggtctggat  10980
ccactctgct atgatagatc accttttcta acatagttca tcctcccatt tgctctcgct  11040
cacctagtgc ctccatcgct gagatcaatg ataagtacca agtgtacgat gaatcccatt  11100
tgtcatgcgt cttgcaagaa tggttggtcc gcttgcagtg ccggtccagc tatggaccca  11160
ggggcctatg tcataactca agcaagacca taccccccata tgctaccaag atgcctttta  11220
agaatcctgg taaaagaaat cggtggaaga cgactcaacg actatcaggc cccatttttt  11280
gggaccatgc tcaaggattt ggctttagca aaagtagata acactatttt ggggagcttg  11340
atctcaagga cacatgaagg aataaagcta ttttagtcaa gacgtcctta aggaacacaa  11400
taagacccta ggtccctaat gactagtgtg ttatatgttt cgagacgctc ctacacctaa  11460
gttcttttag ctatttccat tcacaatgat ggtatatgac ctaggtacca atgccccacg  11520
gagtttctaa cattaagaat gatctaaaac ataaggaccc tagagccagg gcactcctgg  11580
tattaaaaca tttaccagcc cgggccgtcg accacgcgtg ccctatagta ag          11632
```

```
SEQ ID NO: 136         moltype = DNA  length = 1451
FEATURE                Location/Qualifiers
source                 1..1451
                       mol_type = genomic DNA
                       organism = Zea mays
SEQUENCE: 136
ggttacagcc tgggctgatc tgtggacggt ggaccatgca aggttgtact gggcttgcaa  60
ggttgtactg ggcctactgg aacagtcata gcccgtgccg tcgtggtgac cgtcgtacgc  120
ggccgatctg gcagactggg caggtcgctg ctccgtgctg tttgtggatg caatgcaact  180
atgcaagagt gatcacggaa aacggacgga gcctgtctgt cctgttgcga cgtagtacaa  240
```

```
gcgcctgaac agtgacgcta cgctatgcca cgagcctacg agtggtaggt agtagtacac  300
tggtcagaat ccagcagtgc acccacgccg ctgctgactt tgctgatgag agggaggggt  360
cgagcgagtc tgtgtgaaac cgtgaacccc gccggggcct tcagtacgta cgataccacg  420
agcagtagaa aaaacaacgc caagatggca gagtcaacaa ccgatcacag tacgtatcgc  480
attcacatca agattttaag aacgaccccc ggctggccaa tggcaggcca cttggttgcc  540
cgtgcccgac agagggacac ggcgccatgc cctccgcgcc gcacggacga ggtgtcgtga  600
gaaccggcaa aaaaaaaatc atcgcaagtg cgctgaagtg aagtgccttc ccccgcgttt  660
ccttgcccct ggccggtacc catttggcgc cgattctttt cttgcccccc ggccggccgc  720
tcgctcgcct ttggattctt ccaaagccgc tgatgggatg gtggcgaaca cacccaccac  780
ccgtctttgc ccaaagcgac ccggcacagg ccgcgccggc ttcactaacc actagcgctt  840
gtactaataa aatggtttct agcgtttgtt gctctccttt ttcttttttc gccggttctt  900
cggagccgtg tggacactgg acagcgtcca gtccagcagg catagggtgg tctcggcggc  960
ggtcgtccga cgacgatcga tctccatgag attccgcgac aggccaggac ggaaagctgg  1020
gcccttctca ccaattcgcg tcggagccgg aacaagattc cctcccccaa tcatttcgac  1080
gcgccctttc ttcgccaccc ctcgtggccg tgtttcgcgg ccggccctta tctccttccc  1140
gtgacgcgtt cttttgtagc ttagcggccg gcacgttgct aaccaggcta gcttcgttcg  1200
tttttaatct gcctatcgag aagagaagaa aaattcgtcc atggggccac ggcctcttct  1260
gcaggcattt ggcatgtgaa ggaacccgaa ccagtgaatg gagatggacg gatgctgctc  1320
agatacgcag tcaaacctgc cggcgaaatt acggggggag ctggctggct ggctggctgg  1380
acgccagatc acacatggat gacgcggcac ggcagctagc cgagcaggcg ctctgcgcac  1440
gcaattcaac a                                                      1451
```

```
SEQ ID NO: 137         moltype = DNA  length = 1766
FEATURE                Location/Qualifiers
source                 1..1766
                       mol_type = genomic DNA
                       organism = Zea mays
SEQUENCE: 137
agttggtggt acgggtactt taactaacga ggtgtgtcgc gcagcgctcc tgcacggatg  60
tagctttgga ttgctggata atgtctcgcg caagcgtcgt atttatttat ttatttatta  120
cagcctccac cgccgtgcgt gctccgtttc ggattataat aaaactaata ttaaataaaa  180
aaatcggatt aaaggatgtt tccgaaataa agatctccac cacaggagcg aaagaaaaaa  240
aaagagaaac gggctatgga gaaatggtgt tgcgagtata cggcggctcc gtcgtcgtcg  300
gatcgacatg tacaaagtag gtgcacaaaa ggcaaagcaa aatcacctca tcaaagacca  360
aaagcggagc aaagaatcga tactaaatcc acatgttttt tttgttcctg tctactacgt  420
gctgtgcctg tgcgtgaagc acgattagta cgtgtactca ctcttgtcat attcttttta  480
gtgtcttgtc actagtcaca tggagtagca accatggctg gcgataccg cgataaataa  540
aaaaaagaga gagggagtaa tatattagat actcacccat tataaattat aaaatatttt  600
agagtttgaa taggtagttc ttgtatattt atttatagac cttcaagttt gtccgcctct  660
cgagagccga actttgttgc ccatgcttcc ccggctcagg tcatgccacc tccttcacca  720
agggcacacg gaagatctgg tggagcttgt catcaccccg cgcccttcaa acatgtgagg  780
atgcgtcgtc gctggcacta gtagcactca ttgtaggcac tacattgaca gtttcctcca  840
gatatgtagt gaggaaacac ttgaacaaca cgtttgggat tacatatgat gttttgtttg  900
ttcatcaatg ataattcctt cttcttgctt aatgattggc tctagaaccg atacatggca  960
catttcatca ggaagggcgc atgcacgaaa ttaaactgtt atcgatgttt cggtttctaa  1020
gttgaagaaa acaatggcta acaactagcc catgtgagca taacgacaag gcctacaaac  1080
aaaacccaag aaatagctaa atcatggtct ggatccactc tgctatgata gatcaccttt  1140
tctaacatag ttcatcctcc catttgctct cgctcaccta gtgcctccat cgctgagatc  1200
aatgataagt accaagtgta cgatgaatcc catttgtcat gcgtcttgca agaatggttg  1260
gtccgcttgc agtgccggtc cagctatgga cccaggggcc tatgtcataa ctcaagcaag  1320
accatacccc catatgctac caagatgcct tttaagaatc ctggtaaaag aaatcggtgg  1380
aagacgactc aacgactatc aggccccatt ttttgggacc atgctcaagg atttggcttt  1440
agcaaaagta gataacacta ttttggggag cttgatctca aggacacatg aaggaataaa  1500
gctattttag tcaagacgtc cttaaggaac acaataagac cctaggtccc taatgactag  1560
tgtgttatat gtttcgagac gctcctacac ctaagttctt ttagctattt ccattcacaa  1620
tgatggtata tgacctaggt accaatgccc cacggagttt ctaacattaa gaatgatcta  1680
aaacataagg accctagagc cagggcactc ctggtattaa aacatttacc agcccgggcc  1740
gtcgaccacg cgtgccctat agtaag                                      1766
```

```
SEQ ID NO: 138         moltype = DNA  length = 10818
FEATURE                Location/Qualifiers
source                 1..10818
                       mol_type = genomic DNA
                       organism = Zea mays
SEQUENCE: 138
ccattaaatc gacgaaagca actagatcct gattttgatt acgattacga ttgacgagta  60
tggatcatga ttttattgca tattttatga ttttattgca tattttatta ttttattgtc  120
gatttatgta ctaacttgtt tttgttaaaa taggatgtca aagaaaatga agtctttagc  180
tcgtagtttg cttgggtcga ggaggagctc gaggagcagc tcgaggggtg aggattcagt  240
ttttcagggc acaggttcta ccatgagcag acggagagcg ctggcagaac atttgcctcc  300
acaagatgta agttagttgt taaattacat tatttgagtt acttaatatt gtatgatgta  360
agttatttgt ttcataggat gctgaaattg aggaaccagt ggtagaggat catgcaagag  420
atgatgttga agatgatggt ggagataatg tgggagatga tgctggagac gacgctggtg  480
gggattctgg ggctggggat tctggggctg gtggagattc tgcagctggg tctggaactt  540
ctcgagttaa gagaacgagg aagctgcatt ttgttggacc acctccagag cttccacccg  600
aatctcgggt tgtaataaag cctagtggaa agtgagtgac atatctttgc ttaaatgtta  660
ttgaaagtta tgttttaatt tctacattga tttctgtttg caggacttgg atcgacgact  720
cgttcacagg cacaggacac tacaggcagg tgaacatggt tcttggtaat cttgttcgtc  780
tgcactggcc tggtcttgtg actttgccta ctggcgagtc tgtccccgcc accacttggg  840
```

-continued

```
agcattatcg ctatggtgtc tgtagaacgt ttggcaacac acaggcacta gtttgggatg  900
cattctgggt atgacttgtt tatactattt tagttattcc atatatgttt gcttttatga  960
taacactatg gtttttgcag aaacggtaca agttgccgga cgatggatca tatgatatga  1020
acgctcgtta cgtgtttgag tttaacgcga acgatgtcgt tgcagatgca atgtactatg  1080
cacgaattca ggctataaag gcatggtaca gagcaaatgc tgatgatcga ccgatgccaa  1140
atacaaaggc cgagtggtca tcaatttact tgacggagga gcaataccta gaggtaaaca  1200
ggttgttgcc tctcatatcg cacaaagcca tgtatttgct tgctttattt aaaaattttg  1260
atgtaggtgt cggtgccgtg gatggccacc cgaccagacg gttatcgggc attgtgcaga  1320
tggtgggctt cccctgactt tcgtgccatt tccgaaagga acaggggaaa ccgtgggact  1380
gagtcgttcc acaactacgg cggtgatggt catgtgcgct tggctaagcg aatggtaagt  1440
cacagtttgt cgtaactttg aatcacatag caaatgtgtc attataactt ttatgtacag  1500
gaagtcaaat ccggccgtac gcccacggat gtggaggtgt atatgcaagg gcatagggcc  1560
ataggggttc tgatcctcag aatcctgatg tgttatgcac tcagacggcc accgaccgtc  1620
tagtgagttt ttgatactct attatgtgtg ttgatattgt ttgcaagggc ataggggtta  1680
tgcacttata tttgatattg tttgcctcca ggcttcgtat gggcaggaga tggttcaacg  1740
ccatggggag gagtacgatt ggaggagcca gccaatcgac cctcagacag catatgctag  1800
cgcaggagga caagctcatg gacggtgaga ttatttgatt tggttttcaa aattgtcatc  1860
atatgcttgc gattcaactg agccatgagt tactatacta agtgcatggt tcactcttgt  1920
aggttgggta tttttgattc tacgattgat tccagagagc tgagacgccg tggacgacaa  1980
tccacatcgt cgtcttcaca gtcgtcccgt tcacgatcag cagcccatga gatagagctt  2040
gcagtgttgc gtcaacaggc agagtaccat caatcagtct tgagggaaca attggagtac  2100
cagaggcaac aatctgaata ccagagacaa caagccgagt accagaagaa gagggacgag  2160
tattatgcaa gcctccaggc ccaaaatcaa gctcttctct cggtaagttg aagtaacatt  2220
ttgtagctta ttttgcaaaa cacttgatgt gtatcttgtt tgttcaacaa tgacttgtat  2280
ataatttgta gcaactagcc caacaagcgg gcgtcccgat gccgacatat gggatgccgc  2340
ctccggactt tgcactgcca atgccaatgt tggcgcctcc acctccacct ccgcctccgc  2400
ctacgtcaca attccctatg gtatgtacac atatgcgtgt gtgacatgtt catagatgtc  2460
ttatgtgttt aaatgaacaa ctgagtggtt actatttcat gtgcttgtgt tatagggatt  2520
tcagacacca cccgcttcag ttgccgcacc tggagatggg tctgggcaag acgacacaac  2580
acattcgtgg gtcaacaacc tattcaacac gcagagtcca gccggaggag gtggctactt  2640
gaaccatcca gacgatggat atgattgatg tgtcgtgatg tttatttatg aaacactttg  2700
caacacttgt ttgtgagaca caatttcagt ttgcaacaac cgtcgaacct atatgttgat  2760
gttaaatttg tgaatgttat tatttatgtg agaatatttg tgattgtgaa tacttattag  2820
aatgtgtata tttgtgattg tgaatgtgaa tgtgtatatg tgcatgaatc tgttttcgtt  2880
ttgtaaatgt cagatttttt aaaaaacaga attttgtgta aattctgtaa tttgttatgt  2940
ccgacggcct agtggtagcc gtcggacata acacatggtt atgtccgacg gcattaacta  3000
ccgtcggaca taagggatgc ttatgtccga cggcctagtg gtagccgtcg gacttaatcc  3060
tgtggggccc acattccgac cggtaaaacg gttgggattt gttatctccg acgggcacac  3120
gcagccgtcg gagatagctt atgtccgacg gctgccgtcg gacattgcac tatttccgac  3180
gagttatctc cgacggctta aagccgtcgg agataaggct ttgccgtcgg aaataatcta  3240
tttccgacgg tttattcctt atgtccgacg gttttggcca tcggacgttt ctccgtttac  3300
tgtagtggaa gggagtgcag tagaagtgca atggcctaat gtccttcacc ataaaaaaaa  3360
caaagttcaa atctttcaga tttatttact cttggagtag catagcatag gtgtacaagg  3420
gaagtgctta taataatggt aacaagatac tcatcctctc atacctgccg tctcactgac  3480
aggaaacggt aggtggcaag ttggtaagct tttcggtttt agccatgtcc gatcccatgt  3540
gtggatcctg tactgtacat cgacatgcga catcttggtt ggcctatctg atctttaatg  3600
tcgccgcgca cagagaggag atccggtctc atgaagtggc tccgcagatt cctcaagggg  3660
ccgaagcccg gcgaaccgag ccgccggcgg ccccaggtgg cggccgggga agaggaggac  3720
gcgctttggc accaacgacc agctagacca aaggtactac tactaccact gtactagtga  3780
ctgagttcct cccttcttct tctacagttc gtctctgtct ctccaaatgg ctctttgatc  3840
tatccaaaca tgccgtttca cagcttcaca tccgattcaa ctcgcatcca ttgcagtgcc  3900
atcttaaact cttagctccg aaaaaggaag ttgctaaaga ctagtacaat atctttcttc  3960
gctgtttcca gatcgatcca cctaggaacg agaatgagga actagtggac cgtgccattg  4020
ccgagcctct tgcagaggct gtcaaaccgc ccagaggtag taccgtagat ggacgaatcc  4080
agatacacat tccatgtcag catggtataa atttctctga aaccgtttca tccctgcatc  4140
ccgttgctgt aaattgctgc gccagagaaa acccataggg gagaagacag caacgacgac  4200
gaagatctgg caagagccgt acaggacagt ctgaatatga acccttacac gccttacaac  4260
ccctatccac cctctcaggc ccaacctaga gggcacaggt caaccgctat cacaatcacc  4320
atttactggc accctaagat attctctaac gcgccaaagc agctcaatgc cgtcagtgtc  4380
cgtgctgcag ggtatgcgga ggctgcaagc atgagatagg gcgtggccat tacttgagct  4440
gcatgggcat ttactggcac cctcagtgct tccgctgcag gtcctgcggt caccttatcc  4500
gtgagaccga ggtaattaag ctcttgcatt ttctttcacc gtggaagtgt gttacagtgt  4560
taccagagat gagatcatat ccgttattct tttcgtcgtg ccttccagtt caccttgctg  4620
ggtgcggatt cgtaccacaa gctgtgctac aaggagctgc atcatccaaa atgcgacgtc  4680
tgccttcagt ttgtaaggcc tcgtgtcctc ggaaaacctg agcgatctgc actacagact  4740
gataaactgc gtacgcgtta gcatttctac accgtgccgt ctcgtcagtg taatgagagg  4800
ctcattcttt gtagatgtgt ttctgcagat cccaacgaac gggagtggct tgatagagta  4860
cagagcccac ccgttctggg gccagaagta ttgcccttcg catgagcgcg acaggacgcc  4920
acgttgctgc agctgtgaga aaatggaggt acaggtacag atactagata gaaaatgtgg  4980
tcgcagtccg atcactcgtt ttcaaactag gttgtacatt gcctgatcat attcaagggc  5040
atcacttttc ggttgtgatt gtgcagccaa ggaacacgaa gtacatgtcg ctgggagacg  5100
gacgcggcct gtgcatggaa tgcctgggat ctgcagtgat ggacacgagc gagtgccagc  5160
ctctgtacca ttctatcaga gactactacg aggggatgga catgagactg gaccagcaga  5220
tacccgtgct cttggttgag cggcaagcgc tcaacgaagc catggaaggg gagagtaaag  5280
tgagtgtttc ttctggttct gccccttttt tttgtgtgtg tttctgcaaa acgtacagcc  5340
ttcggaaaca ctaacgctga ccgcatctgc gaaatccagg gcccacgcca catgcctgag  5400
actaggggcc tatgtctgtc cgaggagcgg actgtgagca gtgtaagtgt tcaacaactc  5460
aagctgtggc ggttactgct gggatgctta gcccacaatg cgacagtttc tgctcttctg  5520
actgtgtgtt acttctgcag atacttagga ggcccagaat tggtggaaac aaccggttac  5580
```

-continued

```
tagacatgag aactcggcca cagaagctga ctaggagatg tgaagttact gcaatacttg  5640
tcctgtatgg cctccccagg tctggcaatt ttttttttat ctctggagtc tggaggacat  5700
cactttttg tacctaccgg attcaaatac tgcggttctt ctcacgttct gtgaccggtg  5760
gtgtcgtcgt ttgtgtcaca acgctattgc aggctactga caggttccat cctcgcccat  5820
gagctgatgc acgggtggct gcgtctcaaa ggtacatccg tatatggatg gatggacaaa  5880
acatttcata cacccattta tcatctttat ttatgaattt tcttggaaag ctctaccgga  5940
tcgtactttt cattcaggtt accgaaacct aaacgcggag gtggaagaag gcatatgcca  6000
ggtcatgtct tacttgtggc tggaatcaga gattcttccg tcatcctcga ggcacgcgca  6060
gccttcatca tcctatccag caacatcatc cgagaaaggt ggaatatctc ataccgggaa  6120
gaagctgggc gagttcttca tgcaccagat tgccaatgac acgtcgacgg cctatggtga  6180
cgggttcaga actgcgtacg ctgccgtcaa caagtatggc cttcgccaaa cactgagcca  6240
tatacgccta acaggaggtt tccctgtata ataagagtga aaaaaacata aaatgtccat  6300
gcatgatcat atcgatatca aaaggttata tacatattgg gatgaagttg gctatggaac  6360
actggatgca tagtgattca atttcggtga cctttgagtt ttcaaagagg taatgtcgga  6420
gtaaatcaga aagtaaaccc gtataaagca tggttgagac gattgtttac tctatagtga  6480
tgcatgctac atgcatggcc aagaagagag caacgggcca taggaccatc gttattaccc  6540
atcgttgtta atcaaattta gggctagata aatagtaaac catctatagg aacatccaga  6600
gtcaatctac tctatgtatc ataccgacca ggggcggatc taggtaaaat aaccattgat  6660
gtcatctcca ttaaattata gtatcatcaa cctatttaag tgctaacaat catacatttt  6720
aatgaagatt attaaaatcc attggtgtca catgacacca caaaaatggc ctagatccgc  6780
ccctgatacc gacaaaccta gaaaaatttg taactgagaa ctgatgacca tacacatgaa  6840
catgaattag gactttcaaa gagtccaatc aaagtaaaca attagactaa gcatgtaaga  6900
tagggtgcca gatgttgtat caggcttttg agcacatgtg caacttgtat gtcgtggaac  6960
gtgacaaccg gtcaaggaat gcgcatgtga cggtgtaaaa tcaatataac aacatgaaga  7020
acaatcataa gtataggttg aaactacaca tgataactag tatatctttc taacaacaat  7080
gattagtaca atatgtaccg tggtaaagtg gtgacaccat tagagatcgc attagaacgg  7140
catggcgctt actttaaaaa atgttagaga agcggttatg gtcaaacaga atattatgtg  7200
aatatgcggg aagatgaaca aatctataac acagaaacga aggaaccaaa taggatcagc  7260
ggagagtaca gtgccaacgc gcgacgaaac gaggaagcca gaaaggcacc gccgcatgcc  7320
cgcaccgcgt gactgtcgaa ggcggccgtg agcgctccga catcgaagga gtttatttca  7380
aaaatgggac gaccaacatt gcgcttttca catttgtttc ctaacgttgc actctttcac  7440
atatggcacc gagacacgca atcttgttga caccgctcgt agtccggtcc gggcagtgag  7500
gtcttacctg tcgtggtttc agaaaccggg gataataaga tttgtgttcg gtaaggacgc  7560
agcgcggact cactctgaat ggtcagagga ctcaatgatg gatctgagac aaggggttat  7620
actggtttag gcttgcgccc tagtccaatg ttgatcatag tattgcttag agcgtgttac  7680
agttgagtgc tcgtatctag aagatggggg ttgtcttgct cttttatagc tcaaggatag  7740
atcttacaat gagacttgta ttctgttggg gtcgagctca gcttcctact tctgggtgac  7800
gtagctcctc cggtatcgtc tgctgggtcg tgcgccatcg tatccctggt atggcgtcgc  7860
gtcttatccg ttcgccgtat gagttcttgt agctattctg atgcaaacgt agtggtgcct  7920
ggtgggtctc gcagagtcgg tttgtggtga ggtttagggg cgtctttagt acaacttcat  7980
cttccatcat tccctatgcg tcaccttcca gcatgcgtag gcgtacgctt cgtacagcgt  8040
attaccgcgt cccttctgga cttctggtat gtaggtcact gtagagaccc aatgctgggt  8100
tgattggtcc caccggtcag cgaggatgct ctctagaatg tatctggcgt cgtgattggc  8160
agaggccttc ggtactgctc ccatggttca gacgtggctt ggtggtgatc tgtctcatcg  8220
tgctgacgtg acttgatagt actaggtcgg ctcttacctc ctatagatgt gctcgctaga  8280
aagtccattg tcatcttgct gggttgctcg gcatgtaggt tgatcggtaa atccgcctcg  8340
tcgagttgct cgataatgtt gctcggcggg cgggtatgta ggtagtccga cctcaccggg  8400
ttgttcggca atcccgcctc gccgagttgc tcggtgaacg ggttggtcgg cagccccacc  8460
tcgccaggtt gtttggcaca cgtgttggtc tgttggtggg tcgtcgagag ccctttttggg  8520
ctttttttggg cacccggttt ctggtacccc acaatacccg agctagagtt ccacatttgc  8580
ccctaccttc cttcccggct ccggcgacaa gcccaggatc ctggtgtaat ggggcgagga  8640
gaagcagttc ttgacggagg agaccagctc catgatcccc aacaaaatga aggagacaac  8700
cgaggcctac ctcggcgtca ccatcaataa cactgttgtc accgtcccag tctatttcaa  8760
tgagtcccag cgccagacta ccaaaaacgt cgccgtcatc tccggccttc accgtcatgc  8820
gcatcatcaa cgagcccacc actgtcgcca tcacctacgg gctcgacaag aaatcgagca  8880
gcaacaacga gaataatgtc gtcatcttcg acctcgacgg cggtaccttt gacgtcgcgc  8940
tccggcggct aaggaccgca ctgccgacga gggcatgagt ggcgccgaga tggaagagaa  9000
gaggagcaca aatggcggtc gtcggcaaag acaaagagaa ctcgagcgtg agtggaggaa  9060
ggggcaaatg tgtaactcca gcttggatat gactccactg accagattac gagcgacatc  9120
aactagattg tgtgtctcag tggctcagtg ccattttttg aggtttgggt gccaatattt  9180
tttcgtagtg gaaggcaccg cgcccatcgg gttttgggag ccaaacgcca aacccgctcg  9240
cctcatattc cgcaacgtac agcggtttca tgggctggtt gaaggcccgg gccgcaaacc  9300
aaccgagtcg ggccgacgcc ctgggagatc cgcacggctg gtctggccca agcaacctgg  9360
tgggttggtg ccaggttaca gcctgggctg atctgtggac ggtggaccat gcaaggttgt  9420
actgggcttg caaggttgta ctgggcctac tggaacagtc atagcccgtg ccgtcgtggt  9480
gaccgtcgta cgcggccgat ctggcagact gggcaggtcg ctgctccgtg ctgtttgtgg  9540
atgcaatgca actatgcaag agtgatcacg gaaaacggac ggagcctgtc tgtcctgttg  9600
cgacgtagta caagcgcctg aacagtgacg ctacgctatg ccacgagcct acgagtggta  9660
ggtagtagta cactggtcag aatccagcag tgcacccacg ccgctgctga ctttgctgat  9720
gagagggagg ggtcgagcga gtctgtgtga aaccgtgaac cccgccgggg ccttcagtac  9780
gtacgatacc acgagcagta gaaaaaacaa cgccaagatg gcagagtcaa caaccgatca  9840
cagtacgtat cgcattcaca tcaagatttt aagaacgacc cccggctggc caatggcagg  9900
ccacttggtt gcccgtgccc gacagaggga cacggcgcca tgccctccgc gccgcacgga  9960
cgaggtgtcg tgagaaccgg caaaaaaaaa aatcatcgca agtgcgctga agtgaagtgc  10020
cttccccgc gtttccttgc ccctggccgg tacccatttg gcgccgattc ttttcttgcc  10080
ccccggccgg ccgctcgctc gcctttggat tcttccaaag ccgctgatgg gatggtggcg  10140
aacacaccca ccacccgtct ttgcccaaag cgacccggca caggccgcgc cggcttcact  10200
aaccactagc gcttgtacta ataaaatggt ttctagcgtt tgttgctctc cttttcttt  10260
tttcgccggt tcttcggagc cgtgtggaca ctggacagcg tccagtccag caggcatagg  10320
```

```
gtggtctcgg cggcggtcgt ccgacgacga tcgatctcca tgagattccg cgacaggcca  10380
ggacggaaag ctgggccctt ctcaccaatt cgcgtcggag ccggaacaag attccctccc  10440
ccaatcattt cgacgcgccc tttcttcgcc acccctcgtg gccgtgtttc gcggccggcc  10500
cttatctcct tcccgtgacg cgttcttttg tagcttagcg gccggcacgt tgctaaccag  10560
gctagcttcg ttcgttttta atctgcctat cgagaagaga agaaaaattc gtccatgggg  10620
ccacggcctc ttctgcaggc atttggcatg tgaaggaacc cgaaccagtg aatggagatg  10680
gacggatgct gctcagatac gcagtcaaac ctgccggcga aattacgggg ggagctggct  10740
ggctggctgg ctggacgcca gatcacacat ggatgacgcg gcacggcagc tagccgagca  10800
ggcgctctgc gcacgcaa                                                10818

SEQ ID NO: 139          moltype = DNA  length = 6300
FEATURE                 Location/Qualifiers
source                  1..6300
                        mol_type = genomic DNA
                        organism = Zea mays
SEQUENCE: 139
gcactgcact gcactgcacg gatgcagctt tggcaacgag gtgtgtcgcg cagcgctcct  60
gcacggatgt agctttggat tgctggataa tgtctcgcgc aagcgtcgta tttatttatt  120
tatttattac agcctccacc gccgtgcgtg ctccgtttcg gattataata aaactaatat  180
taaataaaaa aatcggatta aaggatgttt ccgaaataaa gatctccacc acaggagcga  240
aagaaaaaaa aagagaaacg ggctatggag aaatggtgtt gcgagtatac ggcggctccg  300
tcgtcgtcgg atcgacatgt acaaagtagg tgcacaaaag gcaaagcaaa atcacctcat  360
caaagaccaa aagcggagca aagaatcgat actaaatcca catgtttttt ttgttcctgt  420
ctactacgtg ctgtgcctgt gcgtgaagca cgattagtac gtgtactcac tcttgtcata  480
ttctttttag tgtcttgtca ctagtcacat ggagtagcaa ccatggctgg cgatacccgc  540
gataaataaa aaaaagagag agggagtaat atattagata ctcacccatt ataaattata  600
aaatatttta gagtttgaat aggtagttct tgtatattta tttatagacc ttcaagtttg  660
tccgcctctc gagagccgaa ctttgttgcc catgcttccc cggctcaggt catgccacct  720
ccttcaccaa gggcacacgg aagatctggt ggagcttgtc atcacccccgc gcccttcaaa  780
catgtgagga tgcgtcgtcg ctggcactag tagcactcat tgtaggcact acattgacag  840
tttcctccag atatgtagtg aggaaacact tgaacaacac gtttgggatt acatatgatg  900
ttttgtttgt tcatcaatga taattccttc ttcttgctta atgattggct ctagaaccga  960
tacatggcac atttcatcag gaagggcgca tgcacgaaat taaactgtta tcgatgtttc  1020
ggtttctaag ttgaagaaaa caatggctaa caactagccc atgtgagcat aacgacaagg  1080
cctacaaaca aaacccaaga aatagctaaa tcatggtctg gatccactct gctatgatag  1140
atcacctttt ctaacatagt tcatcctccc atttgctctc gctcacctag tgcctccatc  1200
gctgagatca atgataagta ccaagtgtac gatgaatccc atttgtcatg cgtcttgcaa  1260
gaatggttgg tccgcttgca gtgccggtcc agctatggac ccaggggcct atgtcataac  1320
tcaagcaaga ccatacccccc atatgctacc aagatgcctt ttaagaatcc tggtaaaaga  1380
aatcggtgga agacgactca acgactatca ggccccattt tttgggacca tgctcaagga  1440
tttggcttta gcaaaagtag ataacactat tttggggagc ttgatctcaa ggacacatga  1500
aggaataaag ctattttagt caagacgtcc ttaaggaaca caataagacc ctaggtccct  1560
aatgactagt gtgttatatg tttcgagacg ctcctacacc taagttcttt tagctatttc  1620
cattcacaat gatggtatat gacctaggta ccaatgcccc acggagtttc taacattaag  1680
aatgatctaa aacataagga ccctagagcc agggcactcc tggtattaaa acatttaaac  1740
cctattgcct tagtgctgat ttttgttttt tgtttgtagg aggagaaacg agcacttgtt  1800
gcctctcgcg acaatcttga taggctgtac cgtgatgcca gtaactcctt gaccatccta  1860
gagaggagcc accgcttcac catgtctgac ctagatcatc accaccatga gctgcaggcg  1920
tctcaagatg aagtcttgca acttggacga ttgttgtcga ctaaggattc caccatcaag  1980
gatctgcgct tctaaaaagc tcgtcccgca ggagctagag gcggcccagc ttgctattaa  2040
gactctaaag gacaactgca ccgtcctgaa gacccagcgc gataaagcta tggataaagt  2100
tgttcgcgct ggacggatcc tgatgaggag gcacggcgtt gtggtgcctg acgatattgt  2160
tgtcgatgtc aaggccgcgc ctgatgctac aagtcgtccc tctttttctg ttgctcctgc  2220
gaaggatacc gtctgcaagg atgtttcgat gcagtgatgt cctgtaaaac actttactta  2280
ttgagttagt atctccttgg aggatggatg taatatggat tcaatgtgca tgcgacaatt  2340
gtgttagaac tcgaatattc tacgaacagg gtgccggaaa acggccctag cactggcaag  2400
taagatgttc tcttttcctg aagtgttttc aattttagcc ggttgttatg ctattagggt  2460
atagtggtca ccctaaacag cgcaaatgca agtataccgc gttggcttaa ggtgtgttcc  2520
gacttaagtc agttgccttg ctggtagggc atagtggtca ccctgagtaa agtaagtcag  2580
agtatattgc accgacctaa gtcgattgca ctactagcag ggtatagtga tcaccctaag  2640
tcaagtaagc atgagcatat cgcaccgact taggtcatca ccgacttaag ccgattgttc  2700
tgttagcagg gtataatggt caccctaagt cagataagca tgagcatgtc acaccggctt  2760
aagtcgttgc cgacttaagc cgattgctcc gtcagcaggg tatagtggtc accctaataa  2820
gtcaggtaag catgagcata tcgcactggc ttaagtcgtt gccgacttaa gccgattgct  2880
ccgtcagtag ggtatagtgg tcaccctaag tcaagtaagc gtgagcatgt cgcactggct  2940
taagtcgatt gctccgtcag cagggtataa tggtcacttt aagtcaagta agtgtgagca  3000
tgtcgcacca gcttaagtca tcgccgactt aagctgattg ctccattagc agggtatagt  3060
ggtcacccta agttaggtaa tcgtgctgat ttcaagtcta gcccaatcaa agtcagttgt  3120
aagtcaagag tatgaatgcc tttggagaat gaaaacttta ttgatgatga aattctcgga  3180
tttacagagt acaatgttcc ttcaagaatt ttgaggcctt gctaaggata gaattttctg  3240
aggtgttcta tgttccatga gttcccttct gtgccgtcca tttgagtaag ccggtatggt  3300
cccggccgag tgaccgcctc taatatgatg aacgatcctt cccacagtgg tgatagcttg  3360
tgccgccctt cccccgttag aattcggcga aggaccaagt ctcccactgc aaaggatcgg  3420
tgccgcatag ctttatcatg gtagcacctc aaggtctgct ggtacctagc cgactgaatt  3480
actgtgttca atagttcttc ttccagtaca tcaatatctt ccagtctggt cgcttctgct  3540
tcagctatgc tttcgaaagt taatcttggt gccctgaaga ttaggtcagc gggcagcact  3600
gcctctaacc cataaaccat gaaaaacggg gtatttctat gcagagctcg actgggttga  3660
gttctcaggc tctagaccac gtatggcagc tctctgatcc atttcctgc aagcttttca  3720
ctcttgtcaa atattttctt cctgagtgct tctagtatca ttccgttggt tctttctacc  3780
```

-continued

```
tggccattgg ctcttgggtg tgctactgat gcatacttaa cctggaagct ccgttgctcg  3840
cagaaatcga gttcagagct ggtgaagttg gatcccagat cggtgatgat gttgtttggt  3900
atcccaaacc tgaatattat gtcttgtata aactccacca ctttggctga ggtcaaggaa  3960
gcaattggct tgtactttat ccattttgtg aatttgttaa tggcaaccag tacatgagta  4020
tagcctccct gagccttctt aaaaggtccg atcatgtcca gcccacagca tgcgaacggc  4080
catgttacag gaatggtctg cagctgctgc gcgggtaagt gttgttgctt tgataggaat  4140
tggcatgctt cacacttctg gactaactcg gcaacatcgt tctttattgt tggccaatag  4200
aaaccggatc taaaagcctt cccgaccaga gtccttgacg ctgcatgtat tccacactgc  4260
ccggcgtgga tttcatccaa caattgtttc tcggtagtcg agtgaataca tttcatgagg  4320
actcttgctg cacctctcct gtacagtaag ccccatatga tggtgtagtg ggccaactgc  4380
ctcgcgatgc attccactgc agccttgtca tctggctctt cttcattttt atatacctga  4440
tgataggctc tctccagtcg ttggggtccg actctggttg gctcaaggta ttgcacactt  4500
ccacctgatc caagatgatg cttggttgtg atatttcttg gacgaagatc ccaggtggag  4560
cctgggcccg actggatccc agcttcgaca acgcgtctgc tgctgcgttg cggtctcgtt  4620
ccacatgatg gaactctaat ccttcaaatt tgtcctctag ttttcgcaca accgcgcagt  4680
atttgcccat ggagtcagtc gagcagtcct agtctttgct tatctggatt atgaccacta  4740
gcgaatcacc atataccatc agtttcttga tgccgagtga tacaacaatg cttaaaccat  4800
ggatcagttc ttcatacttt gctgcattat ttgacgctgg aaatagtagc tggagtgcat  4860
aattgtgttg ctcacctcca ggagcaataa agagaatccc tgcacccgct ccctatagtt  4920
tcaacgagcc atcaaagtac attttccaca cctcgataac ctctgggcta tctgggacct  4980
gatgttcagt ccactctgat acgaagtcaa ccagcgcctg agtcttgatt gccgtgcggg  5040
gccagaactc tatgttgtga gctccaagct cacacgccca cttggcgatc cttccaatag  5100
cttctttgtt gtggagaatg tcccctattg ggaatcctat gaccactatg actttgtggt  5160
cgtcaaagta gtgtcggagt ttgcgtgcgg ttagaagtac tgcatacaac aacttctgta  5220
cttgaggata ccttatcttt gagggcccga ggacttcact gatgaagtag actggatgtt  5280
gcaccgggta cacatgtcct tcctccaccc gcttgactac taacgtggtg cttaccacgt  5340
gagtcgtgct ggagatgtat aacatcaaat cttccaccaa ctgattcagc gtagctcgtc  5400
gtggcggctt gagcactggt ggtgtagtca aaaaatttta gttcctctag agcttcctgc  5460
gcctctgtgg tccactgaaa cttgtccacc tttttgagca atttgtagaa ggccatgcct  5520
tgctccccta gtcttgatat gaacctgctc agggctgcca tgcatccagt aagcctctgt  5580
accttttct atgatcgcaa cacttccatt ctcatgatgg ccttgacctt ttccgggtta  5640
gcttcaatcc cttggtgact gacaatgaat ctgagtaact tccctgcctg tactctgaaa  5700
acacactttt ctgggttgag cttccaccgg taatgcctca ggctattgaa gactagctgc  5760
aaatcttcaa tgaagttttc tgttttgatc accacatcat caacataggc ttccacccgc  5820
ttgccccagt ggtcggctaa gcatgtctga atggctctct ggtaagttgc tcccgtgttc  5880
ttgaggtcga atgacatgaa ggtgtaatag aaagctccaa atggggtgat gaaagcattc  5940
ttctcctcat cttcttttgc taagcagata tgatggtatc tagaatagca gtctaggaag  6000
gacaacatag aacagccagc ggtcgaatca accacctgat ctattctagg gagcccgaag  6060
ggatctttgg tgtctcagac ctgggggacc ctcaaccaaa tcgacaagtg aattttgtgt  6120
cgcgtgtccc tgcccagatg gattagtgca agatgaaaca caagaggagg ggtgaggttt  6180
atattatctt gcaccagggt gcttgcagta ggggatacaa tctttgcgag agagggaacg  6240
gatcccaggt ctcttgagag atctagtgtt gtgaagggga gttcgatgtt tgagcaagcc  6300

SEQ ID NO: 140          moltype = DNA  length = 90
FEATURE                 Location/Qualifiers
source                  1..90
                        mol_type = other DNA
                        organism = Zea mays
SEQUENCE: 140
cgctgcgcga cacacctcgt tgccaaagct gcatccgtgc agtgcagtgc agtgcaggac  60
aggacctcct ttgtttagga cgcgatgctg                                  90
```